(12) United States Patent
Simons, Jr. et al.

(10) Patent No.: US 7,867,500 B2
(45) Date of Patent: Jan. 11, 2011

(54) COFACTOR THAT MODULATES STEROID RECEPTOR ACTIVITIES

(75) Inventors: S. Stoney Simons, Jr., Bethesda, MD (US); Yuanzheng He, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 992 days.

(21) Appl. No.: 11/510,859

(22) Filed: Aug. 25, 2006

(65) Prior Publication Data
US 2007/0128627 A1    Jun. 7, 2007

Related U.S. Application Data

(63) Continuation-in-part of application No. PCT/US2005/006393, filed on Feb. 25, 2005.

(60) Provisional application No. 60/548,039, filed on Feb. 26, 2004.

(51) Int. Cl.
*A61K 39/00* (2006.01)
*A61K 38/00* (2006.01)
(52) U.S. Cl. .................... 424/198.1; 424/185.1; 514/12
(58) Field of Classification Search .................... None
See application file for complete search history.

(56) References Cited

U.S. PATENT DOCUMENTS

2002/0197679 A1* 12/2002 Tang et al. .................. 435/69.1
2005/0181375 A1*  8/2005 Aziz et al. ...................... 435/6

OTHER PUBLICATIONS

He et al. 2007. Mol and Cell Biology, 27:1467-1485.*
Glass et al. 1997. Curr Opin. Cell Biol. 9:222-232.*
Wang et al. 2004. J. Steroid Biochem and Mol Biol. 91:197-210.*
Database EMBL 'Online! Apr. 9, 1999, "Homo Sapiens mRNA for KIAA0998 protein, partial cds." XP002332405, retrieved from EBI accession No. EM_PRO:ABO23215. Database accession No. AB023215 abstract.
Database Geneseq 'Online! Oct. 22, 2001, "Human polynucleotide SEQ ID No. 464." XP002332406 retrieved from EBI accession No. GSN:AAI58261. Database accession No. AAI58261 abstract.
Szapary Daniele et al. "Opposing effects of corepressor and coactivators in determining the dose-response curve of agonists, and residual agonist activity of antagonists, for glucocorticoid receptor-regulated gene expression," Molecular Endocrinology, 13(12):2108-2121, Dec. 1999.
Chen Shiyou et al. "A second pathway for modulating glucocorticoid receptor transactivation properties," Molecular and Cellular Endocrinology 199(1-2):129-142, Jan. 2003.
He Yuanzheng et al., "Modulation of induction properties of glucocorticoid receptor-agonist and —antagonist complexes by coactivators involves binding to receptors but is independent of ability of coactivators to augment transactivation." J. Biological Chemistry 277(51):49256-49266, Dec. 2002.

* cited by examiner

*Primary Examiner*—Shulamith H. Shafer
(74) *Attorney, Agent, or Firm*—Swanson & Bratschun, L.L.C.

(57) ABSTRACT

The invention provides a new glucocorticoid receptor coactivator named STAMP (Steroid receptor coactivator-1 and Transcription intermediary factor-2 Associated Modulatory Protein) that can modulate transcription of glucocorticoid-, progesterone-, mineralocorticoid- and androgen-responsive genes. The invention also provides antibodies that can bind STAMP and modulate its activity. In addition, the invention provides antisense, ribozyme and siRNA STAMP nucleic acids that can modulate the expression of STAMP. Also provided are compositions and methods for modulating glucocorticoid-responsive gene expression and for treating a variety of diseases and conditions.

3 Claims, 36 Drawing Sheets

```
151 tgaatctgctaggaaaggtctctgaggcccccgtctgctgactgcatgac 200
    |||||||||||||||||||||||||||||||||| |||||||||||||||
  1 tgaatctgctaggaaaggtctctgaggcccccgtctgccgactgcatgac 50

201 aaaccctaaaggaaatgccaatcgtgatgggcccgggacctggaggaaaca 250
    ||||||||||||||||||||| ||||||||||||||||||||||||||||
 51 aaaccctaaaggaaatgccagtcgtgatgggcccgggacctggaggaaaca 100

251 gcatcatcctcagaggatgaggaggtcataagtcaagaggatcatccatg 300
    ||||||||||||||||||||||||||||||||||||||||||||||||||
101 gcatcatcctcagaggatgaggaggtcataagtcaagaggatcatccatg 150

301 catcatgtggactggaggctgcaggagaattccagttttggtattccatg 350
    ||||||||||||||||||| ||||||||||||||||||||||||||||||
151 catcatgtggactggaggctgtaggagaattccagttttggtattccatg 200

351 ccgacgctattcttacaaaggacaacaatattagagtaattggagaacgt 400
    ||||||||||||||||||||||||||||||||||||||||||||||||||
201 ccgacgctattcttacaaaggacaacaatattagagtaattggagaacgt 250

401 tatcatttgtcttataagattgtacgaacggacagtcgcctagtacgcag 450
    ||||||||||||||||||||||||||||||||||||||||||||||||||
251 tatcatttgtcttataagattgtacgaacggacagtcgcctagtacgcag 300

451 cattctgacagcccatggatttcatgaagttcacccaagcagcactgact 500
    ||||||||||||||||||||||||||||||||||||||||||||||||||
301 cattctgacagcccatggatttcatgaagttcacccaagcagcactgact 350

501 ataacctaatgtggacaggatcccacctgaagcccttcttactgcgcacc 550
    ||||||||||||||||||||||||||||||||||||||||||||||||||
351 ataacctaatgtggacaggatcccacctgaagcccttcttactgcgcacc 400

551 ctctctgaagcacaaaaagttaatcactttcccaggtcttatgaacttac 600
    ||||||||||||||||||||||||||||||||||||||||||||||||||
401 ctctctgaagcacaaaaagttaatcactttcccaggtcttatgaacttac 450

601 ccggaaggaccgactgtacaaaaacattattcgaatgcagcatacacatg 650
    ||||||||||||||||||||||||||||||||||||||||||||||||||
451 ccggaaggaccgactgtacaaaaacattattcgaatgcagcatacacatg 500

651 gattcaaggttttcacatcctcccccagaccttcctcctgccagctgag 700
    ||||||| ||||||||||||||||||||||||||||||||||||||||||
501 gattcaaggcttttcacatcctcccccagaccttcctcctgccagctgag 550

701 tacgcggaattttgtaattcatattcgaaggaccggggaccttggatagt 750
    ||||||||||||||||||||||||||||||||||||||||||||||||||
551 tacgcggaattttgtaattcatattcgaaggaccggggaccttggatagt 600

751 aaaaccagtggcatcttcaaggggcggggcgtctacctgatcaacaatc 800
    ||||||||||||||||| |||||||||||||||||||||||||||||||
601 aaaaccagtggcatcttctaggggcggggcgtctacctgatcaacaatc 650

801 caaaccagatctccctggaagagaacattttggtctcccgttacattaac 850
    |||||||||| ||||||||||| ||||| |||||||||||||| |||||
651 caaaccagatttccctggaagaaaacattctggtctcccgttatattaac 700

851 aaccccctgctcatagatgatttcaagtttgacgtgcgcctctatgtgct 900
    |||||||||||||||||||||||||||||| |||||||||||||||||||
701 aaccccctgctcatagatgatttcaagtttgatgtgcgcctctatgtgct 750

901 cgtgacttcctatgatcctcttgtcatctatctctatgaagaaggattgg 950
    |||||||||||||||||||||||||||||||||||||||||||||||||
751 ggtgacttcctatgatcctcttgtcatctatctctatgaagaaggattgg 800

951 ctaggtttgcaactgtgcgatatgatcaaggagccaagaacattcggaac 1000
    ||||||||||||||||||||||||||||||||||||||||||||||||||
801 ctaggtttgcaactgtgcgatatgatcaaggagccaagaacattcggaac 850

1001 cagttcatgcatctgacaaactacagtgtcaacaagaaaagtggagatta 1050
     |||||||||||||||||||||||||||||||| ||||| ||||||||| |
 851 cagttcatgcatctgacaaactacagtgtgaacaagaagagtggagacta 900

1051 cgtcagttgtgacgatccagaagtggaggattatggaaacaaatggagca 1100
     |||||||||||| |||||||||||||||| ||||||||||||||||||||
 901 cgtcagttgtgatgatccagaagtggaggactatggaaacaaatggagca 950

1101 tgagtgctatgcttaggtacctgaaacaagaaggcagagatacaaccgca 1150
     ||||||||||||||||||||||||||||||||||||||||||||||| |||
 951 tgagtgctatgcttaggtacctgaaacaagaaggcagagatacaactgca 1000

1151 ttgatggcccatgtagaagacctgatcattaagactataatctctgctga 1200
     ||||||||||||||||||||||||||||||||||||||||||||||||||
1001 ttgatggcccatgtagaagacctgatcattaagactataatctctgctga 1050

1201 actagctattgctactgcctgtaaaaccttttgttcctcatcgcagcagtt 1250
     ||||||||||||||||||||||||||||||||||||||||||||||||||
1051 actagctattgctactgcctgtaaaaccttttgttcctcatcgcagcagtt 1100

1251 gttttgaactctatggctttgacgtgctcatagattctactctgaagcca 1300
     ||||||||||||||||||||||||||||||||| ||||||||||||||||
1101 gttttgaactctatggctttgacgtgctcatagatgctactctgaagcca 1150
```

FIG. 3D1

```
1301 tggttgttggaagtgaatctctctccttctttggcctgtgatgcgcctct 1350
     ||||||||||||||||||||||||||||||||||||||||||||| |||||
1151 tggttgttggaagtgaatctctctccttctttggcctgtgatgcacctct 1200

1351 ggacctaaagattaaagccagtatgatttcagatatgttcactgttgtag 1400
     |||||||||||||||||||||||||||||||||||||||||||||||| |
1201 ggacctaaagattaaagccagtatgatttcagatatgttcactgttgttg 1250

1401 gatttgtgtgccaagatcctgcccagcgggcatcaactcggccaatttat 1450
     |||||||||||||||||||||||||||||||||||  |||||||||||||
1251 gatttgtgtgccaagatcctgcccagcgggcatcaacccggccaatttat 1300

1451 cccacctttgagtcttccaggcgaaaccctttccagaaacct........ 1492
     ||||||||||||||||||||||||||||||||||||||||||
1301 cccacctttgagtcttccaggcgaaaccctttccagaaacctcagcgtcc 1350

1493 ..........................cagcgttgccgtccac 1508
                               |||||||  |||||||||
1351 acttccagcacagtttcattcatcagagccaaagcagcgttcccgtccac 1400

1509 tctctgccagtgatgcggaaatgaaaaacctcgtgggctcagcccgggag 1558
     |||||||||||||||||||||||||||||||||||||||||||||||||
1401 tctctgccagtgatgcggaaatgaaaaacctcgtgggctcagcccgggag 1450

1559 aaagggccagggaagttgggtggttctgtgcttggtctgtcaatggagga 1608
     ||||||||||||||||||||||||||||||||||||||||||||||||||
1451 aaagggccagggaagttgggtggttctgtgcttggtctgtcaatggagga 1500

1609 gatcaaagttttacgaagggtgaaggaggagaatgatcggcgaggtggat 1658
     ||||||||||||| ||||||||||||||||||||||||| ||||||||||
1501 gatcaaagttttacggagggtgaaggaggagaatgatcggagaggtggat 1550

1659 ttattcgcatatttcctacatctgagacatgggaaatatatgggtcctac 1708
     ||||||||||||||||||||||||||||||||||||||||||||||||||
1551 ttattcgcatatttcctacatctgagacatgggaaatatatgggtcctac 1600

1709 ctcgagcataagacctcaatgaactatatgctggcaacacgcctcttcca 1758
     ||||||||||||||||||||||||||||||||||||||||||||||||||
1601 ctcgagcataagacctcaatgaactatatgctggcaacacgcctcttcca 1650

1759 ggacagaatgactgctgatggagcgccagaattgaagatagagagtctga 1808
     |||||||||||||||||||||||| |||||||||||||||||| | ||||
1651 ggacagaatgactgctgatggagcaccagaattgaagatagagggctga 1700

1809 attcaaaggccaagctgcatgctgcactttacgagaggaagctcctgtct 1858
     ||||||||||||||||||||||||||||||||||||||||||||||||||
1701 attcaaaggccaagctgcatgctgcactttacgagaggaagctcctgtct 1750

1859 ctggaggtgcgaaaacgtagacgacggagtagcagattgagggcaatgag 1908
     ||||||||||||||||||||||||||||||||||||||||||||||||||
1751 ctggaggtgcgaaaacgtagacgacggagtagcagattgagggcaatgag 1800

1909 gccaaaataccccagtgattacccaaccagctgaaatgaatgttaaaactg 1958
     ||||||||||||||||||||||||||||||||||||||||||||||||||
1801 gccaaaataccccagtgattacccaaccagctgaaatgaatgttaaaactg 1850

1959 agacagagagtgaagaggaggaagaagtcgcattagataatgaagatgaa 2008
     |||||||||||||||||||||||||||||||||||| |||||||||||||
1851 agacagagagtgaagaggaggaagaagtcgcattagacaatgaagatgaa 1900

2009 gaacaggaggcttcccaggaggagtctgcaggatttcttagagaaaatca 2058
     || ||||| ||||||||||||||||||||||||||||||||||||||||
1901 gagcaggaagcttcccaggaggagtctgcaggatttcttagagaaaatca 1950

2059 agccaaatatacaccctcattgacagctttggtagaaaatacacccaaag 2108
     ||||||| ||||||||||||||||| ||||||||||||||||||||||||
1951 agccaaagatacaccctcattgacaactttggtagaaaatacacccaaag 2000

2109 aaaattccatgaaagttcgtgaatggaataataaaggtggacactgctgc 2158
     |||||||| ||||||||||||||||||| ||| ||||||| || |||||
2001 aaaattccgtgaaagttcgtgaatggagtaaaaaggtgaacggtgctgc 2050

2159 aaacttgagactcaggagctagagcctaaatttaacctgatgcagattct 2208
     ||||||||| ||||||||| |||||||||||||||||||||||| |||||
2051 aaacttgagactcaggagctggagcctaaatttaacctgatgcaggttct 2100

2209 tcaagataatggcaatcttagcaaaatgcaggcccgaatagcattctctg 2258
     |||||||| |||||||||||||||| ||||||||||||||||||||||| 
2101 tcaagataacggcaatcttagcaaagtgcaggcccgaatagcattctcta 2150

2259 cctatctccagcatgttcaaattcgcctgatgaaagacagtggcggtcag 2308
     |||||||||||||||||||||||||||||||||||||||||||| |||||
2151 cctatctccagcatgttcaaattcgcctgatgaaagacagtggaggtcag 2200

2309 acgttcagtgccagttgggctgccaaagaggatgaacagatggagctggt 2358
     ||||||||||||||||||||||||||||||||||||||||||||||||||
2201 acgttcagtgccagttgggctgccaaagaggatgaacagatggagctggt 2250

2359 tgttcgtttcctcaagcgagcatcaaataacctccagcattcactgagga 2408
     ||||||||||||||||||||||||||||||||||| |||| |||||||||
2251 cgttcgtttcctcaagcgagcatcaaataaccttcagcagtcactgagga 2300
```

FIG. 3D2

```
2409 tggtattacccagtcgacgattggcacttctggaacgcagaagaatcctg 2458
     ||||||||||||| |||||||||||||||||||||||||||||||||||
2301 tggtattacccagccgacgattggcacttctggaacgcagaagaatcctg 2350

2459 gcccaccagctgggtgactttatcattgtatacaacaaggaaacagaaca 2508
     ||||||||||||||||||||||||||||||||||||||||||||||||||
2351 gcccaccagctgggtgactttatcattgtatacaacaaggaaacagaaca 2400

2509 aatggctgaaaagaaatcaaagaagaaagttgaggaagaagaggaagatg 2558
     ||||||||||||||||||||||||||||||||| |||||||| ||||
2401 aatggctgaaaagaaatcaaagaagaaagttgaagaagaagagggaggatg 2450

2559 gggtgaatatggaaaactttcaggagttcatcagacaagcaagtgaggct 2608
     | |||||||||||||||||||||||||||||||||||||||||||||||
2451 gagtgaatatggaaaactttcaggagttcatcagacaagcaagtgaggct 2500

2609 gaactggaggaggtgttgacttttatacccaaaagaacaagtctgctag 2658
     |||||||||||||||||||||||||||||||||||||||||||||||||
2501 gaactggaggaggtgttgacttttatacccaaaagaacaagtctgctag 2550

2659 tgtcttcctggggactcactctaaaatttctaagaacaacaacaattatt 2708
     |||||||||||||||||||||||||| ||||||||||||||| ||||
2551 tgtcttcctggggactcactctaaaagttctaagaacaacaacagttatt 2600

2709 ctgatagtggggcaaaaggtgatcaccctgagactataatggaagaagtg 2758
     |||||||||||||||||||||||||||||||||| ||||||||||| |
2601 ctgatagtggggcaaaaggtgatcaccctgagactgtaatggaagaagcg 2650

2759 aaaataaagccacctaaacagcaacagacgacagaaattcattctgataa 2808
     ||||| ||||| |||||||||||||||||| |||||||||| |||||||
2651 aaaatgaagccgcctaaacagcaacagacaacagaaattcactctgataa 2700

2809 attatctcgatttaccacttcagcagaaaaagaggcaaaattagtttata 2858
     |||||||||||||||||||||||||||||||||||||||||||||||||
2701 attatctcgatttaccacttcagcagaaaaagaggcaaaattagtttata 2750

2859 gcaattcctc..........ctctggtcctactgctactctgcagaaa 2896
     || ||| ||           |||||||||||||||||||||||||
2751 ccagttcttcgtcgactcctttctctggtcctactgctactctgcagaaa 2800

2897 attcccaacacccatttgtcatctgttacaacctctgacctctctccagg 2946
     |||||||||||||||||||||||||||||||| |||||||||||||||
2801 attcccaacacccatttgtcatctgttacaacctcagacctctctccagg 2850

2947 gccttgccaccattcttctttatctcaaattccttcagctatccccagca 2996
     |||| ||||||||||||||||||||||||||||||||||||||||||||
2851 gcctggccaccattcttctttatctcaaattccttcagctatccccagca 2900

2997 tgcctcaccagccaacaatttactgaacacagtctctgccagtgcttct 3046
     |||||||||||||||||||||||||||||||||||||||||||||||||
2901 tgcctcaccagccaacaatttactgaacacagtctctgccagtgcttct 2950

3047 ccctgcctacatcccggggcacagaacatcccaagccctactggcctgcc 3096
     ||||  |||||||| ||| |||||||||||||||||||| |||||||||
2951 ccctcctacatcctgggacacagaacatcccaagccctgctggcctgcc 3000

3097 acgctgtcgatcaggaagtcacaccattggtcccttttcttccttcaaa 3146
     | |||||||||||||||||||||||||||||  |||||||||||||||
3001 tcgctgtcgatcaggaagtcacaccattggctccttttcttccttcaaa 3050

3147 gtgctgcacacatctatagccagaaactgtctcgtccctcttcagcaaag 3196
     ||||||||||||||||||||||||||||||||||||||||||||||||||
3051 gtgctgcacacatctatagccagaaactgtctcgtccctcttcagcaaag 3100

3197 gcaggatcgtgctatctaaacaagcatcattcaggaatagccaaaacaca 3246
     ||||||||||||||||||||||||||||||||||||||||||||||||||
3101 gcaggatcgtgctatctaaacaagcatcattcaggaatagccaaaacaca 3150

3247 aaaagagggagaagatgcttctttatatagcaaacggtacaaccaaagta 3296
     | ||||||||||||||||||||||||||||||||||||||||||||||
3151 acaagagggagaagatgcttctttatatagcaaacggtacaaccaaagta 3200

3297 tggttacagctgaacttcagcggctagctgagaagcaggcagcgagacag 3346
     ||||||| |||||||||||||||||||||||||||||||||||||||||
3201 tggttacagctgaacttcagcggctagctgagaagcaggcagcgagacag 3250

3347 tattctccatccagccacatcaacctcctcacccaacaggtaacaaacct 3396
     |||||||||||||||||||||||||||||||||||||||| |||||| |
3251 tattctccatccagccacatcaacctcctcacccaacaggtgacaaactt 3300

3397 gaatttggcaactggcatcataaacagaagcagtgcttcagctcccccaa 3446
     ||||||||  ||||||||||||||||||||||||||||||| ||||| |
3301 gaatttggccactggcatcataaacagaagcagtgcttcaactccccca 3350

3447 ccctccgacccatcatcagtcctagtggcccgacatggtctacacagtca 3496
     |||||  ||||||||||||| |||||||||| |||||||| ||||| |
3351 ccctccaacccatcatcagcccagtggcccca catggttggtgcagtcg 3400

3497 gaccccaagctcccgagaatcactccagctctcctggaagcaggagcct 3546
     |||||  |||||||  ||||||||||||| |||| |||||||||||||
3401 gaccctcaagctcctgagaatcactccagccctcccagaagcaggagcct 3450
```

FIG. 3D3

```
3547 gcagacaggggggatttgcctgggaaggagaagtagaaaacaacgtgtaca 3596
     ||||||||  ||  ||||||||||||||||| |||||||||||||||||
3451 ccagacaggtgggtttgcctgggaaggagaggtagaaaacaacgtgtaca 3500

3597 gccaggctacaggggtggtcccccagcacaagtatcaccccacagcaggc 3646
     ||  |||||||  ||||||||||||||||||||||||||||||||||||
3501 gcaaggctaccggggtggtcccccagcacaagtatcaccccacagcaggc 3550

3647 agctatcagcttcaatttgccctgcagcaacttgaacaacaaaaacttca 3696
     |||||||||||  ||  |||||||||||||||||||||||| |||||||
3551 agctatcagctccattttgccctgcagcaacttgaacaacaaaaacttca 3600

3697 gtcccggcagctcctggaccagagtcgagcccggcaccaggcaatctttg 3746
     ||||||||||||||||||||||||||||||||||||||||||||||||||
3601 gtcccggcagctcctggaccagagtcgagcccggcaccaggcaatctttg 3650

3747 gcagccagacactacctaactccaatttatggacaatgaataatggtgca 3796
     ||||||||||||||||||||||||||||||||||||||||||||||||||
3651 gcagccagacactacctaactccaatttatggacaatgaataatggtgca 3700

3797 ggttgtagaatttccagtgccacagctagtggccagaagccaaccactct 3846
     ||||||||||||||||||||||||||||||||||||||||||||||||||
3701 ggttgtagaatttccagtgccacagctagtggccagaagccaaccactct 3750

3847 gccacaaaaagtggtaccacctccaagttcttgcgcctccctggttccca 3896
     |||||||||| |||||||||||||||| ||||||||||||||| ||||
3751 gccacaaaaagcagtaccacctccaagctcttgcgcctccctggtcccca 3800

3897 aaccccacccaaccacgaacaagtgctcagaagggcaacatcccagaaa 3946
     ||||||| ||||||||| ||||||||||||||||||||||||||||||
3801 aaccccctcccaaccacaaacaagtgctcagaagggcaacatcccagagg 3850

3947 gcttccaaagggtcctccgcggaagggcagctgaatggactccagagcag 3996
     |||||||||||||||||| ||   |  ||||||||||||||||||||||
3851 gcttccaaagggtcctcggcatatgcgcagctgaatggactccagagcag 3900

3997 ccttaaccctgcagcctctgtgcccatcaccagctctacagatcctgctc 4046
     |||||||||||||||||||||||||||||||||  |||||||||||||
3901 ccttaaccctgcagcctctgtgcccatcaccagctccacagatcctgctc 3950

4047 acactaaaatatgaaccacaaacacacagagaaacaacctgttcaccact 4096
     ||||||||  |||||||||||||||||||||||| |||||||||||||
3951 acactaaaagatgaaccacaaacacacagagaaacgacctgttcaccact 4000

4097 cctggggtgcatgattgagggtgaagcatccaccagcacttcaaggggtcc 4146
     ||||||          |  |||   |
4001 cctggggtgcatctagagcat...................... 4021
```

FIG. 3D4

```
  1 MPIVMARDLEETASSSEDEEVISQEDHPCIMWTGGCRRIPVLVFHADAIL  50
    ||:|||||||||||||||||||||||||||||||||||||||||||||||
  1 MPVVMARDLEETASSSEDEEVISQEDHPCIMWTGGCRRIPVLVFHADAIL  50

51 TKDNNIRVIGERYHLSYKIVRTDSRLVRSILTAHGFHEVHPSSTDYNLMW 100
    |||||||||||||||||||||||||||||||||||||||||||||||||
 51 TKDNNIRVIGERYHLSYKIVRTDSRLVRSILTAHGFHEVHPSSTDYNLMW 100

101 TGSHLKPFLLRTLSEAQKVNHFPRSYELTRKDRLYKNIIRMQHTHGFKVF 150
    |||||||||||||||||||||||||||||||||||||||||||||||| |
101 TGSHLKPFLLRTLSEAQKVNHFPRSYELTRKDRLYKNIIRMQHTHGFKAF 150

151 HILPQTFLLPAEYAEFCNSYSKDRGPWIVKPVASSRGRGVYLINNPNQIS 200
    |||||||||||||||||||||||||||||||||||||||||||||||||
151 HILPQTFLLPAEYAEFCNSYSKDRGPWIVKPVASSRGRGVYLINNPNQIS 200

201 LEENILVSRYINNPLLIDDFKFDVRLYVLVTSYDPLVIYLYEEGLARFAT 250
    |||||||||||||||||||||||||||||||||||||||||||||||||
201 LEENILVSRYINNPLLIDDFKFDVRLYVLVTSYDPLVIYLYEEGLARFAT 250

251 VRYDQGAKNIRNQFMHLTNYSVNKKSGDYVSCDDPEVEDYGNKWSMSAML 300
    |||||||||||||||||||||||||||||||||||||||||||||||||
251 VRYDQGAKNIRNQFMHLTNYSVNKKSGDYVSCDDPEVEDYGNKWSMSAML 300

301 RYLKQEGRDTTALMAHVEDLIIKTIISAELAIATACKTFVPHRSSCFELY 350
    |||||||||||||||||||||||||||||||||||||||||||||||||
301 RYLKQEGRDTTALMAHVEDLIIKTIISAELAIATACKTFVPHRSSCFELY 350

351 GFDVLIDSTLKPWLLEVNLSPSLACDAPLDLKIKASMISDMFTVVGFVCQ 400
    |||||||.|||||||||||||||||||||||||||||||||||||||||
351 GFDVLIDATLKPWLLEVNLSPSLACDAPLDLKIKASMISDMFTVVGFVCQ 400

401 DPAQRASTRPIYPTFESSRRNPFQKP..............QRCRPLSASD 436
    |||||||||||||||||||||||||||             || |||||||
401 DPAQRASTRPIYPTFESSRRNPFQKPQRPLPAQFHSSEPKQRSRPLSASD 450

437 AEMKNLVGSAREKGPGKLGGSVLGLSMEEIKVLRRVKEENDRRGGFIRIF 486
    |||||||||||||||||||||||||||||||||||||||||||||||||
451 AEMKNLVGSAREKGPGKLGGSVLGLSMEEIKVLRRVKEENDRRGGFIRIF 500

487 PTSETWEIYGSYLEHKTSMNYMLATRLFQDRMTADGAPELKIESLNSKAK 536
    ||||||||||||||||||||||||||||||||||||||||||| |||||
501 PTSETWEIYGSYLEHKTSMNYMLATRLFQDRMTADGAPELKIEGLNSKAK 550

537 LHAALYERKLLSLEVRKRRRRSSRLRAMRPKYPVITQPAEMNVKTETESE 586
    |||||||||||||||||||||||||||||||||||||||||||||||||
551 LHAALYERKLLSLEVRKRRRRSSRLRAMRPKYPVITQPAEMNVKTETESE 600

587 EEEEVALDNEDEEQEASQEESAGFLRENQAKYTPSLTALVENTPKENSMK 636
    ||||||||||||||||||||||||||||||||||||.| ||||||||.|
601 EEEEVALDNEDEEQEASQEESAGFLRENQAKDTPSLTTLVENTPKENSVK 650

637 VREWNNKGGHCCKLETQELEPKFNLMQILQDNGNLSKMQARIAFSAYLQH 686
    ||||. || |||||||||||||||||||:|||||||||.|||||| |||
651 VREWSKKGERCCKLETQELEPKFNLMQVLQDNGNLSKVQARIAFSTYLQH 700
```

FIG. 3E1

```
687  VQIRLMKDSGGQTFSASWAAKEDEQMELVVRFLKRASNNLQHSLRMVLPS  736
     |||||||||||||||||||||||||||||||||||||||||| |||||||
701  VQIRLMKDSGGQTFSASWAAKEDEQMELVVRFLKRASNNLQQSLRMVLPS  750

737  RRLALLERRRILAHQLGDFIIVYNKETEQMAEKKSKKKVEEEEEDGVNME  786
     |||||||||||||||||||||||||||||||||||||||||||||||||
751  RRLALLERRRILAHQLGDFIIVYNKETEQMAEKKSKKKVEEEEEDGVNME  800

787  NFQEFIRQASEAELEEVLTFYTQKNKSASVFLGTHSKISKNNNNYSDSGA  836
     ||||||||||||||||||||||||||||||||||||| |||| ||||||
801  NFQEFIRQASEAELEEVLTFYTQKNKSASVFLGTHSKSSKNNNSYSDSGA  850

837  KGDHPETIMEEVKIKPPKQQQTTEIHSDKLSRFTTSAEKEAKLVYSNSS.  885
     |||||||:||| |.||||||||||||||||||||||||||||||||..||
851  KGDHPETVMEEAKMKPPKQQQTTEIHSDKLSRFTTSAEKEAKLVYTSSSS  900

886  ...SGPTATLQKIPNTHLSSVTTSDLSPGPCHHSSLSQIPSAIPSMPHQP  932
        |||||||||||||||||||||||||| ||||||||||||||||||||
901  TPFSGPTATLQKIPNTHLSSVTTSDLSPGPGHHSSLSQIPSAIPSMPHQP  950

933  TILLNTVSASASPCLHPGAQNIPSPTGLPRCRSGSHTIGPFSSFQSAAHI  982
     |||||||||||| |||| ||||| ||||||||||||||| |||||||||
951  TILLNTVSASASPSLHPGTQNIPSPAGLPRCRSGSHTIGSFSSFQSAAHI 1000

983  YSQKLSRPSSAKAGSCYLNKHHSGIAKTQKEGEDASLYSKRYNQSMVTAE 1032
     ||||||||||||||||||||||||||||||.|||||||||||||||||||
1001 YSQKLSRPSSAKAGSCYLNKHHSGIAKTQQEGEDASLYSKRYNQSMVTAE 1050

1033 LQRLAEKQAARQYSPSSHINLLTQQVTNLNLATGIINRSSASAPPTLRPI 1082
     |||||||||||||||||||||||||||||||||||||||| ||||| ||
1051 LQRLAEKQAARQYSPSSHINLLTQQVTNLNLATGIINRSSASTPPTLQPI 1100

1083 ISPSGPTWSTQSDPQAPENHSSSPGSRSLQTGGFAWEGEVENNVYSQATG 1132
     ||||||| |||||||||||||| |||||||||||||||||||||||.|||
1101 ISPSGPTWLVQSDPQAPENHSSPPRSRSLQTGGFAWEGEVENNVYSKATG 1150

1133 VVPQHKYHPTAGSYQLQFALQQLEQQKLQSRQLLDQSRARHQAIFGSQTL 1182
     ||||||||||||||||| |||||||||||||||||||||||||||||||
1151 VVPQHKYHPTAGSYQLHFALQQLEQQKLQSRQLLDQSRARHQAIFGSQTL 1200

1183 PNSNLWTMNNGAGCRISSATASGQKPTTLPQKVVPPPSSCASLVPKPPPN 1232
     ||||||||||||||||||||||||||||||| |||||||||||||||||
1201 PNSNLWTMNNGAGCRISSATASGQKPTTLPQKAVPPPSSCASLVPKPPPN 1250

1233 HEQVLRRATSQKASKGSSAEGQLNGLQSSLNPAASVPITSSTDPAHTKI  1281
     |.|||||||||:||||||| ||||||||||||||||||||||||||||
1251 HKQVLRRATSQRASKGSSAYAQLNGLQSSLNPAASVPITSSTDPAHTKR . 1299
```

FIG. 3E2

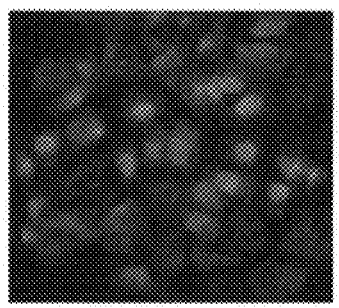
FIG. 3F1
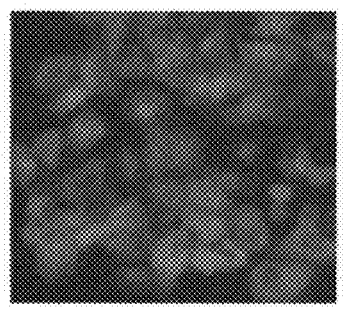
FIG. 3F2
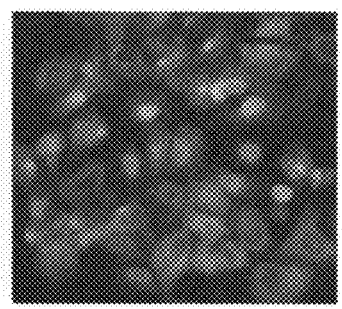
FIG. 3F3
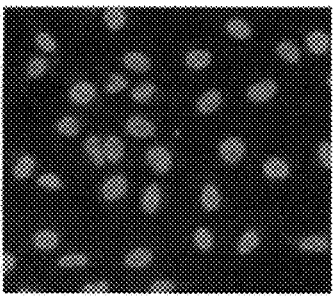
FIG. 3F4
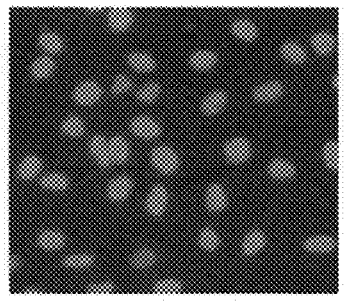
FIG. 3F5
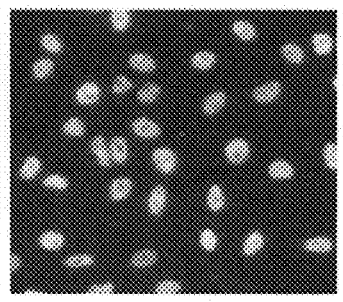
FIG. 3F6

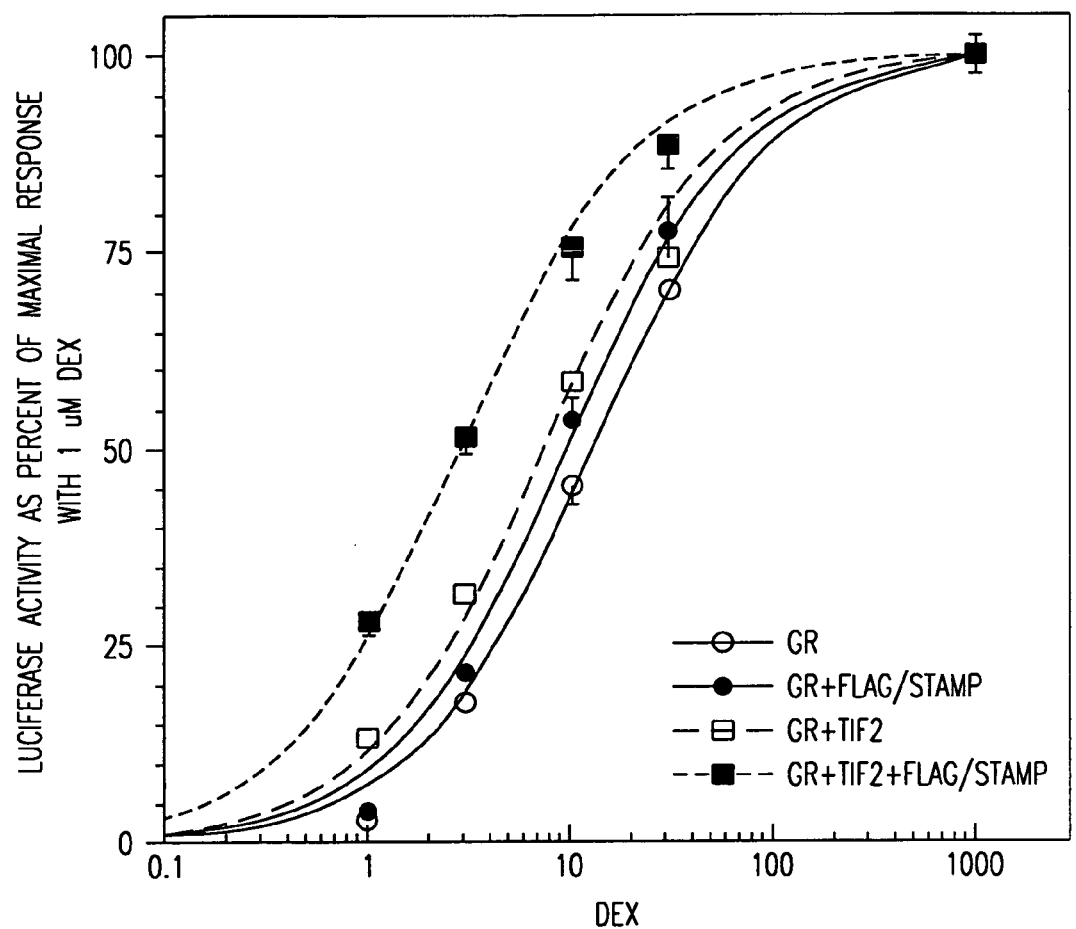
FIG. 4A1

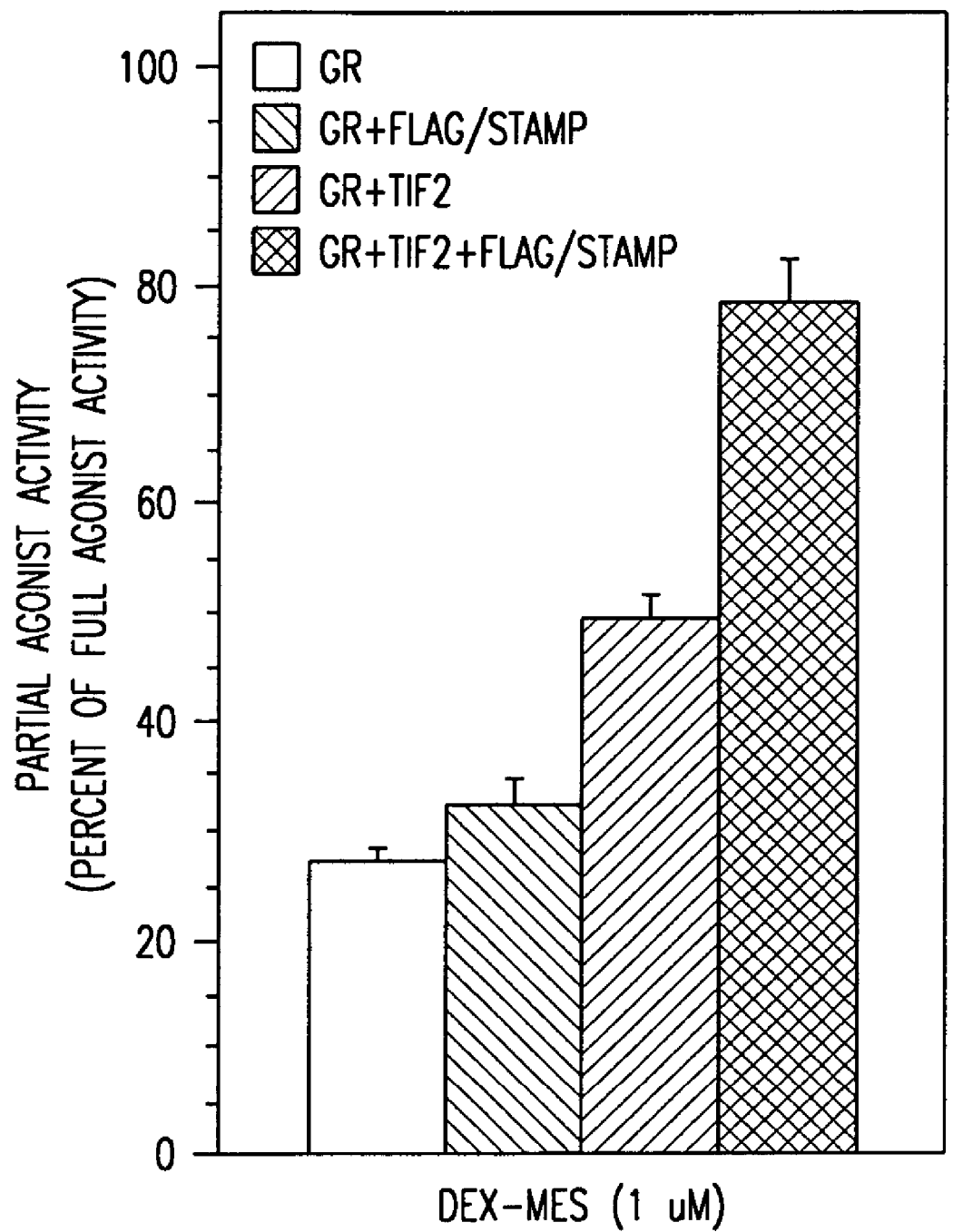
FIG. 4A2

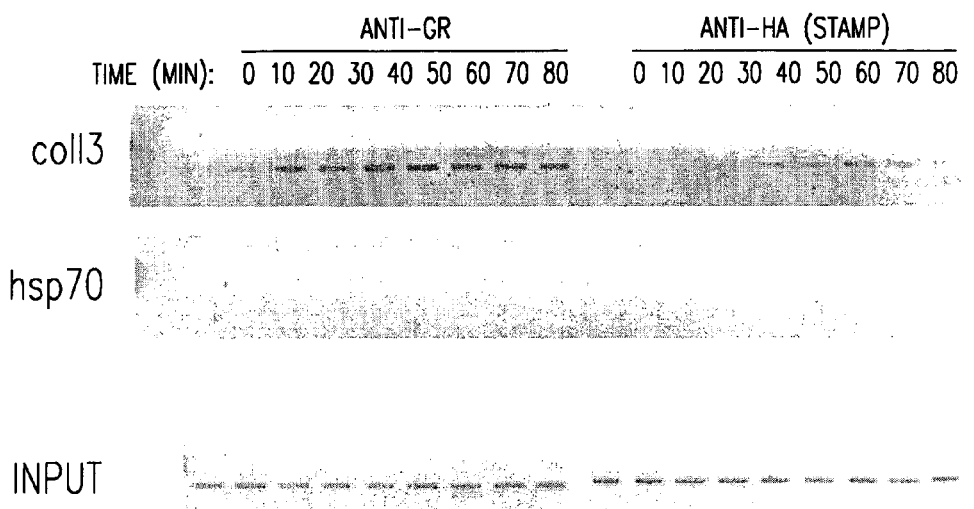
FIG. 5C
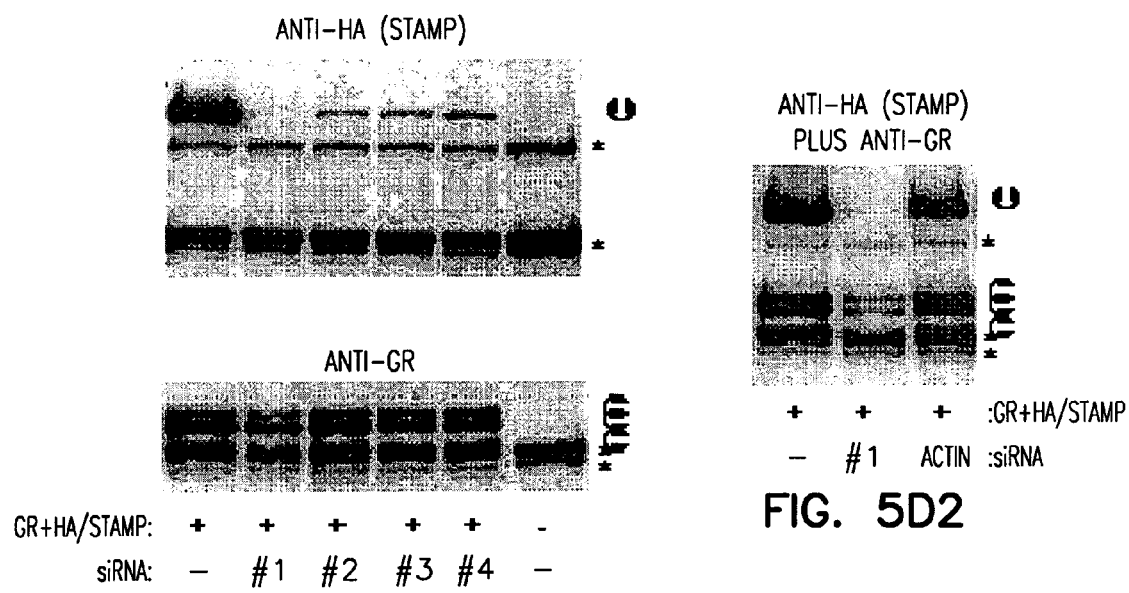
FIG. 5D1
FIG. 5D2

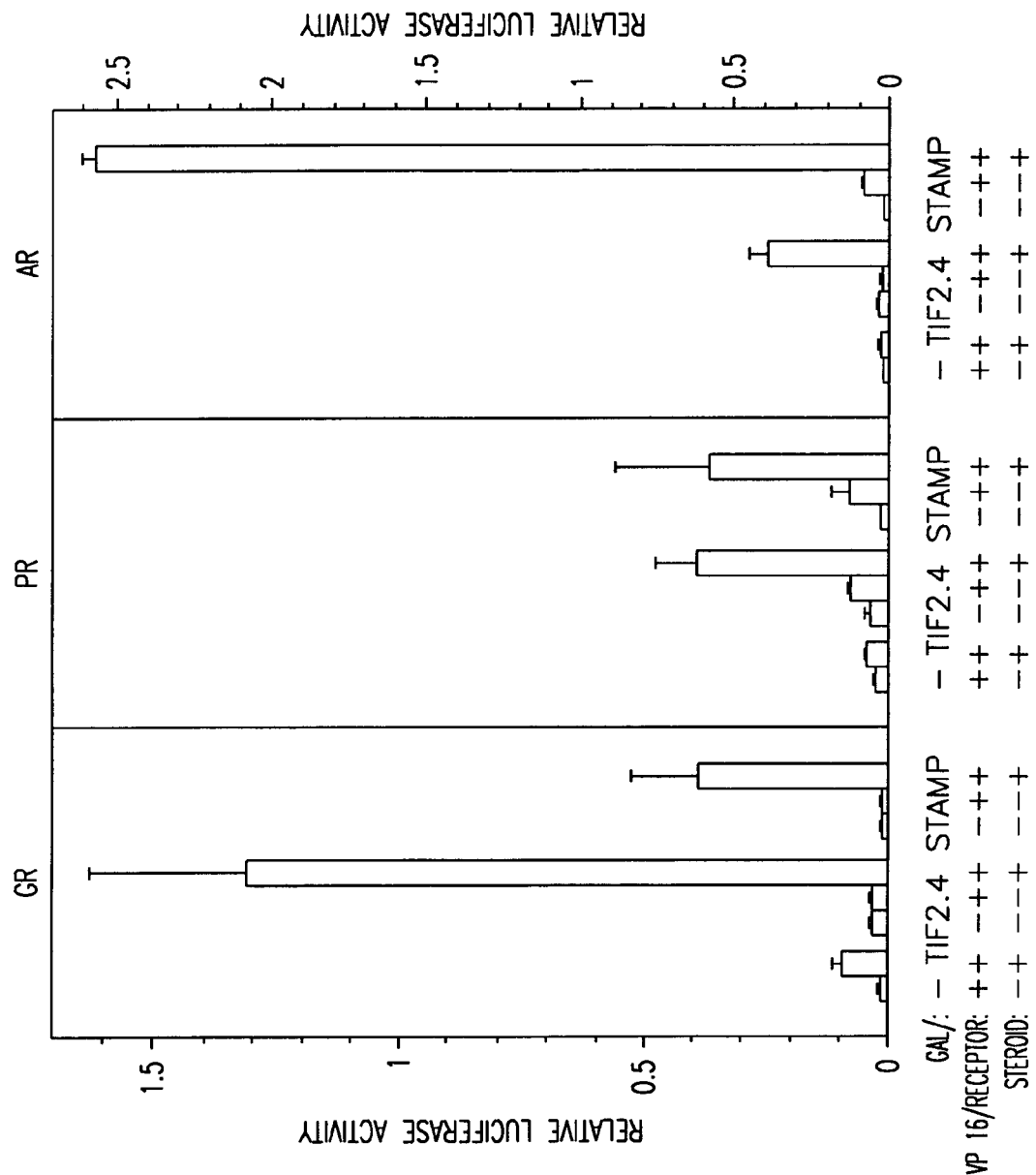
FIG. 6C1

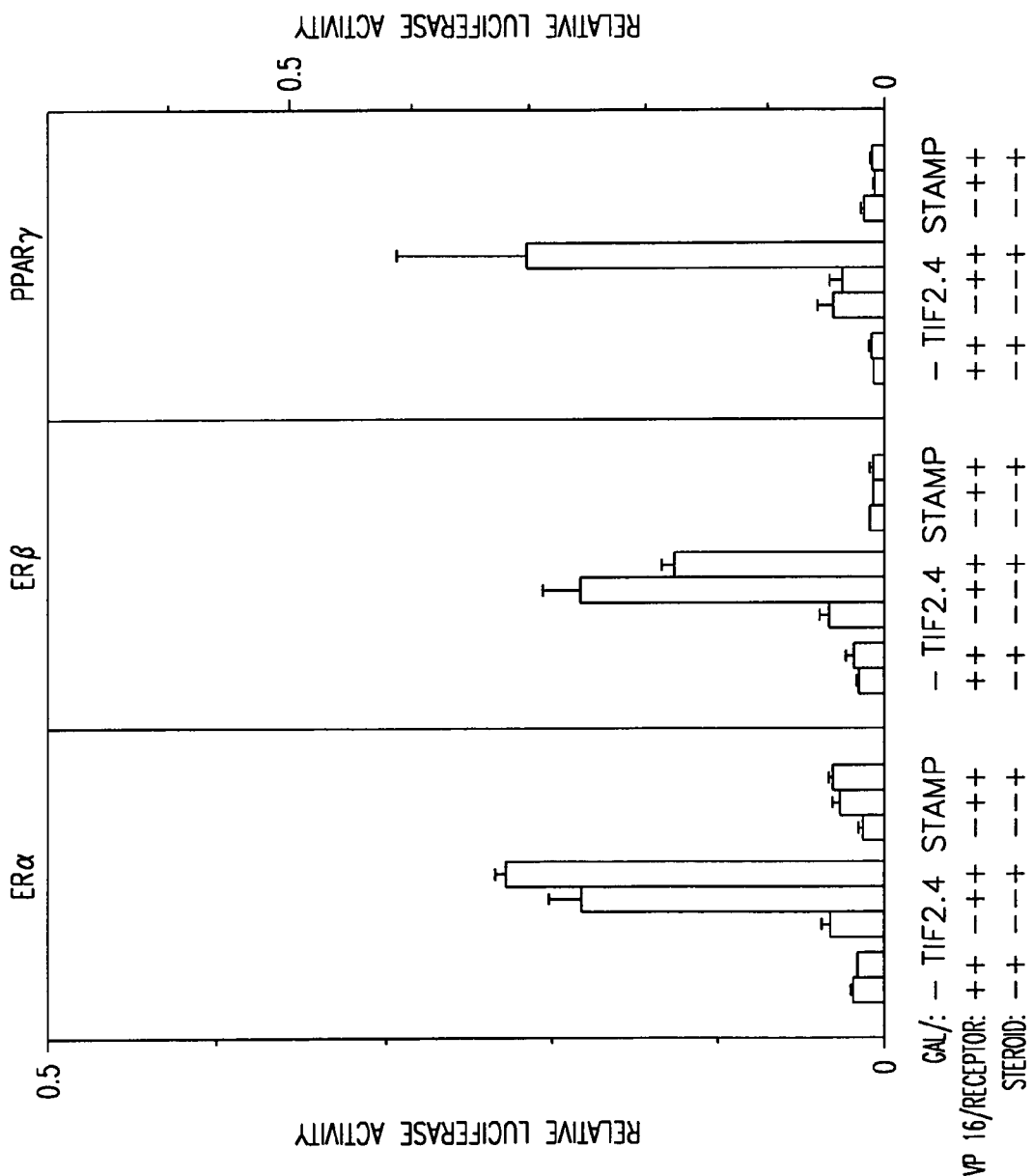
FIG. 6C2

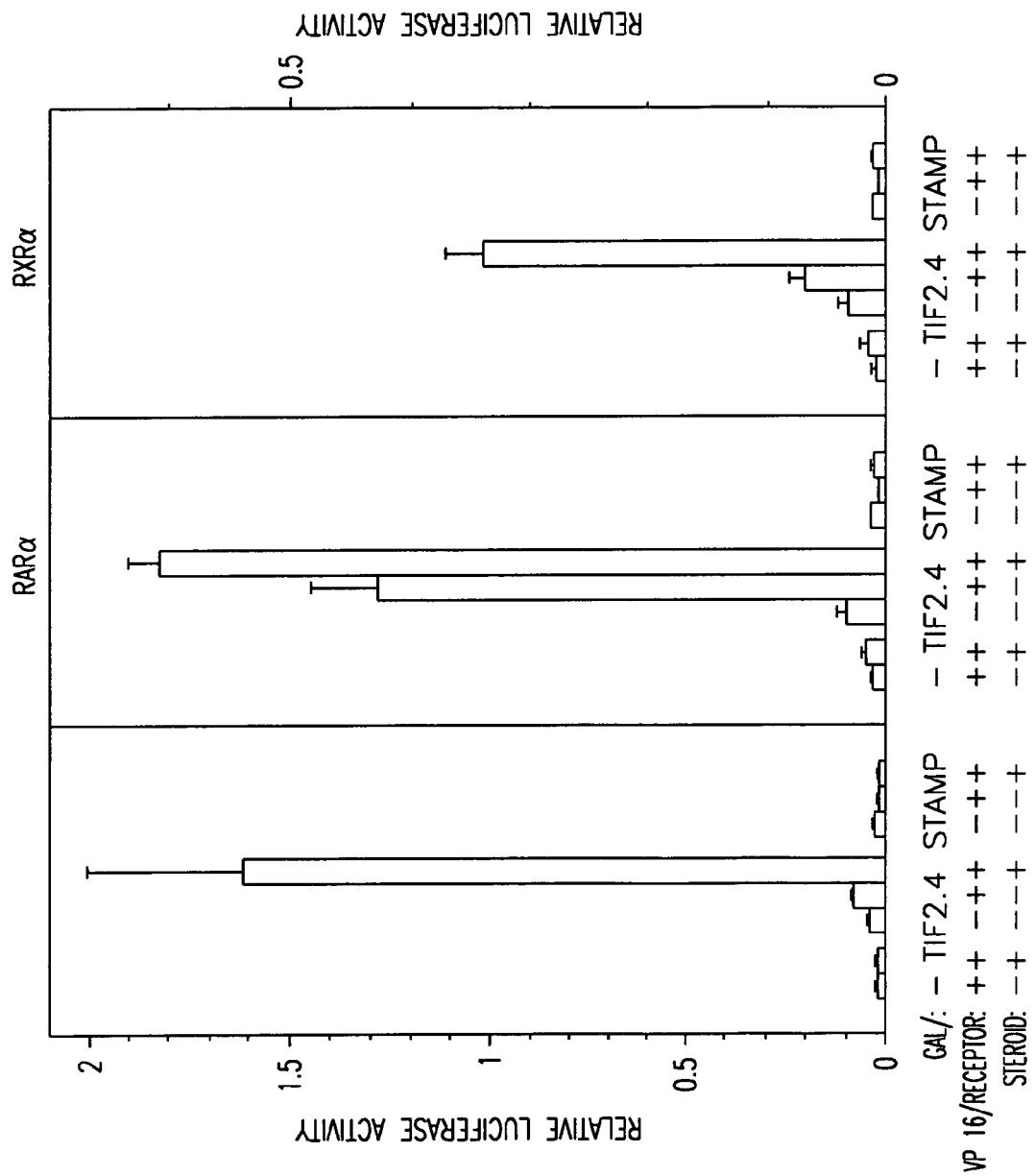
FIG. 6C3

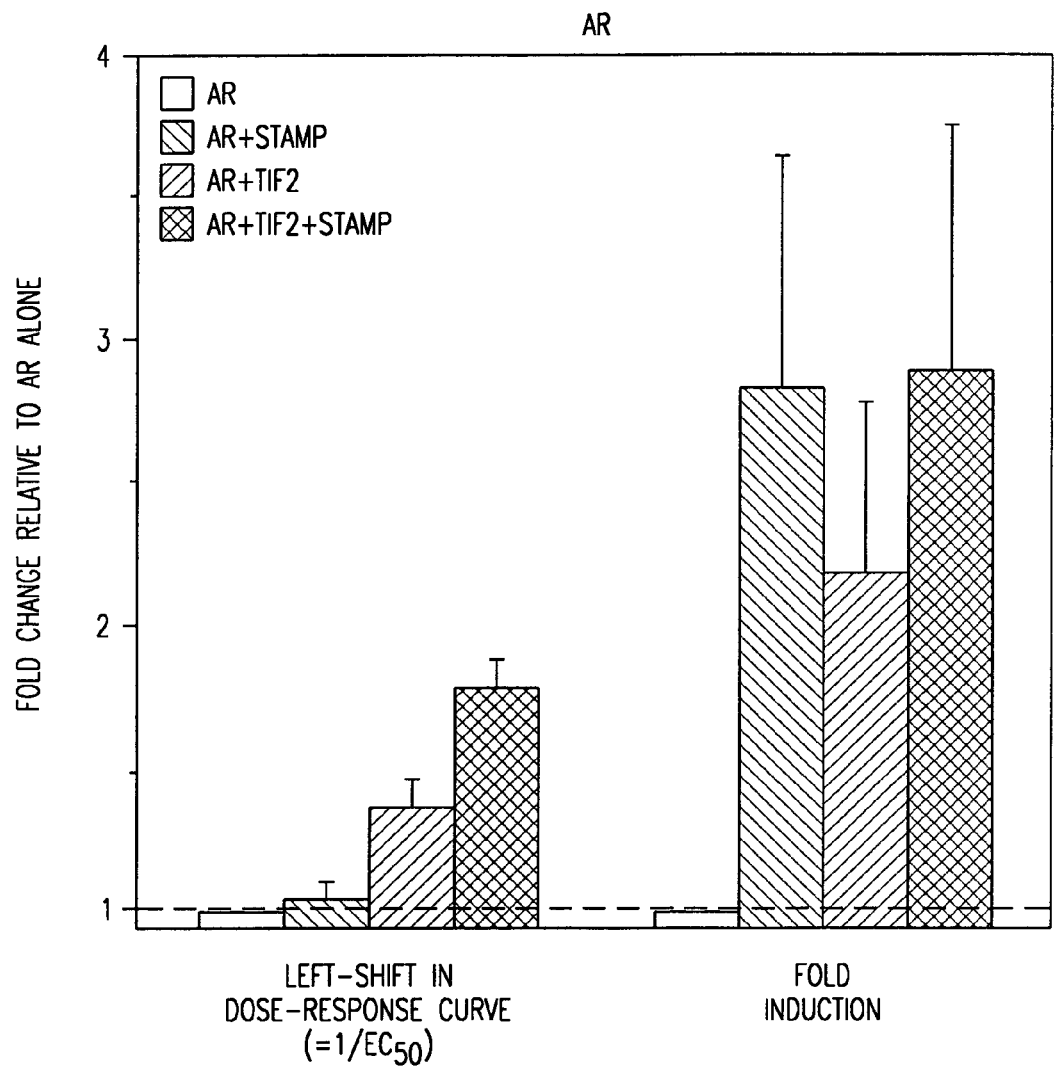
FIG. 6D1

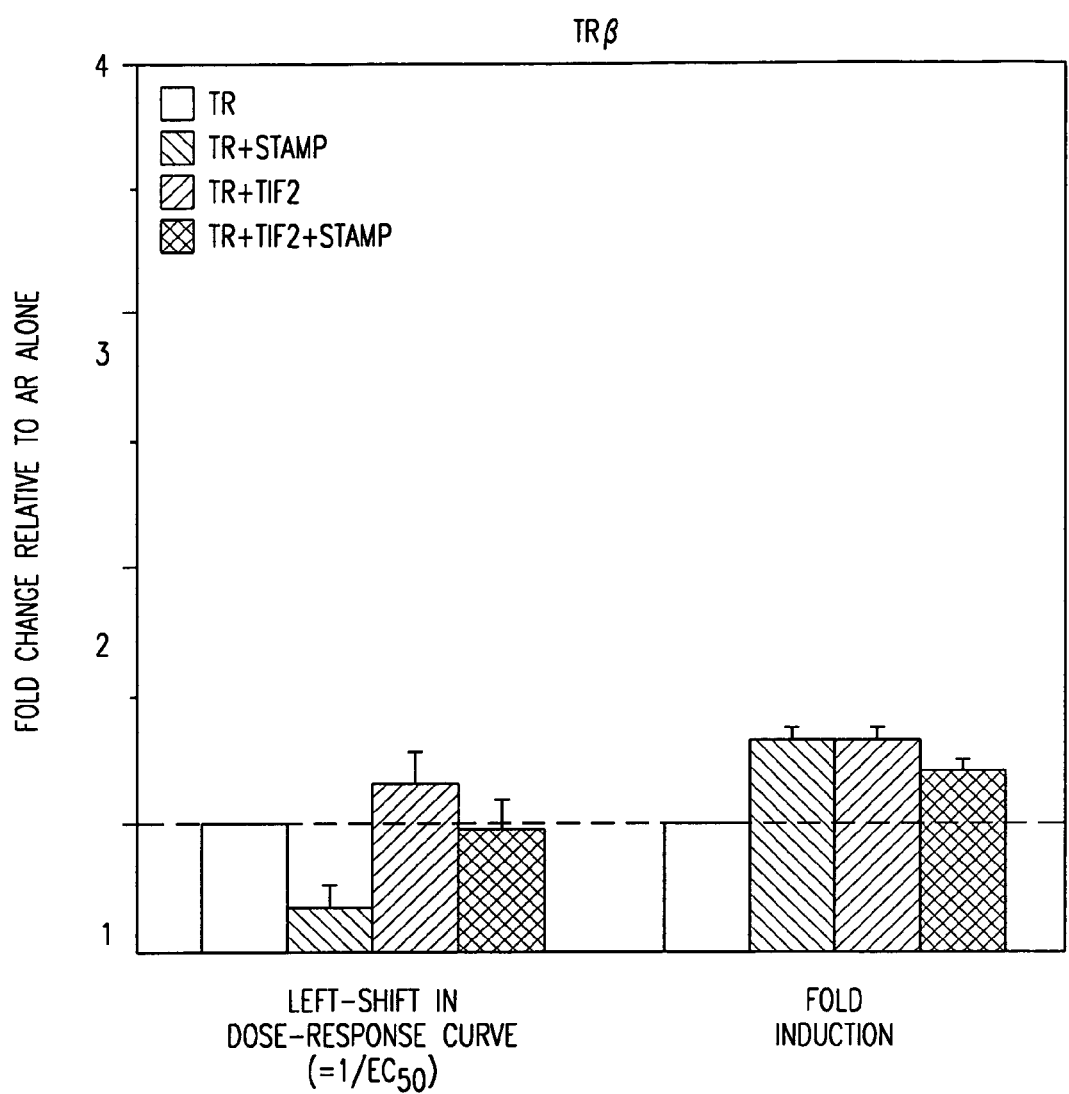
FIG. 6D2

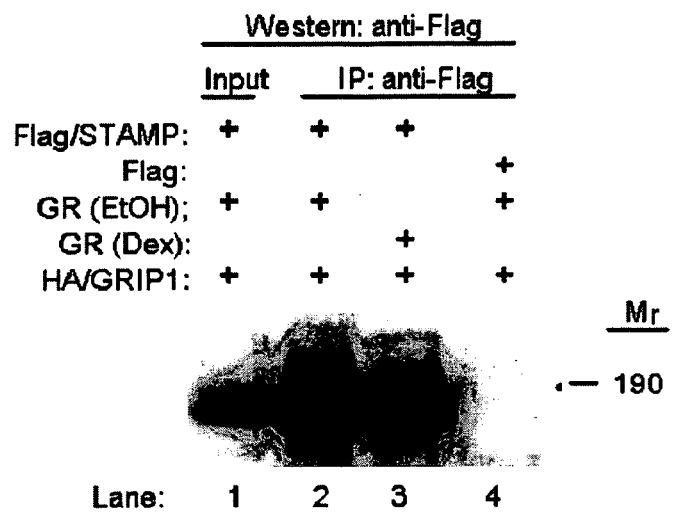
FIG. 7C1
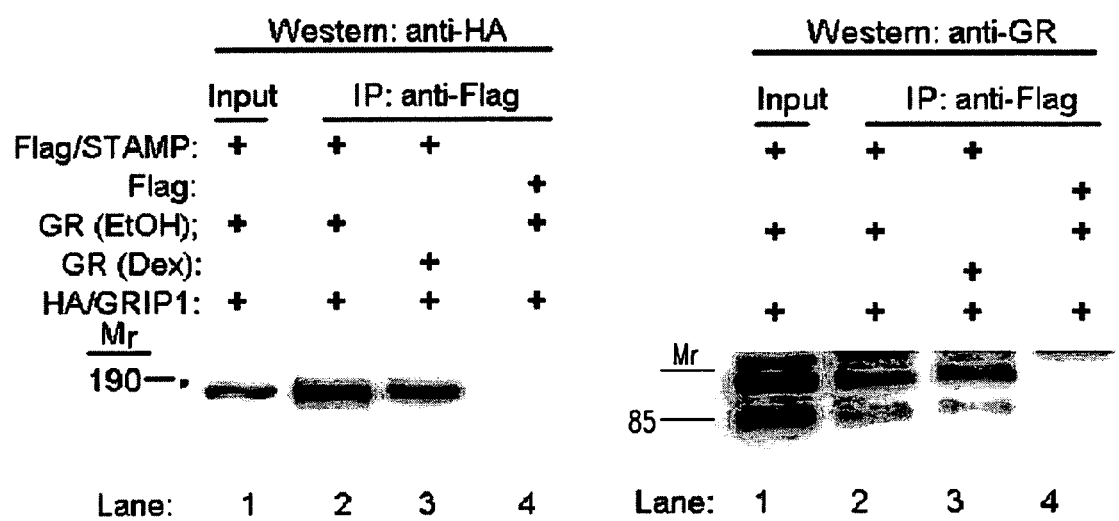
FIG. 7C2
FIG. 7C3

SEQUENCE LISTING

<160> NUMBER OF SEQ ID NOS: 74

<210> SEQ ID NO 1
<211> LENGTH: 1277
<212> TYPE: PRT
<213> ORGANISM: Homo sapiens

<400> SEQUENCE: 1

```
Met Ala Arg Asp Leu Glu Glu Thr Ala Ser Ser Glu Asp Glu Glu
 1               5                  10                  15

Val Ile Ser Gln Glu Asp His Pro Cys Ile Met Trp Thr Gly Gly Cys
                20                  25                  30

Arg Arg Ile Pro Val Leu Val Phe His Ala Asp Ala Ile Leu Thr Lys
                35                  40                  45

Asp Asn Asn Ile Arg Val Ile Gly Glu Arg Tyr His Leu Ser Tyr Lys
            50                  55                  60

Ile Val Arg Thr Asp Ser Arg Leu Val Arg Ser Ile Leu Thr Ala His
65                  70                  75                  80

Gly Phe His Glu Val His Pro Ser Ser Thr Asp Tyr Asn Leu Met Trp
                85                  90                  95

Thr Gly Ser His Leu Lys Pro Phe Leu Leu Arg Thr Leu Ser Glu Ala
                100                 105                 110

Gln Lys Val Asn His Phe Pro Arg Ser Tyr Glu Leu Thr Arg Lys Asp
                115                 120                 125

Arg Leu Tyr Lys Asn Ile Ile Arg Met Gln His Thr His Gly Phe Lys
            130                 135                 140

Val Phe His Ile Leu Pro Gln Thr Phe Leu Leu Pro Ala Glu Tyr Ala
145                 150                 155                 160

Glu Phe Cys Asn Ser Tyr Ser Lys Asp Arg Gly Pro Trp Ile Val Lys
                165                 170                 175

Pro Val Ala Ser Ser Arg Gly Arg Gly Val Tyr Leu Ile Asn Asn Pro
                180                 185                 190

Asn Gln Ile Ser Leu Glu Glu Asn Ile Leu Val Ser Arg Tyr Ile Asn
                195                 200                 205

Asn Pro Leu Leu Ile Asp Asp Phe Lys Phe Asp Val Arg Leu Tyr Val
            210                 215                 220

Leu Val Thr Ser Tyr Asp Pro Leu Val Ile Tyr Leu Tyr Glu Glu Gly
225                 230                 235                 240

Leu Ala Arg Phe Ala Thr Val Arg Tyr Asp Gln Gly Ala Lys Asn Ile
                245                 250                 255

Arg Asn Gln Phe Met His Leu Thr Asn Tyr Ser Val Asn Lys Lys Ser
                260                 265                 270

Gly Asp Tyr Val Ser Cys Asp Asp Pro Glu Val Glu Asp Tyr Gly Asn
                275                 280                 285

Lys Trp Ser Met Ser Ala Met Leu Arg Tyr Leu Lys Gln Glu Gly Arg
            290                 295                 300

Asp Thr Thr Ala Leu Met Ala His Val Glu Asp Leu Ile Ile Lys Thr
305                 310                 315                 320

Ile Ile Ser Ala Glu Leu Ala Ile Ala Thr Ala Cys Lys Thr Phe Val
                325                 330                 335

Pro His Arg Ser Ser Cys Phe Glu Leu Tyr Gly Phe Asp Val Leu Ile
                340                 345                 350

Asp Ser Thr Leu Lys Pro Trp Leu Leu Glu Val Asn Leu Ser Pro Ser
```

```
                355                 360                 365
Leu Ala Cys Asp Ala Pro Leu Asp Leu Lys Ile Lys Ala Ser Met Ile
    370                 375                 380

Ser Asp Met Phe Thr Val Val Gly Phe Val Cys Gln Asp Pro Ala Gln
385                 390                 395                 400

Arg Ala Ser Thr Arg Pro Ile Tyr Pro Thr Phe Glu Ser Ser Arg Arg
                405                 410                 415

Asn Pro Phe Gln Lys Pro Gln Arg Cys Arg Pro Leu Ser Ala Ser Asp
            420                 425                 430

Ala Glu Met Lys Asn Leu Val Gly Ser Ala Arg Glu Lys Gly Pro Gly
        435                 440                 445

Lys Leu Gly Gly Ser Val Leu Gly Leu Ser Met Glu Glu Ile Lys Val
    450                 455                 460

Leu Arg Arg Val Lys Glu Glu Asn Asp Arg Arg Gly Gly Phe Ile Arg
465                 470                 475                 480

Ile Phe Pro Thr Ser Glu Thr Trp Glu Ile Tyr Gly Ser Tyr Leu Glu
                485                 490                 495

His Lys Thr Ser Met Asn Tyr Met Leu Ala Thr Arg Leu Phe Gln Asp
            500                 505                 510

Arg Met Thr Ala Asp Gly Ala Pro Glu Leu Lys Ile Glu Ser Leu Asn
        515                 520                 525

Ser Lys Ala Lys Leu His Ala Ala Leu Tyr Glu Arg Lys Leu Leu Ser
    530                 535                 540

Leu Glu Val Arg Lys Arg Arg Arg Ser Ser Arg Leu Arg Ala Met
545                 550                 555                 560

Arg Pro Lys Tyr Pro Val Ile Thr Gln Pro Ala Glu Met Asn Val Lys
                565                 570                 575

Thr Glu Thr Glu Ser Glu Glu Glu Val Ala Leu Asp Asn Glu
            580                 585                 590

Asp Glu Glu Gln Glu Ala Ser Gln Glu Ser Ala Gly Phe Leu Arg
        595                 600                 605

Glu Asn Gln Ala Lys Tyr Thr Pro Ser Leu Thr Ala Leu Val Glu Asn
    610                 615                 620

Thr Pro Lys Glu Asn Ser Met Lys Val Arg Glu Trp Asn Asn Lys Gly
625                 630                 635                 640

Gly His Cys Cys Lys Leu Glu Thr Gln Glu Leu Glu Pro Lys Phe Asn
                645                 650                 655

Leu Met Gln Ile Leu Gln Asp Asn Gly Asn Leu Ser Lys Met Gln Ala
            660                 665                 670

Arg Ile Ala Phe Ser Ala Tyr Leu Gln His Val Gln Ile Arg Leu Met
        675                 680                 685

Lys Asp Ser Gly Gly Gln Thr Phe Ser Ala Ser Trp Ala Ala Lys Glu
    690                 695                 700

Asp Glu Gln Met Glu Leu Val Val Arg Phe Leu Lys Arg Ala Ser Asn
705                 710                 715                 720

Asn Leu Gln His Ser Leu Arg Met Val Leu Pro Ser Arg Arg Leu Ala
                725                 730                 735

Leu Leu Glu Arg Arg Arg Ile Leu Ala His Gln Leu Gly Asp Phe Ile
            740                 745                 750

Ile Val Tyr Asn Lys Glu Thr Glu Gln Met Ala Glu Lys Lys Ser Lys
        755                 760                 765

Lys Lys Val Glu Glu Glu Glu Glu Asp Gly Val Asn Met Glu Asn Phe
    770                 775                 780
```

```
Gln Glu Phe Ile Arg Gln Ala Ser Glu Ala Glu Leu Glu Glu Val Leu
785                 790                 795                 800

Thr Phe Tyr Thr Gln Lys Asn Lys Ser Ala Ser Val Phe Leu Gly Thr
                805                 810                 815

His Ser Lys Ile Ser Lys Asn Asn Asn Tyr Ser Asp Ser Gly Ala
                820                 825                 830

Lys Gly Asp His Pro Glu Thr Ile Met Glu Val Lys Ile Lys Pro
            835                 840                 845

Pro Lys Gln Gln Gln Thr Thr Glu Ile His Ser Asp Lys Leu Ser Arg
    850                 855                 860

Phe Thr Thr Ser Ala Glu Lys Glu Ala Lys Leu Val Tyr Ser Asn Ser
865                 870                 875                 880

Ser Ser Gly Pro Thr Ala Thr Leu Gln Lys Ile Pro Asn Thr His Leu
                885                 890                 895

Ser Ser Val Thr Thr Ser Asp Leu Ser Pro Gly Pro Cys His His Ser
                900                 905                 910

Ser Leu Ser Gln Ile Pro Ser Ala Ile Pro Ser Met Pro His Gln Pro
            915                 920                 925

Thr Ile Leu Leu Asn Thr Val Ser Ala Ser Ala Ser Pro Cys Leu His
    930                 935                 940

Pro Gly Ala Gln Asn Ile Pro Ser Pro Thr Gly Leu Pro Arg Cys Arg
945                 950                 955                 960

Ser Gly Ser His Thr Ile Gly Pro Phe Ser Ser Phe Gln Ser Ala Ala
                965                 970                 975

His Ile Tyr Ser Gln Lys Leu Ser Arg Pro Ser Ser Ala Lys Ala Gly
            980                 985                 990

Ser Cys Tyr Leu Asn Lys His His Ser Gly Ile Ala Lys Thr Gln Lys
    995                 1000                1005

Glu Gly Glu Asp Ala Ser Leu Tyr Ser Lys Arg Tyr Asn Gln Ser Met
    1010                1015                1020

Val Thr Ala Glu Leu Gln Arg Leu Ala Glu Lys Gln Ala Ala Arg Gln
1025                1030                1035                1040

Tyr Ser Pro Ser Ser His Ile Asn Leu Leu Thr Gln Gln Val Thr Asn
                1045                1050                1055

Leu Asn Leu Ala Thr Gly Ile Ile Asn Arg Ser Ser Ala Ser Ala Pro
                1060                1065                1070

Pro Thr Leu Arg Pro Ile Ile Ser Pro Ser Gly Pro Thr Trp Ser Thr
            1075                1080                1085

Gln Ser Asp Pro Gln Ala Pro Glu Asn His Ser Ser Ser Pro Gly Ser
    1090                1095                1100

Arg Ser Leu Gln Thr Gly Gly Phe Ala Trp Glu Gly Glu Val Glu Asn
1105                1110                1115                1120

Asn Val Tyr Ser Gln Ala Thr Gly Val Val Pro Gln His Lys Tyr His
                1125                1130                1135

Pro Thr Ala Gly Ser Tyr Gln Leu Gln Phe Ala Leu Gln Gln Leu Glu
                1140                1145                1150

Gln Gln Lys Leu Gln Ser Arg Gln Leu Leu Asp Gln Ser Arg Ala Arg
            1155                1160                1165

His Gln Ala Ile Phe Gly Ser Gln Thr Leu Pro Asn Ser Asn Leu Trp
    1170                1175                1180

Thr Met Asn Asn Gly Ala Gly Cys Arg Ile Ser Ser Ala Thr Ala Ser
1185                1190                1195                1200
```

Gly Gln Lys Pro Thr Thr Leu Pro Gln Lys Val Pro Pro Pro Ser
                1205                1210                1215

Ser Cys Ala Ser Leu Val Pro Lys Pro Pro Asn His Glu Gln Val
                1220                1225                1230

Leu Arg Arg Ala Thr Ser Gln Lys Ala Ser Lys Gly Ser Ser Ala Glu
        1235                1240                1245

Gly Gln Leu Asn Gly Leu Gln Ser Ser Leu Asn Pro Ala Ala Ser Val
    1250                1255                1260

Pro Ile Thr Ser Ser Thr Asp Pro Ala His Thr Lys Ile
1265                1270                1275

<210> SEQ ID NO 2
<211> LENGTH: 4692
<212> TYPE: DNA
<213> ORGANISM: Homo sapiens

<400> SEQUENCE: 2
ggcacgaggg ggaagcagcc gtcggcggct gccctgagcc ttcctgggga aggaggaggg      60
aggtaggcgc agagcgcggt ccacgcctgc tcgccccgaa ccatgggaag atgagacagg     120
aatctgtgcc atccaaattg cttgatccag tgaatctgct aggaaaggtc tctgaggccc     180
ccgtctgctg actgcatgac aaaccctaaa ggaaatgcca atcgtgatgg cccgggacct     240
ggaggaaaca gcatcatcct cagaggatga ggaggtcata agtcaagagg atcatccatg     300
catcatgtgg actggaggct gcaggagaat tccagttttg gtattccatg ccgacgctat     360
tcttacaaag gacaacaata ttagagtaat tggagaacgt tatcatttgt cttataagat     420
tgtacgaacg gacagtcgcc tagtacgcag cattctgaca gcccatggat tcatgaagt      480 tcacccaagc agcactgact ataacctaat gtggacagga tcccacctga agcccttctt     540
actgcgcacc ctctctgaag cacaaaaagt taatcacttt cccaggtctt atgaacttac     600
ccggaaggac cgactgtaca aaacattat tcgaatgcag catacacatg gattcaaggt      660
ttttcacatc ctcccccaga ccttcctcct gccagctgag tacgcggaat tttgtaattc     720
atattcgaag gaccggggac cttggatagt aaaaccagtg gcatcttcaa gggggcgggg     780
cgtctacctg atcaacaatc caaccagat ctccctggaa gagaacattt tggtctcccg      840
ttacattaac aaccccctgc tcatagatga tttcaagttt gacgtgcgcc tctatgtgct     900
cgtgacttcc tatgatcctc ttgtcatcta tctctatgaa gaaggattgg ctaggttgc      960 aactgtgcga tatgatcaag gagccaagaa cattcggaac cagttcatgc atctgacaaa    1020
ctacagtgtc aacaagaaaa gtggagatta cgtcagttgt gacgatccag aagtggagga    1080
ttatggaaac aaatggagca tgagtgctat gcttaggtac ctgaaacaag aaggcagaga    1140
tacaaccgca ttgatggccc atgtagaaga cctgatcatt aagactataa tctctgctga    1200
actagctatt gctactgcct gtaaaacctt tgttcctcat cgcagcagtt gttttgaact    1260
ctatggcttt gacgtgctca tagattctac tctgaagcca tggttgttgg aagtgaatct    1320
ctctccttct ttggcctgtg atgcgcctct ggacctaaag attaaagcca gtatgatttc    1380
agatatgttc actgttgtag gatttgtgtg ccaagatcct gcccagcggg catcaactcg    1440
gccaatttat cccaccttg agtcttccag gcgaaaccct ttccagaaac ctcagcgttg    1500
ccgtccactc tctgccagtg atgcggaaat gaaaaacctc gtgggctcag cccggggaaa    1560
agggccaggg aagttgggtg gttctgtgct tggtctgtca atggaggaga tcaaagtttt    1620
acgaagggtg aaggaggaga atgatcggcg aggtggattt attcgcatat ttcctacatc    1680

-continued

```
tgagacatgg gaaatatatg ggtcctacct cgagcataag acctcaatga actatatgct    1740
ggcaacacgc ctcttccagg acagaatgac tgctgatgga gcgccagaat tgaagataga    1800
gagtctgaat tcaaaggcca agctgcatgc tgcactttac gagaggaagc tcctgtctct    1860
ggaggtgcga aaacgtagac gacggagtag cagattgagg gcaatgaggc caaaataccc    1920
agtgattacc caaccagctg aaatgaatgt taaaactgag acagagagtg aagaggagga    1980
agaagtcgca ttagataatg aagatgaaga acaggaggct tcccaggagg agtctgcagg    2040
atttcttaga gaaaatcaag ccaaatatac accctcattg acagctttgg tagaaaatac    2100
acccaaagaa aattccatga aagttcgtga atggaataat aaaggtggac actgctgcaa    2160
acttgagact caggagctag agcctaaatt taacctgatg cagattcttc aagataatgg    2220
caatcttagc aaaatgcagg cccgaatagc attctctgcc tatctccagc atgttcaaat    2280
tcgcctgatg aaagacagtg gcggtcagac gttcagtgcc agttgggctg ccaaagagga    2340
tgaacagatg gagctggttg ttcgtttcct caagcgagca tcaaataacc tccagcattc    2400
actgaggatg gtattaccca gtcgacgatt ggcacttctg gaacgcagaa gaatcctggc    2460
ccaccagctg ggtgacttta tcattgtata caacaaggaa acagaacaaa tggctgaaaa    2520
gaaatcaaag aagaaagttg aggaagaaga ggaagatggg gtgaatatgg aaaactttca    2580
ggagttcatc agacaagcaa gtgaggctga actggaggag gtgttgactt tttataccca    2640
aaagaacaag tctgctagtg tcttcctggg gactcactct aaaatttcta agaacaacaa    2700
caattattct gatagtgggg caaaaggtga tcaccctgag actataatgg aagaagtgaa    2760
aataaagcca cctaaacagc aacagacgac agaaattcat tctgataaat tatctcgatt    2820
taccacttca gcagaaaaag aggcaaaatt agtttatagc aattcctcct ctggtcctac    2880
tgctactctg cagaaaattc ccaacaccca tttgtcatct gttacaacct ctgacctctc    2940
tccagggcct tgccaccatt cttctttatc tcaaattcct tcagctatcc ccagcatgcc    3000
tcaccagcca acaattttac tgaacacagt ctctgccagt gcttctccct gcctacatcc    3060
cggggcacag aacatcccaa gccctactgg cctgccacgc tgtcgatcag gaagtcacac    3120
cattggtccc ttttcttcct tccaaagtgc tgcacacatc tatagccaga aactgtctcg    3180
tccctcttca gcaaaggcag gatcgtgcta tctaaacaag catcattcag gaatagccaa    3240
aacacaaaaa gagggagaag atgcttcttt atatagcaaa cggtacaacc aaagtatggt    3300
tacagctgaa cttcagcggc tagctgagaa gcaggcagcg agacagtatt ctccatccag    3360
ccacatcaac ctcctcaccc aacaggtaac aaacctgaat ttggcaactg gcatcataaa    3420
cagaagcagt gcttcagctc ccccaacccet ccgacccatc atcagtccta gtggcccgac    3480
atggtctaca cagtcagacc cccaagctcc cgagaatcac tccagctctc ctggaagcag    3540
gagcctgcag acaggggat ttgcctggga aggagaagta gaaaacaacg tgtacagcca    3600
ggctacaggg gtggtccccc agcacaagta tcacccaca gcaggcagct atcagcttca    3660
atttgccctg cagcaacttg aacaacaaaa acttcagtcc cggcagctcc tggaccagag    3720
tcgagcccgg caccaggcaa tctttggcag ccagacacta cctaactcca atttatggac    3780
aatgaataat ggtgcaggtt gtagaatttc cagtgccaca gctagtggcc agaagccaac    3840
cactctgcca caaaaagtgg taccacctcc aagttcttgc gcctccctgg ttcccaaacc    3900
cccacccaac cacgaacaag tgctcagaag ggcaacatcc cagaaagctt ccaaagggtc    3960
ctccgcggaa gggcagctga atggactcca gagcagcctt aaccctgcag cctctgtgcc    4020
catcaccagc tctacagatc ctgctcacac taaaatatga accacaaaca cacagagaaa    4080
```

```
caacctgttc accactcctg ggtgcatgat tgagggtgaa gcatccacca gcacttcaag    4140
gggtccatag tatttttttt tttgctgcct caaagtcccc aaagccttcg agcagaagtg    4200
gcagtagatg gttgccaatc agccaatgca gactttcact gggacaacaa gaaagcagat    4260
cttctgggtt ttgatggaac ttggcagtgg ggacattcag ctgatgcatt atatacccg     4320 tcagagcaca cttgtatctt ttaccttccc tttgccccat gccccaaac tgcttaggtc      4380 ttctctgtcc ctttactgct gctgcacaga gatgatataa aagaggctct ttggctattt    4440
gcattttgct tcctcttctt ttccagatta cagtatgaag cttattttc tttgtacaag      4500 cttaaaattt caacatcatc atccgccaaa gttgttcctc ccttttcgga ggatctaggg    4560
ggaaagagga gcattcatca caagtttcct agagagagga gacaaatcgg tgtgccattg    4620
acaacatgag ccagggtaaa ggcaccctttt ggaattactg atttcaaaga ttaataaagt   4680 aattctatt tt                                                          4692
```

<210> SEQ ID NO 3
<211> LENGTH: 212
<212> TYPE: PRT
<213> ORGANISM: Homo sapiens

<400> SEQUENCE: 3

```
Glu Asn Thr Pro Lys Glu Asn Ser Met Lys Val Arg Glu Trp Asn Asn
  1               5                  10                  15

Lys Gly Gly His Cys Cys Lys Leu Glu Thr Gln Glu Leu Glu Pro Lys
             20                  25                  30

Phe Asn Leu Met Gln Ile Leu Gln Asp Asn Gly Asn Leu Ser Lys Met
         35                  40                  45

Gln Ala Arg Ile Ala Phe Ser Ala Tyr Leu Gln His Val Gln Ile Arg
     50                  55                  60

Leu Met Lys Asp Ser Gly Gly Gln Thr Phe Ser Ala Ser Trp Ala Ala
 65                  70                  75                  80

Lys Glu Asp Glu Gln Met Glu Leu Val Val Arg Phe Leu Lys Arg Ala
                 85                  90                  95

Ser Asn Asn Leu Gln His Ser Leu Arg Met Val Leu Pro Ser Arg Arg
            100                 105                 110

Leu Ala Leu Leu Glu Arg Arg Arg Ile Leu Ala His Gln Leu Gly Asp
        115                 120                 125

Phe Ile Ile Val Tyr Asn Lys Glu Thr Glu Gln Met Ala Glu Lys Lys
    130                 135                 140

Ser Lys Lys Lys Val Glu Glu Glu Glu Asp Gly Val Asn Met Glu
145                 150                 155                 160

Asn Phe Gln Glu Phe Ile Arg Gln Ala Ser Glu Ala Glu Leu Glu Glu
                165                 170                 175

Val Leu Thr Phe Tyr Thr Gln Lys Asn Lys Ser Ala Ser Val Phe Leu
            180                 185                 190

Gly Thr His Ser Lys Ile Ser Lys Asn Asn Asn Tyr Ser Asp Ser
        195                 200                 205

Gly Ala Lys Gly
    210
```

<210> SEQ ID NO 4
<211> LENGTH: 444
<212> TYPE: PRT
<213> ORGANISM: Homo sapiens

<400> SEQUENCE: 4

```
Gly Asp His Pro Glu Thr Ile Met Glu Val Lys Ile Lys Pro Pro
  1               5                  10                  15

Lys Gln Gln Gln Thr Thr Glu Ile His Ser Asp Lys Leu Ser Arg Phe
             20                  25                  30

Thr Thr Ser Ala Glu Lys Glu Ala Lys Leu Val Tyr Ser Asn Ser Ser
             35                  40                  45

Ser Gly Pro Thr Ala Thr Leu Gln Lys Ile Pro Asn Thr His Leu Ser
         50                  55                  60

Ser Val Thr Thr Ser Asp Leu Ser Pro Gly Pro Cys His His Ser Ser
 65                  70                  75                  80

Leu Ser Gln Ile Pro Ser Ala Ile Pro Ser Met Pro His Gln Pro Thr
                 85                  90                  95

Ile Leu Leu Asn Thr Val Ser Ala Ser Ala Ser Pro Cys Leu His Pro
                100                 105                 110

Gly Ala Gln Asn Ile Pro Ser Pro Thr Gly Leu Pro Arg Cys Arg Ser
            115                 120                 125

Gly Ser His Thr Ile Gly Pro Phe Ser Ser Phe Gln Ser Ala Ala His
        130                 135                 140

Ile Tyr Ser Gln Lys Leu Ser Arg Pro Ser Ser Ala Lys Ala Gly Ser
145                 150                 155                 160

Cys Tyr Leu Asn Lys His His Ser Gly Ile Ala Lys Thr Gln Lys Glu
                165                 170                 175

Gly Glu Asp Ala Ser Leu Tyr Ser Lys Arg Tyr Asn Gln Ser Met Val
            180                 185                 190

Thr Ala Glu Leu Gln Arg Leu Ala Glu Lys Gln Ala Ala Arg Gln Tyr
        195                 200                 205

Ser Pro Ser Ser His Ile Asn Leu Leu Thr Gln Gln Val Thr Asn Leu
    210                 215                 220

Asn Leu Ala Thr Gly Ile Ile Asn Arg Ser Ser Ala Ser Ala Pro Pro
225                 230                 235                 240

Thr Leu Arg Pro Ile Ile Ser Pro Ser Gly Pro Thr Trp Ser Thr Gln
                245                 250                 255

Ser Asp Pro Gln Ala Pro Glu Asn His Ser Ser Ser Pro Gly Ser Arg
            260                 265                 270

Ser Leu Gln Thr Gly Gly Phe Ala Trp Glu Gly Glu Val Glu Asn Asn
        275                 280                 285

Val Tyr Ser Gln Ala Thr Gly Val Val Pro Gln His Lys Tyr His Pro
    290                 295                 300

Thr Ala Gly Ser Tyr Gln Leu Gln Phe Ala Leu Gln Gln Leu Glu Gln
305                 310                 315                 320

Gln Lys Leu Gln Ser Arg Gln Leu Leu Asp Gln Ser Arg Ala Arg His
                325                 330                 335

Gln Ala Ile Phe Gly Ser Gln Thr Leu Pro Asn Ser Asn Leu Trp Thr
            340                 345                 350

Met Asn Asn Gly Ala Gly Cys Arg Ile Ser Ser Ala Thr Ala Ser Gly
        355                 360                 365

Gln Lys Pro Thr Thr Leu Pro Gln Lys Val Val Pro Pro Ser Ser
    370                 375                 380

Cys Ala Ser Leu Val Pro Lys Pro Pro Asn His Glu Gln Val Leu
385                 390                 395                 400

Arg Arg Ala Thr Ser Gln Lys Ala Ser Lys Gly Ser Ser Ala Glu Gly
                405                 410                 415
```

-continued

```
Gln Leu Asn Gly Leu Gln Ser Ser Leu Asn Pro Ala Ala Ser Val Pro
            420                 425                 430

Ile Thr Ser Ser Thr Asp Pro Ala His Thr Lys Ile
        435                 440

<210> SEQ ID NO 5
<211> LENGTH: 655
<212> TYPE: PRT
<213> ORGANISM: Homo sapiens

<400> SEQUENCE: 5

Glu Asn Thr Pro Lys Glu Asn Ser Met Lys Val Arg Glu Trp Asn Asn
1               5                   10                  15

Lys Gly Gly His Cys Cys Lys Leu Glu Thr Gln Glu Leu Glu Pro Lys
            20                  25                  30

Phe Asn Leu Met Gln Ile Leu Gln Asp Asn Gly Asn Leu Ser Lys Met
        35                  40                  45

Gln Ala Arg Ile Ala Phe Ser Ala Tyr Leu Gln His Val Gln Ile Arg
    50                  55                  60

Leu Met Lys Asp Ser Gly Gly Thr Phe Ser Ala Ser Trp Ala Ala
65                  70                  75                  80

Lys Glu Asp Glu Gln Met Glu Leu Val Val Arg Phe Leu Lys Arg Ala
                85                  90                  95

Ser Asn Asn Leu Gln His Ser Leu Arg Met Val Leu Pro Ser Arg Arg
            100                 105                 110

Leu Ala Leu Leu Glu Arg Arg Arg Ile Leu Ala His Gln Leu Gly Asp
        115                 120                 125

Phe Ile Ile Val Tyr Asn Lys Glu Thr Glu Gln Met Ala Glu Lys Lys
    130                 135                 140

Ser Lys Lys Lys Val Glu Glu Glu Glu Asp Gly Val Asn Met Glu
145                 150                 155                 160

Asn Phe Gln Glu Phe Ile Arg Gln Ala Ser Glu Ala Glu Leu Glu Glu
                165                 170                 175

Val Leu Thr Phe Tyr Thr Gln Lys Asn Lys Ser Ala Ser Val Phe Leu
            180                 185                 190

Gly Thr His Ser Lys Ile Ser Lys Asn Asn Asn Tyr Ser Asp Ser
        195                 200                 205

Gly Ala Lys Gly Asp His Pro Glu Thr Ile Met Glu Glu Val Lys Ile
    210                 215                 220

Lys Pro Pro Lys Gln Gln Gln Thr Thr Glu Ile His Ser Asp Lys Leu
225                 230                 235                 240

Ser Arg Phe Thr Thr Ser Ala Glu Lys Glu Ala Lys Leu Val Tyr Ser
                245                 250                 255

Asn Ser Ser Ser Gly Pro Thr Ala Thr Leu Gln Lys Ile Pro Asn Thr
            260                 265                 270

His Leu Ser Ser Val Thr Thr Ser Asp Leu Ser Pro Gly Pro Cys His
        275                 280                 285

His Ser Ser Leu Ser Gln Ile Pro Ser Ala Ile Pro Ser Met Pro His
    290                 295                 300

Gln Pro Thr Ile Leu Leu Asn Thr Val Ser Ala Ser Ala Ser Pro Cys
305                 310                 315                 320

Leu His Pro Gly Ala Gln Asn Ile Pro Ser Pro Thr Gly Leu Pro Arg
                325                 330                 335

Cys Arg Ser Gly Ser His Thr Ile Gly Pro Phe Ser Ser Phe Gln Ser
```

```
                340             345             350
Ala Ala His Ile Tyr Ser Gln Lys Leu Ser Arg Pro Ser Ser Ala Lys
            355                 360                 365

Ala Gly Ser Cys Tyr Leu Asn Lys His His Ser Gly Ile Ala Lys Thr
            370                 375                 380

Gln Lys Glu Gly Glu Asp Ala Ser Leu Tyr Ser Lys Arg Tyr Asn Gln
385                 390                 395                 400

Ser Met Val Thr Ala Glu Leu Gln Arg Leu Ala Glu Lys Gln Ala Ala
                405                 410                 415

Arg Gln Tyr Ser Pro Ser Ser His Ile Asn Leu Leu Thr Gln Gln Val
            420                 425                 430

Thr Asn Leu Asn Leu Ala Thr Gly Ile Ile Asn Arg Ser Ser Ala Ser
            435                 440                 445

Ala Pro Pro Thr Leu Arg Pro Ile Ile Ser Pro Ser Gly Pro Thr Trp
            450                 455                 460

Ser Thr Gln Ser Asp Pro Gln Ala Pro Glu Asn His Ser Ser Ser Pro
465                 470                 475                 480

Gly Ser Arg Ser Leu Gln Thr Gly Gly Phe Ala Trp Glu Gly Glu Val
                485                 490                 495

Glu Asn Asn Val Tyr Ser Gln Ala Thr Gly Val Val Pro Gln His Lys
                500                 505                 510

Tyr His Pro Thr Ala Gly Ser Tyr Gln Leu Gln Phe Ala Leu Gln Gln
            515                 520                 525

Leu Glu Gln Gln Lys Leu Gln Ser Arg Gln Leu Leu Asp Gln Ser Arg
            530                 535                 540

Ala Arg His Gln Ala Ile Phe Gly Ser Gln Thr Leu Pro Asn Ser Asn
545                 550                 555                 560

Leu Trp Thr Met Asn Asn Gly Ala Gly Cys Arg Ile Ser Ser Ala Thr
                565                 570                 575

Ala Ser Gly Gln Lys Pro Thr Thr Leu Pro Gln Lys Val Val Pro Pro
            580                 585                 590

Pro Ser Ser Cys Ala Ser Leu Val Pro Lys Pro Pro Asn His Glu
            595                 600                 605

Gln Val Leu Arg Arg Ala Thr Ser Gln Lys Ala Ser Lys Gly Ser Ser
610                 615                 620

Ala Glu Gly Gln Leu Asn Gly Leu Gln Ser Ser Leu Asn Pro Ala Ala
625                 630                 635                 640

Ser Val Pro Ile Thr Ser Ser Thr Asp Pro Ala His Thr Lys Ile
                645                 650                 655

<210> SEQ ID NO 6
<211> LENGTH: 760
<212> TYPE: PRT
<213> ORGANISM: Homo sapiens

<400> SEQUENCE: 6

Gly Ala Pro Glu Leu Lys Ile Glu Ser Leu Asn Ser Lys Ala Lys Leu
1               5                   10                  15

His Ala Ala Leu Tyr Glu Arg Lys Leu Leu Ser Leu Glu Val Arg Lys
                20                  25                  30

Arg Arg Arg Arg Ser Ser Arg Leu Arg Ala Met Arg Pro Lys Tyr Pro
            35                  40                  45

Val Ile Thr Gln Pro Ala Glu Met Asn Val Lys Thr Glu Thr Glu Ser
        50                  55                  60
```

-continued

```
Glu Glu Glu Glu Glu Val Ala Leu Asp Asn Glu Asp Glu Glu Gln Glu
 65                  70                  75                  80

Ala Ser Gln Glu Glu Ser Ala Gly Phe Leu Arg Glu Asn Gln Ala Lys
                 85                  90                  95

Tyr Thr Pro Ser Leu Thr Ala Leu Val Glu Asn Thr Pro Lys Glu Asn
            100                 105                 110

Ser Met Lys Val Arg Glu Trp Asn Asn Lys Gly Gly His Cys Cys Lys
        115                 120                 125

Leu Glu Thr Gln Glu Leu Glu Pro Lys Phe Asn Leu Met Gln Ile Leu
    130                 135                 140

Gln Asp Asn Gly Asn Leu Ser Lys Met Gln Ala Arg Ile Ala Phe Ser
145                 150                 155                 160

Ala Tyr Leu Gln His Val Gln Ile Arg Leu Met Lys Asp Ser Gly Gly
                165                 170                 175

Gln Thr Phe Ser Ala Ser Trp Ala Ala Lys Glu Asp Glu Gln Met Glu
            180                 185                 190

Leu Val Val Arg Phe Leu Lys Arg Ala Ser Asn Asn Leu Gln His Ser
        195                 200                 205

Leu Arg Met Val Leu Pro Ser Arg Arg Leu Ala Leu Leu Glu Arg Arg
    210                 215                 220

Arg Ile Leu Ala His Gln Leu Gly Asp Phe Ile Ile Val Tyr Asn Lys
225                 230                 235                 240

Glu Thr Glu Gln Met Ala Glu Lys Lys Ser Lys Lys Val Glu Glu
                245                 250                 255

Glu Glu Glu Asp Gly Val Asn Met Glu Asn Phe Gln Glu Phe Ile Arg
            260                 265                 270

Gln Ala Ser Glu Ala Glu Leu Glu Glu Val Leu Thr Phe Tyr Thr Gln
        275                 280                 285

Lys Asn Lys Ser Ala Ser Val Phe Leu Gly Thr His Ser Lys Ile Ser
    290                 295                 300

Lys Asn Asn Asn Asn Tyr Ser Asp Ser Gly Ala Lys Gly Asp His Pro
305                 310                 315                 320

Glu Thr Ile Met Glu Glu Val Lys Ile Lys Pro Pro Lys Gln Gln Gln
                325                 330                 335

Thr Thr Glu Ile His Ser Asp Lys Leu Ser Arg Phe Thr Thr Ser Ala
            340                 345                 350

Glu Lys Glu Ala Lys Leu Val Tyr Ser Asn Ser Ser Gly Pro Thr
        355                 360                 365

Ala Thr Leu Gln Lys Ile Pro Asn Thr His Leu Ser Ser Val Thr Thr
    370                 375                 380

Ser Asp Leu Ser Pro Gly Pro Cys His His Ser Ser Leu Ser Gln Ile
385                 390                 395                 400

Pro Ser Ala Ile Pro Ser Met Pro His Gln Pro Thr Ile Leu Leu Asn
                405                 410                 415

Thr Val Ser Ala Ser Ala Ser Pro Cys Leu His Pro Gly Ala Gln Asn
            420                 425                 430

Ile Pro Ser Pro Thr Gly Leu Pro Arg Cys Arg Ser Gly Ser His Thr
        435                 440                 445

Ile Gly Pro Phe Ser Ser Phe Gln Ser Ala Ala His Ile Tyr Ser Gln
    450                 455                 460

Lys Leu Ser Arg Pro Ser Ser Ala Lys Ala Gly Ser Cys Tyr Leu Asn
465                 470                 475                 480

Lys His His Ser Gly Ile Ala Lys Thr Gln Lys Glu Gly Glu Asp Ala
```

```
                485                 490                 495
Ser Leu Tyr Ser Lys Arg Tyr Asn Gln Ser Met Val Thr Ala Glu Leu
            500                 505                 510

Gln Arg Leu Ala Glu Lys Gln Ala Arg Gln Tyr Ser Pro Ser Ser
        515                 520                 525

His Ile Asn Leu Leu Thr Gln Gln Val Thr Asn Leu Asn Leu Ala Thr
            530                 535                 540

Gly Ile Ile Asn Arg Ser Ser Ala Ser Ala Pro Pro Thr Leu Arg Pro
545                 550                 555                 560

Ile Ile Ser Pro Ser Gly Pro Thr Trp Ser Thr Gln Ser Asp Pro Gln
                565                 570                 575

Ala Pro Glu Asn His Ser Ser Pro Gly Ser Arg Ser Leu Gln Thr
            580                 585                 590

Gly Gly Phe Ala Trp Glu Gly Glu Val Glu Asn Asn Val Tyr Ser Gln
                595                 600                 605

Ala Thr Gly Val Val Pro Gln His Lys Tyr His Pro Thr Ala Gly Ser
            610                 615                 620

Tyr Gln Leu Gln Phe Ala Leu Gln Gln Leu Glu Gln Gln Lys Leu Gln
625                 630                 635                 640

Ser Arg Gln Leu Leu Asp Gln Ser Arg Ala Arg His Gln Ala Ile Phe
                645                 650                 655

Gly Ser Gln Thr Leu Pro Asn Ser Asn Leu Trp Thr Met Asn Asn Gly
            660                 665                 670

Ala Gly Cys Arg Ile Ser Ser Ala Thr Ala Ser Gly Lys Pro Thr
                675                 680                 685

Thr Leu Pro Gln Lys Val Val Pro Pro Ser Ser Cys Ala Ser Leu
            690                 695                 700

Val Pro Lys Pro Pro Asn His Glu Gln Val Leu Arg Arg Ala Thr
705                 710                 715                 720

Ser Gln Lys Ala Ser Lys Gly Ser Ser Ala Glu Gly Gln Leu Asn Gly
                725                 730                 735

Leu Gln Ser Ser Leu Asn Pro Ala Ala Ser Val Pro Ile Thr Ser Ser
            740                 745                 750

Thr Asp Pro Ala His Thr Lys Ile
        755                 760

<210> SEQ ID NO 7
<211> LENGTH: 808
<212> TYPE: PRT
<213> ORGANISM: Homo sapiens

<400> SEQUENCE: 7

Met Lys Asn Leu Val Gly Ser Ala Arg Glu Lys Gly Pro Gly Lys Leu
1               5                   10                  15

Gly Gly Ser Val Leu Gly Leu Ser Met Glu Glu Ile Lys Val Leu Arg
            20                  25                  30

Arg Val Lys Glu Glu Asn Asp Arg Arg Gly Gly Phe Ile Arg Ile Phe
        35                  40                  45

Pro Thr Ser Glu Thr Trp Glu Ile Tyr Gly Ser Tyr Leu Glu His Lys
    50                  55                  60

Thr Ser Met Asn Tyr Met Leu Ala Thr Arg Leu Phe Gln Asp Arg Met
65                  70                  75                  80

Thr Ala Asp Gly Ala Pro Glu Leu Lys Ile Glu Ser Leu Asn Ser Lys
                85                  90                  95
```

```
Ala Lys Leu His Ala Ala Leu Tyr Glu Arg Lys Leu Leu Ser Leu Glu
            100                 105                 110

Val Arg Lys Arg Arg Arg Ser Ser Arg Leu Arg Ala Met Arg Pro
            115                 120                 125

Lys Tyr Pro Val Ile Thr Gln Pro Ala Glu Met Asn Val Lys Thr Glu
        130                 135                 140

Thr Glu Ser Glu Glu Glu Glu Val Ala Leu Asp Asn Glu Asp Glu
145                 150                 155                 160

Glu Gln Glu Ala Ser Gln Glu Ser Ala Gly Phe Leu Arg Glu Asn
                165                 170                 175

Gln Ala Lys Tyr Thr Pro Ser Leu Thr Ala Leu Val Glu Asn Thr Pro
            180                 185                 190

Lys Glu Asn Ser Met Lys Val Arg Glu Trp Asn Asn Lys Gly Gly His
            195                 200                 205

Cys Cys Lys Leu Glu Thr Gln Glu Leu Glu Pro Lys Phe Asn Leu Met
    210                 215                 220

Gln Ile Leu Gln Asp Asn Gly Asn Leu Ser Lys Met Gln Ala Arg Ile
225                 230                 235                 240

Ala Phe Ser Ala Tyr Leu Gln His Val Gln Ile Arg Leu Met Lys Asp
                245                 250                 255

Ser Gly Gly Gln Thr Phe Ser Ala Ser Trp Ala Ala Lys Glu Asp Glu
            260                 265                 270

Gln Met Glu Leu Val Val Arg Phe Leu Lys Arg Ala Ser Asn Asn Leu
        275                 280                 285

Gln His Ser Leu Arg Met Val Leu Pro Ser Arg Arg Leu Ala Leu Leu
        290                 295                 300

Glu Arg Arg Arg Ile Leu Ala His Gln Leu Gly Asp Phe Ile Ile Val
305                 310                 315                 320

Tyr Asn Lys Glu Thr Glu Gln Met Ala Glu Lys Lys Ser Lys Lys Lys
                325                 330                 335

Val Glu Glu Glu Glu Glu Asp Gly Val Asn Met Glu Asn Phe Gln Glu
            340                 345                 350

Phe Ile Arg Gln Ala Ser Glu Ala Glu Leu Glu Glu Val Leu Thr Phe
        355                 360                 365

Tyr Thr Gln Lys Asn Lys Ser Ala Ser Val Phe Leu Gly Thr His Ser
    370                 375                 380

Lys Ile Ser Lys Asn Asn Asn Tyr Ser Asp Ser Gly Ala Lys Gly
385                 390                 395                 400

Asp His Pro Glu Thr Ile Met Glu Glu Val Lys Ile Lys Pro Pro Lys
                405                 410                 415

Gln Gln Gln Thr Thr Glu Ile His Ser Asp Lys Leu Ser Arg Phe Thr
            420                 425                 430

Thr Ser Ala Glu Lys Glu Ala Lys Leu Val Tyr Ser Asn Ser Ser Ser
        435                 440                 445

Gly Pro Thr Ala Thr Leu Gln Lys Ile Pro Asn Thr His Leu Ser Ser
    450                 455                 460

Val Thr Thr Ser Asp Leu Ser Pro Gly Pro Cys His His Ser Ser Leu
465                 470                 475                 480

Ser Gln Ile Pro Ser Ala Ile Pro Ser Met Pro His Gln Pro Thr Ile
                485                 490                 495

Leu Leu Asn Thr Val Ser Ala Ser Ala Ser Pro Cys Leu His Pro Gly
            500                 505                 510

Ala Gln Asn Ile Pro Ser Pro Thr Gly Leu Pro Arg Cys Arg Ser Gly
```

```
                 515                 520                 525
Ser His Thr Ile Gly Pro Phe Ser Ser Phe Gln Ser Ala Ala His Ile
    530                 535                 540

Tyr Ser Gln Lys Leu Ser Arg Pro Ser Ala Lys Ala Gly Ser Cys
545                 550                 555                 560

Tyr Leu Asn Lys His His Ser Gly Ile Ala Lys Thr Gln Lys Glu Gly
                565                 570                 575

Glu Asp Ala Ser Leu Tyr Ser Lys Arg Tyr Asn Gln Ser Met Val Thr
            580                 585                 590

Ala Glu Leu Gln Arg Leu Ala Glu Lys Gln Ala Ala Arg Gln Tyr Ser
        595                 600                 605

Pro Ser Ser His Ile Asn Leu Leu Thr Gln Gln Val Thr Asn Leu Asn
    610                 615                 620

Leu Ala Thr Gly Ile Ile Asn Arg Ser Ser Ala Ser Ala Pro Pro Thr
625                 630                 635                 640

Leu Arg Pro Ile Ile Ser Pro Ser Gly Pro Thr Trp Ser Thr Gln Ser
                645                 650                 655

Asp Pro Gln Ala Pro Glu Asn His Ser Ser Ser Pro Gly Ser Arg Ser
            660                 665                 670

Leu Gln Thr Gly Gly Phe Ala Trp Glu Gly Val Glu Asn Asn Val
        675                 680                 685

Tyr Ser Gln Ala Thr Gly Val Val Pro Gln His Lys Tyr His Pro Thr
    690                 695                 700

Ala Gly Ser Tyr Gln Leu Gln Phe Ala Leu Gln Leu Glu Gln Gln
705                 710                 715                 720

Lys Leu Gln Ser Arg Gln Leu Leu Asp Gln Ser Arg Ala Arg His Gln
                725                 730                 735

Ala Ile Phe Gly Ser Gln Thr Leu Pro Asn Ser Asn Leu Trp Thr Met
            740                 745                 750

Asn Asn Gly Ala Gly Cys Arg Ile Ser Ser Ala Thr Ala Ser Gly Gln
        755                 760                 765

Lys Pro Thr Thr Leu Pro Gln Lys Val Val Pro Pro Ser Ser Cys
770                 775                 780

Ala Ser Leu Val Pro Lys Pro Pro Asn His Glu Gln Val Leu Arg
785                 790                 795                 800

Arg Ala Thr Ser Gln Lys Ala Ser
                805

<210> SEQ ID NO 8
<211> LENGTH: 669
<212> TYPE: PRT
<213> ORGANISM: Homo sapiens

<400> SEQUENCE: 8

Lys Ile Lys Ala Ser Met Ile Ser Asp Met Phe Thr Val Val Gly Phe
  1               5                  10                  15

Val Cys Gln Asp Pro Ala Gln Arg Ala Ser Thr Arg Pro Ile Tyr Pro
             20                  25                  30

Thr Phe Glu Ser Ser Arg Arg Asn Pro Phe Gln Lys Pro Gln Arg Cys
         35                  40                  45

Arg Pro Leu Ser Ala Ser Asp Ala Glu Met Lys Asn Leu Val Gly Ser
     50                  55                  60

Ala Arg Glu Lys Gly Pro Gly Lys Leu Gly Gly Ser Val Leu Gly Leu
65                  70                  75                  80
```

-continued

```
Ser Met Glu Glu Ile Lys Val Leu Arg Arg Val Lys Glu Glu Asn Asp
            85                  90                  95
Arg Arg Gly Gly Phe Ile Arg Ile Phe Pro Thr Ser Glu Thr Trp Glu
            100                 105                 110
Ile Tyr Gly Ser Tyr Leu Glu His Lys Thr Ser Met Asn Tyr Met Leu
            115                 120                 125
Ala Thr Arg Leu Phe Gln Asp Arg Met Thr Ala Asp Gly Ala Pro Glu
    130                 135                 140
Leu Lys Ile Glu Ser Leu Asn Ser Lys Ala Lys Leu His Ala Ala Leu
145                 150                 155                 160
Tyr Glu Arg Lys Leu Leu Ser Leu Glu Val Arg Lys Arg Arg Arg Arg
                165                 170                 175
Ser Ser Arg Leu Arg Ala Met Arg Pro Lys Tyr Pro Val Ile Thr Gln
            180                 185                 190
Pro Ala Glu Met Asn Val Lys Thr Glu Thr Glu Ser Glu Glu Glu Glu
            195                 200                 205
Glu Val Ala Leu Asp Asn Glu Asp Glu Glu Gln Glu Ala Ser Gln Glu
    210                 215                 220
Glu Ser Ala Gly Phe Leu Arg Glu Asn Gln Ala Lys Tyr Thr Pro Ser
225                 230                 235                 240
Leu Thr Ala Leu Val Glu Asn Thr Pro Lys Glu Asn Ser Met Lys Val
                245                 250                 255
Arg Glu Trp Asn Asn Lys Gly Gly His Cys Cys Lys Leu Glu Thr Gln
            260                 265                 270
Glu Leu Glu Pro Lys Phe Asn Leu Met Gln Ile Leu Gln Asp Asn Gly
        275                 280                 285
Asn Leu Ser Lys Met Gln Ala Arg Ile Ala Phe Ser Ala Tyr Leu Gln
    290                 295                 300
His Val Gln Ile Arg Leu Met Lys Asp Ser Gly Gly Gln Thr Phe Ser
305                 310                 315                 320
Ala Ser Trp Ala Ala Lys Glu Asp Glu Gln Met Glu Leu Val Val Arg
                325                 330                 335
Phe Leu Lys Arg Ala Ser Asn Asn Leu Gln His Ser Leu Arg Met Val
            340                 345                 350
Leu Pro Ser Arg Arg Leu Ala Leu Leu Glu Arg Arg Arg Ile Leu Ala
        355                 360                 365
His Gln Leu Gly Asp Phe Ile Ile Val Tyr Asn Lys Glu Thr Glu Gln
    370                 375                 380
Met Ala Glu Lys Lys Ser Lys Lys Val Glu Glu Glu Glu Asp
385                 390                 395                 400
Gly Val Asn Met Glu Asn Phe Gln Glu Phe Ile Arg Gln Ala Ser Glu
                405                 410                 415
Ala Glu Leu Glu Glu Val Leu Thr Phe Tyr Thr Gln Lys Asn Lys Ser
            420                 425                 430
Ala Ser Val Phe Leu Gly Thr His Ser Lys Ile Ser Lys Asn Asn Asn
        435                 440                 445
Asn Tyr Ser Asp Ser Gly Ala Lys Gly Asp His Pro Glu Thr Ile Met
    450                 455                 460
Glu Glu Val Lys Ile Lys Pro Pro Lys Gln Gln Thr Thr Glu Ile
465                 470                 475                 480
His Ser Asp Lys Leu Ser Arg Phe Thr Thr Ser Ala Glu Lys Glu Ala
                485                 490                 495
Lys Leu Val Tyr Ser Asn Ser Ser Ser Gly Pro Thr Ala Thr Leu Gln
```

```
                    500                 505                 510
Lys Ile Pro Asn Thr His Leu Ser Ser Val Thr Thr Ser Asp Leu Ser
            515                 520                 525

Pro Gly Pro Cys His His Ser Ser Leu Ser Gln Ile Pro Ser Ala Ile
        530                 535                 540

Pro Ser Met Pro His Gln Pro Thr Ile Leu Leu Asn Thr Val Ser Ala
545                 550                 555                 560

Ser Ala Ser Pro Cys Leu His Pro Gly Ala Gln Asn Ile Pro Ser Pro
                565                 570                 575

Thr Gly Leu Pro Arg Cys Arg Ser Gly Ser His Thr Ile Gly Pro Phe
            580                 585                 590

Ser Ser Phe Gln Ser Ala Ala His Ile Tyr Ser Gln Lys Leu Ser Arg
        595                 600                 605

Pro Ser Ser Ala Lys Ala Gly Ser Cys Tyr Leu Asn Lys His His Ser
    610                 615                 620

Gly Ile Ala Lys Thr Gln Lys Glu Gly Glu Asp Ala Ser Leu Tyr Ser
625                 630                 635                 640

Lys Arg Tyr Asn Gln Ser Met Val Thr Ala Glu Leu Gln Arg Leu Ala
                645                 650                 655

Glu Lys Gln Ala Ala Arg Gln Tyr Ser Pro Ser Ser His
            660                 665

<210> SEQ ID NO 9
<211> LENGTH: 406
<212> TYPE: PRT
<213> ORGANISM: Homo sapiens

<400> SEQUENCE: 9

Ser Ala Ser Asp Ala Glu Met Lys Asn Leu Val Gly Ser Ala Arg Glu
1               5                   10                  15

Lys Gly Pro Gly Lys Leu Gly Gly Ser Val Leu Gly Leu Ser Met Glu
            20                  25                  30

Glu Ile Lys Val Leu Arg Arg Val Lys Glu Glu Asn Asp Arg Arg Gly
        35                  40                  45

Gly Phe Ile Arg Ile Phe Pro Thr Ser Glu Thr Trp Glu Ile Tyr Gly
    50                  55                  60

Ser Tyr Leu Glu His Lys Thr Ser Met Asn Tyr Met Leu Ala Thr Arg
65                  70                  75                  80

Leu Phe Gln Asp Arg Met Thr Ala Asp Gly Ala Pro Glu Leu Lys Ile
                85                  90                  95

Glu Ser Leu Asn Ser Lys Ala Lys Leu His Ala Ala Leu Tyr Glu Arg
            100                 105                 110

Lys Leu Leu Ser Leu Glu Val Arg Lys Arg Arg Arg Ser Ser Arg
        115                 120                 125

Leu Arg Ala Met Arg Pro Lys Tyr Pro Val Ile Thr Gln Pro Ala Glu
    130                 135                 140

Met Asn Val Lys Thr Glu Thr Glu Ser Glu Glu Glu Glu Val Ala
145                 150                 155                 160

Leu Asp Asn Glu Asp Glu Glu Gln Ala Ser Gln Glu Glu Ser Ala
                165                 170                 175

Gly Phe Leu Arg Glu Asn Gln Ala Lys Tyr Thr Pro Ser Leu Thr Ala
            180                 185                 190

Leu Val Glu Asn Thr Pro Lys Glu Asn Ser Met Lys Val Arg Glu Trp
        195                 200                 205
```

```
Asn Asn Lys Gly Gly His Cys Cys Lys Leu Glu Thr Gln Glu Leu Glu
210                 215                 220

Pro Lys Phe Asn Leu Met Gln Ile Leu Gln Asp Asn Gly Asn Leu Ser
225                 230                 235                 240

Lys Met Gln Ala Arg Ile Ala Phe Ser Ala Tyr Leu Gln His Val Gln
                245                 250                 255

Ile Arg Leu Met Lys Asp Ser Gly Gln Thr Phe Ser Ala Ser Trp
                260                 265                 270

Ala Ala Lys Glu Asp Glu Gln Met Glu Leu Val Val Arg Phe Leu Lys
                275                 280                 285

Arg Ala Ser Asn Asn Leu Gln His Ser Leu Arg Met Val Leu Pro Ser
290                 295                 300

Arg Arg Leu Ala Leu Leu Glu Arg Arg Ile Leu Ala His Gln Leu
305                 310                 315                 320

Gly Asp Phe Ile Ile Val Tyr Asn Lys Glu Thr Glu Gln Met Ala Glu
                325                 330                 335

Lys Lys Ser Lys Lys Val Glu Glu Glu Glu Asp Gly Val Asn
                340                 345                 350

Met Glu Asn Phe Gln Glu Phe Ile Arg Gln Ala Ser Glu Ala Glu Leu
                355                 360                 365

Glu Glu Val Leu Thr Phe Tyr Thr Gln Lys Asn Lys Ser Ala Ser Val
370                 375                 380

Phe Leu Gly Thr His Ser Lys Ile Ser Lys Asn Asn Asn Tyr Ser
385                 390                 395                 400

Asp Ser Gly Ala Lys Gly
                405

<210> SEQ ID NO 10
<211> LENGTH: 317
<212> TYPE: PRT
<213> ORGANISM: Homo sapiens

<400> SEQUENCE: 10

Gly Ala Pro Glu Leu Lys Ile Glu Ser Leu Asn Ser Lys Ala Lys Leu
1               5                   10                  15

His Ala Ala Leu Tyr Glu Arg Lys Leu Leu Ser Leu Glu Val Arg Lys
                20                  25                  30

Arg Arg Arg Arg Ser Ser Arg Leu Arg Ala Met Arg Pro Lys Tyr Pro
                35                  40                  45

Val Ile Thr Gln Pro Ala Glu Met Asn Val Lys Thr Glu Thr Glu Ser
                50                  55                  60

Glu Glu Glu Glu Val Ala Leu Asp Asn Glu Asp Glu Glu Gln Glu
65                  70                  75                  80

Ala Ser Gln Glu Glu Ser Ala Gly Phe Leu Arg Glu Asn Gln Ala Lys
                85                  90                  95

Tyr Thr Pro Ser Leu Thr Ala Leu Val Glu Asn Thr Pro Lys Glu Asn
                100                 105                 110

Ser Met Lys Val Arg Glu Trp Asn Asn Lys Gly Gly His Cys Cys Lys
                115                 120                 125

Leu Glu Thr Gln Glu Leu Glu Pro Lys Phe Asn Leu Met Gln Ile Leu
                130                 135                 140

Gln Asp Asn Gly Asn Leu Ser Lys Met Gln Ala Arg Ile Ala Phe Ser
145                 150                 155                 160

Ala Tyr Leu Gln His Val Gln Ile Arg Leu Met Lys Asp Ser Gly Gly
                165                 170                 175
```

```
Gln Thr Phe Ser Ala Ser Trp Ala Ala Lys Glu Asp Glu Gln Met Glu
                180                 185                 190

Leu Val Val Arg Phe Leu Lys Arg Ala Ser Asn Asn Leu Gln His Ser
            195                 200                 205

Leu Arg Met Val Leu Pro Ser Arg Arg Leu Ala Leu Leu Glu Arg Arg
        210                 215                 220

Arg Ile Leu Ala His Gln Leu Gly Asp Phe Ile Ile Val Tyr Asn Lys
225                 230                 235                 240

Glu Thr Glu Gln Met Ala Glu Lys Lys Ser Lys Lys Val Glu Glu
                245                 250                 255

Glu Glu Glu Asp Gly Val Asn Met Glu Asn Phe Gln Glu Phe Ile Arg
                260                 265                 270

Gln Ala Ser Glu Ala Glu Leu Glu Glu Val Leu Thr Phe Tyr Thr Gln
                275                 280                 285

Lys Asn Lys Ser Ala Ser Val Phe Leu Gly Thr His Ser Lys Ile Ser
                290                 295                 300

Lys Asn Asn Asn Asn Tyr Ser Asp Ser Gly Ala Lys Gly
305                 310                 315

<210> SEQ ID NO 11
<211> LENGTH: 322
<212> TYPE: PRT
<213> ORGANISM: Homo sapiens

<400> SEQUENCE: 11

Leu Pro Arg Cys Arg Ser Gly Ser His Thr Ile Gly Pro Phe Ser Ser
1               5                   10                  15

Phe Gln Ser Ala Ala His Ile Tyr Ser Gln Lys Leu Ser Arg Pro Ser
                20                  25                  30

Ser Ala Lys Ala Gly Ser Cys Tyr Leu Asn Lys His His Ser Gly Ile
            35                  40                  45

Ala Lys Thr Gln Lys Glu Gly Glu Asp Ala Ser Leu Tyr Ser Lys Arg
        50                  55                  60

Tyr Asn Gln Ser Met Val Thr Ala Glu Leu Gln Arg Leu Ala Glu Lys
65                  70                  75                  80

Gln Ala Ala Arg Gln Tyr Ser Pro Ser Ser His Ile Asn Leu Leu Thr
                85                  90                  95

Gln Gln Val Thr Asn Leu Asn Leu Ala Thr Gly Ile Ile Asn Arg Ser
                100                 105                 110

Ser Ala Ser Ala Pro Pro Thr Leu Arg Pro Ile Ile Ser Pro Ser Gly
            115                 120                 125

Pro Thr Trp Ser Thr Gln Ser Asp Pro Gln Ala Pro Glu Asn His Ser
        130                 135                 140

Ser Ser Pro Gly Ser Arg Ser Leu Gln Thr Gly Gly Phe Ala Trp Glu
145                 150                 155                 160

Gly Glu Val Glu Asn Asn Val Tyr Ser Gln Ala Thr Gly Val Val Pro
                165                 170                 175

Gln His Lys Tyr His Pro Thr Ala Gly Ser Tyr Gln Leu Gln Phe Ala
                180                 185                 190

Leu Gln Gln Leu Glu Gln Lys Leu Gln Ser Arg Gln Leu Leu Asp
            195                 200                 205

Gln Ser Arg Ala Arg His Gln Ala Ile Phe Gly Ser Gln Thr Leu Pro
        210                 215                 220

Asn Ser Asn Leu Trp Thr Met Asn Asn Gly Ala Gly Cys Arg Ile Ser
```

```
                    225                 230                 235                 240
Ser Ala Thr Ala Ser Gly Gln Lys Pro Thr Thr Leu Pro Gln Lys Val
                245                 250                 255

Val Pro Pro Pro Ser Ser Cys Ala Ser Leu Val Pro Lys Pro Pro Pro
            260                 265                 270

Asn His Glu Gln Val Leu Arg Arg Ala Thr Ser Gln Lys Ala Ser Lys
        275                 280                 285

Gly Ser Ser Ala Glu Gly Gln Leu Asn Gly Leu Gln Ser Ser Leu Asn
    290                 295                 300

Pro Ala Ala Ser Val Pro Ile Thr Ser Ser Thr Asp Pro Ala His Thr
305                 310                 315                 320

Lys Ile

<210> SEQ ID NO 12
<211> LENGTH: 172
<212> TYPE: PRT
<213> ORGANISM: Homo sapiens

<400> SEQUENCE: 12

Leu Pro Arg Cys Arg Ser Gly Ser His Thr Ile Gly Pro Phe Ser Ser
  1               5                  10                  15

Phe Gln Ser Ala Ala His Ile Tyr Ser Gln Lys Leu Ser Arg Pro Ser
             20                  25                  30

Ser Ala Lys Ala Gly Ser Cys Tyr Leu Asn Lys His His Ser Gly Ile
         35                  40                  45

Ala Lys Thr Gln Lys Glu Gly Glu Asp Ala Ser Leu Tyr Ser Lys Arg
     50                  55                  60

Tyr Asn Gln Ser Met Val Thr Ala Glu Leu Gln Arg Leu Ala Glu Lys
 65                  70                  75                  80

Gln Ala Ala Arg Gln Tyr Ser Pro Ser Ser His Ile Asn Leu Leu Thr
                 85                  90                  95

Gln Gln Val Thr Asn Leu Asn Leu Ala Thr Gly Ile Ile Asn Arg Ser
            100                 105                 110

Ser Ala Ser Ala Pro Pro Thr Leu Arg Pro Ile Ile Ser Pro Ser Gly
        115                 120                 125

Pro Thr Trp Ser Thr Gln Ser Asp Pro Gln Ala Pro Glu Asn His Ser
    130                 135                 140

Ser Ser Pro Gly Ser Arg Ser Leu Gln Thr Gly Gly Phe Ala Trp Glu
145                 150                 155                 160

Gly Glu Val Glu Asn Asn Val Tyr Ser Gln Ala Thr
                165                 170

<210> SEQ ID NO 13
<211> LENGTH: 151
<212> TYPE: PRT
<213> ORGANISM: Homo sapiens

<400> SEQUENCE: 13

Thr Gly Val Val Pro Gln His Lys Tyr His Pro Thr Ala Gly Ser Tyr
  1               5                  10                  15

Gln Leu Gln Phe Ala Leu Gln Leu Glu Gln Lys Leu Gln Ser
             20                  25                  30

Arg Gln Leu Leu Asp Gln Ser Arg Ala Arg His Gln Ala Ile Phe Gly
         35                  40                  45

Ser Gln Thr Leu Pro Asn Ser Asn Leu Trp Thr Met Asn Asn Gly Ala
     50                  55                  60
```

```
Gly Cys Arg Ile Ser Ser Ala Thr Ala Ser Gly Gln Lys Pro Thr Thr
 65                  70                  75                  80

Leu Pro Gln Lys Val Val Pro Pro Ser Ser Cys Ala Ser Leu Val
                 85                  90                  95

Pro Lys Pro Pro Pro Asn His Glu Gln Val Leu Arg Arg Ala Thr Ser
            100                 105                 110

Gln Lys Ala Ser Lys Gly Ser Ser Ala Glu Gly Gln Leu Asn Gly Leu
            115                 120                 125

Gln Ser Ser Leu Asn Pro Ala Ala Ser Val Pro Ile Thr Ser Ser Thr
130                 135                 140

Asp Pro Ala His Thr Lys Ile
145                 150

<210> SEQ ID NO 14
<211> LENGTH: 834
<212> TYPE: PRT
<213> ORGANISM: Homo sapiens

<400> SEQUENCE: 14

Met Ala Arg Asp Leu Glu Glu Thr Ala Ser Ser Ser Glu Asp Glu Glu
  1               5                  10                  15

Val Ile Ser Gln Glu Asp His Pro Cys Ile Met Trp Thr Gly Gly Cys
                 20                  25                  30

Arg Arg Ile Pro Val Leu Val Phe His Ala Asp Ala Ile Leu Thr Lys
             35                  40                  45

Asp Asn Asn Ile Arg Val Ile Gly Glu Arg Tyr His Leu Ser Tyr Lys
 50                  55                  60

Ile Val Arg Thr Asp Ser Arg Leu Val Arg Ser Ile Leu Thr Ala His
 65                  70                  75                  80

Gly Phe His Glu Val His Pro Ser Ser Thr Asp Tyr Asn Leu Met Trp
                 85                  90                  95

Thr Gly Ser His Leu Lys Pro Phe Leu Leu Arg Thr Leu Ser Glu Ala
            100                 105                 110

Gln Lys Val Asn His Phe Pro Arg Ser Tyr Glu Leu Thr Arg Lys Asp
            115                 120                 125

Arg Leu Tyr Lys Asn Ile Ile Arg Met Gln His Thr His Gly Phe Lys
130                 135                 140

Val Phe His Ile Leu Pro Gln Thr Phe Leu Leu Pro Ala Glu Tyr Ala
145                 150                 155                 160

Glu Phe Cys Asn Ser Tyr Ser Lys Asp Arg Gly Pro Trp Ile Val Lys
                165                 170                 175

Pro Val Ala Ser Ser Arg Gly Arg Gly Val Tyr Leu Ile Asn Asn Pro
            180                 185                 190

Asn Gln Ile Ser Leu Glu Glu Asn Ile Leu Val Ser Arg Tyr Ile Asn
            195                 200                 205

Asn Pro Leu Leu Ile Asp Asp Phe Lys Phe Asp Val Arg Leu Tyr Val
        210                 215                 220

Leu Val Thr Ser Tyr Asp Pro Leu Val Ile Tyr Leu Tyr Glu Glu Gly
225                 230                 235                 240

Leu Ala Arg Phe Ala Thr Val Arg Tyr Asp Gln Gly Ala Lys Asn Ile
                245                 250                 255

Arg Asn Gln Phe Met His Leu Thr Asn Tyr Ser Val Asn Lys Lys Ser
            260                 265                 270

Gly Asp Tyr Val Ser Cys Asp Asp Pro Glu Val Glu Asp Tyr Gly Asn
```

-continued

```
                275                 280                 285
Lys Trp Ser Met Ser Ala Met Leu Arg Tyr Leu Lys Gln Glu Gly Arg
290                     295                 300

Asp Thr Thr Ala Leu Met Ala His Val Glu Asp Leu Ile Ile Lys Thr
305                 310                 315                 320

Ile Ile Ser Ala Glu Leu Ala Ile Ala Thr Ala Cys Lys Thr Phe Val
                325                 330                 335

Pro His Arg Ser Ser Cys Phe Glu Leu Tyr Gly Phe Asp Val Leu Ile
            340                 345                 350

Asp Ser Thr Leu Lys Pro Trp Leu Leu Glu Val Asn Leu Ser Pro Ser
        355                 360                 365

Leu Ala Cys Asp Ala Pro Leu Asp Leu Lys Ile Lys Ala Ser Met Ile
    370                 375                 380

Ser Asp Met Phe Thr Val Val Gly Phe Val Cys Gln Asp Pro Ala Gln
385                 390                 395                 400

Arg Ala Ser Thr Arg Pro Ile Tyr Pro Thr Phe Glu Ser Ser Arg Arg
                405                 410                 415

Asn Pro Phe Gln Lys Pro Gln Arg Cys Arg Pro Leu Ser Ala Ser Asp
            420                 425                 430

Ala Glu Met Lys Asn Leu Val Gly Ser Ala Arg Glu Lys Gly Pro Gly
        435                 440                 445

Lys Leu Gly Gly Ser Val Leu Gly Leu Ser Met Glu Glu Ile Lys Val
    450                 455                 460

Leu Arg Arg Val Lys Glu Glu Asn Asp Arg Arg Gly Gly Phe Ile Arg
465                 470                 475                 480

Ile Phe Pro Thr Ser Glu Thr Trp Glu Ile Tyr Gly Ser Tyr Leu Glu
                485                 490                 495

His Lys Thr Ser Met Asn Tyr Met Leu Ala Thr Arg Leu Phe Gln Asp
            500                 505                 510

Arg Met Thr Ala Asp Gly Ala Pro Glu Leu Lys Ile Glu Ser Leu Asn
        515                 520                 525

Ser Lys Ala Lys Leu His Ala Ala Leu Tyr Glu Arg Lys Leu Leu Ser
    530                 535                 540

Leu Glu Val Arg Lys Arg Arg Arg Ser Ser Arg Leu Arg Ala Met
545                 550                 555                 560

Arg Pro Lys Tyr Pro Val Ile Thr Gln Pro Ala Glu Met Asn Val Lys
                565                 570                 575

Thr Glu Thr Glu Ser Glu Glu Glu Val Ala Leu Asp Asn Glu
            580                 585                 590

Asp Glu Glu Gln Glu Ala Ser Gln Glu Glu Ser Ala Gly Phe Leu Arg
        595                 600                 605

Glu Asn Gln Ala Lys Tyr Thr Pro Ser Leu Thr Ala Leu Val Glu Asn
    610                 615                 620

Thr Pro Lys Glu Asn Ser Met Lys Val Arg Glu Trp Asn Asn Lys Gly
625                 630                 635                 640

Gly His Cys Cys Lys Leu Glu Thr Gln Glu Leu Glu Pro Lys Phe Asn
                645                 650                 655

Leu Met Gln Ile Leu Gln Asp Asn Gly Asn Leu Ser Lys Met Gln Ala
            660                 665                 670

Arg Ile Ala Phe Ser Ala Tyr Leu Gln His Val Gln Ile Arg Leu Met
        675                 680                 685

Lys Asp Ser Gly Gly Gln Thr Phe Ser Ala Ser Trp Ala Ala Lys Glu
    690                 695                 700
```

```
Asp Glu Gln Met Glu Leu Val Val Arg Phe Leu Lys Arg Ala Ser Asn
705                 710                 715                 720

Asn Leu Gln His Ser Leu Arg Met Val Leu Pro Ser Arg Arg Leu Ala
            725                 730                 735

Leu Leu Glu Arg Arg Arg Ile Leu Ala His Gln Leu Gly Asp Phe Ile
        740                 745                 750

Ile Val Tyr Asn Lys Glu Thr Glu Gln Met Ala Glu Lys Lys Ser Lys
            755                 760                 765

Lys Lys Val Glu Glu Glu Glu Asp Gly Val Asn Met Glu Asn Phe
        770                 775                 780

Gln Glu Phe Ile Arg Gln Ala Ser Glu Ala Glu Leu Glu Glu Val Leu
785                 790                 795                 800

Thr Phe Tyr Thr Gln Lys Asn Lys Ser Ala Ser Val Phe Leu Gly Thr
                805                 810                 815

His Ser Lys Ile Ser Lys Asn Asn Asn Tyr Ser Asp Ser Gly Ala
            820                 825                 830

Lys Gly

<210> SEQ ID NO 15
<211> LENGTH: 623
<212> TYPE: PRT
<213> ORGANISM: Homo sapiens

<400> SEQUENCE: 15

Met Ala Arg Asp Leu Glu Glu Thr Ala Ser Ser Glu Asp Glu Glu
1               5                   10                  15

Val Ile Ser Gln Glu Asp His Pro Cys Ile Met Trp Thr Gly Gly Cys
            20                  25                  30

Arg Arg Ile Pro Val Leu Val Phe His Ala Asp Ala Ile Leu Thr Lys
        35                  40                  45

Asp Asn Asn Ile Arg Val Ile Gly Glu Arg Tyr His Leu Ser Tyr Lys
    50                  55                  60

Ile Val Arg Thr Asp Ser Arg Leu Val Arg Ser Ile Leu Thr Ala His
65                  70                  75                  80

Gly Phe His Glu Val His Pro Ser Ser Thr Asp Tyr Asn Leu Met Trp
                85                  90                  95

Thr Gly Ser His Leu Lys Pro Phe Leu Leu Arg Thr Leu Ser Glu Ala
            100                 105                 110

Gln Lys Val Asn His Phe Pro Arg Ser Tyr Glu Leu Thr Arg Lys Asp
        115                 120                 125

Arg Leu Tyr Lys Asn Ile Ile Arg Met Gln His Thr His Gly Phe Lys
    130                 135                 140

Val Phe His Ile Leu Pro Gln Thr Phe Leu Leu Pro Ala Glu Tyr Ala
145                 150                 155                 160

Glu Phe Cys Asn Ser Tyr Ser Lys Asp Arg Gly Pro Trp Ile Val Lys
                165                 170                 175

Pro Val Ala Ser Ser Arg Gly Arg Gly Val Tyr Leu Ile Asn Asn Pro
            180                 185                 190

Asn Gln Ile Ser Leu Glu Glu Asn Ile Leu Val Ser Arg Tyr Ile Asn
        195                 200                 205

Asn Pro Leu Leu Ile Asp Asp Phe Lys Phe Asp Val Arg Leu Tyr Val
    210                 215                 220

Leu Val Thr Ser Tyr Asp Pro Leu Val Ile Tyr Leu Tyr Glu Glu Gly
225                 230                 235                 240
```

```
Leu Ala Arg Phe Ala Thr Val Arg Tyr Asp Gln Gly Ala Lys Asn Ile
                245                 250                 255

Arg Asn Gln Phe Met His Leu Thr Asn Tyr Ser Val Asn Lys Lys Ser
            260                 265                 270

Gly Asp Tyr Val Ser Cys Asp Pro Glu Val Glu Asp Tyr Gly Asn
        275                 280                 285

Lys Trp Ser Met Ser Ala Met Leu Arg Tyr Leu Lys Gln Gly Arg
    290                 295                 300

Asp Thr Thr Ala Leu Met Ala His Val Glu Asp Leu Ile Ile Lys Thr
305                 310                 315                 320

Ile Ile Ser Ala Glu Leu Ala Ile Ala Thr Ala Cys Lys Thr Phe Val
                325                 330                 335

Pro His Arg Ser Ser Cys Phe Glu Leu Tyr Gly Phe Asp Val Leu Ile
            340                 345                 350

Asp Ser Thr Leu Lys Pro Trp Leu Leu Glu Val Asn Leu Ser Pro Ser
            355                 360                 365

Leu Ala Cys Asp Ala Pro Leu Asp Leu Lys Ile Lys Ala Ser Met Ile
    370                 375                 380

Ser Asp Met Phe Thr Val Val Gly Phe Val Cys Gln Asp Pro Ala Gln
385                 390                 395                 400

Arg Ala Ser Thr Arg Pro Ile Tyr Pro Thr Phe Glu Ser Ser Arg Arg
                405                 410                 415

Asn Pro Phe Gln Lys Pro Gln Arg Cys Arg Pro Leu Ser Ala Ser Asp
            420                 425                 430

Ala Glu Met Lys Asn Leu Val Gly Ser Ala Arg Glu Lys Gly Pro Gly
    435                 440                 445

Lys Leu Gly Gly Ser Val Leu Gly Leu Ser Met Glu Glu Ile Lys Val
450                 455                 460

Leu Arg Arg Val Lys Glu Glu Asn Asp Arg Arg Gly Gly Phe Ile Arg
465                 470                 475                 480

Ile Phe Pro Thr Ser Glu Thr Trp Glu Ile Tyr Gly Ser Tyr Leu Glu
                485                 490                 495

His Lys Thr Ser Met Asn Tyr Met Leu Ala Thr Arg Leu Phe Gln Asp
            500                 505                 510

Arg Met Thr Ala Asp Gly Ala Pro Glu Leu Lys Ile Glu Ser Leu Asn
    515                 520                 525

Ser Lys Ala Lys Leu His Ala Ala Leu Tyr Glu Arg Lys Leu Leu Ser
    530                 535                 540

Leu Glu Val Arg Lys Arg Arg Arg Ser Ser Arg Leu Arg Ala Met
545                 550                 555                 560

Arg Pro Lys Tyr Pro Val Ile Thr Gln Pro Ala Glu Met Asn Val Lys
                565                 570                 575

Thr Glu Thr Glu Ser Glu Glu Glu Val Ala Leu Asp Asn Glu
            580                 585                 590

Asp Glu Glu Gln Glu Ala Ser Gln Glu Ser Ala Gly Phe Leu Arg
    595                 600                 605

Glu Asn Gln Ala Lys Tyr Thr Pro Ser Leu Thr Ala Leu Val Glu
    610                 615                 620

<210> SEQ ID NO 16
<211> LENGTH: 123
<212> TYPE: PRT
<213> ORGANISM: Homo sapiens
```

-continued

```
<400> SEQUENCE: 16

Gly Asp His Pro Glu Thr Ile Met Glu Val Lys Ile Lys Pro Pro
1               5                   10                  15

Lys Gln Gln Gln Thr Thr Glu Ile His Ser Asp Lys Leu Ser Arg Phe
            20                  25                  30

Thr Thr Ser Ala Glu Lys Glu Ala Lys Leu Val Tyr Ser Asn Ser Ser
        35                  40                  45

Ser Gly Pro Thr Ala Thr Leu Gln Lys Ile Pro Asn Thr His Leu Ser
    50                  55                  60

Ser Val Thr Thr Ser Asp Leu Ser Pro Gly Pro Cys His His Ser Ser
65                  70                  75                  80

Leu Ser Gln Ile Pro Ser Ala Ile Pro Ser Met Pro His Gln Pro Thr
                85                  90                  95

Ile Leu Leu Asn Thr Val Ser Ala Ser Ala Ser Pro Cys Leu His Pro
            100                 105                 110

Gly Ala Gln Asn Ile Pro Ser Pro Thr Gly Leu
        115                 120

<210> SEQ ID NO 17
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 17
aagcagccgu cggcggcugu u                                            21

<210> SEQ ID NO 18
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 18
aaccauggga agaugagacu u                                            21

<210> SEQ ID NO 19
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 19
aaucugugcc auccaaauuu u                                            21

<210> SEQ ID NO 20
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 20
aaaggucucu gaggccccu u                                             21

<210> SEQ ID NO 21
<211> LENGTH: 21
<212> TYPE: RNA
<213> ORGANISM: Artificial Sequence
```

```
<220> FEATURE:
<223> OTHER INFORMATION: A synthetic siRNA

<400> SEQUENCE: 21
aaacccuaaa ggaaaugccu u                                              21

<210> SEQ ID NO 22
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 22
aaacagcauc auccucagau u                                              21

<210> SEQ ID NO 23
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 23
aaaaaguuaa ucacuuuccu u                                              21

<210> SEQ ID NO 24
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 24
aaaacauuau ucgaaugcau u                                              21

<210> SEQ ID NO 25
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 25
aagguuuuuc acauccuccu u                                              21

<210> SEQ ID NO 26
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 26
aauuuuguaa uucauauucu u                                              21

<210> SEQ ID NO 27
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 27
aaggaccggg gaccuuggau u                                              21
```

```
<210> SEQ ID NO 28
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 28
aaaccagugg caucuucaau u                                              21

<210> SEQ ID NO 29
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 29
aacaauccaa accagaucuu u                                              21

<210> SEQ ID NO 30
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 30
aagagaacau uuggucucu u                                               21

<210> SEQ ID NO 31
<211> LENGTH: 22
<212> TYPE: RNA
<213> ORGANISM: Artificial Sequence
<220> FEATURE:
<223> OTHER INFORMATION: A synthetic siRNA

<400> SEQUENCE: 31 aaccccugc ucauagauga uu                                              22

<210> SEQ ID NO 32
<211> LENGTH: 22
<212> TYPE: RNA
<213> ORGANISM: Artificial Sequence
<220> FEATURE:
<223> OTHER INFORMATION: A synthetic siRNA

<400> SEQUENCE: 32
aagaaggauu ggcuagguuu uu                                             22

<210> SEQ ID NO 33
<211> LENGTH: 23
<212> TYPE: RNA
<213> ORGANISM: Artificial Sequence
<220> FEATURE:
<223> OTHER INFORMATION: A synthetic siRNA

<400> SEQUENCE: 33
cagcacugac uauaaccuaa uuu                                            23

<210> SEQ ID NO 34
<211> LENGTH: 23
<212> TYPE: RNA
<213> ORGANISM: Artificial Sequence
<220> FEATURE:
<223> OTHER INFORMATION: A synthetic siRNA
```

```
<400> SEQUENCE: 34
cacccucucu gaagcacaaa auu                                          23

<210> SEQ ID NO 35
<211> LENGTH: 23
<212> TYPE: RNA
<213> ORGANISM: Artificial Sequence
<220> FEATURE:
<223> OTHER INFORMATION: A synthetic siRNA

<400> SEQUENCE: 35
gccagcugag uacgcggaau uuu                                          23

<210> SEQ ID NO 36
<211> LENGTH: 23
<212> TYPE: RNA
<213> ORGANISM: Artificial Sequence
<220> FEATURE:
<223> OTHER INFORMATION: A synthetic siRNA

<400> SEQUENCE: 36
gagggcaaug aggccaaaau auu                                          23

<210> SEQ ID NO 37
<211> LENGTH: 21
<212> TYPE: DNA
<213> ORGANISM: Homo sapiens

<400> SEQUENCE: 37
cagcactgac tataacctaa t                                            21

<210> SEQ ID NO 38
<211> LENGTH: 21
<212> TYPE: DNA
<213> ORGANISM: Homo sapiens

<400> SEQUENCE: 38
caccctctct gaagcacaaa a                                            21

<210> SEQ ID NO 39
<211> LENGTH: 21
<212> TYPE: DNA
<213> ORGANISM: Homo sapiens

<400> SEQUENCE: 39
gccagctgag tacgcggaat t                                            21

<210> SEQ ID NO 40
<211> LENGTH: 21
<212> TYPE: DNA
<213> ORGANISM: Homo sapiens

<400> SEQUENCE: 40
gagggcaatg aggccaaaat a                                            21

<210> SEQ ID NO 41
<211> LENGTH: 6
<212> TYPE: DNA
<213> ORGANISM: Homo sapiens

<400> SEQUENCE: 41 tgttct                                                              6
```

<210> SEQ ID NO 42
<211> LENGTH: 1464
<212> TYPE: PRT
<213> ORGANISM: Homo sapiens

<400> SEQUENCE: 42

```
Met Ser Gly Met Gly Glu Asn Thr Ser Asp Pro Ser Arg Ala Glu Thr
 1               5                  10                  15

Arg Lys Arg Lys Glu Cys Pro Asp Gln Leu Gly Pro Ser Pro Lys Arg
                20                  25                  30

Asn Thr Glu Lys Arg Asn Arg Glu Gln Glu Asn Lys Tyr Ile Glu Glu
            35                  40                  45

Leu Ala Glu Leu Ile Phe Ala Asn Phe Asn Asp Ile Asp Asn Phe Asn
        50                  55                  60

Phe Lys Pro Asp Lys Cys Ala Ile Leu Lys Glu Thr Val Lys Gln Ile
 65                  70                  75                  80

Arg Gln Ile Lys Glu Gln Glu Lys Ala Ala Ala Asn Ile Asp Glu
                85                  90                  95

Val Gln Lys Ser Asp Val Ser Ser Thr Gly Gln Gly Val Ile Asp Lys
            100                 105                 110

Asp Ala Leu Gly Pro Met Met Leu Glu Ala Leu Asp Gly Phe Phe Phe
        115                 120                 125

Val Val Asn Leu Glu Gly Asn Val Val Phe Val Ser Glu Asn Val Thr
130                 135                 140

Gln Tyr Leu Arg Tyr Asn Gln Glu Glu Leu Met Asn Lys Ser Val Tyr
145                 150                 155                 160

Ser Ile Leu His Val Gly Asp His Thr Glu Phe Val Lys Asn Leu Leu
                165                 170                 175

Pro Lys Ser Ile Val Asn Gly Gly Ser Trp Ser Gly Glu Pro Pro Arg
            180                 185                 190

Arg Asn Ser His Thr Phe Asn Cys Arg Met Leu Val Lys Pro Leu Pro
        195                 200                 205

Asp Ser Glu Glu Glu Gly His Asp Asn Gln Glu Ala His Gln Lys Tyr
    210                 215                 220

Glu Thr Met Gln Cys Phe Ala Val Ser Gln Pro Lys Ser Ile Lys Glu
225                 230                 235                 240

Glu Gly Glu Asp Leu Gln Ser Cys Leu Ile Cys Val Ala Arg Arg Val
                245                 250                 255

Pro Met Lys Glu Arg Pro Val Leu Pro Ser Ser Glu Ser Phe Thr Thr
            260                 265                 270

Arg Gln Asp Leu Gln Gly Lys Ile Thr Ser Leu Asp Thr Ser Thr Met
        275                 280                 285

Arg Ala Ala Met Lys Pro Gly Trp Glu Asp Leu Val Arg Arg Cys Ile
    290                 295                 300

Gln Lys Phe His Ala Gln His Glu Gly Glu Ser Val Ser Tyr Ala Lys
305                 310                 315                 320

Arg His His His Glu Val Leu Arg Gln Gly Leu Ala Phe Ser Gln Ile
                325                 330                 335

Tyr Arg Phe Ser Leu Ser Asp Gly Thr Leu Val Ala Ala Gln Thr Lys
            340                 345                 350

Ser Lys Leu Ile Arg Ser Gln Thr Thr Asn Glu Pro Gln Leu Val Ile
        355                 360                 365

Ser Leu His Met Leu His Arg Glu Gln Asn Val Cys Val Met Asn Pro
    370                 375                 380
```

```
Asp Leu Thr Gly Gln Thr Met Gly Lys Pro Leu Asn Pro Ile Ser Ser
385                 390                 395                 400

Asn Ser Pro Ala His Gln Ala Leu Cys Ser Gly Asn Pro Gly Gln Asp
            405                 410                 415

Met Thr Leu Ser Ser Asn Ile Asn Phe Pro Ile Asn Gly Pro Lys Glu
            420                 425                 430

Gln Met Gly Met Pro Met Gly Arg Phe Gly Ser Gly Gly Met Asn
        435                 440                 445

His Val Ser Gly Met Gln Ala Thr Thr Pro Gln Gly Ser Asn Tyr Ala
        450                 455                 460

Leu Lys Met Asn Ser Pro Ser Gln Ser Ser Pro Gly Met Asn Pro Gly
465                 470                 475                 480

Gln Pro Thr Ser Met Leu Ser Pro Arg His Arg Met Ser Pro Gly Val
            485                 490                 495

Ala Gly Ser Pro Arg Ile Pro Pro Ser Gln Phe Ser Pro Ala Gly Ser
            500                 505                 510

Leu His Ser Pro Val Gly Val Cys Ser Ser Thr Gly Asn Ser His Ser
            515                 520                 525

Tyr Thr Asn Ser Ser Leu Asn Ala Leu Gln Ala Leu Ser Glu Gly His
            530                 535                 540

Gly Val Ser Leu Gly Ser Ser Leu Ala Ser Pro Asp Leu Lys Met Gly
545                 550                 555                 560

Asn Leu Gln Asn Ser Pro Val Asn Met Asn Pro Pro Leu Ser Lys
                565                 570                 575

Met Gly Ser Leu Asp Ser Lys Asp Cys Phe Gly Leu Tyr Gly Glu Pro
            580                 585                 590

Ser Glu Gly Thr Thr Gly Gln Ala Glu Ser Ser Cys His Pro Gly Glu
        595                 600                 605

Gln Lys Glu Thr Asn Asp Pro Asn Leu Pro Pro Ala Val Ser Ser Glu
    610                 615                 620

Arg Ala Asp Gly Gln Ser Arg Leu His Asp Ser Lys Gly Gln Thr Lys
625                 630                 635                 640

Leu Leu Gln Leu Leu Thr Thr Lys Ser Asp Gln Met Glu Pro Ser Pro
                645                 650                 655

Leu Ala Ser Ser Leu Ser Asp Thr Asn Lys Asp Ser Thr Gly Ser Leu
            660                 665                 670

Pro Gly Ser Gly Ser Thr His Gly Thr Ser Leu Lys Glu Lys His Lys
            675                 680                 685

Ile Leu His Arg Leu Leu Gln Asp Ser Ser Ser Pro Val Asp Leu Ala
        690                 695                 700

Lys Leu Thr Ala Glu Ala Thr Gly Lys Asp Leu Ser Gln Glu Ser Ser
705                 710                 715                 720

Ser Thr Ala Pro Gly Ser Glu Val Thr Ile Lys Gln Glu Pro Val Ser
            725                 730                 735

Pro Lys Lys Lys Glu Asn Ala Leu Leu Arg Tyr Leu Leu Asp Lys Asp
            740                 745                 750

Asp Thr Lys Asp Ile Gly Leu Pro Glu Ile Thr Pro Lys Leu Glu Arg
        755                 760                 765

Leu Asp Ser Lys Thr Asp Pro Ala Ser Asn Thr Lys Leu Ile Ala Met
        770                 775                 780

Lys Thr Glu Lys Glu Glu Met Ser Phe Glu Pro Gly Asp Gln Pro Gly
785                 790                 795                 800
```

-continued

```
Ser Glu Leu Asp Asn Leu Glu Ile Leu Asp Asp Leu Gln Asn Ser
                805                 810                 815

Gln Leu Pro Gln Leu Phe Pro Asp Thr Arg Pro Gly Ala Pro Ala Gly
                820                 825                 830

Ser Val Asp Lys Gln Ala Ile Ile Asn Asp Leu Met Gln Leu Thr Ala
                835                 840                 845

Glu Asn Ser Pro Val Thr Pro Val Gly Ala Gln Lys Thr Ala Leu Arg
    850                 855                 860

Ile Ser Gln Ser Thr Phe Asn Asn Pro Arg Pro Gly Gln Leu Gly Arg
865                 870                 875                 880

Leu Leu Pro Asn Gln Asn Leu Pro Leu Asp Ile Thr Leu Gln Ser Pro
                885                 890                 895

Thr Gly Ala Gly Pro Phe Pro Pro Ile Arg Asn Ser Ser Pro Tyr Ser
                900                 905                 910

Val Ile Pro Gln Pro Gly Met Met Gly Asn Gln Gly Met Ile Gly Asn
                915                 920                 925

Gln Gly Asn Leu Gly Asn Ser Ser Thr Gly Met Ile Gly Asn Ser Ala
    930                 935                 940

Ser Arg Pro Thr Met Pro Ser Gly Glu Trp Ala Pro Gln Ser Ser Ala
945                 950                 955                 960

Val Arg Val Thr Cys Ala Ala Thr Thr Ser Ala Met Asn Arg Pro Val
                965                 970                 975

Gln Gly Gly Met Ile Arg Asn Pro Ala Ala Ser Ile Pro Met Arg Pro
                980                 985                 990

Ser Ser Gln Pro Gly Gln Arg Gln Thr Leu Gln Ser Gln Val Met Asn
                995                 1000                1005

Ile Gly Pro Ser Glu Leu Glu Met Asn Met Gly Gly Pro Gln Tyr Ser
    1010                1015                1020

Gln Gln Gln Ala Pro Pro Asn Gln Thr Ala Pro Trp Pro Glu Ser Ile
1025                1030                1035                1040

Leu Pro Ile Asp Gln Ala Ser Phe Ala Ser Gln Asn Arg Gln Pro Phe
                1045                1050                1055

Gly Ser Ser Pro Asp Asp Leu Leu Cys Pro His Pro Ala Ala Glu Ser
                1060                1065                1070

Pro Ser Asp Glu Gly Ala Leu Leu Asp Gln Leu Tyr Leu Ala Leu Arg
                1075                1080                1085

Asn Phe Asp Gly Leu Glu Glu Ile Asp Arg Ala Leu Gly Ile Pro Glu
                1090                1095                1100

Leu Val Ser Gln Ser Gln Ala Val Asp Pro Glu Gln Phe Ser Ser Gln
1105                1110                1115                1120

Asp Ser Asn Ile Met Leu Glu Gln Lys Ala Pro Val Phe Pro Gln Gln
                1125                1130                1135

Tyr Ala Ser Gln Ala Gln Met Ala Gln Gly Ser Tyr Ser Pro Met Gln
                1140                1145                1150

Asp Pro Asn Phe His Thr Met Gly Gln Arg Pro Ser Tyr Ala Thr Leu
                1155                1160                1165

Arg Met Gln Pro Arg Pro Gly Leu Arg Pro Thr Gly Leu Val Gln Asn
                1170                1175                1180

Gln Pro Asn Gln Leu Arg Leu Gln Leu Gln His Arg Leu Gln Ala Gln
1185                1190                1195                1200

Gln Asn Arg Gln Pro Leu Met Asn Gln Ile Ser Asn Val Ser Asn Val
                1205                1210                1215

Asn Leu Thr Leu Arg Pro Gly Val Pro Thr Gln Ala Pro Ile Asn Ala
```

```
                1220               1225               1230
Gln Met Leu Ala Gln Arg Gln Arg Glu Ile Leu Asn Gln His Leu Arg
        1235               1240               1245
Gln Arg Gln Met His Gln Gln Gln Val Gln Gln Arg Thr Leu Met
    1250               1255               1260
Met Arg Gly Gln Gly Leu Asn Met Thr Pro Ser Met Val Ala Pro Ser
1265               1270               1275               1280
Gly Met Pro Ala Thr Met Ser Asn Pro Arg Ile Pro Gln Ala Asn Ala
                1285               1290               1295
Gln Gln Phe Pro Phe Pro Pro Asn Tyr Gly Ile Ser Gln Gln Pro Asp
            1300               1305               1310
Pro Gly Phe Thr Gly Ala Thr Thr Pro Gln Ser Pro Leu Met Ser Pro
        1315               1320               1325
Arg Met Ala His Thr Gln Ser Pro Met Met Gln Gln Ser Gln Ala Asn
    1330               1335               1340
Pro Ala Tyr Gln Ala Pro Ser Asp Ile Asn Gly Trp Ala Gln Gly Asn
1345               1350               1355               1360
Met Gly Gly Asn Ser Met Phe Ser Gln Gln Ser Pro Pro His Phe Gly
                1365               1370               1375
Gln Gln Ala Asn Thr Ser Met Tyr Ser Asn Asn Met Asn Ile Asn Val
            1380               1385               1390
Ser Met Ala Thr Asn Thr Gly Met Ser Ser Met Asn Gln Met Thr
        1395               1400               1405
Gly Gln Ile Ser Met Thr Ser Val Thr Ser Val Pro Thr Ser Gly Leu
    1410               1415               1420
Ser Ser Met Gly Pro Glu Gln Val Asn Asp Pro Ala Leu Arg Gly Gly
1425               1430               1435               1440
Asn Leu Phe Pro Asn Gln Leu Pro Gly Met Asp Met Ile Lys Gln Glu
                1445               1450               1455
Gly Asp Thr Thr Arg Lys Tyr Cys
        1460

<210> SEQ ID NO 43
<211> LENGTH: 1440
<212> TYPE: PRT
<213> ORGANISM: Homo sapiens

<400> SEQUENCE: 43

Met Ser Gly Leu Gly Asp Ser Ser Ser Asp Pro Ala Asn Pro Asp Ser
 1               5                  10                  15
His Lys Arg Lys Gly Ser Pro Cys Asp Thr Leu Ala Ser Ser Thr Glu
            20                  25                  30
Lys Arg Arg Arg Glu Gln Glu Asn Lys Tyr Leu Glu Glu Leu Ala Glu
        35                  40                  45
Leu Leu Ser Ala Asn Ile Ser Asp Ile Asp Ser Leu Ser Val Lys Pro
    50                  55                  60
Asp Lys Cys Lys Ile Leu Lys Lys Thr Val Asp Gln Ile Gln Leu Met
65                  70                  75                  80
Lys Arg Met Glu Gln Glu Lys Ser Thr Thr Asp Asp Val Gln Lys
                85                  90                  95
Ser Asp Ile Ser Ser Ser Ser Gln Gly Val Ile Glu Lys Glu Ser Leu
            100                 105                 110
Gly Pro Leu Leu Leu Glu Ala Leu Asp Gly Phe Phe Phe Val Val Asn
        115                 120                 125
```

```
Cys Glu Gly Arg Ile Val Phe Val Ser Glu Asn Val Thr Ser Tyr Leu
    130                 135                 140

Gly Tyr Asn Gln Glu Glu Leu Met Asn Thr Ser Val Tyr Ser Ile Leu
145                 150                 155                 160

His Val Gly Asp His Ala Glu Phe Val Lys Asn Leu Leu Pro Lys Ser
                165                 170                 175

Leu Val Asn Gly Val Pro Trp Pro Gln Glu Ala Thr Arg Arg Asn Ser
            180                 185                 190

His Thr Phe Asn Cys Arg Met Leu Ile His Pro Pro Asp Glu Pro Gly
        195                 200                 205

Thr Glu Asn Gln Glu Ala Cys Gln Arg Tyr Glu Val Met Gln Cys Phe
210                 215                 220

Thr Val Ser Gln Pro Lys Ser Ile Gln Glu Asp Gly Glu Asp Phe Gln
225                 230                 235                 240

Ser Cys Leu Ile Cys Ile Ala Arg Arg Leu Pro Arg Pro Pro Ala Ile
                245                 250                 255

Thr Gly Val Glu Ser Phe Met Thr Lys Gln Asp Thr Thr Gly Lys Ile
            260                 265                 270

Ile Ser Ile Asp Thr Ser Ser Leu Arg Ala Ala Gly Arg Thr Gly Trp
        275                 280                 285

Glu Asp Leu Val Arg Lys Cys Ile Tyr Ala Phe Phe Gln Pro Gln Gly
290                 295                 300

Arg Glu Pro Ser Tyr Ala Arg Gln Leu Phe Gln Glu Val Met Thr Arg
305                 310                 315                 320

Gly Thr Ala Ser Ser Pro Ser Tyr Arg Phe Ile Leu Asn Asp Gly Thr
                325                 330                 335

Met Leu Ser Ala His Thr Lys Cys Lys Leu Cys Tyr Pro Gln Ser Pro
            340                 345                 350

Asp Met Gln Pro Phe Ile Met Gly Ile His Ile Ile Asp Arg Glu His
        355                 360                 365

Ser Gly Leu Ser Pro Gln Asp Asp Thr Asn Ser Gly Met Ser Ile Pro
370                 375                 380

Arg Val Asn Pro Ser Val Asn Pro Ser Ile Ser Pro Ala His Gly Val
385                 390                 395                 400

Ala Arg Ser Ser Thr Leu Pro Pro Ser Asn Ser Asn Met Val Ser Thr
                405                 410                 415

Arg Ile Asn Arg Gln Gln Ser Ser Asp Leu His Ser Ser Ser His Ser
            420                 425                 430

Asn Ser Ser Asn Ser Gln Gly Ser Phe Gly Cys Ser Pro Gly Ser Gln
        435                 440                 445

Ile Val Ala Asn Val Ala Leu Asn Gln Gly Gln Ala Ser Ser Gln Ser
450                 455                 460

Ser Asn Pro Ser Leu Asn Leu Asn Asn Ser Pro Met Glu Gly Thr Gly
465                 470                 475                 480

Ile Ser Leu Ala Gln Phe Met Ser Pro Arg Arg Gln Val Thr Ser Gly
                485                 490                 495

Leu Ala Thr Arg Pro Arg Met Pro Asn Asn Ser Phe Pro Pro Asn Ile
            500                 505                 510

Ser Thr Leu Ser Ser Pro Val Gly Met Thr Ser Ala Cys Asn Asn
        515                 520                 525

Asn Asn Arg Ser Tyr Ser Asn Ile Pro Val Thr Ser Leu Gln Gly Met
530                 535                 540

Asn Glu Gly Pro Asn Asn Ser Val Gly Phe Ser Ala Ser Ser Pro Val
```

-continued

```
                545                 550                 555                 560
Leu Arg Gln Met Ser Ser Gln Asn Ser Pro Ser Arg Leu Asn Ile Gln
                565                 570                 575
Pro Ala Lys Ala Glu Ser Lys Asp Asn Lys Glu Ile Ala Ser Ile Leu
                580                 585                 590
Asn Glu Met Ile Gln Ser Asp Asn Ser Ser Asp Gly Lys Pro Leu
                595                 600                 605
Asp Ser Gly Leu Leu His Asn Asn Asp Arg Leu Ser Asp Gly Asp Ser
                610                 615                 620
Lys Tyr Ser Gln Thr Ser His Lys Leu Val Gln Leu Leu Thr Thr Thr
625                 630                 635                 640
Ala Glu Gln Gln Leu Arg His Ala Asp Ile Asp Thr Ser Cys Lys Asp
                645                 650                 655
Val Leu Ser Cys Thr Gly Thr Ser Asn Ser Ala Ser Ala Asn Ser Ser
                660                 665                 670
Gly Gly Ser Cys Pro Ser Ser His Ser Ser Leu Thr Glu Arg His Lys
                675                 680                 685
Ile Leu His Arg Leu Leu Gln Glu Gly Ser Pro Ser Asp Ile Thr Thr
                690                 695                 700
Leu Ser Val Glu Pro Asp Lys Lys Asp Ser Ala Ser Thr Ser Val Ser
705                 710                 715                 720
Val Thr Gly Gln Val Gln Gly Asn Ser Ser Ile Lys Leu Glu Leu Asp
                725                 730                 735
Ala Ser Lys Lys Lys Glu Ser Lys Asp His Gln Leu Leu Arg Tyr Leu
                740                 745                 750
Leu Asp Lys Asp Glu Lys Asp Leu Arg Ser Thr Pro Asn Leu Ser Leu
                755                 760                 765
Asp Asp Val Lys Val Lys Val Glu Lys Lys Glu Gln Met Asp Pro Cys
                770                 775                 780
Asn Thr Asn Pro Thr Pro Met Thr Lys Pro Thr Pro Glu Glu Ile Lys
785                 790                 795                 800
Leu Glu Ala Gln Ser Gln Phe Thr Ala Asp Leu Asp Gln Phe Asp Gln
                805                 810                 815
Leu Leu Pro Thr Leu Glu Lys Ala Ala Gln Leu Pro Gly Leu Cys Glu
                820                 825                 830
Thr Asp Arg Met Asp Gly Ala Val Thr Ser Val Thr Ile Lys Ser Glu
                835                 840                 845
Ile Leu Pro Ala Ser Leu Gln Ser Ala Thr Ala Arg Pro Thr Ser Arg
                850                 855                 860
Leu Asn Arg Leu Pro Glu Leu Glu Leu Glu Ala Ile Asp Asn Gln Phe
865                 870                 875                 880
Gly Gln Pro Gly Thr Gly Asp Gln Ile Pro Trp Thr Asn Asn Thr Val
                885                 890                 895
Thr Ala Ile Asn Gln Ser Lys Ser Glu Asp Gln Cys Ile Ser Ser Gln
                900                 905                 910
Leu Asp Glu Leu Leu Cys Pro Pro Thr Thr Val Glu Gly Arg Asn Asp
                915                 920                 925
Glu Lys Ala Leu Leu Glu Gln Leu Val Ser Phe Leu Ser Gly Lys Asp
                930                 935                 940
Glu Thr Glu Leu Ala Glu Leu Asp Arg Ala Leu Gly Ile Asp Lys Leu
945                 950                 955                 960
Val Gln Gly Gly Gly Leu Asp Val Leu Ser Glu Arg Phe Pro Pro Gln
                965                 970                 975
```

-continued

```
Gln Ala Thr Pro Pro Leu Ile Met Glu Glu Arg Pro Asn Leu Tyr Ser
            980                 985                 990

Gln Pro Tyr Ser Ser Pro Ser Pro Thr Ala Asn Leu Pro Ser Pro Phe
            995                 1000                1005

Gln Gly Met Val Arg Gln Lys Pro Ser Leu Gly Thr Met Pro Val Gln
            1010                1015                1020

Val Thr Pro Pro Arg Gly Ala Phe Ser Pro Gly Met Gly Met Gln Pro
1025                1030                1035                1040

Arg Gln Thr Leu Asn Arg Pro Pro Ala Ala Pro Asn Gln Leu Arg Leu
                1045                1050                1055

Gln Leu Gln Gln Arg Leu Gln Gly Gln Gln Gln Leu Ile His Gln Asn
                1060                1065                1070

Arg Gln Ala Ile Leu Asn Gln Phe Ala Ala Thr Ala Pro Val Gly Ile
                1075                1080                1085

Asn Met Arg Ser Gly Met Gln Gln Gln Ile Thr Pro Gln Pro Pro Leu
                1090                1095                1100

Asn Ala Gln Met Leu Ala Gln Arg Gln Arg Glu Leu Tyr Ser Gln Gln
1105                1110                1115                1120

His Arg Gln Arg Gln Leu Ile Gln Gln Gln Arg Ala Met Leu Met Arg
                1125                1130                1135

Gln Gln Ser Phe Gly Asn Asn Leu Pro Pro Ser Ser Gly Leu Pro Val
                1140                1145                1150

Gln Met Gly Asn Pro Arg Leu Pro Gln Gly Ala Pro Gln Gln Phe Pro
                1155                1160                1165

Tyr Pro Pro Asn Tyr Gly Thr Asn Pro Gly Thr Pro Pro Ala Ser Thr
                1170                1175                1180

Ser Pro Phe Ser Gln Leu Ala Ala Asn Pro Glu Ala Ser Leu Ala Asn
1185                1190                1195                1200

Arg Asn Ser Met Val Ser Arg Gly Met Thr Gly Asn Ile Gly Gly Gln
                1205                1210                1215

Phe Gly Thr Gly Ile Asn Pro Gln Met Gln Gln Asn Val Phe Gln Tyr
                1220                1225                1230

Pro Gly Ala Gly Met Val Pro Gln Gly Glu Ala Asn Phe Ala Pro Ser
                1235                1240                1245

Leu Ser Pro Gly Ser Ser Met Val Pro Met Pro Ile Pro Pro Pro Gln
                1250                1255                1260

Ser Ser Leu Leu Gln Gln Thr Pro Pro Ala Ser Gly Tyr Gln Ser Pro
1265                1270                1275                1280

Asp Met Lys Ala Trp Gln Gln Gly Ala Ile Gly Asn Asn Asn Val Phe
                1285                1290                1295

Ser Gln Ala Val Gln Asn Gln Pro Thr Pro Ala Gln Pro Gly Val Tyr
                1300                1305                1310

Asn Asn Met Ser Ile Thr Val Ser Met Ala Gly Gly Asn Thr Asn Val
                1315                1320                1325

Gln Asn Met Asn Pro Met Met Ala Gln Met Gln Met Ser Ser Leu Gln
                1330                1335                1340

Met Pro Gly Met Asn Thr Val Cys Pro Glu Gln Ile Asn Asp Pro Ala
1345                1350                1355                1360

Leu Arg His Thr Gly Leu Tyr Cys Asn Gln Leu Ser Ser Thr Asp Leu
                1365                1370                1375

Leu Lys Thr Glu Ala Asp Gly Thr Gln Val Gln Gln Val Gln Val Phe
                1380                1385                1390
```

```
Ala Asp Val Gln Cys Thr Val Asn Leu Val Gly Gly Asp Pro Tyr Leu
    1395                1400                1405

Asn Gln Pro Gly Pro Leu Gly Thr Gln Lys Pro Thr Ser Gly Pro Gln
    1410                1415                1420

Thr Pro Gln Ala Gln Gln Lys Ser Leu Leu Gln Gln Leu Leu Thr Glu
1425                1430                1435                1440

<210> SEQ ID NO 44
<211> LENGTH: 777
<212> TYPE: PRT
<213> ORGANISM: Homo sapiens

<400> SEQUENCE: 44

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
                20                  25                  30

Leu Arg Gly Gly Ala Thr Val Lys Val Ser Ala Ser Ser Pro Ser Leu
            35                  40                  45

Ala Val Ala Ser Gln Ser Asp Ser Lys Gln Arg Arg Leu Leu Val Asp
50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
            115                 120                 125

Leu Asn Arg Ser Thr Ser Val Pro Glu Asn Pro Lys Ser Ser Ala Ser
130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
            195                 200                 205

Asn Glu Ser Pro Trp Arg Ser Asp Leu Leu Ile Asp Glu Asn Cys Leu
        210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
            275                 280                 285

Pro Gly Val Ile Lys Gln Glu Lys Leu Gly Thr Val Tyr Cys Gln Ala
        290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335
```

```
Asn Thr Ala Ser Leu Ser Gln Gln Asp Gln Lys Pro Ile Phe Asn
            340                 345                 350
Val Ile Pro Pro Ile Pro Val Gly Ser Glu Asn Trp Asn Arg Cys Gln
            355                 360                 365
Gly Ser Gly Asp Asp Asn Leu Thr Ser Leu Gly Thr Leu Asn Phe Pro
        370                 375                 380
Gly Arg Thr Val Phe Ser Asn Gly Tyr Ser Ser Pro Ser Met Arg Pro
385                 390                 395                 400
Asp Val Ser Ser Pro Ser Ser Ser Thr Ala Thr Thr Gly Pro
                405                 410                 415
Pro Pro Lys Leu Cys Leu Val Cys Ser Asp Glu Ala Ser Gly Cys His
                420                 425                 430
Tyr Gly Val Leu Thr Cys Gly Ser Cys Lys Val Phe Phe Lys Arg Ala
            435                 440                 445
Val Glu Gly Gln His Asn Tyr Leu Cys Ala Gly Arg Asn Asp Cys Ile
        450                 455                 460
Ile Asp Lys Ile Arg Arg Lys Asn Cys Pro Ala Cys Arg Tyr Arg Lys
465                 470                 475                 480
Cys Leu Gln Ala Gly Met Asn Leu Glu Ala Arg Lys Thr Lys Lys Lys
                485                 490                 495
Ile Lys Gly Ile Gln Gln Ala Thr Thr Gly Val Ser Gln Glu Thr Ser
            500                 505                 510
Glu Asn Pro Gly Asn Lys Thr Ile Val Pro Ala Thr Leu Pro Gln Leu
        515                 520                 525
Thr Pro Thr Leu Val Ser Leu Leu Glu Val Ile Glu Pro Glu Val Leu
    530                 535                 540
Tyr Ala Gly Tyr Asp Ser Ser Val Pro Asp Ser Thr Trp Arg Ile Met
545                 550                 555                 560
Thr Thr Leu Asn Met Leu Gly Gly Arg Gln Val Ile Ala Ala Val Lys
                565                 570                 575
Trp Ala Lys Ala Ile Pro Gly Phe Arg Asn Leu His Leu Asp Asp Gln
            580                 585                 590
Met Thr Leu Leu Gln Tyr Ser Trp Met Phe Leu Met Ala Phe Ala Leu
        595                 600                 605
Gly Trp Arg Ser Tyr Arg Gln Ser Ser Ala Asn Leu Leu Cys Phe Ala
    610                 615                 620
Pro Asp Leu Ile Ile Asn Glu Gln Arg Met Thr Leu Pro Cys Met Tyr
625                 630                 635                 640
Asp Gln Cys Lys His Met Leu Tyr Val Ser Ser Glu Leu His Arg Leu
                645                 650                 655
Gln Val Ser Tyr Glu Glu Tyr Leu Cys Met Lys Thr Leu Leu Leu Leu
            660                 665                 670
Ser Ser Val Pro Lys Asp Gly Leu Lys Ser Gln Glu Leu Phe Asp Glu
        675                 680                 685
Ile Arg Met Thr Tyr Ile Lys Glu Leu Gly Lys Ala Ile Val Lys Arg
    690                 695                 700
Glu Gly Asn Ser Ser Gln Asn Trp Gln Arg Phe Tyr Gln Leu Thr Lys
705                 710                 715                 720
Leu Leu Asp Ser Met His Glu Val Val Glu Asn Leu Leu Asn Tyr Cys
                725                 730                 735
Phe Gln Thr Phe Leu Asp Lys Thr Met Ser Ile Glu Phe Pro Glu Met
            740                 745                 750
```

```
Leu Ala Glu Ile Ile Thr Asn Gln Ile Pro Lys Tyr Ser Asn Gly Asn
        755                 760                 765

Ile Lys Lys Leu Leu Phe His Gln Lys
        770                 775
```

<210> SEQ ID NO 45
<211> LENGTH: 31
<212> TYPE: DNA
<213> ORGANISM: Artificial Sequence
<220> FEATURE:
<223> OTHER INFORMATION: A synthetic primer

<400> SEQUENCE: 45
gctctagatg cacccaggag tggtgaacag g                          31

<210> SEQ ID NO 46
<211> LENGTH: 23
<212> TYPE: DNA
<213> ORGANISM: Artificial Sequence
<220> FEATURE:
<223> OTHER INFORMATION: A synthetic primer

<400> SEQUENCE: 46
aagatgagac aggaatctgt gcc                                   23

<210> SEQ ID NO 47
<211> LENGTH: 34
<212> TYPE: DNA
<213> ORGANISM: Artificial Sequence
<220> FEATURE:
<223> OTHER INFORMATION: A synthetic primer

<400> SEQUENCE: 47
tacgatatct gatggcccgg gacctggagg aaac                       34

<210> SEQ ID NO 48
<211> LENGTH: 18
<212> TYPE: DNA
<213> ORGANISM: Artificial Sequence
<220> FEATURE:
<223> OTHER INFORMATION: A synthetic primer

<400> SEQUENCE: 48
agtaagaagg gcttcagg                                         18

<210> SEQ ID NO 49
<211> LENGTH: 32
<212> TYPE: DNA
<213> ORGANISM: Artificial Sequence
<220> FEATURE:
<223> OTHER INFORMATION: A synthetic primer

<400> SEQUENCE: 49
cgtctagact accaaagctg tcaatgaggg tg                         32

<210> SEQ ID NO 50
<211> LENGTH: 31
<212> TYPE: DNA
<213> ORGANISM: Artificial Sequence
<220> FEATURE:
<223> OTHER INFORMATION: A synthetic primer

<400> SEQUENCE: 50
ggaattcgaa aatacaccca agaaaattc c                           31

```
<210> SEQ ID NO 51
<211> LENGTH: 31
<212> TYPE: DNA
<213> ORGANISM: Artificial Sequence
<220> FEATURE:
<223> OTHER INFORMATION: A synthetic primer

<400> SEQUENCE: 51
gctctagaca cctttgccc cactatcaga a                              31

<210> SEQ ID NO 52
<211> LENGTH: 29
<212> TYPE: DNA
<213> ORGANISM: Artificial Sequence
<220> FEATURE:
<223> OTHER INFORMATION: A synthetic primer

<400> SEQUENCE: 52
ggaattcgat caccctgaga ctataatgg                                29

<210> SEQ ID NO 53
<211> LENGTH: 31
<212> TYPE: DNA
<213> ORGANISM: Artificial Sequence
<220> FEATURE:
<223> OTHER INFORMATION: A synthetic primer

<400> SEQUENCE: 53
cgtctagagg ccagtagggc ttgggatgtt c                             31

<210> SEQ ID NO 54
<211> LENGTH: 30
<212> TYPE: DNA
<213> ORGANISM: Artificial Sequence
<220> FEATURE:
<223> OTHER INFORMATION: A synthetic primer

<400> SEQUENCE: 54
ggaattcctg ccacgctgtc gatcaggaag                               30

<210> SEQ ID NO 55
<211> LENGTH: 28
<212> TYPE: DNA
<213> ORGANISM: Artificial Sequence
<220> FEATURE:
<223> OTHER INFORMATION: A synthetic primer

<400> SEQUENCE: 55
ggaattcaca ggggtggtcc cccagcac                                 28

<210> SEQ ID NO 56
<211> LENGTH: 33
<212> TYPE: DNA
<213> ORGANISM: Artificial Sequence
<220> FEATURE:
<223> OTHER INFORMATION: A synthetic primer

<400> SEQUENCE: 56
cgtctagata gcctggctgt acacgttgtt ttc                           33

<210> SEQ ID NO 57
<211> LENGTH: 28
<212> TYPE: DNA
<213> ORGANISM: Artificial Sequence
<220> FEATURE:
<223> OTHER INFORMATION: A synthetic primer
```

```
<400> SEQUENCE: 57
ggaattcgca caaatggccc agggtagc                                              28

<210> SEQ ID NO 58
<211> LENGTH: 32
<212> TYPE: DNA
<213> ORGANISM: Artificial Sequence
<220> FEATURE:
<223> OTHER INFORMATION: A synthetic primer

<400> SEQUENCE: 58
cgggatcctc agcaatattt ccgtgttgtg tc                                         32

<210> SEQ ID NO 59
<211> LENGTH: 66
<212> TYPE: DNA
<213> ORGANISM: Artificial Sequence
<220> FEATURE:
<223> OTHER INFORMATION: A synthetic oligonucleotide

<400> SEQUENCE: 59
gaattcccgg gatatcgtcg acccacgcgt ccggggcggc cgctctagag tatccctcga          60
ggatcc                                                                     66

<210> SEQ ID NO 60
<211> LENGTH: 336
<212> TYPE: DNA
<213> ORGANISM: Homo sapiens

<400> SEQUENCE: 60
tagaaaatac acccaaagaa aattccatga aagttcgtga atggaataat aaaggtggac          60
actgctgcaa acttgagact caggagctag agcctaaatt taacctgatg cagattcttc         120
aagataatgg caatcttagc aaaatgcagg cccgaatagc attctctgcc tatctccagc         180
atgttcaaat tcgcctgatg aaagacagtg gcggtcagac gttcagtgcc agttgggctg         240
ccaaagagga tgaacagatg gagctggttg ttcgtttcct caagcgagca tcaaataacc         300
tccagcattc actgaggatg gtattaccca gtcgac                                   336

<210> SEQ ID NO 61
<211> LENGTH: 4021
<212> TYPE: DNA
<213> ORGANISM: Cercopithecus aethiops

<400> SEQUENCE: 61
tgaatctgct aggaaaggtc tctgaggccc ccgtctgccg actgcatgac aaaccctaaa          60
ggaaatgcca gtcgtgatgg cccgggacct ggaggaaaca gcatcatcct cagaggatga        120
ggaggtcata agtcaagagg atcatccatg catcatgtgg actggaggct gtaggagaat        180
tccagttttg gtattccatg ccgacgctat tcttacaaag acaacaata ttagagtaat         240 tggagaacgt tatcatttgt cttataagat tgtacgaacg acagtcgcc tagtacgcag         300 cattctgaca gcccatggat ttcatgaagt tcacccaagc agcactgact ataacctaat        360
gtggacagga tcccacctga agcccttctt actgcgcacc ctctctgaag cacaaaaagt        420
taatcacttt cccaggtctt atgaacttac ccggaaggac cgactgtaca aaacattat         480 tcgaatgcag catacacatg gattcaaggc ttttcacatc ctcccccaga ccttcctcct        540
gccagctgag tacgcggaat tttgtaattc atattcgaag gaccgggac cttggatagt         600 aaaaccagtg gcatcttcta gggggcgggg cgtctacctg atcaacaatc caaaccagat        660
```

```
ttccctggaa gaaacattc  tggtctcccg ttatattaac aaccccctgc tcatagatga    720
tttcaagttt gatgtgcgcc tctatgtgct ggtgacttcc tatgatcctc ttgtcatcta    780
tctctatgaa gaaggattgg ctaggtttgc aactgtgcga tatgatcaag agccaagaa    840
cattcggaac cagttcatgc atctgacaaa ctacagtgtg aacaagaaga gtggagacta    900
cgtcagttgt gatgatccag aagtggagga ctatggaaac aaatggagca tgagtgctat    960
gcttaggtac ctgaaacaag aaggcagaga tacaactgca ttgatggccc atgtagaaga   1020
cctgatcatt aagactataa tctctgctga actagctatt gctactgcct gtaaaacctt   1080
tgttcctcat cgcagcagtt gttttgaact ctatggcttt gacgtgctca tagatgctac   1140
tctgaagcca tggttgttgg aagtgaatct ctctccttct ttggcctgtg atgcacctct   1200
ggacctaaag attaaagcca gtatgatttc agatatgttc actgttgttg gatttgtgtg   1260
ccaagatcct gcccagcggg catcaacccg gccaatttat cccacctttg agtcttccag   1320
gcgaaaccct ttccagaaac ctcagcgtcc acttccagca cagtttcatt catcagagcc   1380
aaagcagcgt tcccgtccac tctctgccag tgatgcggaa atgaaaaacc tcgtgggctc   1440
agcccgggag aaagggccag ggaagttggg tggttctgtg cttggtctgt caatggagga   1500
gatcaaagtt ttacggaggg tgaaggagga gaatgatcgg agaggtggat ttattcgcat   1560
atttcctaca tctgagacat gggaaatata tgggtcctac ctcgagcata agacctcaat   1620
gaactatatg ctggcaacac gcctcttcca ggacagaatg actgctgatg agcaccaga   1680
attgaagata gagggcctga attcaaaggc caagctgcat gctgcacttt acgagaggaa   1740
gctcctgtct ctggaggtgc gaaaacgtag acgacggagt agcagattga gggcaatgag   1800
gccaaaatac ccagtgatta cccaaccagc tgaaatgaat gttaaaactg agacagagag   1860
tgaagaggag gaagaagtcg cattagacaa tgaagatgaa gagcaggaag cttcccagga   1920
ggagtctgca ggatttctta gagaaaatca agccaaagat acaccctcat tgacaacttt   1980
ggtagaaaat acacccaaag aaaattccgt gaaagttcgt gaatggagta aaaaaggtga   2040
acggtgctgc aaacttgaga ctcaggagct ggagcctaaa tttaacctga tgcaggttct   2100
tcaagataac ggcaatctta gcaaagtgca ggcccgaata gcattctcta cctatctcca   2160
gcatgttcaa attcgcctga tgaaagacag tggaggtcag acgttcagtg ccagttgggc   2220
tgccaaagag gatgaacaga tggagctggt cgttcgtttc ctcaagcgag catcaaataa   2280
ccttcagcag tcactgagga tggtattacc cagccgacga ttggcacttc tggaacgcag   2340
aagaatcctg gcccaccagc tgggtgactt tatcattgta tacaacaagg aaacagaaca   2400
aatggctgaa aagaaatcaa agaagaaagt tgaagaagaa gaggaggatg gagtgaatat   2460
ggaaaacttt caggagttca tcagacaagc aagtgaggct gaactggagg aggtgttgac   2520
tttttatacc caaagaaaca agtctgctag tgtcttcctg gggactcact ctaaaagttc   2580
taagaacaac aacagttatt ctgatagtgg ggcaaaaggt gatcaccctg agactgtaat   2640
ggaagaagcg aaaatgaagc cgcctaaaca gcaacagaca acagaaattc actctgataa   2700
attatctcga tttaccactt cagcagaaaa agaggcaaaa ttagtttata ccagttcttc   2760
gtcgactcct ttctctggtc ctactgctac tctgcagaaa attcccaaca cccatttgtc   2820
atctgttaca acctcagacc tctctccagg gcctggccac cattcttctt tatctcaaat   2880
tccttcagct atcccagca  tgcctcacca gccaacaatt ttactgaaca cagtctctgc   2940
cagtgcttct ccctccctac atcctgggac acagaacatc ccaagccctg ctggcctgcc   3000
```

```
tcgctgtcga tcaggaagtc acaccattgg ctcctttct tccttccaaa gtgctgcaca    3060
catctatagc cagaaactgt ctcgtccctc ttcagcaaag gcaggatcgt gctatctaaa    3120
caagcatcat tcaggaatag ccaaaacaca acaagaggga gaagatgctt ctttatatag    3180
caaacggtac aaccaaagta tggttacagc tgaacttcag cggctagctg agaagcaggc    3240
agcgagacag tattctccat ccagccacat caacctcctc acccaacagg tgacaaactt    3300
gaatttggcc actggcatca taaacagaag cagtgcttca actccccca ccctccaacc    3360 catcatcagc cctagtggcc ccacatggtt ggtgcagtcg gaccctcaag ctcctgagaa    3420
tcactccagc cctcccagaa gcaggagcct ccagacaggt gggtttgcct gggaaggaga    3480
ggtagaaaac aacgtgtaca gcaaggctac cggggtggtc ccccagcaca agtatcaccc    3540
cacagcaggc agctatcagc tccattttgc cctgcagcaa cttgaacaac aaaaacttca    3600
gtcccggcag ctcctggacc agagtcgagc ccggcaccag gcaatctttg gcagccagac    3660
actacctaac tccaatttat ggacaatgaa taatggtgca ggttgtagaa tttccagtgc    3720
cacagctagt ggccagaagc caaccactct gccacaaaaa gcagtaccac ctccaagctc    3780
ttgcgcctcc ctggtcccca aaccccctcc caaccacaaa caagtgctca aagggcaac    3840 atcccagagg gcttccaaag ggtcctcggc atatgcgcag ctgaatggac tccagagcag    3900
ccttaaccct gcagcctctg tgcccatcac cagctccaca gatcctgctc acactaaaag    3960
atgaaccaca aacacacaga gaaacgacct gttcaccact cctggggtgc atctagagca    4020
t                                                                   4021

<210> SEQ ID NO 62
<211> LENGTH: 1299
<212> TYPE: PRT
<213> ORGANISM: Cercopithecus aethiops

<400> SEQUENCE: 62

Met Pro Val Val Met Ala Arg Asp Leu Glu Glu Thr Ala Ser Ser Ser
 1               5                  10                  15

Glu Asp Glu Glu Val Ile Ser Gln Glu Asp His Pro Cys Ile Met Trp
            20                  25                  30

Thr Gly Gly Cys Arg Arg Ile Pro Val Leu Val Phe His Ala Asp Ala
        35                  40                  45

Ile Leu Thr Lys Asp Asn Asn Ile Arg Val Ile Gly Glu Arg Tyr His
    50                  55                  60

Leu Ser Tyr Lys Ile Val Arg Thr Asp Ser Arg Leu Val Arg Ser Ile
65                  70                  75                  80

Leu Thr Ala His Gly Phe His Glu Val His Pro Ser Ser Thr Asp Tyr
                85                  90                  95

Asn Leu Met Trp Thr Gly Ser His Leu Lys Pro Phe Leu Leu Arg Thr
            100                 105                 110

Leu Ser Glu Ala Gln Lys Val Asn His Phe Pro Arg Ser Tyr Glu Leu
        115                 120                 125

Thr Arg Lys Asp Arg Leu Tyr Lys Asn Ile Ile Arg Met Gln His Thr
    130                 135                 140

His Gly Phe Lys Ala Phe His Ile Leu Pro Gln Thr Phe Leu Leu Pro
145                 150                 155                 160

Ala Glu Tyr Ala Glu Phe Cys Asn Ser Tyr Ser Lys Asp Arg Gly Pro
                165                 170                 175

Trp Ile Val Lys Pro Val Ala Ser Ser Arg Gly Arg Gly Val Tyr Leu
            180                 185                 190
```

```
Ile Asn Asn Pro Asn Gln Ile Ser Leu Glu Glu Asn Ile Leu Val Ser
        195                 200                 205

Arg Tyr Ile Asn Asn Pro Leu Leu Ile Asp Asp Phe Lys Phe Asp Val
210                 215                 220

Arg Leu Tyr Val Leu Val Thr Ser Tyr Asp Pro Leu Val Ile Tyr Leu
225                 230                 235                 240

Tyr Glu Glu Gly Leu Ala Arg Phe Ala Thr Val Arg Tyr Asp Gln Gly
                245                 250                 255

Ala Lys Asn Ile Arg Asn Gln Phe Met His Leu Thr Asn Tyr Ser Val
            260                 265                 270

Asn Lys Lys Ser Gly Asp Tyr Val Ser Cys Asp Asp Pro Glu Val Glu
        275                 280                 285

Asp Tyr Gly Asn Lys Trp Ser Met Ser Ala Met Leu Arg Tyr Leu Lys
290                 295                 300

Gln Glu Gly Arg Asp Thr Thr Ala Leu Met Ala His Val Glu Asp Leu
305                 310                 315                 320

Ile Ile Lys Thr Ile Ile Ser Ala Glu Leu Ala Ile Ala Thr Ala Cys
                325                 330                 335

Lys Thr Phe Val Pro His Arg Ser Ser Cys Phe Glu Leu Tyr Gly Phe
                340                 345                 350

Asp Val Leu Ile Asp Ala Thr Leu Lys Pro Trp Leu Leu Glu Val Asn
            355                 360                 365

Leu Ser Pro Ser Leu Ala Cys Asp Ala Pro Leu Asp Leu Lys Ile Lys
        370                 375                 380

Ala Ser Met Ile Ser Asp Met Phe Thr Val Val Gly Phe Val Cys Gln
385                 390                 395                 400

Asp Pro Ala Gln Arg Ala Ser Thr Arg Pro Ile Tyr Pro Thr Phe Glu
                405                 410                 415

Ser Ser Arg Arg Asn Pro Phe Gln Lys Pro Gln Arg Pro Leu Pro Ala
            420                 425                 430

Gln Phe His Ser Ser Glu Pro Lys Gln Arg Ser Arg Pro Leu Ser Ala
        435                 440                 445

Ser Asp Ala Glu Met Lys Asn Leu Val Gly Ser Ala Arg Glu Lys Gly
    450                 455                 460

Pro Gly Lys Leu Gly Gly Ser Val Leu Gly Leu Ser Met Glu Glu Ile
465                 470                 475                 480

Lys Val Leu Arg Arg Val Lys Glu Glu Asn Asp Arg Arg Gly Gly Phe
                485                 490                 495

Ile Arg Ile Phe Pro Thr Ser Glu Thr Trp Glu Ile Tyr Gly Ser Tyr
            500                 505                 510

Leu Glu His Lys Thr Ser Met Asn Tyr Met Leu Ala Thr Arg Leu Phe
        515                 520                 525

Gln Asp Arg Met Thr Ala Asp Gly Ala Pro Glu Leu Lys Ile Glu Gly
    530                 535                 540

Leu Asn Ser Lys Ala Lys Leu His Ala Ala Leu Tyr Glu Arg Lys Leu
545                 550                 555                 560

Leu Ser Leu Glu Val Arg Lys Arg Arg Arg Ser Ser Arg Leu Arg
                565                 570                 575

Ala Met Arg Pro Lys Tyr Pro Val Ile Thr Gln Pro Ala Glu Met Asn
            580                 585                 590

Val Lys Thr Glu Thr Glu Ser Glu Glu Glu Glu Val Ala Leu Asp
        595                 600                 605
```

-continued

```
Asn Glu Asp Glu Glu Gln Glu Ala Ser Gln Glu Ser Ala Gly Phe
    610                 615                 620

Leu Arg Glu Asn Gln Ala Lys Asp Thr Pro Ser Leu Thr Thr Leu Val
625                 630                 635                 640

Glu Asn Thr Pro Lys Glu Asn Ser Val Lys Val Arg Glu Trp Ser Lys
                645                 650                 655

Lys Gly Glu Arg Cys Cys Lys Leu Glu Thr Gln Glu Leu Glu Pro Lys
                660                 665                 670

Phe Asn Leu Met Gln Val Leu Gln Asp Asn Gly Asn Leu Ser Lys Val
            675                 680                 685

Gln Ala Arg Ile Ala Phe Ser Thr Tyr Leu Gln His Val Gln Ile Arg
    690                 695                 700

Leu Met Lys Asp Ser Gly Gly Gln Thr Phe Ser Ala Ser Trp Ala Ala
705                 710                 715                 720

Lys Glu Asp Glu Gln Met Glu Leu Val Val Arg Phe Leu Lys Arg Ala
                725                 730                 735

Ser Asn Asn Leu Gln Gln Ser Leu Arg Met Val Leu Pro Ser Arg Arg
            740                 745                 750

Leu Ala Leu Leu Glu Arg Arg Arg Ile Leu Ala His Gln Leu Gly Asp
        755                 760                 765

Phe Ile Ile Val Tyr Asn Lys Glu Thr Glu Gln Met Ala Glu Lys Lys
770                 775                 780

Ser Lys Lys Lys Val Glu Glu Glu Glu Asp Gly Val Asn Met Glu
785                 790                 795                 800

Asn Phe Gln Glu Phe Ile Arg Gln Ala Ser Glu Ala Glu Leu Glu Glu
                805                 810                 815

Val Leu Thr Phe Tyr Thr Gln Lys Asn Lys Ser Ala Ser Val Phe Leu
            820                 825                 830

Gly Thr His Ser Lys Ser Ser Lys Asn Asn Ser Tyr Ser Asp Ser
        835                 840                 845

Gly Ala Lys Gly Asp His Pro Glu Thr Val Met Glu Glu Ala Lys Met
    850                 855                 860

Lys Pro Pro Lys Gln Gln Thr Thr Glu Ile His Ser Asp Lys Leu
865                 870                 875                 880

Ser Arg Phe Thr Thr Ser Ala Glu Lys Glu Ala Lys Leu Val Tyr Thr
                885                 890                 895

Ser Ser Ser Ser Thr Pro Phe Ser Gly Pro Thr Ala Thr Leu Gln Lys
            900                 905                 910

Ile Pro Asn Thr His Leu Ser Ser Val Thr Thr Ser Asp Leu Ser Pro
        915                 920                 925

Gly Pro Gly His His Ser Ser Leu Ser Gln Ile Pro Ser Ala Ile Pro
    930                 935                 940

Ser Met Pro His Gln Pro Thr Ile Leu Leu Asn Thr Val Ser Ala Ser
945                 950                 955                 960

Ala Ser Pro Ser Leu His Pro Gly Thr Gln Asn Ile Pro Ser Pro Ala
                965                 970                 975

Gly Leu Pro Arg Cys Arg Ser Gly Ser His Thr Ile Gly Ser Phe Ser
            980                 985                 990

Ser Phe Gln Ser Ala Ala His Ile Tyr Ser Gln Lys Leu Ser Arg Pro
        995                 1000                1005

Ser Ser Ala Lys Ala Gly Ser Cys Tyr Leu Asn Lys His His Ser Gly
    1010                1015                1020

Ile Ala Lys Thr Gln Gln Glu Gly Glu Asp Ala Ser Leu Tyr Ser Lys
```

-continued

```
             1025                1030                1035                1040

Arg Tyr Asn Gln Ser Met Val Thr Ala Glu Leu Gln Arg Leu Ala Glu
                1045                1050                1055

Lys Gln Ala Ala Arg Gln Tyr Ser Pro Ser Ser His Ile Asn Leu Leu
            1060                1065                1070

Thr Gln Gln Val Thr Asn Leu Asn Leu Ala Thr Gly Ile Ile Asn Arg
        1075                1080                1085

Ser Ser Ala Ser Thr Pro Pro Thr Leu Gln Pro Ile Ile Ser Pro Ser
    1090                1095                1100

Gly Pro Thr Trp Leu Val Gln Ser Asp Pro Gln Ala Pro Glu Asn His
1105                1110                1115                1120

Ser Ser Pro Pro Arg Ser Arg Ser Leu Gln Thr Gly Gly Phe Ala Trp
                1125                1130                1135

Glu Gly Glu Val Glu Asn Asn Val Tyr Ser Lys Ala Thr Gly Val Val
            1140                1145                1150

Pro Gln His Lys Tyr His Pro Thr Ala Gly Ser Tyr Gln Leu His Phe
        1155                1160                1165

Ala Leu Gln Gln Leu Glu Gln Gln Lys Leu Gln Ser Arg Gln Leu Leu
    1170                1175                1180

Asp Gln Ser Arg Ala Arg His Gln Ala Ile Phe Gly Ser Gln Thr Leu
1185                1190                1195                1200

Pro Asn Ser Asn Leu Trp Thr Met Asn Asn Gly Ala Gly Cys Arg Ile
                1205                1210                1215

Ser Ser Ala Thr Ala Ser Gly Gln Lys Pro Thr Thr Leu Pro Gln Lys
            1220                1225                1230

Ala Val Pro Pro Ser Ser Cys Ala Ser Leu Val Pro Lys Pro Pro
    1235                1240                1245

Pro Asn His Lys Gln Val Leu Arg Arg Ala Thr Ser Gln Arg Ala Ser
1250                1255                1260

Lys Gly Ser Ser Ala Tyr Ala Gln Leu Asn Gly Leu Gln Ser Ser Leu
1265                1270                1275                1280

Asn Pro Ala Ala Ser Val Pro Ile Thr Ser Ser Thr Asp Pro Ala His
            1285                1290                1295

Thr Lys Arg

<210> SEQ ID NO 63
<211> LENGTH: 1281
<212> TYPE: PRT
<213> ORGANISM: Homo sapiens

<400> SEQUENCE: 63

Met Pro Ile Val Met Ala Arg Asp Leu Glu Thr Ala Ser Ser Ser
 1               5                  10                  15

Glu Asp Glu Glu Val Ile Ser Gln Glu Asp His Pro Cys Ile Met Trp
            20                  25                  30

Thr Gly Gly Cys Arg Arg Ile Pro Val Leu Val Phe His Ala Asp Ala
        35                  40                  45

Ile Leu Thr Lys Asp Asn Asn Ile Arg Val Ile Gly Glu Arg Tyr His
    50                  55                  60

Leu Ser Tyr Lys Ile Val Arg Thr Asp Ser Arg Leu Val Arg Ser Ile
65                  70                  75                  80

Leu Thr Ala His Gly Phe His Glu Val His Pro Ser Ser Thr Asp Tyr
                85                  90                  95

Asn Leu Met Trp Thr Gly Ser His Leu Lys Pro Phe Leu Leu Arg Thr
```

-continued

```
               100                 105                 110
Leu Ser Glu Ala Gln Lys Val Asn His Phe Pro Arg Ser Tyr Glu Leu
            115                 120                 125
Thr Arg Lys Asp Arg Leu Tyr Lys Asn Ile Ile Arg Met Gln His Thr
        130                 135                 140
His Gly Phe Lys Ala Phe His Ile Leu Pro Gln Thr Phe Leu Leu Pro
145                 150                 155                 160
Ala Glu Tyr Ala Glu Phe Cys Asn Ser Tyr Ser Lys Asp Arg Gly Pro
                165                 170                 175
Trp Ile Val Lys Pro Val Ala Ser Ser Arg Gly Arg Gly Val Tyr Leu
            180                 185                 190
Ile Asn Asn Pro Asn Gln Ile Ser Leu Glu Glu Asn Ile Leu Val Ser
        195                 200                 205
Arg Tyr Ile Asn Asn Pro Leu Leu Ile Asp Asp Phe Lys Phe Asp Val
    210                 215                 220
Arg Leu Tyr Val Leu Val Thr Ser Tyr Asp Pro Leu Val Ile Tyr Leu
225                 230                 235                 240
Tyr Glu Glu Gly Leu Ala Arg Phe Ala Thr Val Arg Tyr Asp Gln Gly
                245                 250                 255
Ala Lys Asn Ile Arg Asn Gln Phe Met His Leu Thr Asn Tyr Ser Val
            260                 265                 270
Asn Lys Lys Ser Gly Asp Tyr Val Ser Cys Asp Pro Glu Val Glu
        275                 280                 285
Asp Tyr Gly Asn Lys Trp Ser Met Ser Ala Met Leu Arg Tyr Leu Lys
    290                 295                 300
Gln Glu Gly Arg Asp Thr Thr Ala Leu Met Ala His Val Glu Asp Leu
305                 310                 315                 320
Ile Ile Lys Thr Ile Ile Ser Ala Glu Leu Ala Ile Ala Thr Ala Cys
                325                 330                 335
Lys Thr Phe Val Pro His Arg Ser Ser Cys Phe Glu Leu Tyr Gly Phe
            340                 345                 350
Asp Val Leu Ile Asp Ser Thr Leu Lys Pro Trp Leu Leu Glu Val Asn
        355                 360                 365
Leu Ser Pro Ser Leu Ala Cys Asp Ala Pro Leu Asp Leu Lys Ile Lys
    370                 375                 380
Ala Ser Met Ile Ser Asp Met Phe Thr Val Val Gly Phe Val Cys Gln
385                 390                 395                 400
Asp Pro Ala Gln Arg Ala Ser Thr Arg Pro Ile Tyr Pro Thr Phe Glu
                405                 410                 415
Ser Ser Arg Arg Asn Pro Phe Gln Lys Pro Gln Arg Cys Arg Pro Leu
            420                 425                 430
Ser Ala Ser Asp Ala Glu Met Lys Asn Leu Val Gly Ser Ala Arg Glu
        435                 440                 445
Lys Gly Pro Gly Lys Leu Gly Gly Ser Val Leu Gly Leu Ser Met Glu
    450                 455                 460
Glu Ile Lys Val Leu Arg Arg Val Lys Glu Glu Asn Asp Arg Arg Gly
465                 470                 475                 480
Gly Phe Ile Arg Ile Phe Pro Thr Ser Glu Thr Trp Glu Ile Tyr Gly
                485                 490                 495
Ser Tyr Leu Glu His Lys Thr Ser Met Asn Tyr Met Leu Ala Thr Arg
            500                 505                 510
Leu Phe Gln Asp Arg Met Thr Ala Asp Gly Ala Pro Glu Leu Lys Ile
        515                 520                 525
```

```
Glu Ser Leu Asn Ser Lys Ala Lys Leu His Ala Ala Leu Tyr Glu Arg
    530                 535                 540

Lys Leu Leu Ser Leu Glu Val Arg Lys Arg Arg Arg Ser Ser Arg
545                 550                 555                 560

Leu Arg Ala Met Arg Pro Lys Tyr Pro Val Ile Thr Gln Pro Ala Glu
                565                 570                 575

Met Asn Val Lys Thr Glu Thr Glu Ser Glu Glu Glu Glu Val Ala
            580                 585                 590

Leu Asp Asn Glu Asp Glu Glu Gln Glu Ala Ser Gln Glu Glu Ser Ala
            595                 600                 605

Gly Phe Leu Arg Glu Asn Gln Ala Lys Tyr Thr Pro Ser Leu Thr Ala
    610                 615                 620

Leu Val Glu Asn Thr Pro Lys Glu Asn Ser Met Lys Val Arg Glu Trp
625                 630                 635                 640

Asn Asn Lys Gly Gly His Cys Cys Lys Leu Glu Thr Gln Glu Leu Glu
                645                 650                 655

Pro Lys Phe Asn Leu Met Gln Ile Leu Gln Asp Asn Gly Asn Leu Ser
                660                 665                 670

Lys Met Gln Ala Arg Ile Ala Phe Ser Ala Tyr Leu Gln His Val Gln
            675                 680                 685

Ile Arg Leu Met Lys Asp Ser Gly Gly Gln Thr Phe Ser Ala Ser Trp
    690                 695                 700

Ala Ala Lys Glu Asp Glu Gln Met Glu Leu Val Val Arg Phe Leu Lys
705                 710                 715                 720

Arg Ala Ser Asn Asn Leu Gln His Ser Leu Arg Met Val Leu Pro Ser
                725                 730                 735

Arg Arg Leu Ala Leu Leu Glu Arg Arg Arg Ile Leu Ala His Gln Leu
                740                 745                 750

Gly Asp Phe Ile Ile Val Tyr Asn Lys Glu Thr Glu Gln Met Ala Glu
    755                 760                 765

Lys Lys Ser Lys Lys Val Glu Glu Glu Glu Asp Gly Val Asn
770                 775                 780

Met Glu Asn Phe Gln Glu Phe Ile Arg Gln Ala Ser Glu Ala Glu Leu
785                 790                 795                 800

Glu Glu Val Leu Thr Phe Tyr Thr Gln Lys Asn Lys Ser Ala Ser Val
                805                 810                 815

Phe Leu Gly Thr His Ser Lys Ile Ser Lys Asn Asn Asn Tyr Ser
                820                 825                 830

Asp Ser Gly Ala Lys Gly Asp His Pro Glu Thr Ile Met Glu Glu Val
    835                 840                 845

Lys Ile Lys Pro Pro Lys Gln Gln Gln Thr Thr Glu Ile His Ser Asp
    850                 855                 860

Lys Leu Ser Arg Phe Thr Thr Ser Ala Glu Lys Glu Ala Lys Leu Val
865                 870                 875                 880

Tyr Ser Asn Ser Ser Ser Gly Pro Thr Ala Thr Leu Gln Lys Ile Pro
                885                 890                 895

Asn Thr His Leu Ser Ser Val Thr Thr Ser Asp Leu Ser Pro Gly Pro
                900                 905                 910

Cys His His Ser Ser Leu Ser Gln Ile Pro Ser Ala Ile Pro Ser Met
                915                 920                 925

Pro His Gln Pro Thr Ile Leu Leu Asn Thr Val Ser Ala Ser Ala Ser
    930                 935                 940
```

Pro Cys Leu His Pro Gly Ala Gln Asn Ile Pro Ser Pro Thr Gly Leu
945                 950                 955                 960

Pro Arg Cys Arg Ser Gly Ser His Thr Ile Gly Pro Phe Ser Ser Phe
            965                 970                 975

Gln Ser Ala Ala His Ile Tyr Ser Gln Lys Leu Ser Arg Pro Ser Ser
            980                 985                 990

Ala Lys Ala Gly Ser Cys Tyr Leu Asn Lys His His Ser Gly Ile Ala
            995                 1000                1005

Lys Thr Gln Lys Glu Gly Glu Asp Ala Ser Leu Tyr Ser Lys Arg Tyr
        1010                1015                1020

Asn Gln Ser Met Val Thr Ala Glu Leu Gln Arg Leu Ala Glu Lys Gln
1025                1030                1035                1040

Ala Ala Arg Gln Tyr Ser Pro Ser Ser His Ile Asn Leu Leu Thr Gln
            1045                1050                1055

Gln Val Thr Asn Leu Asn Leu Ala Thr Gly Ile Ile Asn Arg Ser Ser
            1060                1065                1070

Ala Ser Ala Pro Pro Thr Leu Arg Pro Ile Ile Ser Pro Ser Gly Pro
            1075                1080                1085

Thr Trp Ser Thr Gln Ser Asp Pro Gln Ala Pro Glu Asn His Ser Ser
    1090                1095                1100

Ser Pro Gly Ser Arg Ser Leu Gln Thr Gly Gly Phe Ala Trp Glu Gly
1105                1110                1115                1120

Glu Val Glu Asn Asn Val Tyr Ser Gln Ala Thr Gly Val Val Pro Gln
            1125                1130                1135

His Lys Tyr His Pro Thr Ala Gly Ser Tyr Gln Leu Gln Phe Ala Leu
            1140                1145                1150

Gln Gln Leu Glu Gln Lys Leu Gln Ser Arg Gln Leu Leu Asp Gln
            1155                1160                1165

Ser Arg Ala Arg His Gln Ala Ile Phe Gly Ser Gln Thr Leu Pro Asn
    1170                1175                1180

Ser Asn Leu Trp Thr Met Asn Asn Gly Ala Gly Cys Arg Ile Ser Ser
1185                1190                1195                1200

Ala Thr Ala Ser Gly Gln Lys Pro Thr Thr Leu Pro Gln Lys Val Val
            1205                1210                1215

Pro Pro Pro Ser Ser Cys Ala Ser Leu Val Pro Lys Pro Pro Pro Asn
            1220                1225                1230

His Glu Gln Val Leu Arg Arg Ala Thr Ser Gln Lys Ala Ser Lys Gly
        1235                1240                1245

Ser Ser Ala Glu Gly Gln Leu Asn Gly Leu Gln Ser Ser Leu Asn Pro
    1250                1255                1260

Ala Ala Phe Val Pro Ile Thr Ser Ser Thr Asp Pro Ala His Thr Lys
1265                1270                1275                1280

Ile

<210> SEQ ID NO 64
<211> LENGTH: 1299
<212> TYPE: PRT
<213> ORGANISM: Pongo pygmaeus

<400> SEQUENCE: 64

Met Pro Ile Val Met Ala Arg Asp Leu Glu Glu Thr Ala Ser Ser Ser
 1               5                  10                  15

Glu Asp Glu Glu Val Ile Ser Gln Glu Asp His Pro Cys Ile Met Trp
            20                  25                  30

```
Thr Gly Gly Cys Arg Arg Ile Pro Val Leu Val Phe His Ala Asp Ala
            35                  40                  45

Ile Leu Thr Lys Asp Asn Asn Ile Arg Val Ile Gly Glu Arg Tyr His
 50                  55                  60

Leu Ser Tyr Lys Ile Val Arg Thr Asp Ser Arg Leu Val Arg Ser Ile
 65                  70                  75                  80

Leu Thr Ala His Gly Phe His Glu Val His Pro Ser Ser Thr Asp Tyr
                 85                  90                  95

Asn Leu Met Trp Thr Gly Ser His Leu Lys Pro Phe Leu Leu Arg Thr
            100                 105                 110

Leu Ser Glu Ala Gln Lys Val Asn His Phe Pro Arg Ser Tyr Glu Leu
        115                 120                 125

Thr Arg Lys Asp Arg Leu Tyr Lys Asn Ile Ile Arg Met Gln His Thr
    130                 135                 140

His Gly Phe Lys Ala Phe His Ile Leu Pro Gln Thr Phe Leu Leu Pro
145                 150                 155                 160

Ala Glu Tyr Ala Glu Phe Cys Asn Ser Tyr Ser Lys Asp Arg Gly Pro
                165                 170                 175

Trp Ile Val Lys Pro Val Ala Ser Ser Arg Gly Arg Gly Val Tyr Leu
            180                 185                 190

Ile Asn Asn Pro Asn Gln Ile Ser Leu Glu Glu Asn Ile Leu Val Ser
        195                 200                 205

Arg Tyr Ile Asn Asn Pro Leu Leu Ile Asp Asp Phe Lys Phe Asp Val
    210                 215                 220

Arg Leu Tyr Val Leu Val Thr Ser Tyr Asp Pro Leu Val Ile Tyr Leu
225                 230                 235                 240

Tyr Glu Glu Gly Leu Ala Arg Phe Ala Thr Val Arg Tyr Asp Gln Gly
                245                 250                 255

Ala Lys Asn Ile Arg Asn Gln Phe Met His Leu Thr Asn Tyr Ser Val
            260                 265                 270

Asn Lys Lys Ser Gly Asp Tyr Val Ser Cys Asp Asp Pro Glu Val Glu
        275                 280                 285

Asp Tyr Gly Asn Lys Trp Ser Met Ser Ala Met Leu Arg Tyr Leu Lys
    290                 295                 300

Gln Glu Gly Arg Asp Thr Thr Ala Leu Met Ala His Val Glu Asp Leu
305                 310                 315                 320

Ile Ile Lys Thr Ile Ile Ser Ala Glu Leu Ala Ile Ala Thr Ala Cys
                325                 330                 335

Lys Thr Phe Val Pro His Arg Ser Ser Cys Phe Glu Leu Tyr Gly Phe
            340                 345                 350

Asp Val Leu Ile Asp Ser Thr Leu Lys Pro Trp Leu Leu Glu Val Asn
        355                 360                 365

Leu Ser Pro Ser Leu Ala Cys Asp Ala Pro Leu Asp Leu Lys Ile Lys
    370                 375                 380

Ala Ser Met Ile Ser Asp Met Phe Thr Val Val Gly Phe Val Cys Gln
385                 390                 395                 400

Asp Pro Ala Gln Arg Ala Ser Thr Arg Pro Ile Tyr Pro Thr Phe Glu
                405                 410                 415

Ser Ser Arg Arg Asn Pro Phe Gln Lys Pro Gln Arg Cys Arg Pro Leu
            420                 425                 430

Ser Ala Ser Asp Ala Glu Met Lys Asn Leu Val Gly Ser Ala Arg Glu
        435                 440                 445

Lys Gly Pro Gly Lys Leu Gly Gly Ser Val Leu Gly Leu Ser Met Glu
```

```
        450                 455                 460
Glu Ile Lys Val Leu Arg Arg Val Lys Glu Asn Asp Arg Arg Gly
465                 470                 475                 480

Gly Phe Ile Arg Ile Phe Pro Thr Ser Glu Thr Trp Glu Ile Tyr Gly
                485                 490                 495

Ser Tyr Leu Glu His Lys Thr Ser Met Asn Tyr Met Leu Ala Thr Arg
                500                 505                 510

Leu Phe Gln Asp Arg Gly Asn Pro Arg Arg Ser Leu Leu Thr Gly Arg
                515                 520                 525

Thr Arg Met Thr Ala Asp Gly Ala Pro Glu Leu Lys Ile Glu Ser Leu
530                 535                 540

Asn Ser Lys Ala Lys Leu His Ala Ala Leu Tyr Glu Arg Lys Leu Leu
545                 550                 555                 560

Ser Leu Glu Val Arg Lys Arg Arg Ser Ser Arg Leu Arg Ala
                565                 570                 575

Met Arg Pro Lys Tyr Pro Val Ile Thr Gln Pro Ala Glu Met Asn Val
                580                 585                 590

Lys Thr Glu Thr Glu Ser Glu Glu Glu Glu Val Ala Leu Asp Asn
                595                 600                 605

Glu Glu Glu Glu Gln Glu Ala Ser Gln Glu Glu Ser Ala Gly Phe Leu
                610                 615                 620

Arg Glu Asn Gln Ala Lys Tyr Thr Pro Ser Leu Thr Ala Leu Val Glu
625                 630                 635                 640

Asn Thr Pro Lys Glu His Ser Met Lys Val Arg Glu Trp Asn Asn Lys
                645                 650                 655

Gly Gly His Cys Cys Lys Leu Glu Thr Gln Glu Leu Glu Pro Lys Phe
                660                 665                 670

Asn Leu Val Gln Ile Leu Gln Asp Asn Gly Asn Leu Ser Lys Val Gln
                675                 680                 685

Ala Arg Ile Ala Phe Ser Ala Tyr Leu Gln His Val Gln Ile Arg Leu
                690                 695                 700

Met Lys Asp Ser Gly Gly Gln Thr Phe Ser Ala Ser Trp Ala Ala Lys
705                 710                 715                 720

Glu Asp Glu Gln Met Glu Leu Val Val Arg Phe Leu Lys Arg Ala Ser
                725                 730                 735

Asn Asn Leu Gln His Ser Leu Arg Met Val Leu Pro Ser Arg Arg Leu
                740                 745                 750

Ala Leu Leu Glu Arg Arg Ile Leu Ala His Gln Leu Gly Asp Phe
                755                 760                 765

Ile Ile Val Tyr Asn Lys Glu Thr Gly Gln Met Ala Glu Lys Lys Ser
770                 775                 780

Lys Lys Lys Val Glu Glu Glu Glu Asp Gly Val Asn Met Glu Asn
785                 790                 795                 800

Phe Gln Glu Phe Ile Arg Gln Ala Ser Glu Ala Leu Glu Glu Val
                805                 810                 815

Leu Thr Phe Tyr Thr Gln Lys Asn Lys Ser Ala Ser Val Phe Leu Gly
                820                 825                 830

Thr His Ser Lys Ser Ser Lys Asn Asn Asn Ser Tyr Ser Asp Ser Gly
                835                 840                 845

Ala Lys Gly Asp His Pro Glu Thr Ile Met Glu Glu Val Lys Ile Lys
                850                 855                 860

Pro Pro Lys Gln Gln Thr Thr Glu Ile His Ser Asp Lys Leu Ser
865                 870                 875                 880
```

-continued

```
Arg Phe Thr Thr Ser Ala Glu Lys Glu Ala Lys Leu Val Tyr Ser Asn
                885                 890                 895

Ser Ser Ser Thr Pro Phe Ser Gly Pro Thr Ala Thr Leu Gln Lys Ile
            900                 905                 910

Pro Asn Thr His Leu Ser Ser Val Thr Thr Ser Asp Leu Ser Pro Gly
        915                 920                 925

Pro Gly His His Ser Ser Leu Ser Gln Ile Pro Ser Ala Ile Pro Ser
    930                 935                 940

Met Pro His Gln Pro Thr Val Leu Leu Asn Thr Val Ser Ala Ser Ala
945                 950                 955                 960

Ser Pro Cys Leu His Thr Gly Thr Gln Asn Ile Pro Asn Pro Ala Gly
                965                 970                 975

Leu Pro Arg Cys Arg Ser Gly Ser His Thr Ile Gly Pro Phe Ser Ser
            980                 985                 990

Phe Gln Ser Ala Ala His Ile Tyr Ser Gln Lys Leu Ser Arg Pro Ser
        995                 1000                1005

Ser Ala Lys Ala Ala Gly Ser Cys Tyr Leu Asn Lys His His Ser Gly
    1010                1015                1020

Ile Ala Lys Thr Gln Lys Glu Gly Glu Asp Ala Ser Ser Tyr Ser Lys
1025                1030                1035                1040

Arg Tyr Asn Gln Ser Met Val Thr Ala Glu Leu Gln Arg Leu Ala Glu
                1045                1050                1055

Lys Gln Ala Ala Arg Gln Tyr Ser Pro Ser Ser His Ile Asn Leu Leu
            1060                1065                1070

Thr Gln Gln Val Thr Asn Leu Asn Leu Ala Thr Gly Ile Ile Asn Arg
        1075                1080                1085

Ser Ser Ala Ser Thr Pro Pro Thr Leu Arg Pro Ile Ile Ser Pro Ser
    1090                1095                1100

Gly Pro Thr Trp Ser Thr Gln Ser Asp Pro Gln Ala Pro Glu Asn His
1105                1110                1115                1120

Ser Ser Pro Pro Gly Ser Arg Ser Leu Gln Thr Gly Val Phe Ala Trp
                1125                1130                1135

Glu Gly Glu Val Glu Asn Asn Val Tyr Ser Lys Ala Thr Gly Val Val
            1140                1145                1150

Pro Gln His Lys Tyr His Pro Thr Ala Gly Ser Tyr Gln Leu His Phe
        1155                1160                1165

Ala Leu Gln Gln Leu Glu Gln Gln Lys Leu Gln Ser Arg Gln Leu Leu
    1170                1175                1180

Asp Gln Ser Arg Ala Arg His Gln Ala Ile Phe Gly Ser Gln Thr Leu
1185                1190                1195                1200

Pro Asn Ser Asn Leu Trp Thr Met Asn Asn Gly Ala Gly Cys Arg Ile
                1205                1210                1215

Ser Ser Ala Thr Ala Ser Gly Lys Pro Thr Thr Leu Pro Gln Lys
            1220                1225                1230

Val Val Pro Pro Pro Ser Ser Cys Ala Ser Leu Val Pro Lys Pro Pro
    1235                1240                1245

Pro Asn His Lys Gln Val Leu Arg Arg Ala Thr Ser Gln Arg Ala Ser
    1250                1255                1260

Lys Gly Ser Ser Ala Glu Gly Gln Leu Asn Gly Leu Gln Ser Ser Leu
1265                1270                1275                1280

Asn Pro Ala Ala Phe Val Pro Ile Thr Ser Ser Thr Asp Pro Ala His
                1285                1290                1295
```

-continued

Thr Lys Ile

<210> SEQ ID NO 65
<400> SEQUENCE: 65

000

<210> SEQ ID NO 66
<211> LENGTH: 12
<212> TYPE: DNA
<213> ORGANISM: Homo sapiens

<400> SEQUENCE: 66
atgccaatcg tg                                                              12

<210> SEQ ID NO 67
<211> LENGTH: 4
<212> TYPE: PRT
<213> ORGANISM: Homo sapiens

<400> SEQUENCE: 67

Met Pro Ile Val
 1

<210> SEQ ID NO 68
<211> LENGTH: 12
<212> TYPE: DNA
<213> ORGANISM: Homo sapiens

<400> SEQUENCE: 68
atggcccggg ac                                                              12

<210> SEQ ID NO 69
<211> LENGTH: 4
<212> TYPE: PRT
<213> ORGANISM: Homo sapiens

<400> SEQUENCE: 69

Met Ala Arg Asp
 1

<210> SEQ ID NO 70
<211> LENGTH: 1281
<212> TYPE: PRT
<213> ORGANISM: Homo sapiens

<400> SEQUENCE: 70

Met Pro Ile Val Met Ala Arg Asp Leu Glu Glu Thr Ala Ser Ser
 1               5                  10                  15

Glu Asp Glu Glu Val Ile Ser Gln Glu Asp His Pro Cys Ile Met Trp
            20                  25                  30

Thr Gly Gly Cys Arg Arg Ile Pro Val Leu Val Phe His Ala Asp Ala
        35                  40                  45

Ile Leu Thr Lys Asp Asn Asn Ile Arg Val Ile Gly Glu Arg Tyr His
    50                  55                  60

Leu Ser Tyr Lys Ile Val Arg Thr Asp Ser Arg Leu Val Arg Ser Ile
65                  70                  75                  80

Leu Thr Ala His Gly Phe His Glu Val His Pro Ser Ser Thr Asp Tyr
                85                  90                  95

Asn Leu Met Trp Thr Gly Ser His Leu Lys Pro Phe Leu Leu Arg Thr
            100                 105                 110

```
Leu Ser Glu Ala Gln Lys Val Asn His Phe Pro Arg Ser Tyr Glu Leu
        115                 120                 125

Thr Arg Lys Asp Arg Leu Tyr Lys Asn Ile Ile Arg Met Gln His Thr
    130                 135                 140

His Gly Phe Lys Val Phe His Ile Leu Pro Gln Thr Phe Leu Leu Pro
145                 150                 155                 160

Ala Glu Tyr Ala Glu Phe Cys Asn Ser Tyr Ser Lys Asp Arg Gly Pro
                165                 170                 175

Trp Ile Val Lys Pro Val Ala Ser Ser Arg Gly Arg Gly Val Tyr Leu
            180                 185                 190

Ile Asn Asn Pro Asn Gln Ile Ser Leu Glu Glu Asn Ile Leu Val Ser
        195                 200                 205

Arg Tyr Ile Asn Asn Pro Leu Leu Ile Asp Asp Phe Lys Phe Asp Val
    210                 215                 220

Arg Leu Tyr Val Leu Val Thr Ser Tyr Asp Pro Leu Val Ile Tyr Leu
225                 230                 235                 240

Tyr Glu Glu Gly Leu Ala Arg Phe Ala Thr Val Arg Tyr Asp Gln Gly
                245                 250                 255

Ala Lys Asn Ile Arg Asn Gln Phe Met His Leu Thr Asn Tyr Ser Val
            260                 265                 270

Asn Lys Lys Ser Gly Asp Tyr Val Ser Cys Asp Pro Glu Val Glu
        275                 280                 285

Asp Tyr Gly Asn Lys Trp Ser Met Ser Ala Met Leu Arg Tyr Leu Lys
    290                 295                 300

Gln Glu Gly Arg Asp Thr Thr Ala Leu Met Ala His Val Glu Asp Leu
305                 310                 315                 320

Ile Ile Lys Thr Ile Ile Ser Ala Glu Leu Ala Ile Ala Thr Ala Cys
                325                 330                 335

Lys Thr Phe Val Pro His Arg Ser Ser Cys Phe Glu Leu Tyr Gly Phe
            340                 345                 350

Asp Val Leu Ile Asp Ser Thr Leu Lys Pro Trp Leu Leu Glu Val Asn
        355                 360                 365

Leu Ser Pro Ser Leu Ala Cys Asp Ala Pro Leu Asp Leu Lys Ile Lys
    370                 375                 380

Ala Ser Met Ile Ser Asp Met Phe Thr Val Val Gly Phe Val Cys Gln
385                 390                 395                 400

Asp Pro Ala Gln Arg Ala Ser Thr Arg Pro Ile Tyr Pro Thr Phe Glu
                405                 410                 415

Ser Ser Arg Arg Asn Pro Phe Gln Lys Pro Gln Arg Cys Arg Pro Leu
            420                 425                 430

Ser Ala Ser Asp Ala Glu Met Lys Asn Leu Val Gly Ser Ala Arg Glu
        435                 440                 445

Lys Gly Pro Gly Lys Leu Gly Gly Ser Val Leu Gly Leu Ser Met Glu
    450                 455                 460

Glu Ile Lys Val Leu Arg Arg Val Lys Glu Glu Asn Asp Arg Arg Gly
465                 470                 475                 480

Gly Phe Ile Arg Ile Phe Pro Thr Ser Glu Thr Trp Glu Ile Tyr Gly
                485                 490                 495

Ser Tyr Leu Glu His Lys Thr Ser Met Asn Tyr Met Leu Ala Thr Arg
            500                 505                 510

Leu Phe Gln Asp Arg Met Thr Ala Asp Gly Ala Pro Glu Leu Lys Ile
        515                 520                 525
```

-continued

```
Glu Ser Leu Asn Ser Lys Ala Lys Leu His Ala Ala Leu Tyr Glu Arg
    530                 535                 540
Lys Leu Leu Ser Leu Glu Val Arg Lys Arg Arg Arg Ser Ser Arg
545                 550                 555                 560
Leu Arg Ala Met Arg Pro Lys Tyr Pro Val Ile Thr Gln Pro Ala Glu
                565                 570                 575
Met Asn Val Lys Thr Glu Thr Glu Ser Glu Glu Glu Glu Val Ala
                580                 585                 590
Leu Asp Asn Glu Asp Glu Glu Gln Glu Ala Ser Gln Glu Glu Ser Ala
                595                 600                 605
Gly Phe Leu Arg Glu Asn Gln Ala Lys Tyr Thr Pro Ser Leu Thr Ala
610                 615                 620
Leu Val Glu Asn Thr Pro Lys Glu Asn Ser Met Lys Val Arg Glu Trp
625                 630                 635                 640
Asn Asn Lys Gly Gly His Cys Cys Lys Leu Glu Thr Gln Glu Leu Glu
                645                 650                 655
Pro Lys Phe Asn Leu Met Gln Ile Leu Gln Asp Asn Gly Asn Leu Ser
                660                 665                 670
Lys Met Gln Ala Arg Ile Ala Phe Ser Ala Tyr Leu Gln His Val Gln
                675                 680                 685
Ile Arg Leu Met Lys Asp Ser Gly Gly Gln Thr Phe Ser Ala Ser Trp
690                 695                 700
Ala Ala Lys Glu Asp Glu Gln Met Glu Leu Val Val Arg Phe Leu Lys
705                 710                 715                 720
Arg Ala Ser Asn Asn Leu Gln His Ser Leu Arg Met Val Leu Pro Ser
                725                 730                 735
Arg Arg Leu Ala Leu Leu Glu Arg Arg Arg Ile Leu Ala His Gln Leu
                740                 745                 750
Gly Asp Phe Ile Ile Val Tyr Asn Lys Glu Thr Glu Gln Met Ala Glu
                755                 760                 765
Lys Lys Ser Lys Lys Val Glu Glu Glu Glu Asp Gly Val Asn
                770                 775                 780
Met Glu Asn Phe Gln Glu Phe Ile Arg Gln Ala Ser Glu Ala Glu Leu
785                 790                 795                 800
Glu Glu Val Leu Thr Phe Tyr Thr Gln Lys Asn Lys Ser Ala Ser Val
                805                 810                 815
Phe Leu Gly Thr His Ser Lys Ile Ser Lys Asn Asn Asn Tyr Ser
                820                 825                 830
Asp Ser Gly Ala Lys Gly Asp His Pro Glu Thr Ile Met Glu Glu Val
                835                 840                 845
Lys Ile Lys Pro Pro Lys Gln Gln Gln Thr Thr Glu Ile His Ser Asp
                850                 855                 860
Lys Leu Ser Arg Phe Thr Thr Ser Ala Glu Lys Glu Ala Lys Leu Val
865                 870                 875                 880
Tyr Ser Asn Ser Ser Ser Gly Pro Thr Ala Thr Leu Gln Lys Ile Pro
                885                 890                 895
Asn Thr His Leu Ser Ser Val Thr Thr Ser Asp Leu Ser Pro Gly Pro
                900                 905                 910
Cys His His Ser Ser Leu Ser Gln Ile Pro Ser Ala Ile Pro Ser Met
                915                 920                 925
Pro His Gln Pro Thr Ile Leu Leu Asn Thr Val Ser Ala Ser Ala Ser
                930                 935                 940
Pro Cys Leu His Pro Gly Ala Gln Asn Ile Pro Ser Pro Thr Gly Leu
```

| | | | |
|---|---|---|---|
| | 945 | 950 | 955 | 960 |

Pro Arg Cys Arg Ser Gly Ser His Thr Ile Gly Pro Phe Ser Ser Phe
                       965                          970                        975

Gln Ser Ala Ala His Ile Tyr Ser Gln Lys Leu Ser Arg Pro Ser Ser
        980                        985                        990

Ala Lys Ala Gly Ser Cys Tyr Leu Asn Lys His His Ser Gly Ile Ala
        995                      1000                      1005

Lys Thr Gln Lys Glu Gly Glu Asp Ala Ser Leu Tyr Ser Lys Arg Tyr
    1010                      1015                      1020

Asn Gln Ser Met Val Thr Ala Glu Leu Gln Arg Leu Ala Glu Lys Gln
1025                  1030                  1035                  1040

Ala Ala Arg Gln Tyr Ser Pro Ser Ser His Ile Asn Leu Leu Thr Gln
                1045                  1050                  1055

Gln Val Thr Asn Leu Asn Leu Ala Thr Gly Ile Ile Asn Arg Ser Ser
        1060                      1065                      1070

Ala Ser Ala Pro Pro Thr Leu Arg Pro Ile Ile Ser Pro Ser Gly Pro
            1075                  1080                  1085

Thr Trp Ser Thr Gln Ser Asp Pro Gln Ala Pro Glu Asn His Ser Ser
    1090                      1095                      1100

Ser Pro Gly Ser Arg Ser Leu Gln Thr Gly Gly Phe Ala Trp Glu Gly
1105                  1110                  1115                  1120

Glu Val Glu Asn Asn Val Tyr Ser Gln Ala Thr Gly Val Val Pro Gln
                1125                  1130                  1135

His Lys Tyr His Pro Thr Ala Gly Ser Tyr Gln Leu Gln Phe Ala Leu
        1140                      1145                      1150

Gln Gln Leu Glu Gln Gln Lys Leu Gln Ser Arg Gln Leu Leu Asp Gln
            1155                  1160                  1165

Ser Arg Ala Arg His Gln Ala Ile Phe Gly Ser Gln Thr Leu Pro Asn
    1170                      1175                      1180

Ser Asn Leu Trp Thr Met Asn Asn Gly Ala Gly Cys Arg Ile Ser Ser
1185                  1190                  1195                  1200

Ala Thr Ala Ser Gly Gln Lys Pro Thr Thr Leu Pro Gln Lys Val Val
                1205                  1210                  1215

Pro Pro Pro Ser Ser Cys Ala Ser Leu Val Pro Lys Pro Pro Asn
        1220                      1225                      1230

His Glu Gln Val Leu Arg Arg Ala Thr Ser Gln Lys Ala Ser Lys Gly
            1235                  1240                  1245

Ser Ser Ala Glu Gly Gln Leu Asn Gly Leu Gln Ser Ser Leu Asn Pro
        1250                      1255                      1260

Ala Ala Ser Val Pro Ile Thr Ser Ser Thr Asp Pro Ala His Thr Lys
1265                  1270                  1275                  1280

Ile

```
<210> SEQ ID NO 71
<211> LENGTH: 3996
<212> TYPE: DNA
<213> ORGANISM: Homo sapiens

<400> SEQUENCE: 71
tgaatctgct aggaaaggtc tctgaggccc ccgtctgctg actgcatgac aaaccctaaa     60
ggaaatgcca atcgtgatgg cccgggacct ggaggaaaca gcatcatcct cagaggatga    120
ggaggtcata agtcaagagg atcatccatg catcatgtgg actggaggct gcaggagaat    180
tccagttttg gtattccatg ccgacgctat tcttacaaag gacaacaata ttagagtaat    240
```

```
tggagaacgt tatcatttgt cttataagat tgtacgaacg gacagtcgcc tagtacgcag    300
cattctgaca gcccatggat ttcatgaagt tcacccaagc agcactgact ataacctaat    360
gtggacagga tcccacctga agcccttctt actgcgcacc ctctctgaag cacaaaaagt    420
taatcacttt cccaggtctt atgaacttac ccggaaggac cgactgtaca aaacattat    480
tcgaatgcag catacacatg gattcaaggt ttttcacatc ctcccccaga ccttcctcct    540
gccagctgag tacgcggaat tttgtaattc atattcgaag gaccggggac cttggatagt    600
aaaaccagtg gcatcttcaa gggggcgggg cgtctacctg atcaacaatc caaaccagat    660
ctccctggaa gagaacattt tggtctcccg ttacattaac aaccccctgc tcatagatga    720
tttcaagttt gacgtgcgcc tctatgtgct cgtgacttcc tatgatcctc ttgtcatcta    780
tctctatgaa gaaggattgg ctaggtttgc aactgtgcga tatgatcaag gagccaagaa    840
cattcggaac cagttcatgc atctgacaaa ctacagtgtc aacaagaaaa gtggagatta    900
cgtcagttgt gacgatccag aagtggagga ttatggaaac aaatggagca tgagtgctat    960
gcttaggtac ctgaaacaag aaggcagaga tacaaccgca ttgatggccc atgtagaaga   1020
cctgatcatt aagactataa tctctgctga actagctatt gctactgcct gtaaaacctt   1080
tgttcctcat cgcagcagtt gttttgaact ctatggcttt gacgtgctca tagattctac   1140
tctgaagcca tggttgttgg aagtgaatct ctctccttct ttggcctgtg atgcgcctct   1200
ggacctaaag attaaagcca gtatgatttc agatatgttc actgttgtag gatttgtgtg   1260
ccaagatcct gcccagcggg catcaactcg gccaatttat cccacctttg agtcttccag   1320
gcgaaaccct ttccagaaac ctcagcgttg ccgtccactc tctgccagtg atgcggaaat   1380
gaaaaacctc gtgggctcag cccgggagaa agggccaggg aagttgggtg ttctgtgct   1440
tggtctgtca atggaggaga tcaaagtttt acgaagggtg aaggaggaga atgatcggcg   1500
aggtggattt attcgcatat ttcctacatc tgagacatgg gaaatatatg ggtcctacct   1560
cgagcataag acctcaatga actatatgct ggcaacacgc ctcttccagg acagaatgac   1620
tgctgatgga gcgccagaat tgaagataga gagtctgaat tcaaaggcca agctgcatgc   1680
tgcactttac gagaggaagc tcctgtctct ggaggtgcga aaacgtagac gacggagtag   1740
cagattgagg gcaatgaggc caaaataccc agtgattacc caaccagctg aaatgaatgt   1800
taaaactgag acagagagtg aagaggagga agaagtcgca ttagataatg aagatgaaga   1860
acaggaggct tcccaggagg agtctgcagg atttcttaga gaaaatcaag ccaaatatac   1920
accctcattg acagctttgg tagaaaatac acccaaagaa aattccatga agttcgtga   1980
atggaataat aaaggtggac actgctgcaa acttgagact caggagctag agcctaaatt   2040
taacctgatg cagattcttc aagataatgg caatcttagc aaaatgcagg cccgaatagc   2100
attctctgcc tatctccagc atgttcaaat tcgcctgatg aaagacagtg gcggtcagac   2160
gttcagtgcc agttgggctg ccaaagagga tgaacagatg gagctggttg ttcgtttcct   2220
caagcgagca tcaaataacc tccagcattc actgaggatg gtattaccca gtcgacgatt   2280
ggcacttctg gaacgcagaa gaatcctggc ccaccagctg ggtgactta tcattgtata   2340
caacaaggaa acagaacaaa tggctgaaaa gaaatcaaag aagaaagttg aggaagaaga   2400
ggaagatggg gtgaatatgg aaaactttca ggagttcatc agacaagcaa gtgaggctga   2460
actggaggag gtgttgactt tttataccca aagaacaag tctgctagtg tcttcctggg   2520
gactcactct aaaaatttcta agaacaacaa caattattct gatagtgggg caaaaggtga   2580
```

```
tcaccctgag actataatgg aagaagtgaa aataaagcca cctaaacagc aacagacgac   2640
agaaattcat tctgataaat tatctcgatt taccacttca gcagaaaaag aggcaaaatt   2700
agtttatagc aattcctcct ctggtcctac tgctactctg cagaaaattc ccaacaccca   2760
tttgtcatct gttacaacct ctgacctctc tccagggcct tgccaccatt cttctttatc   2820
tcaaattcct tcagctatcc ccagcatgcc tcaccagcca acaattttac tgaacacagt   2880
ctctgccagt gcttctccct gcctacatcc cggggcacag aacatcccaa gccctactgg   2940
cctgccacgc tgtcgatcag gaagtcacac cattggtccc ttttcttcct tccaaagtgc   3000
tgcacacatc tatagccaga aactgtctcg tccctcttca gcaaaggcag gatcgtgcta   3060
tctaaacaag catcattcag gaatagccaa aacacaaaaa gagggagaag atgcttcttt   3120
atatagcaaa cggtacaacc aaagtatggt tacagctgaa cttcagcggc tagctgagaa   3180
gcaggcagcg agacagtatt ctccatccag ccacatcaac ctcctcaccc aacaggtaac   3240
aaacctgaat ttggcaactg gcatcataaa cagaagcagt gcttcagctc ccccaacccct  3300 ccgacccatc atcagtccta gtggcccgac atggtctaca cagtcagacc cccaagctcc   3360
cgagaatcac tccagctctc ctggaagcag gagcctgcag acaggggggat ttgcctggga  3420 aggagaagta gaaaacaacg tgtacagcca ggctacaggg gtggtcccccc agcacaagta  3480 tcaccccaca gcaggcagct atcagcttca atttgccctg cagcaacttg aacaacaaaa   3540
acttcagtcc cggcagctcc tggaccagag tcgagcccgg caccaggcaa tctttggcag   3600
ccagacacta cctaactcca atttatggac aatgaataat ggtgcaggtt gtagaatttc   3660
cagtgccaca gctagtggcc agaagccaac cactctgcca caaaaagtgg taccacctcc   3720
aagttcttgc gcctccctgg ttcccaaacc cccacccaac cacgaacaag tgctcagaag   3780
ggcaacatcc cagaaagctt ccaaagggtc ctccgcggaa gggcagctga atggactcca   3840
gagcagcctt aaccctgcag cctctgtgcc catcaccagc tctacagatc ctgctcacac   3900
taaaatatga accacaaaca cacagagaaa caacctgttc accactcctg ggtgcatgat   3960
tgagggtgaa gcatccacca gcacttcaag gggtcc                             3996
```

<210> SEQ ID NO 72
<211> LENGTH: 1281
<212> TYPE: PRT
<213> ORGANISM: Homo sapiens

<400> SEQUENCE: 72

```
Met Pro Ile Val Met Ala Arg Asp Leu Glu Glu Thr Ala Ser Ser Ser
 1               5                  10                  15

Glu Asp Glu Glu Val Ile Ser Gln Glu Asp His Pro Cys Ile Met Trp
             20                  25                  30

Thr Gly Gly Cys Arg Arg Ile Pro Val Leu Val Phe His Ala Asp Ala
         35                  40                  45

Ile Leu Thr Lys Asp Asn Asn Ile Arg Val Ile Gly Glu Arg Tyr His
     50                  55                  60

Leu Ser Tyr Lys Ile Val Arg Thr Asp Ser Arg Leu Val Arg Ser Ile
 65                  70                  75                  80

Leu Thr Ala His Gly Phe His Glu Val His Pro Ser Ser Thr Asp Tyr
                 85                  90                  95

Asn Leu Met Trp Thr Gly Ser His Leu Lys Pro Phe Leu Leu Arg Thr
            100                 105                 110

Leu Ser Glu Ala Gln Lys Val Asn His Phe Pro Arg Ser Tyr Glu Leu
        115                 120                 125
```

```
Thr Arg Lys Asp Arg Leu Tyr Lys Asn Ile Ile Arg Met Gln His Thr
    130                 135                 140

His Gly Phe Lys Val Phe His Ile Leu Pro Gln Thr Phe Leu Leu Pro
145                 150                 155                 160

Ala Glu Tyr Ala Glu Phe Cys Asn Ser Tyr Ser Lys Asp Arg Gly Pro
                165                 170                 175

Trp Ile Val Lys Pro Val Ala Ser Ser Arg Gly Arg Gly Val Tyr Leu
            180                 185                 190

Ile Asn Asn Pro Asn Gln Ile Ser Leu Glu Glu Asn Ile Leu Val Ser
        195                 200                 205

Arg Tyr Ile Asn Asn Pro Leu Leu Ile Asp Asp Phe Lys Phe Asp Val
    210                 215                 220

Arg Leu Tyr Val Leu Val Thr Ser Tyr Asp Pro Leu Val Ile Tyr Leu
225                 230                 235                 240

Tyr Glu Glu Gly Leu Ala Arg Phe Ala Thr Val Arg Tyr Asp Gln Gly
                245                 250                 255

Ala Lys Asn Ile Arg Asn Gln Phe Met His Leu Thr Asn Tyr Ser Val
            260                 265                 270

Asn Lys Lys Ser Gly Asp Tyr Val Ser Cys Asp Asp Pro Glu Val Glu
        275                 280                 285

Asp Tyr Gly Asn Lys Trp Ser Met Ser Ala Met Leu Arg Tyr Leu Lys
    290                 295                 300

Gln Glu Gly Arg Asp Thr Thr Ala Leu Met Ala His Val Glu Asp Leu
305                 310                 315                 320

Ile Ile Lys Thr Ile Ile Ser Ala Glu Leu Ala Ile Ala Thr Ala Cys
                325                 330                 335

Lys Thr Phe Val Pro His Arg Ser Ser Cys Phe Glu Leu Tyr Gly Phe
            340                 345                 350

Asp Val Leu Ile Asp Ser Thr Leu Lys Pro Trp Leu Leu Glu Val Asn
        355                 360                 365

Leu Ser Pro Ser Leu Ala Cys Asp Ala Pro Leu Asp Leu Lys Ile Lys
    370                 375                 380

Ala Ser Met Ile Ser Asp Met Phe Thr Val Val Gly Phe Val Cys Gln
385                 390                 395                 400

Asp Pro Ala Gln Arg Ala Ser Thr Arg Pro Ile Tyr Pro Thr Phe Glu
                405                 410                 415

Ser Ser Arg Arg Asn Pro Phe Gln Lys Pro Gln Arg Cys Arg Pro Leu
            420                 425                 430

Ser Ala Ser Asp Ala Glu Met Lys Asn Leu Val Gly Ser Ala Arg Glu
        435                 440                 445

Lys Gly Pro Gly Lys Leu Gly Gly Ser Val Leu Gly Leu Ser Met Glu
    450                 455                 460

Glu Ile Lys Val Leu Arg Arg Val Lys Glu Glu Asn Asp Arg Arg Gly
465                 470                 475                 480

Gly Phe Ile Arg Ile Phe Pro Thr Ser Glu Thr Trp Glu Ile Tyr Gly
                485                 490                 495

Ser Tyr Leu Glu His Lys Thr Ser Met Asn Tyr Met Leu Ala Thr Arg
            500                 505                 510

Leu Phe Gln Asp Arg Met Thr Ala Asp Gly Ala Pro Glu Leu Lys Ile
        515                 520                 525

Glu Ser Leu Asn Ser Lys Ala Lys Leu His Ala Leu Tyr Glu Arg
    530                 535                 540
```

-continued

```
Lys Leu Leu Ser Leu Glu Val Arg Lys Arg Arg Arg Ser Ser Arg
545                 550                 555                 560

Leu Arg Ala Met Arg Pro Lys Tyr Pro Val Ile Thr Gln Pro Ala Glu
            565                 570                 575

Met Asn Val Lys Thr Glu Thr Glu Ser Glu Glu Glu Glu Glu Val Ala
            580                 585                 590

Leu Asp Asn Glu Asp Glu Glu Gln Glu Ala Ser Gln Glu Glu Ser Ala
            595                 600                 605

Gly Phe Leu Arg Glu Asn Gln Ala Lys Tyr Thr Pro Ser Leu Thr Ala
            610                 615                 620

Leu Val Glu Asn Thr Pro Lys Glu Asn Ser Met Lys Val Arg Glu Trp
625                 630                 635                 640

Asn Asn Lys Gly Gly His Cys Cys Lys Leu Glu Thr Gln Glu Leu Glu
                645                 650                 655

Pro Lys Phe Asn Leu Met Gln Ile Leu Gln Asp Asn Gly Asn Leu Ser
            660                 665                 670

Lys Met Gln Ala Arg Ile Ala Phe Ser Ala Tyr Leu Gln His Val Gln
            675                 680                 685

Ile Arg Leu Met Lys Asp Ser Gly Gly Gln Thr Phe Ser Ala Ser Trp
690                 695                 700

Ala Ala Lys Glu Asp Glu Gln Met Glu Leu Val Val Arg Phe Leu Lys
705                 710                 715                 720

Arg Ala Ser Asn Asn Leu Gln His Ser Leu Arg Met Val Leu Pro Ser
            725                 730                 735

Arg Arg Leu Ala Leu Leu Glu Arg Arg Arg Ile Leu Ala His Gln Leu
            740                 745                 750

Gly Asp Phe Ile Ile Val Tyr Asn Lys Glu Thr Glu Gln Met Ala Glu
            755                 760                 765

Lys Lys Ser Lys Lys Lys Val Glu Glu Glu Glu Asp Gly Val Asn
            770                 775                 780

Met Glu Asn Phe Gln Glu Phe Ile Arg Gln Ala Ser Glu Ala Glu Leu
785                 790                 795                 800

Glu Glu Val Leu Thr Phe Tyr Thr Gln Lys Asn Lys Ser Ala Ser Val
            805                 810                 815

Phe Leu Gly Thr His Ser Lys Ile Ser Lys Asn Asn Asn Tyr Ser
            820                 825                 830

Asp Ser Gly Ala Lys Gly Asp His Pro Glu Thr Ile Met Glu Glu Val
            835                 840                 845

Lys Ile Lys Pro Pro Lys Gln Gln Thr Thr Glu Ile His Ser Asp
            850                 855                 860

Lys Leu Ser Arg Phe Thr Thr Ser Ala Glu Lys Glu Ala Lys Leu Val
865                 870                 875                 880

Tyr Ser Asn Ser Ser Ser Gly Pro Thr Ala Thr Leu Gln Lys Ile Pro
                885                 890                 895

Asn Thr His Leu Ser Ser Val Thr Thr Ser Asp Leu Ser Pro Gly Pro
            900                 905                 910

Cys His His Ser Ser Leu Ser Gln Ile Pro Ser Ala Ile Pro Ser Met
            915                 920                 925

Pro His Gln Pro Thr Ile Leu Leu Asn Thr Val Ser Ala Ser Ala Ser
            930                 935                 940

Pro Cys Leu His Pro Gly Ala Gln Asn Ile Pro Ser Pro Thr Gly Leu
945                 950                 955                 960

Pro Arg Cys Arg Ser Gly Ser His Thr Ile Gly Pro Phe Ser Ser Phe
```

```
                965                 970                 975
Gln Ser Ala Ala His Ile Tyr Ser Gln Lys Leu Ser Arg Pro Ser Ser
            980                 985                 990
Ala Lys Ala Gly Ser Cys Tyr Leu Asn Lys His His Ser Gly Ile Ala
            995                 1000                1005
Lys Thr Gln Lys Glu Gly Glu Asp Ala Ser Leu Tyr Ser Lys Arg Tyr
        1010                1015                1020
Asn Gln Ser Met Val Thr Ala Glu Leu Gln Arg Leu Ala Glu Lys Gln
1025                1030                1035                1040
Ala Ala Arg Gln Tyr Ser Pro Ser Ser His Ile Asn Leu Leu Thr Gln
            1045                1050                1055
Gln Val Thr Asn Leu Asn Leu Ala Thr Gly Ile Ile Asn Arg Ser Ser
            1060                1065                1070
Ala Ser Ala Pro Pro Thr Leu Arg Pro Ile Ile Ser Pro Ser Gly Pro
            1075                1080                1085
Thr Trp Ser Thr Gln Ser Asp Pro Gln Ala Pro Glu Asn His Ser Ser
            1090                1095                1100
Ser Pro Gly Ser Arg Ser Leu Gln Thr Gly Gly Phe Ala Trp Glu Gly
1105                1110                1115                1120
Glu Val Glu Asn Asn Val Tyr Ser Gln Ala Thr Gly Val Val Pro Gln
            1125                1130                1135
His Lys Tyr His Pro Thr Ala Gly Ser Tyr Gln Leu Gln Phe Ala Leu
            1140                1145                1150
Gln Gln Leu Glu Gln Lys Leu Gln Ser Arg Gln Leu Leu Asp Gln
            1155                1160                1165
Ser Arg Ala Arg His Gln Ala Ile Phe Gly Ser Gln Thr Leu Pro Asn
            1170                1175                1180
Ser Asn Leu Trp Thr Met Asn Asn Gly Ala Gly Cys Arg Ile Ser Ser
1185                1190                1195                1200
Ala Thr Ala Ser Gly Gln Lys Pro Thr Thr Leu Pro Gln Lys Val Val
            1205                1210                1215
Pro Pro Pro Ser Ser Cys Ala Ser Leu Val Pro Lys Pro Pro Pro Asn
            1220                1225                1230
His Glu Gln Val Leu Arg Arg Ala Thr Ser Gln Lys Ala Ser Lys Gly
            1235                1240                1245
Ser Ser Ala Glu Gly Gln Leu Asn Gly Leu Gln Ser Ser Leu Asn Pro
            1250                1255                1260
Ala Ala Ser Val Pro Ile Thr Ser Ser Thr Asp Pro Ala His Thr Lys
1265                1270                1275                1280
Ile

<210> SEQ ID NO 73

<400> SEQUENCE: 73

000

<210> SEQ ID NO 74
<211> LENGTH: 4691
<212> TYPE: DNA
<213> ORGANISM: Homo sapiens

<400> SEQUENCE: 74
gcacgagggg gaagcagccg tcggcggctg ccctgagcct tcctggggaa ggaggaggga    60
ggtaggcgca gagcgcggtc cacgcctgct cgccccgaac catgggaaga tgagacagga   120
```

```
atctgtgcca tccaaattgc ttgatccagt gaatctgcta ggaaaggtct ctgaggcccc    180
cgtctgctga ctgcatgaca aaccctaaag gaaatgccaa tcgtgatggc ccgggacctg    240
gaggaaacag catcatcctc agaggatgag gaggtcataa gtcaagagga tcatccatgc    300
atcatgtgga ctggaggctg caggagaatt ccagttttgg tattccatgc cgacgctatt    360
cttacaaagg acaacaatat tagagtaatt ggagaacgtt atcatttgtc ttataagatt    420
gtacgaacgg acagtcgcct agtacgcagc attctgacag cccatggatt tcatgaagtt    480
cacccaagca gcactgacta taacctaatg tggacaggat cccacctgaa gcccttctta    540
ctgcgcaccc tctctgaagc acaaaaagtt aatcactttc ccaggtctta tgaacttacc    600
cggaaggacc gactgtacaa aaacattatt cgaatgcagc atacacatgg attcaaggtt    660
tttcacatcc tcccccagac cttcctcctg ccagctgagt acgcggaatt ttgtaattca    720
tattcgaagg accggggacc ttggatagta aaaccagtgg catcttcaag ggggcggggc    780
gtctacctga tcaacaatcc aaaccagatc tccctggaag agaacatttt ggtctcccgt    840
tacattaaca ccccctgct catagatgat ttcaagtttg acgtgcgcct ctatgtgctc    900
gtgacttcct atgatcctct tgtcatctat ctctatgaag aaggattggc taggtttgca    960
actgtgcgat atgatcaagg agccaagaac attcggaacc agttcatgca tctgacaaac    1020
tacagtgtca acaagaaaag tggagattac gtcagttgtg acgatccaga agtggaggat    1080
tatgaaaaca aatggagcat gagtgctatg cttaggtacc tgaaacaaga aggcagagat    1140
acaaccgcat tgatggccca tgtagaagac ctgatcatta agactataat ctctgctgaa    1200
ctagctattg ctactgcctg taaaacctt gttcctcatc gcagcagttg ttttgaactc    1260
tatggctttg acgtgctcat agattctact ctgaagccat ggttgttgga agtgaatctc    1320
tctccttctt tggcctgtga tgcgcctctg gacctaaaga ttaaagccag tatgatttca    1380
gatatgttca ctgttgtagg atttgtgtgc caagatcctg cccagcgggc atcaactcgg    1440
ccaatttatc ccacctttga gtcttccagg cgaaaccctt ccagaaaacc tcagcgttgc    1500
cgtccactct ctgccagtga tgcggaaatg aaaaaacctcg tgggctcagc ccgggagaaa    1560
gggccaggga agttgggtgg ttctgtgctt ggtctgtcaa tggaggagat caaagtttta    1620
cgaagggtga aggaggagaa tgatcggcga ggtggattta ttcgcatatt tcctacatct    1680
gagacatggg aaatatatgg gtcctacctc gagcataaga cctcaatgaa ctatatgctg    1740
gcaacacgcc tcttccagga cagaatgact gctgatggag cgccagaatt gaagatagag    1800
agtctgaatt caaaggccaa gctgcatgct gcactttacg agaggaagct cctgtctctg    1860
gaggtgcgaa aacgtagacg acggagtagc agattgaggg caatgaggcc aaaatacca    1920 gtgattaccc aaccagctga atgaatgtt aaaactgaga cagagagtga agaggaggaa    1980
gaagtcgcat tagataatga agatgaagaa caggaggctt cccaggagga gtctgcagga    2040
tttcttagag aaaatcaagc caaatataca ccctcattga cagctttggt agaaaataca    2100
cccaaagaaa attccatgaa agttcgtgaa tggaataata aaggtggaca ctgctgcaaa    2160
cttgagactc aggagctaga gcctaaattt aacctgatgc agattcttca agataatggc    2220
aatcttagca aaatgcaggc ccgaatagca ttctctgcct atctccagca tgttcaaatt    2280
cgcctgatga agacagtgg cggtcagacg ttcagtgcca gttgggctgc caagaggat    2340 gaacagatgg agctggttgt tcgtttcctc aagcgagcat caaataacct ccagcattca    2400
ctgaggatgg tattacccag tcgacgattg gcacttctgg aacgcagaag aatcctggcc    2460
```

-continued

```
caccagctgg gtgactttat cattgtatac aacaaggaaa cagaacaaat ggctgaaaag      2520
aaatcaaaga agaaagttga ggaagaagag gaagatgggg tgaatatgga aaactttcag      2580
gagttcatca gacaagcaag tgaggctgaa ctggaggagg tgttgacttt ttatacccaa      2640
aagaacaagt ctgctagtgt cttcctgggg actcactcta aaatttctaa gaacaacaac      2700
aattattctg atagtggggc aaaaggtgat caccctgaga ctataatgga agaagtgaaa      2760
ataaagccac ctaaacagca acagacgaca gaaattcatt ctgataaatt atctcgattt      2820
accacttcag cagaaaaaga ggcaaaatta gtttatagca attcctcctc tggtcctact      2880
gctactctgc agaaaattcc caacacccat ttgtcatctg ttacaacctc tgacctctct      2940
ccagggcctt gccaccattc ttctttatct caaattcctt cagctatccc cagcatgcct      3000
caccagccaa caattttact gaacacagtc tctgccagtg cttctccctg cctacatccc      3060
ggggcacaga acatcccaag ccctactggc ctgccacgct gtcgatcagg aagtcacacc      3120
attggtccct tttcttcctt ccaaagtgct gcacacatct atagccagaa actgtctcgt      3180
ccctcttcag caaaggcagg atcgtgctat ctaaacaagc atcattcagg aatagccaaa      3240
acacaaaaag agggagaaga tgcttcttta tatagcaaac ggtacaacca aagtatggtt      3300
acagctgaac ttcagcggct agctgagaag caggcagcga gacagtattc tccatccagc      3360
cacatcaacc tcctcaccca acaggtaaca aacctgaatt tggcaactgg catcataaac      3420
agaagcagtg cttcagctcc cccaaccctc cgacccatca tcagtcctag tggcccgaca      3480
tggtctacac agtcagaccc ccaagctccc gagaatcact ccagctctcc tggaagcagg      3540
agcctgcaga caggggggatt tgcctgggaa ggagaagtag aaaacaacgt gtacagccag      3600
gctacagggg tggtccccca gcacaagtat caccccacag caggcagcta tcagcttcaa      3660
tttgccctgc agcaacttga acaacaaaaa cttcagtccc ggcagctcct ggaccagagt      3720
cgagcccggc accaggcaat ctttggcagc cagacactac ctaactccaa tttatggaca      3780
atgaataatg gtgcaggttg tagaatttcc agtgccacag ctagtggcca gaagccaacc      3840
actctgccac aaaaagtggt accacctcca agttcttgcg cctccctggt tcccaaaccc      3900
ccacccaacc acgaacaagt gctcagaagg gcaacatccc agaaagcttc caaagggtcc      3960
tccgcggaag ggcagctgaa tggactccag agcagcctta accctgcagc ctctgtgccc      4020
atcaccagct ctacagatcc tgctcacact aaaatatgaa ccacaaacac acagagaaac      4080
aacctgttca ccactcctgg gtgcatgatt gagggtgaag catccaccag cacttcaagg      4140
ggtccatagt atttttttttt ttgctgcctc aaagtcccca aagccttcga gcagaagtgg      4200
cagtagatgg ttgccaatca gccaatgcag actttcactg ggacaacaag aaagcagatc      4260
ttctgggttt tgatggaact tggcagtggg gacattcagc tgatgcatta tatacccgt       4320 cagagcacac ttgtatcttt taccttccct ttgccccatg cccccaaact gcttaggtct      4380
tctctgtccc tttactgctg ctgcacagag atgatataaa agaggctctt tggctatttg      4440
cattttgctt cctcttcttt tccagattac agtatgaagc tttattttct ttgtacaagc      4500
ttaaaatttc aacatcatca tccgccaaag ttgttcctcc cttttcggag gatctagggg      4560
gaaagaggag cattcatcac aagtttccta gagagaggag acaaatcggt gtgccattga      4620
caacatgagc cagggtaaag gcacccttttg gaattactga tttcaaagat taataaagta      4680
attctatttt t                                                          4691
```

COFACTOR THAT MODULATES STEROID RECEPTOR ACTIVITIES

This application is a continuation-in-part under 35 U.S.C. 111(a) of International Application No. PCT/US2005/006393 filed Feb. 25, 2005 and published in English as WO 2005/082935 on Sep. 9, 2005, which claimed the benefit of U.S. Provisional Application Ser. No. 60/548,039, filed Feb. 26, 2004, the contents of which applications and publication are incorporated herein in their entireties.

The patent or application file contains at least one drawing executed in color. Copies of this patent or patent application publication with color drawing(s) will be provided by the Office upon request and payment of the necessary fee.

FIELD OF THE INVENTION

The invention relates to a new factor, termed STAMP (Steroid receptor coactivator-1 and Transcription intermediary factor-2 (TIF2) Associated Modulatory Protein), a coactivator that can modulate steroid receptors and glucocorticoid-sensitive gene expression.

BACKGROUND OF THE INVENTION

Nuclear receptors are classically defined as a family of ligand dependent transcription factors that are activated in response to ligand binding. Members of this family include the following receptors: glucocorticoid, mineralocorticoid, androgen, progesterone and estrogen. Naturally occurring ligands to these receptors are low molecular weight molecules that play an important role in health and in many diseases. Excesses or deficiencies of these ligands can have profound physiological consequences. By way of example, glucocorticoid excess results in Cushing's Syndrome, while glucocorticoid insufficiency results in Addison's Disease.

The glucocorticoid receptor (GR) is present in glucocorticoid responsive cells where it resides in the cytosol in an inactive state until it is stimulated by the binding of a ligand. Upon stimulation, the glucocorticoid receptor translocates to the cell nucleus where it specifically interacts with DNA and/or protein(s) and either activates or represses transcription in a glucocorticoid responsive manner. Activation involves glucocorticoid receptor binding to specific DNA sequences (glucocorticoid response elements or GREs) and the association with other factors, including coactivators that were discovered on the basis of their ability to increase the total levels of induced gene product. Repression usually involves glucocorticoid receptor becoming tethered to proteins bound to non-GRE DNA sequences as opposed to the direct binding of glucocorticoid receptors to DNA sequences. Two examples of DNA-bound proteins that interact with glucocorticoid receptors, and participate in glucocorticoid receptor-mediated gene repression, are AP-1 and NFκ-B. These interactions of glucocorticoid receptor are believed to be responsible for some of the anti-inflammatory activity of exogenously administered glucocorticoids. In addition, glucocorticoids may also exert physiologic effects independent of nuclear transcription.

Three distinguishing properties of ligand-regulated gene induction by glucocorticoid receptors are 1) the level of activated gene expression with agonist steroids, 2) the concentration of agonist required for half-maximal induction ($EC_{50}$), and 3) the amount of partial agonist activity with antagonists or antisteroids. The last two properties are independent of the total amount of gene expression, and basal level activity, due to the mathematical method by which they are defined. Physiological concentrations of steroid are often similar to the $EC_{50}$ of inducible genes. Therefore, those regulated genes that have lower $EC_{50}$s, and dose-response curves that are more left-shifted, will be preferentially induced by the circulating hormone, thereby affording differential gene induction during development, differentiation, and homeostasis. Endocrine therapies using antisteroids will be much more specific if one can increase the partial agonist activity for most genes and limit the repression to one or a few regulated genes.

Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from eliciting GR mediated events, including transcription. RU486 is an example of a non-selective glucocorticoid receptor antagonist.

However, while glucocorticoid receptor agonists can be beneficial agents for the treatment or prevention of various diseases and conditions, such treatment is often accompanied by undesirable side effects. These side effects include, for example, metabolic effects, weight gain, muscle wasting, decalcification of the skeleton, osteoporosis, thinning of the skin and thinning of the skeleton. Hence, agents are needed that modulate glucocorticoid receptor activity without causing these types of side effects. Moreover, glucocorticoid antagonists and agonists that act selectively may be desirable in therapies for the selective blockage/enhancement of specific genes without simultaneously influencing other glucocorticoid-responsive genes.

SUMMARY OF THE INVENTION

The invention provides a new factor, termed STAMP (SRC-1 and TIF2 Associated Modulatory Protein) that can modulate transcription of glucocorticoid-responsive genes. In other embodiments, STAMP can influence the activity of a variety of receptors, including glucocorticoid receptors, androgen receptors, estrogen receptors, mineralocorticoid receptors, progesterone receptors, thyroid receptors, retinoid receptors (RAR and RXR), and peroxisome proliferator-activated receptors (PPARs). Hence, STAMP can be included in compositions and methods for modulating such receptors.

Also provided are STAMP nucleic acids, antibodies that can bind STAMP polypeptides from various species, and agents that can modulate the transcription of a STAMP RNA, or the translation or activity of a STAMP polypeptide. Use of STAMP polypeptides, anti-STAMP antibodies, STAMP nucleic acids and agents that can modulate STAMP may reduce the need for steroids and avoid some of the negative side effects observed upon administration of steroids.

Thus, one aspect of the invention is an isolated STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof.

Another aspect of the invention is an isolated antibody that can bind a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof.

Another aspect of the invention is an isolated nucleic acid encoding a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Such a nucleic acid can, for example, comprise SEQ ID NO:2 or SEQ ID NO:61.

Another aspect of the invention is a nucleic acid that can modulate the expression of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Such a nucleic acid can, for example, be an antisense nucleic acid, a ribozyme or a siRNA. These nucleic acids can hybridize to a nucleic acid comprising SEQ ID NO:2 OR SEQ ID NO:61 under physiological conditions. In other embodiments, these nucleic acids can hybridize to a nucleic acid comprising SEQ ID NO:2 or SEQ ID NO:61 under stringent hybridization conditions. Examples of nucleic acids that can modulate the expression of a STAMP polypeptide include a siRNA that consists essentially of a double-stranded RNA with any one of SEQ ID NO:17-36.

According to the present invention, STAMP may be formulated into a composition. Such a composition can contain a therapeutically effective amount of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. The composition can also contain a glucocorticoid receptor coactivator, a glucocorticoid receptor agonist, a glucocorticoid receptor partial agonist or a glucocorticoid receptor antagonist. Examples of coactivators that can be included in the STAMP compositions include, for example, transcription intermediary factor-2 (TIF2) and steroid receptor coactivator-1 (SRC-1). Glucocorticoid receptor and glucocorticoids can also be included in the compositions of the invention.

Another aspect of the invention is a composition comprising a carrier and an agent that can modulate the expression or activity of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. One type of agent that can modulate the expression or activity of a STAMP polypeptide is a nucleic acid that can hybridize to a nucleic acid comprising SEQ ID NO:2 or SEQ ID NO:61 under physiological conditions. In some embodiments, the nucleic acid that can modulate the expression or activity of a STAMP polypeptide is a nucleic acid can hybridize to a nucleic acid comprising SEQ ID NO:2 or SEQ ID NO:61 under stringent hybridization conditions.

In another embodiment, the agent that can modulate the expression or activity of a STAMP polypeptide is an antisense nucleic acid, a ribozyme or a siRNA. Examples of siRNA that may modulate the expression of a STAMP polypeptide include double-stranded RNA molecules with SEQ ID NO:17-36. In another embodiment, the agent that can modulate the expression or activity of a STAMP polypeptide is a sense nucleic acid, for example, a STAMP nucleic acid having SEQ ID NO:2 or SEQ ID NO:61.

In another embodiment, the agent that can modulate the expression or activity of a STAMP polypeptide is an antibody that can bind to a STAMP polypeptide comprising any one of SEQ ID NO:1, SEQ ID NO:3, SEQ ID NO:4, SEQ ID NO:5, SEQ ID NO:6, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof.

Another aspect of the invention is a method of modulating glucocorticoid-responsive gene expression in a mammalian cell comprising contacting the cell with a composition comprising a carrier and an effective amount of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Compositions containing a STAMP polypeptide can contain other active ingredients, as described herein.

Another aspect of the invention is a method of modulating glucocorticoid-responsive gene expression in a mammalian cell comprising contacting the cell with a composition comprising a carrier and an agent that can modulate the expression or activity of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Agents that can modulate the expression or activity of a STAMP polypeptide include nucleic acids that can hybridize to a nucleic acid comprising SEQ ID NO:2 or SEQ ID NO:61, an antisense nucleic acid, a ribozyme, a siRNA or an antibody that can bind to STAMP. Compositions containing an agent that can modulate the expression or activity of a STAMP polypeptide can contain other active ingredients, as described herein.

Another aspect of the invention is a method of modulating glucocorticoid-responsive gene expression in a mammal comprising administering to the mammal a composition comprising a carrier and an effective amount of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Compositions containing a STAMP polypeptide can contain other active ingredients, as described herein. In another embodiment, the method for modulating glucocorticoid-responsive gene expression in a mammal comprises administering to the mammal a composition comprising a carrier and an agent that can modulate the expression or activity of a STAMP polypeptide. Agents that can modulate the expression or activity of a STAMP polypeptide include nucleic acids that can hybridize to a nucleic acid comprising SEQ ID NO:2 or SEQ ID NO:61, an antisense nucleic acid, a ribozyme, a siRNA or an antibody that can bind to STAMP.

Compositions containing an agent that can modulate the expression or activity of a STAMP polypeptide can contain other active ingredients, as described herein.

Another aspect of the invention is a method of treating or preventing a disease or a condition in a mammal comprising administering to the mammal a composition comprising a carrier and an effective amount of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Compositions containing a STAMP polypeptide can contain other active ingredients, as described herein.

Another aspect of the invention is a method of treating or preventing a disease or a condition in a mammal comprising administering to the mammal a composition comprising a carrier and an effective amount of an agent that can modulate the expression or activity of a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof. Agents that can modulate the expression or activity of a STAMP polypeptide include nucleic acids that can hybridize to a nucleic acid comprising SEQ ID NO:2 or SEQ ID NO:61, an antisense nucleic acid, a ribozyme, a siRNA or an antibody that can bind to STAMP. Compositions containing an agent that can modulate the expression or activity of a STAMP polypeptide can contain other active ingredients, as described herein.

Examples of the diseases and conditions that can be treated by the methods and compositions of the invention include conception (contraception), infertility, diabetes, menopause, cancer (e.g., hormone- or steroid-sensitive cancers, such as prostate and breast cancer), hypertension, osteoporosis, and the like. Other examples of diseases and conditions that can be treated by the compositions and methods of the invention are described below.

DESCRIPTION OF THE DRAWINGS

FIG. 2A shows the growth of yeast clones from the Sos-Ras two-hybrid screen for TIF2.4 interacting proteins. Five clones were obtained but only two (clones I and V) contained a protein that was needed for colony growth in the presence of the pSos/TIF2.4 fusion protein. After initial screening, only clone I (also named 6-6CL1) was selected for further investigation. FIG. 2B and FIG. 2C illustrate the selectivity of 6-6CL1 interactions with TIF2.4 in mammalian two-hybrid assays. Triplicate samples of CV-1 cells in 24-well plates were transiently transfected with the indicated GAL-DBD and VP16-AD plasmids along with the GAL4-regulated reporter, pFRLuc. The relative luciferase activity, normalized for the activity of the internal Renilla control, was determined and plotted as the average±S.D. The much lower activity of GAL/TIF2.4m123 was previously shown not to be due to unequal levels of protein expression (He et al., 2002). Similar results were obtained in three additional experiments.

FIG. 3A-F provide STAMP sequences and expression patterns. FIG. 3A1-2 provides the nucleotide sequence for human STAMP (nucleotide sequence: SEQ ID NO:74; amino acid sequence: SEQ ID NO:72). Stop codons that are 5' and 3' to the coding sequence are given in bold type. The double dagger above the DNA sequence indicate the positions of two sets of consensus Kozak sequence nucleotides (positions 211-229) for the start of translation at the first two codons for methionine, which would afford proteins containing either 1281 or 1277 amino acids. The first methionine is thought not to be the major start site as only the nucleotide at −3 to the ATG fits the consensus Kozak sequence (Kozak, 1989). The asterisk marks the end of the predicted, more abundant protein sequence with 1277 amino acids. A poly-A signal sequence is marked by a double underline. FIG. 3B shows a gel with endogenous STAMP mRNA in a human testis library as identified by RT-PCR. The human STAMP cDNA sequence was use to select primers (single underlined sequences in FIG. 3A) that were used to amplify STAMP mRNA sequences present in a human testis mRNA library. The position of the predicted 4.1 kb band is indicated by the arrow. FIG. 3C provides Northern blots of mRNAs from different tissues probed with a [$^{32}$P]labeled STAMP oligonucleotide (bp 2093-2426). The membrane contained mRNAs of the indicated human tissues (BD Clonetech). The presence of a common species at about 4.6 kb was detected in all samples by radioautography. The level of the internal control protein β-actin was determined by probing with a [$^{32}$P]labeled actin fragment (BD Clonetech). FIG. 3D1-4 provide a comparison of human (top; SEQ ID NO:71) vs. monkey (bottom, SEQ ID NO:61) STAMP cDNAs. FIG. 3E1-2 provide a comparison of the predicted human (top; SEQ ID NO:72) vs. monkey (bottom, SEQ ID NO:62) STAMP amino acid sequences.

FIG. 3F1-6 illustrate the immunocytochemical localization of transiently transfected STAMP. U2OS.rGR cells were treated as described in Example 1. Illumination at 570-590 or 330-360 nm was used to locate glucocorticoid receptors (FIG. 3F2 and FIG. 3F5, red) or HA/STAMP (FIG. 3F1 and FIG. 3F4, green), respectively. FIG. 3F1-3 show cells that were not treated with dexamethasone, while FIG. 3F4-6 show cells that were treated with 100 nM dexamethasone. FIG. 3F3 and FIG. 3F6 shows the signal for both glucocorticoid and STAMP together when illuminating at both wavelengths. Colocalization is revealed by the yellow fluorescence of the merged pictures.

Figure 1A:
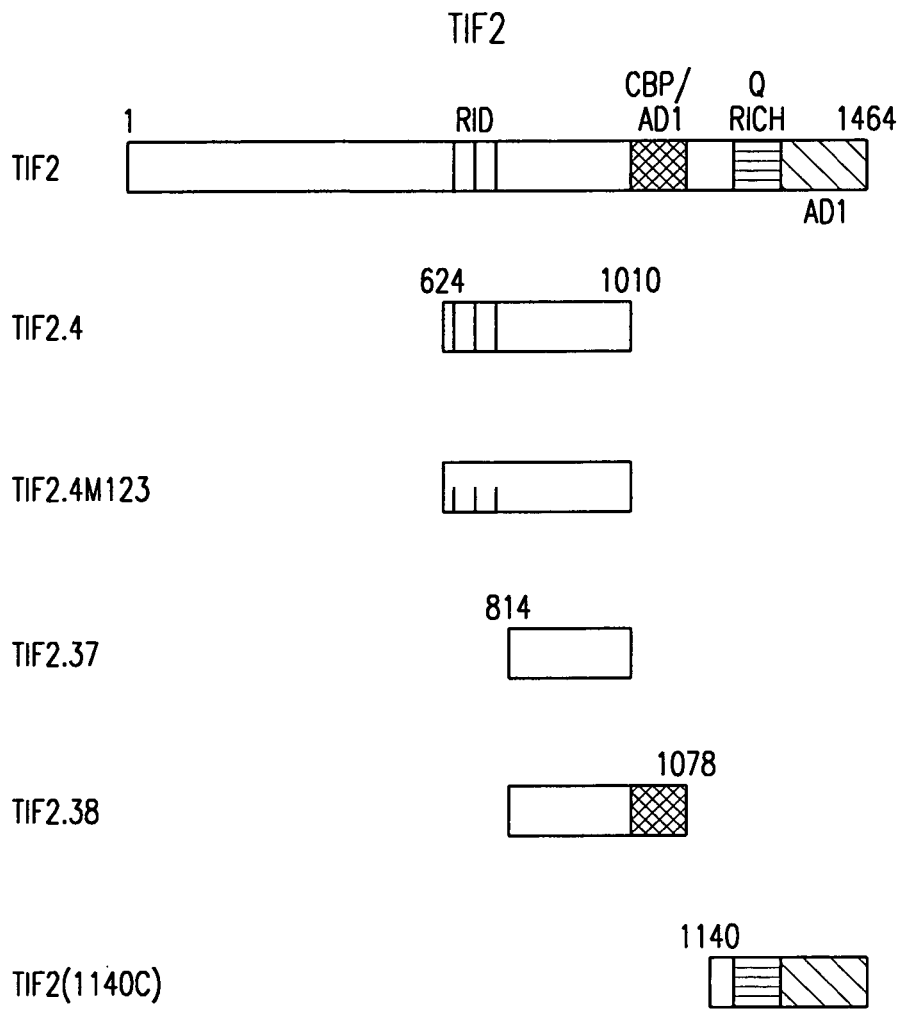
FIG. 1A provides a schematic diagram of the various constructs of the coactivator TIF2 employed in several of the experiments described herein. The amino acid positions of the various domains for TIF2 are given above the schematic diagram of each polypeptide. See Voegel et al., 1998, EMBO J. 17, 507-519; Ma et al., 1999, Mol. Cell. Biol. 19, 6164-6173. The abbreviations for the domains listed above each diagram are as follows: RID, receptor interaction domain; AD1 and AD2, activation domain 1 and 2; CBP, CBP interaction domain; Q-rich, glutamine rich; and Neg, negative suppressor domain. See Onate et al., 1995, Science 270, 1354-1357.
Figure 1B:
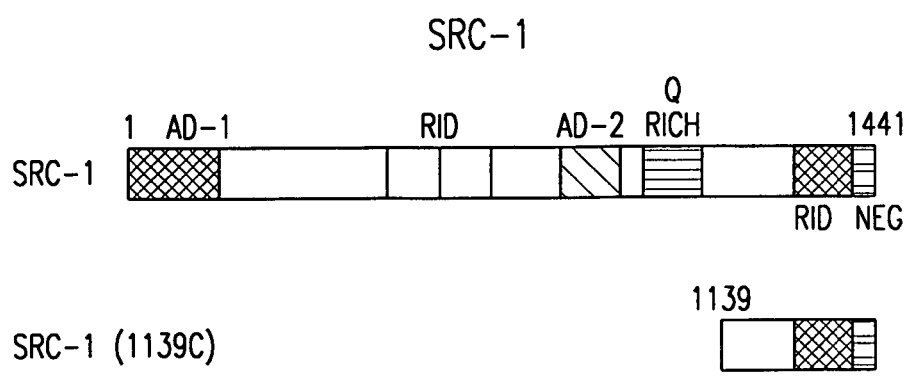
FIG. 1B provides a schematic diagram of the various constructs of the coactivator SRC-1 employed in several of the experiments described herein. The amino acid positions of the domains for the SRC-1 polypeptides are shown. See Onate et al., 1998 J. Biol. Chem. 273, 12101-12108; Kalkhoven et al., 1998, EMBO J. 17, 232-243. The abbreviations for the domains listed above each diagram are as follows: RID, receptor interaction domain; AD1 and AD2, activation domain 1 and 2; CBP, CBP interaction domain; Q-rich, glutamine rich; and Neg, negative suppressor domain. See Onate et al., 1995, Science 270, 1354-1357.
Figure 1C:
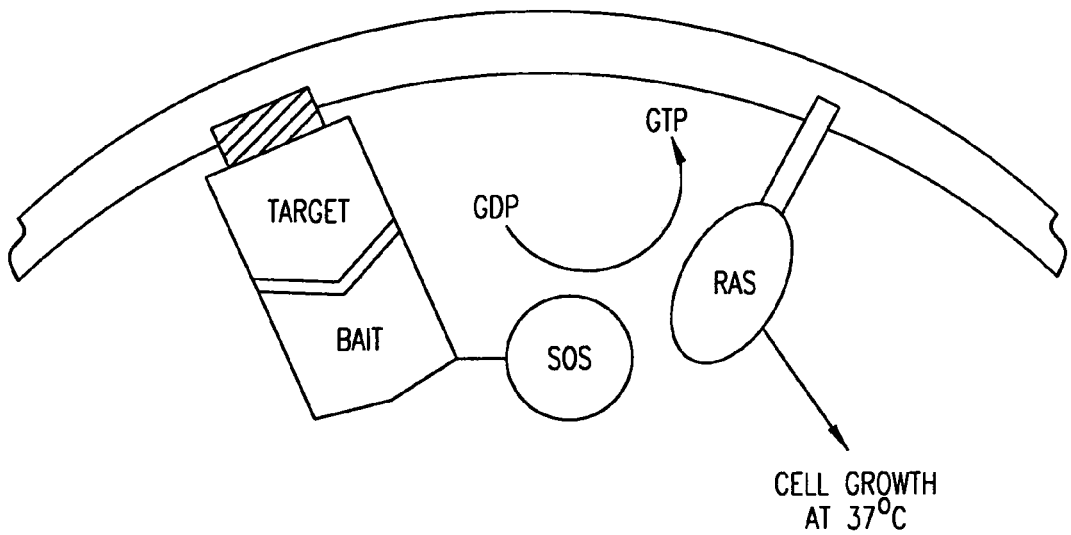
FIG. 1C provides a schematic diagram of a Sos-Ras two-hybrid screen to isolate STAMP. The bait, present as a chimera with Sos, will activate the membrane-bound Ras protein in a GDP-dependent coupled reaction to cause colony growth only if it binds to a target protein that is fused to a membrane localization sequence.
Figure 4B:
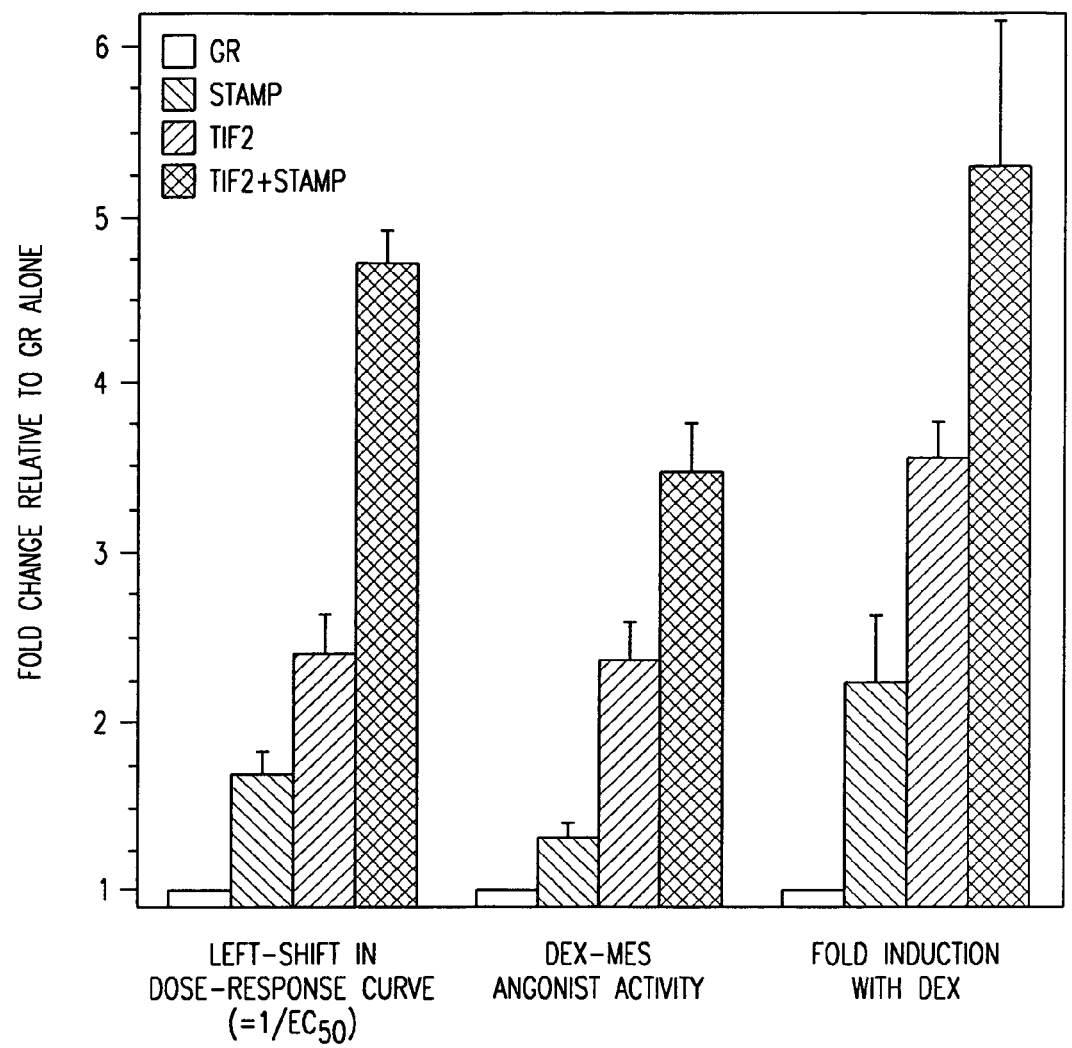

FIGS. 4A1, 4A2 and 4B illustrate STAMP modulation of GR-mediated gene induction. FIG. 4A1-2 show that exogenous STAMP can modulate the dose-response curve and partial agonist activity for GR-regulated induction. Triplicate samples of CV-1 cells were transiently transfected with GR (6 ng)±TIF2 (20 ng)±STAMP (160 ng) plasmids, GREtkLUC reporter, and Renilla control plasmid. Gene expression was induced with EtOH± the indicated concentrations of dexamethasone (Dex) or 1 µM dexamethasone-21-mesylate (Dex-Mes). Luciferase activities, normalized to the internal Renilla control values, were then expressed as a percent of the maximal response with 1 µM Dex as described in Example 1. Similar results were obtained in three additional experiments. FIG. 4B illustrates the fold changes in GR induction parameters by STAMP and TIF2. The absolute value of the $EC_{50}$, the partial agonist activity with 1 µM Dex-Mes, and the fold induction with 1 µM Dex, were determined in four independent experiments as described for FIG. 4A. The fold-increase in each parameter was determined as follows: for $EC_{50}$s, fold increase=$[EC_{50}]_{GR}/[EC_{50}]_{GR+factor}$; for partial agonist activity and fold Dex induction, fold increase=activity$_{GR+factor}$/activity$_{GR}$). The average fold increases were then plotted±S.E.M (n=4).

Figure 5A:
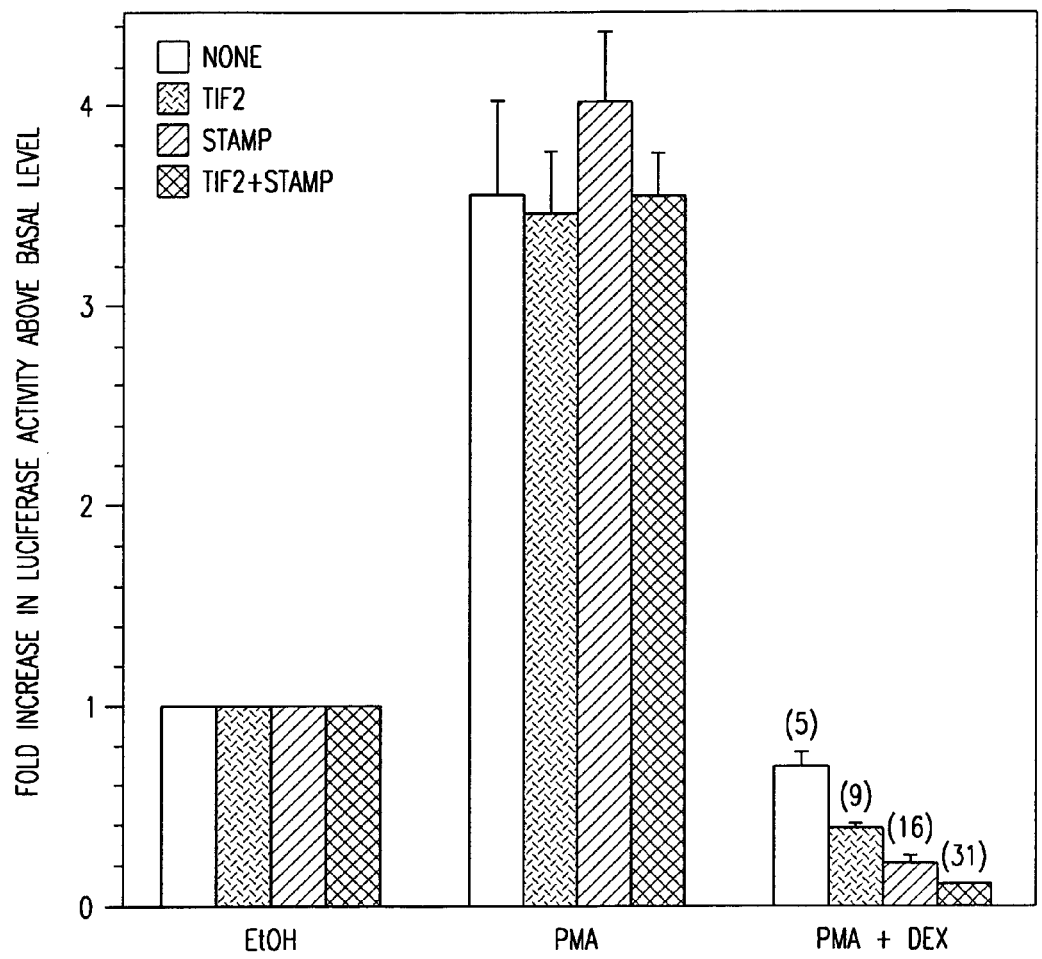

FIG. 5A-F illustrate STAMP modulation of GR-mediated repression. FIG. 5A shows that ectopic STAMP augments GR-repression of an AP-1 induced gene. U2OS.rGR cells were transiently transfected with ±TIF2 (20 ng)±STAMP (100 ng) plasmids, AP-1/Luc reporter (20 ng), and Renilla control (10 ng) plasmid. The cells were induced with ethanol (EtOH) or 25 µM PMA±0.1 µM Dex. The luciferase activities, normalized to the internal Renilla control values, were then expressed as the fold increase over the basal level response with EtOH as described in Example 1. The average values±S.E.M. of four experiments are plotted. The numbers in parentheses above the bars labeled "PMA+Dex" represent the average fold repression caused by Dex± the various factors.

Figure 5B:
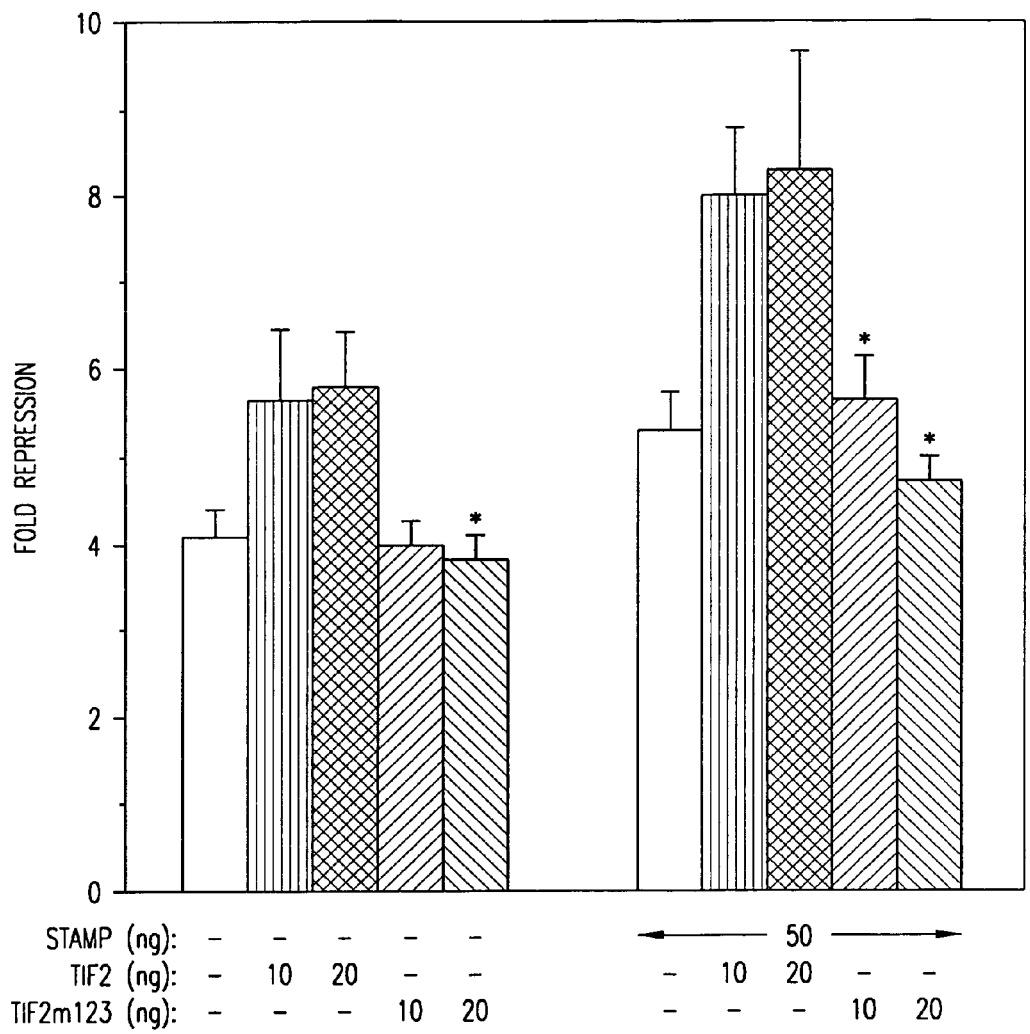

FIG. 5B illustrates that functional TIF2 is needed for optimal STAMP activity. U2OS.rGR cells were transiently transfected and processed as described for FIG. 5A but less STAMP (50 ng) was used and two concentrations of TIF2 or TIF2m123 (10 and 20 ng) were employed. The average values±S.E.M. of 4-5 experiments are plotted. An asterisk indicates a significant difference (P≦0.031) between samples containing equal amounts of TIF2 and TIF2m123.

FIG. 5C illustrates that STAMP and GR are co-localized on the promoter of an endogenous regulated gene as detected by chromatin immunoprecipitation (ChIP) assays. U2OS.rGR cells were treated with 1 µM Dex and then processed after 0 to 80 min as described in Example 1. The binding of GR and STAMP to the coll3 promoter was determined by the ability of PCR to amplify coll3 promoter sequences in the DNA that had been co-immunoprecipitated by anti-GR and anti-HA (to immobilize HA/STAMP) antibodies, respectively (upper panel). As a control for specificity, the same treatment does not co-precipitate hsp70DNA sequences (lower panel). Similar results were obtained in two additional experiments.

FIGS. 5D1 and 5D2 illustrate selective repression of STAMP protein levels by STAMP siRNAs. Cos-7 cells were transiently transfected with HA/STAMP (2 µg) and GR (1 µg) plasmids and ±5 µg of one out of the four STAMP siRNAs, or a β-actin siRNA, per 60 mm dish. Cytoplasmic extracts were separated on SDS-PAGE gels and Western blotted with anti-HA (for STAMP) or anti-GR antibodies to detect STAMP (downward pointing open arrow) and GR (thin sideway pointing arrows). The specificity of the effects of the siRNAs is exemplified by the lack of effect on the other, non-specifically detected proteins (*). Major decreases in protein level were seen only for STAMP (open downward pointing arrow) in the presence of STAMP siRNA and not in the presence of β-actin siRNA (FIGS. 5D1 and 5D2).

Figure 5E:
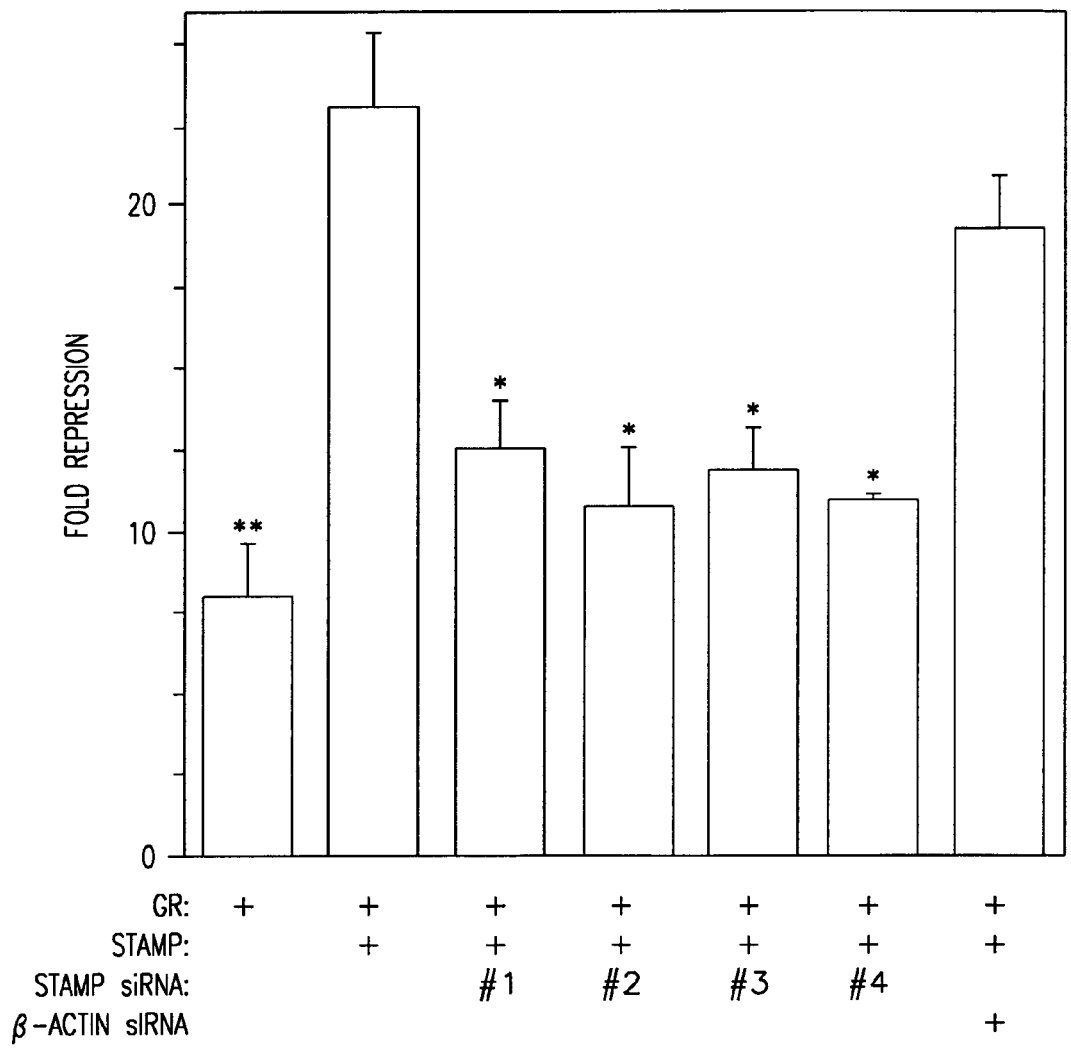
Figure 5F:
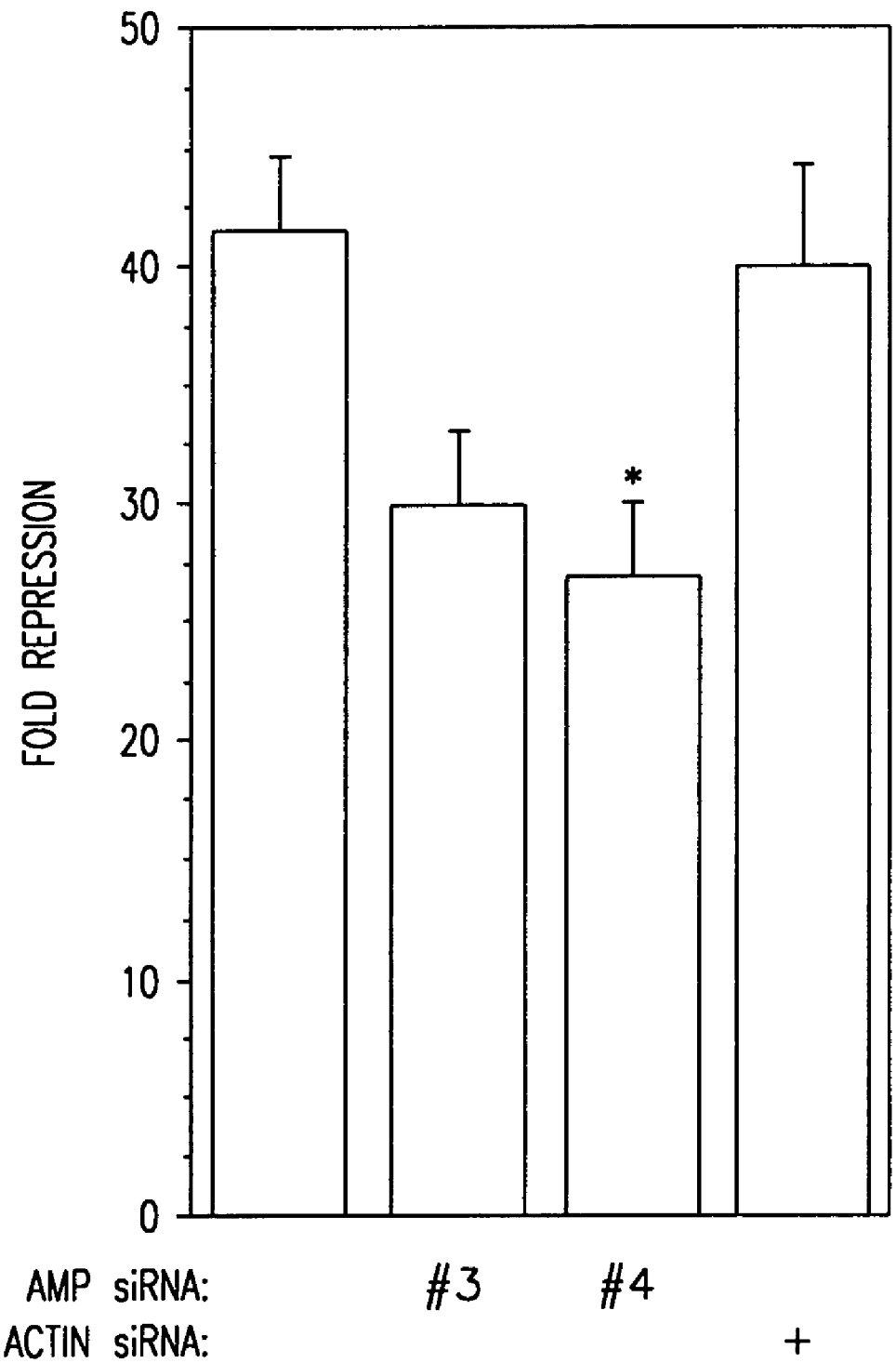

FIGS. 5E and 5F show that STAMP siRNAs significantly inhibit increased repression by exogenous (E) and endogenous (F) STAMP in U2OS.rGR cells relative to β-actin siRNA. U2OS.rGR cells were transiently transfected with (FIG. 5E) or without (FIG. 5F) HA/STAMP plasmid (100 ng) and ±500 ng of STAMP siRNA, or β-actin siRNA, plus AP-1/Luc reporter (20 ng) and the Renilla control (10 ng) plasmid. The cells were processed and the fold repression with each treatment was calculated as described in FIG. 5A. The average values were then plotted (±S.E.M., n=4-5 (FIG. 5D) and 7 (FIG. 5E); *, P≦0.032; **, P=0.0022).

Figure 6A:
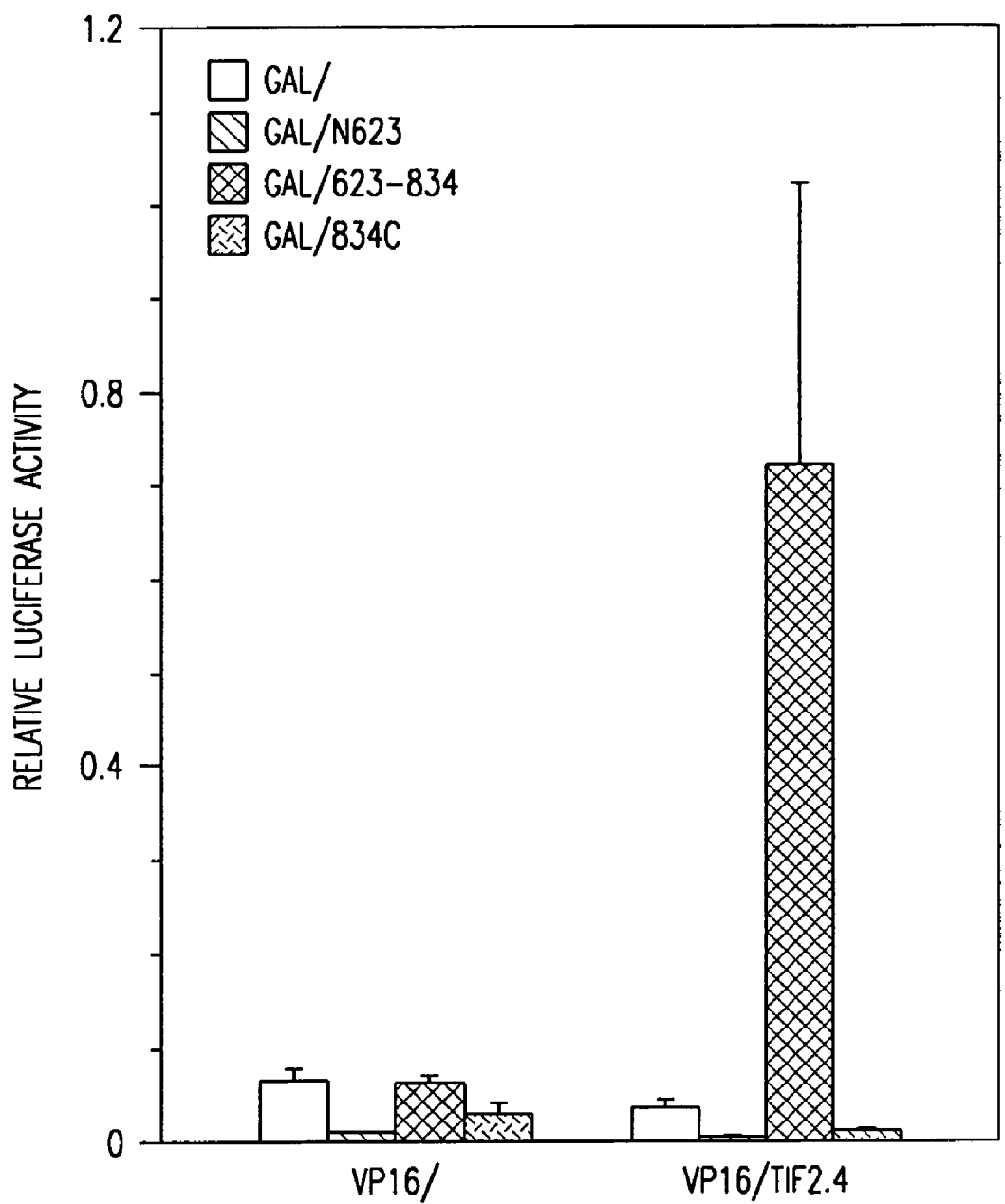
Figure 6B:
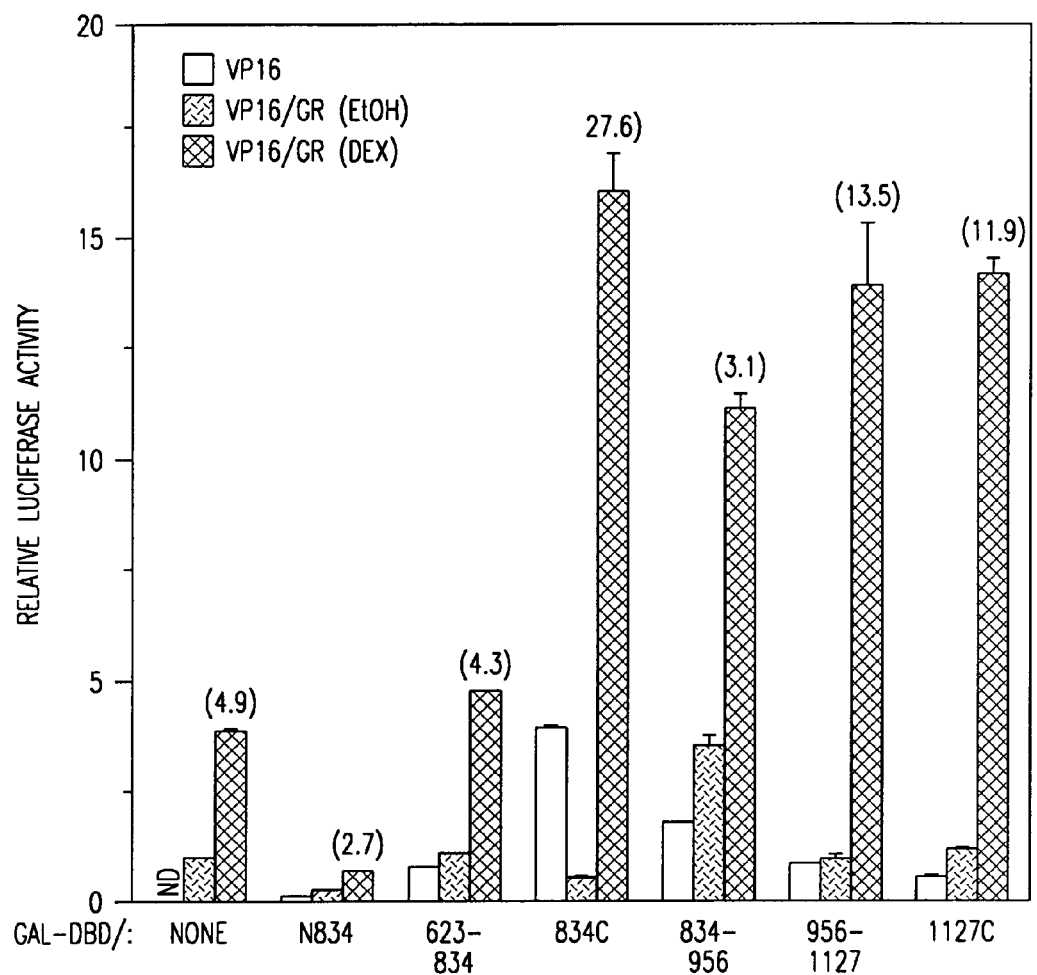

FIGS. 6A and 6B illustrate the domains of STAMP that interact with TIF2.4 (FIG. 6A) and GR (FIG. 6B) in the mammalian two-hybrid assay. Triplicate samples of CV-1 cells were transiently transfected with VP16 or VP16/TIF2.4 in FIG. 6A experiments. In FIG. 6B experiments, triplicate samples of CV-1 cells were transiently transfected with VP16 or VP16/GR±1 µM Dex. These CV-1 cells were also transfected with GAL fused to the indicated segments of STAMP along with the FRLuc reporter and Renilla control plasmids. After determining the relative luciferase activities as described in FIG. 2B and 2C, the average values±S.E.M. from 2-5 experiments were plotted. The average fold increase for VP16/TIF2.4 with GAL/STAMP(623-834) in FIG. 6A was 11.0±3.0 (SEM, n=5) above the VP16 control. The values in parentheses above the data bars in FIG. 6B indicate the fold increased interaction ±1 µM Dex.

FIG. 6C1-3 illustrate the association of STAMP with assorted steroid/nuclear receptors, including glucocorticoid receptors (GRs), progesterone receptors (PRs), androgen receptors (ARs), estrogen receptors (ER α or β), PPARγ2 receptors, thyroid receptor beta (TR), and retinoid (α) receptors (RAR α or RXR α). Triplicate samples of CV-1 cells were transfected (as described for FIG. 6B) with GAL, or GAL fused to TIF2.4 or STAMP834C, plus VP16 fused to the indicated full length receptors and incubated with the appropriate steroid (1 µM Dex, 20 nM R5020, 1 nM R1881, 0.1 µM triiodothyronine, or 1 µM estradiol, roziglitazone, or 9-cis-retinoic acid). The average relative luciferase activities of 2-3 experiments±S.E.M. were then plotted. FIG. 6C1 illustrates the effects of STAMP association upon GR, PR and AR induced expression. FIG. 6C2 illustrates the effects of STAMP association upon ERα, ERβ and PPARγ2 induced expression. FIG. 6C3 illustrates the effects of STAMP association upon TR, RARα and RXRα induced expression.

FIG. 6D1-2 illustrate the effects of STAMP and TIF2 on androgen receptor (AR, FIG. 6D1) and thyroid receptor β (TRβ, FIG. 6D2) expression. CV-1 cells were transiently transfected with AR (2 ng) or TRβ (10 ng)±TIF2 (20 ng)±STAMP (160 ng) plasmids, GREtkLUC reporter, and Renilla control plasmid, and induced with ethanol±various concentrations of R1881 or triiodothyronine. Luciferase activities, normalized to the internal Renilla control values, and the fold changes in $EC_{50}$ and fold induction were determined and plotted as in FIG. 4B. The average fold increases were then plotted±S.E.M (n=3-4).

Figure 7A:
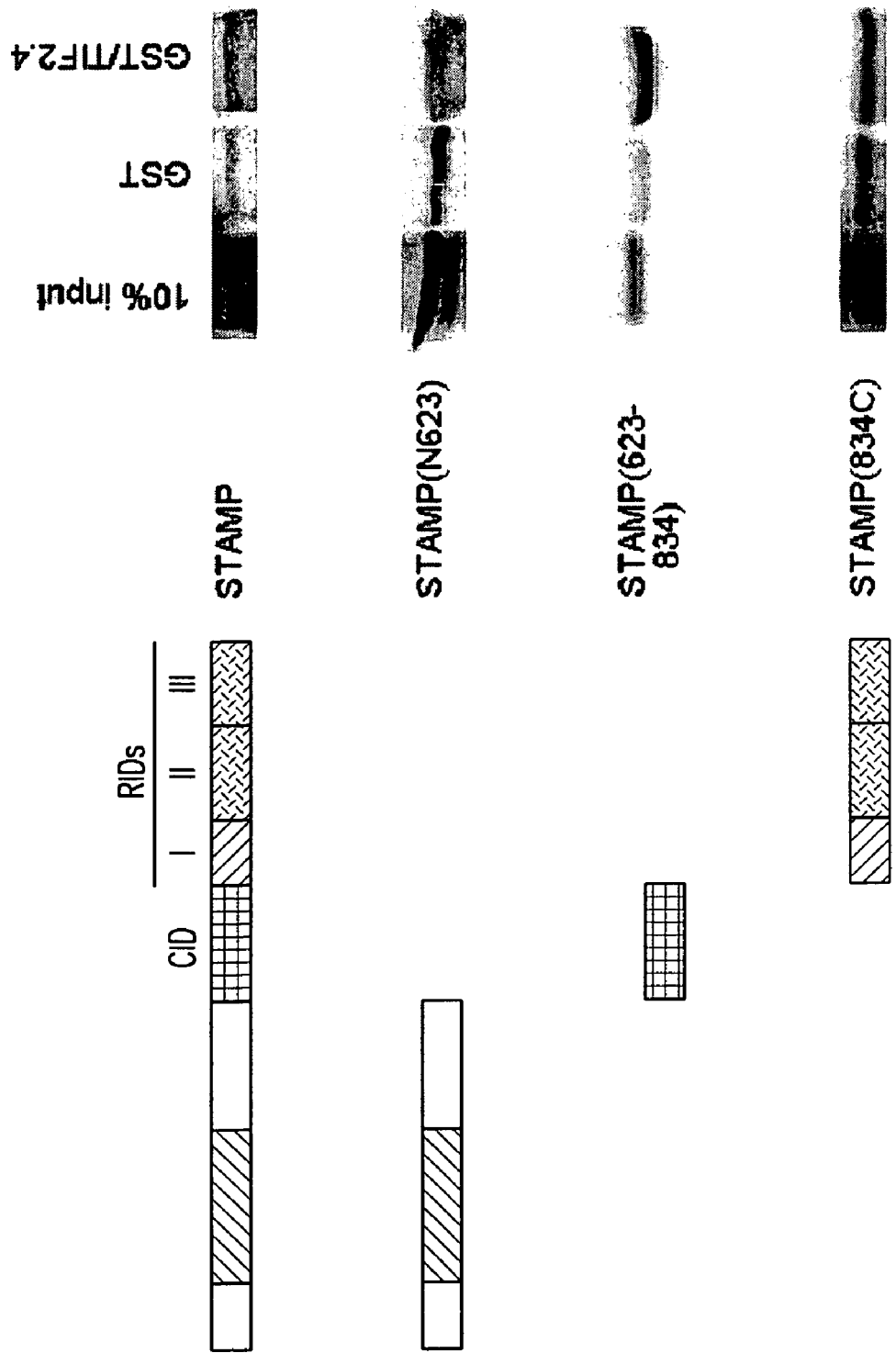
Figure 7B:
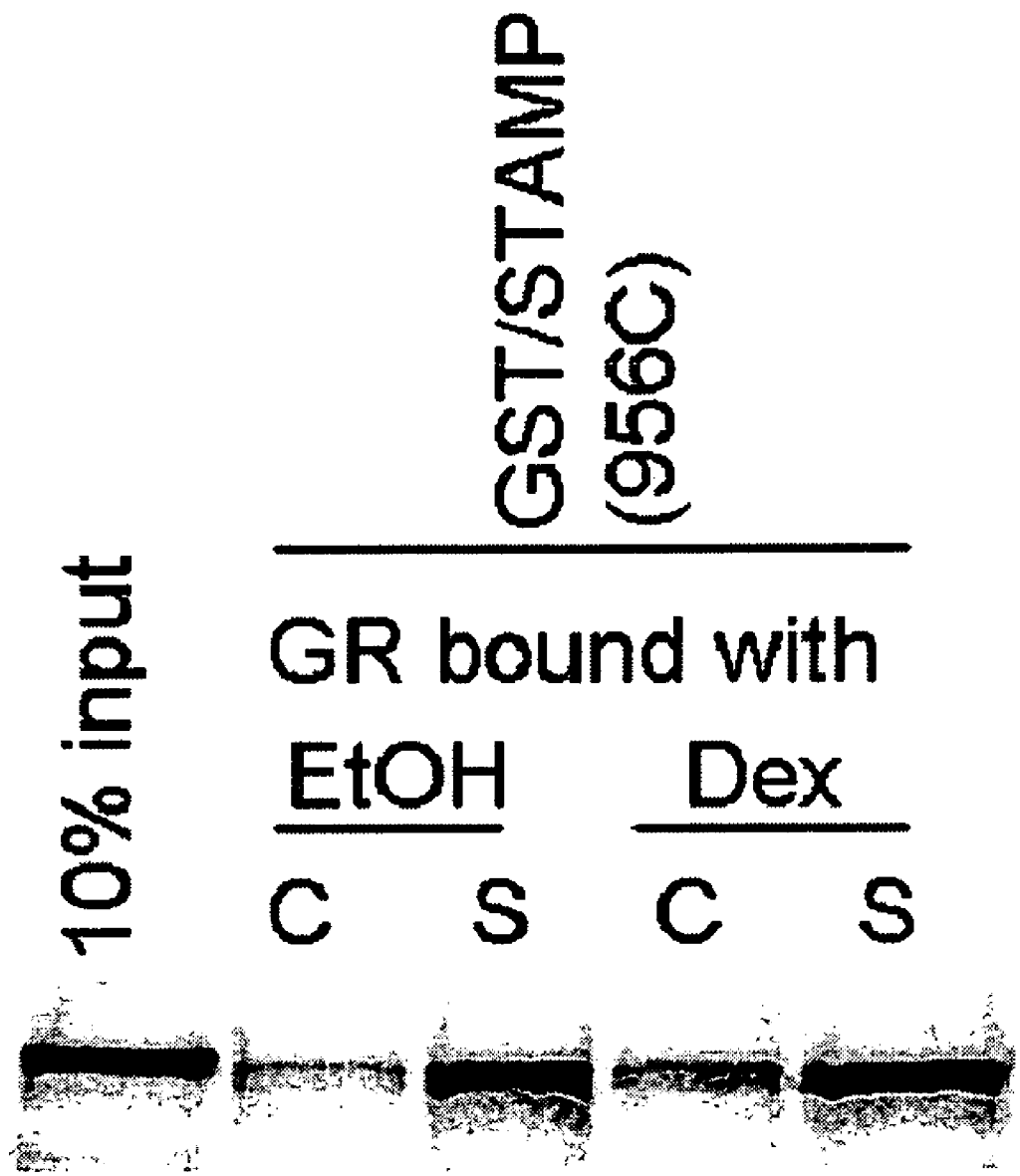

FIGS. 7A and 7B illustrate the domains of STAMP that bind to TIF2.4 (FIG. 7A) and GR (FIG. 7B) in cell-free pulldown assays. Bacterially expressed GST-chimeras (GST/TIF2.4 in FIG. 7A and GST/STAMP segments in FIG. 7B) were immobilized on glutathione-Sepharose beads. The [$^{35}$S] methionine labeled STAMP fragments (FIG. 7A) or wild type GR (FIG. 7B) that were retained on the matrix by binding to the GST chimeras were separated on SDS PAGE gels and visualized by autoradiography. Specific binding was seen as when the GST/TIF2.4 or GST/STAMP bands were darker than the GST control bands. "10% input" shows 10% of the [$^{35}$S]methionine label that was initially loaded onto the matrix beads. Similar results were obtained in a second experiment.

FIG. 7C1-3 illustrate whole cell co-immunoprecipitation of STAMP, GR, and TIF2/GRIP1. Cos-7 cells that had been co-transfected with Flag/STAMP (or Flag itself), HA/GRIP1, and GR plasmids (10 µg of each/150 mm dish) for 48 hr were treated for 2 hr with EtOH±1 µM Dex before being lysed as described in Example 1. Lysate was either analyzed on SDS-PAGE gels or treated with anti-Flag antibody to immunoprecipitate Flag/STAMP. The pellets were separated on SDS-PAGE gels and Western blotted with anti-Flag (FIG. 7C1), anti-HA (FIG. 7C2), or anti-GR antibodies (FIG. 7C3). In each panel, lane 1=5.7% of input lysate, lane 2=IP pellet of Flag/STAMP, HA/GRIP1, and GR+EtOH, lane 3=IP pellet of Flag/STAMP, HA/GRIP1, and GR+Dex, and lane 4=control IP pellet of Flag, HA/GRIP1, and GR+EtOH. Similar results were obtained in a second experiment.

Figure 8A:
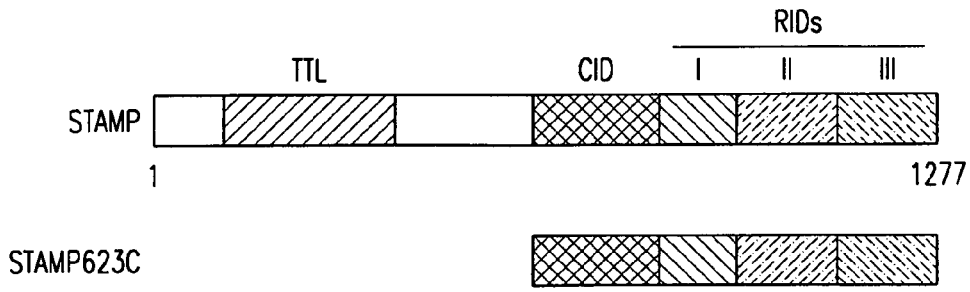
Figure 8B:
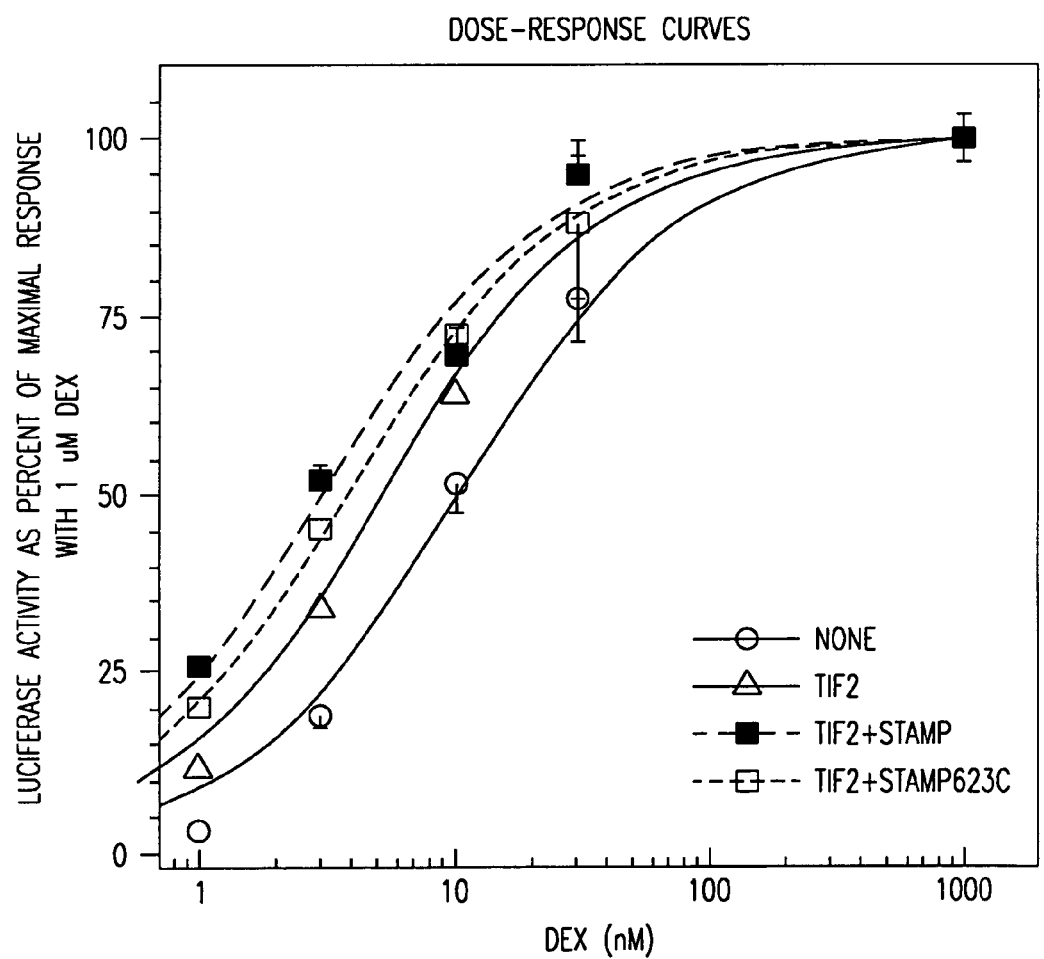
Figure 8C:
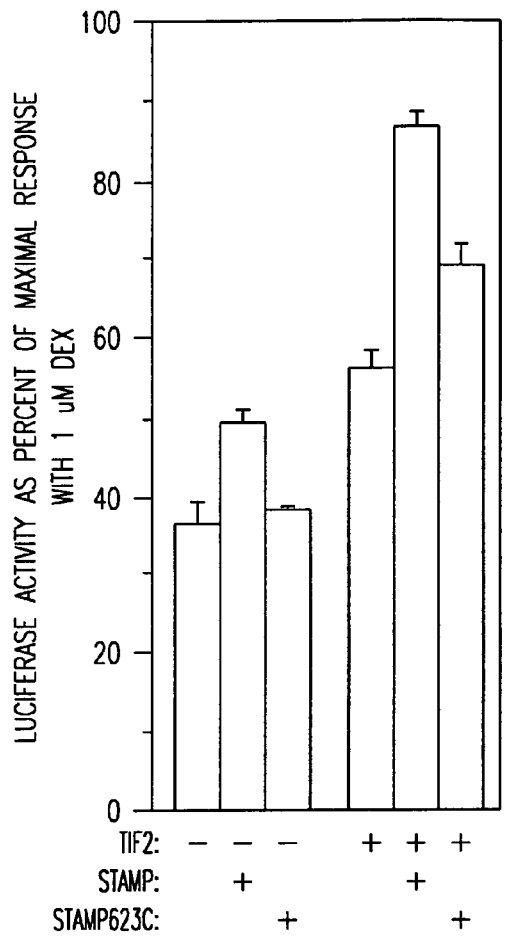
Figure 8D:
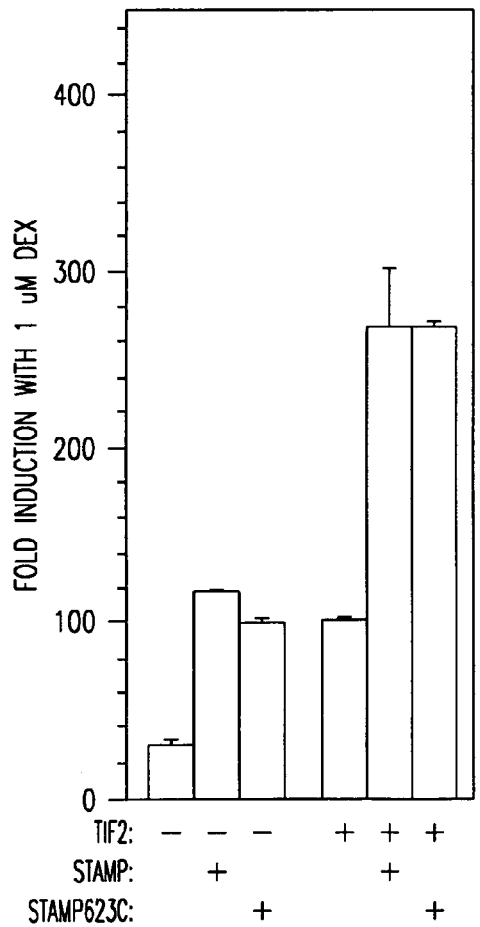

FIG. 8A-D illustrate the modulatory activity of STAMP versus STAMP623C on glucocorticoid receptor (GR) mediated gene induction. FIG. 8A schematically illustrates the structural domains of STAMP compared to the truncated STAMP polypeptide, STAMP623C. FIG. 8B graphically illustrates the degree of gene induction at various dexamethasone concentration by various factors, including TIF2 (open triangles), TIF2+STAMP (closed squares) and TIF2+STAMP623C (open squares), compared to a control where no such factor was present (open circles). FIG. 8C-D illustrate the percent of maximal response and fold induction, respectively, of GR-induced gene expression by various factors, as shown. CV-1 cells were transiently transfected with GR (6 ng)±TIF2 (20 ng)±STAMP (160 ng) plasmids, GREtkLUC reporter, and Renilla control plasmid, and induced with ethanol± the indicated concentrations of Dex. Luciferase activities, normalized to the internal Renilla control values, were then expressed as percent of the maximal response with 1 µM Dex as described in Example 1 and plotted as in FIG. 4. Similar results were obtained in two additional experiments.

DETAILED DESCRIPTION OF THE INVENTION

The invention provides a new factor that can modulate glucocorticoids-responsive gene expression. This new factor is termed STAMP ((SRC-1 and TIF2 Associated Modulatory Protein). STAMP polypeptides can bind to glucocorticoid receptors as well as to a variety of glucocorticoid receptor coactivators, for example, the TIF2 and SRC-1 glucocorticoid receptor co-activators. One target of STAMP (i.e., TIF2) can modulate the dose-response curve and partial agonist activity of several steroid receptors and can affect the properties of steroid and nuclear receptors. Examples of receptors that can be influenced by STAMP-TIF2 include androgen receptors, estrogen receptors, mineralocorticoid receptors, progesterone receptors, thyroid receptors, retinoid receptors (RAR and RXR), and peroxisome proliferator-activated receptors (PPARs). Hence, STAMP can be included in compositions and methods for modulating such receptors. STAMP polypeptides, anti-STAMP antibodies, and STAMP nucleic acids (including, for example, antisense nucleic acids, ribozymes and siRNAs) can be used to modulate the activity of such receptors and gene expression that is controlled by such receptors. The compositions and methods of the invention can also be used to treat or prevent a variety of conditions and diseases.

Stamp

The full-length STAMP polypeptide is about 1277 amino acid long with a predicted molecular weight of about 143 kDa. Note that an alternate start codon would give rise to a 1281 amino acid STAMP polypeptide. However, the 1277 amino acid STAMP polypeptide is predicted to be more abundant. The full-length amino acid sequence for the 1277 human STAMP polypeptide is provided below (SEQ ID NO:1).

```
  1 MARDLEETAS SSEDEEVISQ EDHPCIMWTG GCRRIPVLVF

41 HADAILTKDN NIRVIGERYH LSYKIVRTDS RLVRSILTAH

81 GFHEVHPSST DYNLMWTGSH LKPFLLRTLS EAQKVNHFPR

121 SYELTRKDRL YKNIIRMQHT HGEKVFHILP QTFLLPAEYA

161 EFCNSYSKDR GPWIVKPVAS SRGRGVYLIN NPNQISLEEN

201 ILVSRYINNP LLIDDFKFDV RLYVLVTSYD PLVIYLYEEG

241 LARFATVRYD QGAKNIRNQF MHLTNYSVNK KSGDYVSCDD

281 PEVEDYGNKW SMSAMLRYLK QEGRDTTALM AHVEDLIIKT

321 ITSAELAIAT ACKTFVPHRS SCFELYGFDV LIDSTLKPWL

361 LEVNLSPSLA CDAPLDLKIK ASMISDMFTV VGFVCQDPAQ

401 RASTRPIYPT FESSRRNPFQ KPQRCRPLSA SDAEMKNLVG

441 SAREKGPGKL GGSVLGLSME EIKVLRRVKE ENDRRGGFIR

481 IFPTSETWEI YGSYLEHKTS MNYMLATRLF QDRMTADGAP

521 ELKIESLNSK AKLHAALYER KLLSLEVRKR RRRSSRLRAM

561 RPKYPVITQP AEMNVKTETE SEEEEEVALD NEDEEQEASQ

601 EESAGFLREN QAKYTPSLTA LVENTPKENS MKVREWNNKG

641 GHCCKLETQE LEPKFNLMQI LQDNGNLSKM QARIAFSAYL

681 QHVQIRLMKD SGGQTFSASW AAKEDEQMEL VVRFLKRASN

721 NLQHSLRMVL PSRRLALLER RRILAHQLGD FIIVYNKETE

761 QMAEKKSKKK VEEEEEDGVN MENFQEFIRQ ASEAELEEVL

801 TFYTQKNKSA SVFLGTHSKI SKNNNNYSDS GAKGDHPETI

841 MEEVKIKPPK QQQTTEIHSD KLSRFTTSAE KEAKLVYSNS

881 SSGPTATLQK IPNTHLSSVT TSDLSPGPCH HSSLSQIPSA

921 IPSMPHQPTI LLNTVSASAS PCLHPGAQNI PSPTGLPRCR
```

-continued

```
 961 SGSHTIGPES SFQSAAHIYS QKLSRPSSAK AGSCYLNKHH

1001 SGIAKTQKEG EDASLYSKRY NQSMVTAELQ RLAEKQAARQ

1041 YSPSSHINLL TQQVTNLNLA TGIINRSSAS APPTLRPIIS

1081 PSGPTWSTQS DPQAPENHSS SPGSRSLQTG GFAWEGEVEN

1121 NVYSQATGVV PQHKYHPTAG SYQLQFALQQ LEQQKLQSRQ

1161 LLDQSRARHQ AIFGSQTLPN SNLWTMNNGA GCRISSATAS

1201 GQKPTTLPQK VVPPPSSCAS LVPKPPPNHE QVLRRATSQK

1241 ASKGSSAEGQ LNGLQSSLNP AASVPITSST DPAHTKI
```

This human STAMP polypeptide is encoded within a 4.6 kb cDNA (newly deposited as Genbank Accession No. AY237126). As indicated above, two start codons are found in naturally occurring human STAMP nucleic acids. The first codon starts at about nucleotide 227 of the human STAMP cDNA and has the sequence ATGCCAATCGTG (SEQ ID NO:66), which encodes Met-Pro-Ile-Val (SEQ ID NO:67), while the second start codon starts immediately thereafter at ATGGCCCGGGAC (SEQ ID NO:68), which encodes Met-Ala-Arg-Asp (SEQ ID NO:69).

The sequence for this STAMP cDNA is as follows (SEQ ID NO:2).

```
   1 GGCACGAGGG GGAAGCAGCC GTCGGCGGCT GCCCTGAGCC

41 TTCCTGGGGA AGGAGGAGGG AGGTAGGCGC AGAGCGCGGT

81 CCACGCCTGC TCGCCCCGAA CCATGGGAAG ATGAGACAGG

121 AATCTGTGCC ATCCAAATTG CTTGATCCAG TGAATCTGCT

161 AGGAAAGGTC TCTGAGGCCC CCGTCTGCTG ACTGCATGAC

201 AAACCCTAAA GGAAATGCCA ATCGTGATGG CCCGGGACCT

241 GGAGGAAACA GCATCATCCT CAGAGGATGA GGAGGTCATA

281 AGTCAAGAGG ATCATCCATG CATCATGTGG ACTGGAGGCT

321 GCAGGAGAAT TCCAGTTTTG GTATTCCATG CCGACGCTAT

361 TCTTACAAAG GACAACAATA TTAGAGTAAT TGGAGAACGT

401 TATCATTTGT CTTATAAGAT TGTACGAACG GACAGTCGCC

441 TAGTACGCAG CATTCTGACA GCCCATGGAT TTCATGAAGT

481 TCACCCAAGC AGCACTGACT ATAACCTAAT GTGGACAGGA

521 TCCCACCTGA AGCCCTTCTT ACTGCGCACC CTCTCTGAAG

561 CACAAAAAGT TAATCACTTT CCCAGGTCTT ATGAACTTAC

601 CCGGAAGGAC CGACTGTACA AAAACATTAT TCGAATGCAG

641 CATACACATG GATTCAAGGT TTTTCACATC CTCCCCCAGA

681 CCTTCCTCCT GCCAGCTGAG TACGCGGAAT TTTGTAATTC

721 ATATTCGAAG GACCGGGGAC CTTGGATAGT AAAACCAGTG

761 GCATCTTCAA GGGGGCGGGG CGTCTACCTG ATCAACAATC

801 CAAACCAGAT CTCCCTGGAA GAGAACATTT TGGTCTCCCG

841 TTACATTAAC AACCCCCTGC TCATAGATGA TTTCAAGTTT

881 GACGTGCGCC TCTATGTGCT CGTGACTTCC TATGATCCTC
```

-continued

```
 921 TTGTCATCTA TCTCTATGAA GAAGGATTGG CTAGGTTTGC

961 AACTGTGCGA TATGATCAAG GAGCCAAGAA CATTCGGAAC

1001 CAGTTCATGC ATCTGACAAA CTACAGTGTC AACAAGAAAA

1041 GTGGAGATTA CGTCAGTTGT GACGATCCAA AGTGGAGGA

1081 TTATGGAAAC AAATGGAGCA TGAGTGCTAT GCTTAGGTAC

1121 CTGAAACAAG AAGGCAGAGA TACAACCGCA TTGATGGCCC

1161 ATGTAGAAGA CCTGATCATT AAGACTATAA TCTCTGCTGA

1201 ACTAGCTATT GCTACTGCCT GTAAAACCTT TGTTCCTCAT

1241 CGCAGCAGTT GTTTTGAACT CTATGGCTTT GACGTGCTCA

1281 TAGATTCTAC TCTGAAGCCA TGGTTGTTGG AAGTGAATCT

1321 CTCTCCTTCT TTGGCCTGTG ATGCGCCTCT GGACCTAAAG

1361 ATTAAAGCCA GTATGATTTC AGATATGTTC ACTGTTGTAG

1401 GATTTGTGTG CCAAGATCCT GCCCAGCGGG CATCAACTCG

1441 GCCAATTTAT CCCACCTTTG AGTCTTCCAG GCGAAACCCT

1481 TTCCAGAAAC CTCAGCGTTG CCGTCCACTC TCTGCCAGTG

1521 ATGCGGAAAT GAAAACCTC GTGGGCTCAG CCCGGGAGAA

1561 AGGGCCAGGG AAGTTGGGTG GTTCTGTGCT TGGTCTGTCA

1601 ATGGAGGAGA TCAAAGTTTT ACGAAGGGTG AAGGAGGAGA

1641 ATGATCGGCG AGGTGGATTT ATTCGCATAT TTCCTACATC

1681 TGAGACATGG GAAATATATG GGTCCTACCT CGAGCATAAG

1721 ACCTCAATGA ACTATATGCT GGCAACACGC CTCTTCCAGG

1761 ACAGAATGAC TGCTGATGGA GCGCCAGAAT TGAAGATAGA

1801 GAGTCTGAAT TCAAAGGCCA AGCTGCATGC TGCACTTTAC

1841 GAGAGGAAGC TCCTGTCTCT GGAGGTGCGA AAACGTAGAC

1881 GACGGAGTAG CAGATTGAGG GCAATGAGGC CAAAATACCC

1921 AGTGATTACC CAACCAGCTG AAATGAATGT TAAAACTGAG

1961 ACAGAGAGTG AAGAGGAGGA AGAAGTCGCA TTAGATAATG

2001 AAGATGAAGA ACAGGAGGCT TCCCAGGAGG AGTCTGCAGG

2041 ATTTCTTAGA GAAAATCAAG CCAAATATAC ACCCTCATTG

2081 ACAGCTTTGG TAGAAAATAC ACCCAAAGAA AATTCCATGA

2121 AAGTTCGTGA ATGGAATAAT AAAGGTGGAC ACTGCTGCAA

2161 ACTTGAGACT CAGGAGCTAG AGCCTAAATT TAACCTGATG

2201 CAGATTCTTC AAGATAATGG CAATCTTAGC AAAATGCAGG

2241 CCCGAATAGC ATTCTCTGCC TATCTCCAGC ATGTTCAAAT

2281 TCGCCTGATG AAAGACAGTG GCGGTCAGAC GTTCAGTGCC

2321 AGTTGGGCTG CCAAAGAGGA TGAACAGATG GAGCTGGTTG

2361 TTCGTTTCCT CAAGCGAGCA TCAAATAACC TCCAGCATTC

2401 ACTGAGGATG GTATTACCCA GTCGACGATT GGCACTTCTG

2441 GAACGCAGAA GAATCCTGGC CCACCAGCTG GGTGACTTTA

2481 TCATTGTATA CAACAAGGAA ACAGAACAAA TGGCTGAAAA
```

```
2521 GAAATCAAAG AAGAAAGTTG AGGAAGAAGA GGAAGATGGG
2561 GTGAATATGG AAAACTTTCA GGAGTTCATC AGACAAGCAA
2601 GTGAGGCTGA ACTGGAGGAG GTGTTGACTT TTTATACCCA
2641 AAAGAACAAG TCTGCTAGTG TCTTCCTGGG GACTCACTCT
2681 AAAATTTCTA AGAACAACAA CAATTATTCT GATAGTGGGG
2721 CAAAAGGTGA TCACCCTGAG ACTATAATGG AAGAAGTGAA
2761 AATAAAGCCA CCTAAACAGC AACAGACGAC AGAAATTCAT
2801 TCTGATAAAT TATCTCGATT TACCACTTCA GCAGAAAAAG
2841 AGGCAAAATT AGTTTATAGC AATTCCTCCT CTGGTCCTAC
2881 TGCTACTCTG CAGAAAATTC CCAACACCCA TTTGTCATCT
2921 GTTACAACCT CTGACCTCTC TCCAGGGCCT TGCCACCATT
2961 CTTCTTTATC TCAAATTCCT TCAGCTATCC CCAGCATGCC
3001 TCACCAGCCA ACAATTTTAC TGAACACAGT CTCTGCCAGT
3041 GCTTCTCCCT GCCTACATCC CGGGGCACAG AACATCCCAA
3081 GCCCTACTGG CCTGCCACGC TGTCGATCAG GAAGTCACAC
3121 CATTGGTCCC TTTTCTTCCT TCCAAAGTGC TGCACACATC
3161 TATAGCCAGA AACTGTCTCG TCCCTCTTCA GCAAAGGCAG
3201 GATCGTGCTA TCTAAACAAG CATCATTCAG GAATAGCCAA
3241 AACACAAAAA GAGGGAGAAG ATGCTTCTTT ATATAGCAAA
3281 CGGTACAACC AAAGTATGGT TACAGCTGAA CTTCAGCGGC
3321 TAGCTGAGAA GCAGGCAGCG AGACAGTATT CTCCATCCAG
3361 CCACATCAAC CTCCTCACCC AACAGGTAAC AAACCTGAAT
3401 TTGGCAACTG GCATCATAAA CAGAAGCAGT GCTTCAGCTC
3441 CCCCAACCCT CCGACCCATC ATCAGTCCTA GTGGCCCGAC
3481 ATGGTCTACA CAGTCAGACC CCCAAGCTCC CGAGAATCAC
3521 TCCAGCTCTC CTGGAAGCAG GAGCCTGCAG ACAGGGGGAT
3561 TTGCCTGGGA AGGAGAAGTA GAAAACAACG TGTACAGCCA
3601 GGCTACAGGG GTGGTCCCCC AGCACAAGTA TCACCCCACA
3641 GCAGGCAGCT ATCAGCTTCA ATTTGCCCTG CAGCAACTTG
3681 AACAACAAAA ACTTCAGTCC CGGCAGCTCC TGGACCAGAG
3721 TCGAGCCCGG CACCAGGCAA TCTTTGGCAG CCAGACACTA
3761 CCTAACTCCA ATTTATGGAC AATGAATAAT GGTGCAGGTT
3801 GTAGAATTTC CAGTGCCACA GCTAGTGGCC AGAAGCCAAC
3841 CACTCTGCCA CAAAAAGTGG TACCACCTCC AAGTTCTTGC
3881 GCCTCCCTGG TTCCCAAACC CCCACCCAAC CACGAACAAG
3921 TGCTCAGAAG GCAACATCC CAGAAAGCTT CCAAAGGGTC
3961 CTCCGCGGAA GGGCAGCTGA ATGGACTCCA GAGCAGCCTT
4001 AACCCTGCAG CCTCTGTGCC CATCACCAGC TCTACAGATC
4041 CTGCTCACAC TAAAATATGA ACCACAAACA CACAGAGAAA
4081 CAACCTGTTC ACCACTCCTG GGTGCATGAT TGAGGGTGAA
4121 GCATCCACCA GCACTTCAAG GGGTCCATAG TATTTTTTTT
4161 TTTGCTGCCT CAAAGTCCCC AAAGCCTTCG AGCAGAAGTG
4201 GCAGTAGATG GTTGCCAATC AGCCAATGCA GACTTTCACT
4241 GGGACAACAA GAAAGCAGAT CTTCTGGGTT TTGATGGAAC
4281 TTGGCACTGG GGACATTCAG CTGATGCATT ATATACCCCG
4321 TCAGAGCACA CTTGTATCTT TTACCTTCCC TTTGCCCCAT
4361 GCCCCCAAAC TGCTTAGGTC TTCTCTGTCC CTTTACTGCT
4401 GCTGCACAGA GATGATATAA AAGAGGCTCT TTGGCTATTT
4441 GCATTTTGCT TCCTCTTCTT TTCCAGATTA CAGTATGAAG
4481 CTTTATTTTC TTTGTACAAG CTTAAAATTT CAACATCATC
4521 ATCCGCCAAA GTTGTTCCTC CCTTTTCGGA GGATCTAGGG
4561 GGAAAGAGGA GCATTCATCA CAAGTTTCCT AGAGAGAGGA
4601 GACAAATCGG TGTGCCATTG ACAACATGAG CCAGGGTAAA
4641 GGCACCCTTT GGAATTACTG ATTTCAAAGA TTAATAAAGT
4681 AATTCTATTT TT
```

The human STAMP gene is located on chromosome 14q24.3 and has 32 introns (GenBank Accession No. NM_015072).

According to the invention, STAMP and related STAMP polypeptides (like those STAMP-related polypeptides provided herein) can modulate transcription of glucocorticoid-responsive genes. As used herein, modulating transcription of glucocorticoid-responsive genes means that STAMP can inhibit or enhance transcription from genes that are glucocorticoid-responsive. In some embodiments, when modulation of transcription from glucocorticoid-responsive genes is by an agonist, modulating transcription of glucocorticoid-responsive genes means that the concentration at which the glucocorticoid agonist exhibits 50% of maximal activity is shifted, meaning that more or less glucocorticoid is needed to observe 50% activity. In other embodiments, when modulation of transcription from glucocorticoid-responsive genes is by an antisteroid, modulation of transcription from glucocorticoid-responsive genes means that the amount of partial agonist activity of an antisteroid changes, meaning that the ability of the antisteroid to repress the induction of that gene by agonist steroids is increased or decreased.

STAMP and STAMP-related polypeptides have a number of domains, including a coactivator interaction domain (CID), a receptor interaction domain (RID) and a tubulin-tyrosine ligase (TTL) domain. The coactivator interaction domain in SEQ ID NO:1 is found at about amino acid 623 to about amino acid 834. The receptor interaction domain is found in SEQ ID NO:1 at about amino acid 834 to about amino acid 1277. The tubulin-tyrosine ligase domain in SEQ ID NO:1 is found at about amino acid 113 to about amino acid 391. These domains can readily be identified in STAMP-related polypeptides by aligning the STAMP-related polypeptide sequences with SEQ ID NO:1 and identifying regions of sequence identity or homology.

STAMP nucleic acids were cloned using a Sos-Ras based yeast two-hybrid assay, generally as described by Aronheim, 1997, Nucleic Acids Res 25, 3373-3374. This assay was used to detect polypeptides that bind to a TIF2 fragment (TIF2.4).

The first STAMP clone isolated using this assay encoded only amino acids 623-834 of the STAMP polypeptide, and therefore had the following sequence (SEQ ID NO:3).

```
 623                       ENTPKENS MKVREWNNKG
 641 GHCCKLETQE LEPKFNLMQI LQDNGNLSKM QARIAFSAYL
 681 QHVQIRLMKD SGGQTFSASW AAKEDEQMEL VVRFLKRASN
 721 NLQHSLRMVL PSRRLALLER RRILAHQLGD FIIVYNKETE
 761 QMAEKKSKKK VEEEEEDGVN MENFQEFIRQ ASEAELEEVL
 801 TFYTQKNKSA SVFLGTHSKI SKNNNNYSDS GAKG
```

This STAMP fragment can bind to TIF2 and acts as a coactivator interaction domain (CID). This STAMP polypeptide fragment can also be incorporated into compositions for modulating glucocorticoid-responsive gene expression.

A region of STAMP that is C-terminal to the CID region interacts with GR in a steroid-responsive manner. This region of STAMP includes amino acids 834-1277 and has the following sequence (SEQ ID NO:4).

```
 834                                GDHPETI
 841 MEEVKIKPPK QQQTTEIHSD KLSRFTTSAE KEAKLVYSNS
 881 SSGPTATLQK IPNTHLSSVT TSDLSPGPCH HSSLSQIPSA
 921 IPSMPHQPTI LLNTVSASAS PCLHPGAQNI PSPTGLPRCR
 961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TGIINRSSAS APPTLRPIIS
1081 PSGPTWSTQS DPQAPENHSS SPGSRSLQTG GFAWEGEVEN
1121 NVYSQATGVV PQHKYHPTAG SYQLQFALQQ LEQQKLQSRQ
1161 LLDQSRARHQ AIFGSQTLPN SNLWTMNNGA GCRISSATAS
1201 GQKPTTLPQK VVPPPSSCAS LVPKPPPNHE QVLRRATSQK
1241 ASKGSSAEGQ LNGLQSSLNP AASVPITSST DPAHTKI
```

This C-terminal STAMP fragment can bind to glucocorticoid receptor and provides a receptor interaction domain (RID). This STAMP polypeptide fragment can be incorporated into compositions for modulating glucocorticoid-responsive gene expression.

Other STAMP peptidyl fragments also have utility. For example, the following STAMP polypeptide fragment, with amino acids 623 to 1277 has the CID and the RID regions of STAMP (SEQ ID NO:5), but not the tubulin-tyrosine ligase (TTL) domain

```
 601                       ENTPKENS MKVREWNNKG
 641 GHCCKLETQE LEPKFNLMQI LQDNGNLSKM QARIAFSAYL
 681 QHVQIRLMKD SGGQTFSASW AAKEDEQMEL VVRFLKRASN
 721 NLQHSLRMVL PSRRLALLER RRILAHQLGD FIIVYNKETE
 761 QMAEKKSKKK VEEEEEDGVN MENFQEFIRQ ASEAELEEVL
```

```
                  -continued
 801 TFYTQKNKSA SVFLGTHSKI SKNNNNYSDS GAKGDHPETI
 841 MEEVKIKPPK QQQTTEIHSD KLSRFTTSAE KEAKLVYSNS
 881 SSGPTATLQK IPNTHLSSVT TSDLSPGPCH HSSLSQIPSA
 921 IPSMPHQPTI LLNTVSASAS PCLHPGAQNI PSPTGLPRCR
 961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TGIINRSSAS APPTLRPIIS
1081 PSGPTWSTQS DPQAPENHSS SPGSRSLQTG GFAWEGEVEN
1121 NVYSQATGVV PQHKYHPTAG SYQLQEALQQ LEQQKLQSRQ
1161 LLDQSRARHQ AIFGSQTLPN SNLWTMNNGA GCRISSATAS
1201 GQKPTTLPQK VVPPPSSCAS LVPKPPPNHE QVLRRATSQK
1241 ASKGSSAEGQ LNGLQSSLNP AASVPITSST DPAHTKT
```

This STAMP polypeptide fragment (SEQ ID NO:5) can also be incorporated into compositions for modulating glucocorticoid-responsive gene expression.

The following STAMP polypeptide fragment, with amino acids 518 to 1277 has the CID and the RID regions of STAMP, as well as part of the region between the tubulin-tyrosine ligase (TTL) domain and the CID region(SEQ ID NO:6).

```
 518                                    GAP
 521 ELKIESLNSK AKLHAALYER KLLSLEVRKR RRRSSRLRAM
 561 RPKYPVITQP AEMNVKTETE SEEEEEVALD NEDEEQEASQ
 601 EESAGFLREN QAKYTPSLTA LVENTPKENS MKVREWNNKG
 641 GHCCKLETQE LEPKFNLMQI LQDNGNLSKM QARIAFSAYL
 681 QHVQIRLMKD SGGQTFSASW AAKEDEQMEL VVRFLKRASN
 721 NLQHSLRMVL PSRRLALLER RRILAHQLGD FIIVYNKETE
 761 QMAEKKSKKK VEEEEEDGVN MENFQEFIRQ ASEAELEEVL
 801 TFYTQKNKSA SVFLGTHSKI SKNNNNYSDS GAKGDHPETI
 841 MEEVKIKPPK QQQTTEIHSD KLSRFTTSAE KEAKLVYSNS
 881 SSGPTATLQK IPNTHLSSVT TSDLSPGPCH HSSLSQIPSA
 921 IPSMPHQPTI LLNTVSASAS PCLHPGAQNI PSPTGLPRCR
 961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TGIINRSSAS APPTLRPIIS
1081 PSGPTWSTQS DPQAPENHSS SPGSRSLQTG GFAWEGEVEN
1121 NVYSQATGVV PQHKYHPTAG SYQLQFALQQ LEQQKLQSRQ
1161 LLDQSRARHQ AIFGSQTLPN SNLWTMNNGA GCRISSATAS
1201 GQKPTTLPQK VVPPPSSCAS LVPKPPPNHE QVLRRATSQK
1241 ASKGSSAEGQ LNGLQSSLNP AASVPITSST DPAHTKT
```

This STAMP polypeptide fragment (SEQ ID NO:6) can also be incorporated into compositions for modulating glucocorticoid-responsive gene expression.

The following STAMP polypeptide fragment, with amino acids 435 to 1242 has the CID and most of the RID regions of STAMP (SEQ ID NO:7).

```
435                                          MKNLVG
441 SAREKGPGKL GGSVLGLSME EIKVLRRVKE ENDRRGGFIR
481 IFPTSETWEI YGSYLEHKTS MNYMLATRLF QDRMTADGAP
521 ELKIESLNSK AKLHAALYER KLLSLEVRKR RRRSSRLRAM
561 RPKYPVITQP AEMNVKTETE SEEEEEVALD NEDEEQEASQ
601 EESAGFLREN QAKYTPSLTA LVENTPKENS MKVREWNNKG
641 GHCCKLETQE LEPKFNLMQI LQDNGNLSKM QARIAFSAYL
681 QHVQIRLMKD SGGQTFSASW AAKEDEQMEL VVRFLKRASN
721 NLQHSLRMVL PSRRLALLER RRILAHQLGD FIIVYNKETE
761 QMAEKKSKKK VEEEEEDGVN MENFQEFIRQ ASEAELEEVL
801 TFYTQKNKSA SVFLGTHSKI SKNNNNYSDS GAKGDHPETI
841 MEEVKIKPPK QQQTTEIHSD KLSRFTTSAE KEAKLVYSNS
881 SSGPTATLQK IPNTHLSSVT TSDLSPGPCH HSSLSQIPSA
921 IPSMPHQPTI LLNTVSASAS PCLHPGAQNI PSPTGLPRCR
961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TGIINRSSAS APPTLRPIIS
1081 PSGPTWSTQS DPQAPENHSS SPGSRSLQTG GFAWEGEVEN
1121 NVYSQATGVV PQHKYHPTAG SYQLQEALQQ LEQQKLQSRQ
1161 LLDQSRARHQ AIFGSQTLPN SNLWTMNNGA GCRISSATAS
1201 GQKPTTLPQK VVPPPSSCAS LVPKPPPNHE QVLRRATSQK
1242 AS
```

This STAMP polypeptide fragment (SEQ ID NO:7) can also be incorporated into compositions for modulating glucocorticoid-responsive gene expression.

The following STAMP polypeptide fragment, with amino acids 378 to 1046, also has the CID region and somewhat less of the RID regions of STAMP (SEQ ID NO:8).

```
378                KIK ASMISDMFTV VCFVCQDPAQ
401 RASTRPIYPT FESSRRNPFQ KPQRCRPLSA SDAEMKNLVG
441 SAREKGPGKL GGSVLGLSME EIKVLRRVKE ENDRRGGFIR
481 IFPTSETWEI YGSYLEHKTS MNYMLATRLF QDRMTADGAP
521 ELKIESLNSK AKLHAALYER KLLSLEVRKR RRRSSRLRAM
561 RPKYPVITQP AEMNVKTETE SEEEEEVALD NEDEEQEASQ
601 EESAGFLREN QAKYTPSLTA LVENTPKENS MKVREWNNKG
641 GHCCKLETQE LEPKFNLMQI LQDNGNLSKM QARIAFSAYL
681 QHVQIRLMKD SGGQTFSASW AAKEDEQMEL VVRFLKRASN
721 NLQHSLRMVL PSRRLALLER RRILAHQLGD FIIVYNKETE
761 QMAEKKSKKK VEEEEEDGVN MENFQEFIRQ ASEAELEEVL
801 TFYTQKNKSA SVFLGTHSKI SKNNNNYSDS GAKGDHPETI
841 MEEVKIKPPK QQQTTEIHSD KLSRFTTSAE KEAKLVYSNS
881 SSGPTATLQK IPNTHLSSVT TSDLSPGPCH HSSLSQIPSA
921 IPSMPHQPTI LLNTVSASAS PCLHPGAQNI PSPTGLPRCR
961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSH
```

This STAMP polypeptide fragment (SEQ ID NO:8) can also be incorporated into compositions for modulating glucocorticoid-responsive gene expression.

The following STAMP polypeptide fragment, with amino acids 429 to 834, has the CID region but not the RID regions of STAMP (SEQ ID NO:9).

```
429                                    SA SDAEMKNLVG
441 SAREKGPGKL GGSVLGLSME EIKVLRRVKE ENDRRGGFIR
481 IFPTSETWEI YGSYLEHKTS MNYMLATRLF QDRMTADGAP
521 ELKIESLNSK AKLHAALYER KLLSLEVRKR RRRSSRLRAM
561 RPKYPVITQP AEMNVKTETE SEEEEEVALD NEDEEQEASQ
601 EESAGFLREN QAKYTPSLTA LVENTPKENS MKVREWNNKG
641 GHCCKLETQE LEPKFNLMQI LQDNGNLSKM QARIAFSAYL
681 QHVQIRLMKD SGGQTFSASW AAKEDEQMEL VVRFLKRASN
721 NLQHSLRMVL PSRRLALLER RRILAHQLGD FIIVYNKETE
761 QMAEKKSKKK VEEEEEDGVN MENFQEFIRQ ASEAELEEVL
801 TFYTQKNKSA SVFLGTHSKI SKNNNNYSDS GAKG
```

This STAMP polypeptide fragment (SEQ ID NO:9) can also be incorporated into compositions for modulating glucocorticoid-responsive gene expression.

The following STAMP polypeptide fragment, with amino acids 518 to 834, has the CID region but not the RID regions of STAMP (SEQ ID NO:10).

```
518                                             GAP
521 ELKIESLNSK AKLHAALYER KLLSLEVRKR RRRSSRLRAM
561 RPKYPVITQP AEMNVKTETE SEEEEEVALD NEDEEQEASQ
601 EESAGFLREN QAKYTPSLTA LVENTPKENS MKVREWNNKG
641 GHCCKLETQE LEPKFNLMQI LQDNGNLSKM QARIAFSAYL
681 QHVQIRLMKD SGGQTFSASW AAKEDEQMEL VVRFLKRASN
721 NLQHSLRMVL PSRRLALLER RRILAHQLGD FIIVYNKETE
761 QMAEKKSKKK VEEEEEDGVN MENFQEFIRQ ASEAELEEVL
801 TPYTQKNKSA SVFLGTHSKI SKNNNNYSDS GAKG
```

This STAMP polypeptide fragment (SEQ ID NO:10) can also be incorporated into compositions for modulating glucocorticoid-responsive gene expression.

The following STAMP polypeptide fragment, with amino acids 956 to 1277 has most of the RID regions of STAMP but no CID region (SEQ ID NO:11).

```
 956                                            LPRCR
 961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TGIINRSSAS APPTLRPIIS
1081 PSGPTWSTQS DPQAPENHSS SPGSRSLQTG GFAWEGEVEN
1121 NVYSQATGVV PQHKYHPTAG SYQLQFALQQ LEQQKLQSRQ
1161 LLDQSRARHQ AIFGSQTLPN SNLWTMNNGA GCRISSATAS
1201 CQKPTTLPQK VVPPPSSCAS LVPKPPPNHE QVLRRATSQK
1241 ASKGSSAEGQ LNGLQSSLNP AASVPITSST DPAHTKI
```

This STAMP polypeptide fragment (SEQ ID NO:11) can also be incorporated into compositions for modulating glucocorticoid-responsive gene expression.

The following STAMP polypeptide fragment, with amino acids 956 to 1127 has a portion of the RID region of STAMP (SEQ ID NO:12).

```
 956                                            LPRCR
 961 SGSHTIGPFS SFQSAAHIYS QKLSRPSSAK AGSCYLNKHH
1001 SGIAKTQKEG EDASLYSKRY NQSMVTAELQ RLAEKQAARQ
1041 YSPSSHINLL TQQVTNLNLA TCIINRSSAS APPTLRPIIS
1081 PSGPTWSTQS DPQAPENHSS SPGSRSLQTG GFAWEGEVEN
1121 NVYSQAT
```

This STAMP polypeptide fragment (SEQ ID NO:12) can also be incorporated into compositions for modulating glucocorticoid-responsive gene expression.

The following STAMP polypeptide fragment, with amino acids 1127 to 1277 has the C-terminal part of the RID regions of STAMP (SEQ ID NO:13).

```
1127        TGVV PQHKYHPTAG SYQLQFALQQ LEQQKLQSRQ
1161 LLDQSRARHQ AIFGSQTLPN SNLWTMNNGA GCRISSATAS
1201 GQKPTTLPQK VVPPPSSCAS LVPKPPPNHE QVLRRATSQK
1241 ASKGSSAEGQ LNGLQSSLNP AASVPITSST DPAHTKI
```

This STAMP polypeptide fragment (SEQ ID NO:13) can also be incorporated into compositions for modulating glucocorticoid-responsive gene expression.

The following STAMP polypeptide fragment, with amino acids 1-834 has the tubulin-tyrosine ligase (TTL) domain (at amino acids 113-391) and the CID region (SEQ ID NO:14).

```
   1 MARDLEETAS SSEDEEVISQ EDHPCIMWTG GCRRIPVLVF
  41 HADAILTKDN NIRVIGERYH LSYKIVRTDS RLVRSILTAH
  81 GFHEVHPSST DYNLMWTGSH LKPFLLRTLS EAQKVNHFPR
 121 SYELTRKDRL YKNIIRMQHT HGFKVFHILP QTFLLPAEYA
 161 EFCNSYSKDR GPWIVKPVAS SRGRGVYLIN NPNQISLEEN
 201 ILVSRYINNP LLIDDFKFDV RLYVLVTSYD PLVIYLYEEG
 241 LARFATVRYD QGAKNIRNQF MHLTNYSVNK KSGDYVSCDD
 281 PEVEDYGNKW SMSAMLRYLK QEGRDTTALM AHVEDLIIKT
 321 IISAELAIAT ACKTFVPHRS SCFELYGFDV LIDSTLKPWL
 361 LEVNLSPSLA CDAPLDLKIK ASMISDMFTV VGFVCQDPAQ
 401 RASTRPIYPT FESSRRNPFQ KPQRCRPLSA SDAEMKNLVG
 441 SAREKGPGKL GGSVLGLSME EIKVLRRVKE ENDRRGGFIR
 481 IFPTSETWEI YGSYLEHKTS MNYMLATRLF QDRMTADGAP
 521 ELKIESLNSK AKLHAALYER KLLSLEVRKR RRRSSRLRAM
 561 RPKYPVITQP AEMNVKTETE SEEEEEVALD NEDEEQEASQ
 601 EESAGFLREN QAKYTPSLTA LVENTPKENS MKVREWNNKG
 641 GHCCKLETQE LEPKFNLMQI LQDNGNLSKM QARIAFSAYL
 681 QHVQIRLMKD SGGQTFSASW AAKEDEQMEL VVRFLKRASN
 721 NLQHSLRMVL PSRRLALLER RRILAHQLGD FIIVYNKETE
 761 QMAEKKSKKK VEEEEEDGVN MENFQEFIRQ ASEAELEEVL
 801 TFYTQKNKSA SVFLGTHSKI SKNNNNYSDS GAKG
```

This STAMP polypeptide fragment (SEQ ID NO:14) can also be incorporated into compositions for modulating glucocorticoid-responsive gene expression.

The following STAMP polypeptide fragment, with amino acids 1-623 has the tubulin-tyrosine ligase (TTL) domain (at amino acids 113-391) but not the CID region (SEQ ID NO:15).

```
   1 MARDLEETAS SSEDEEVISQ EDHPCIMWTG GCRRIPVLVF
  41 HADAILTKDN NIRVIGERYH LSYKIVRTDS RLVRSILTAH
  81 GFHEVHPSST DYNLMWTGSH LKPFLLRTLS EAQKVNHFPR
 121 SYELTRKDRL YKNIIRMQHT HGFKVFHILP QTFLLPAEYA
 161 EFCNSYSKDR GPWIVKPVAS SRGRGVYLIN NPNQISLEEN
 201 ILVSRYINNP LLIDDFKFDV RLYVLVTSYD PLVIYLYEEG
 241 LARFATVRYD QGAKNIRNQF MHLTNYSVNK KSGDYVSCDD
 281 PEVEDYGNKW SMSAMLRYLK QEGRDTTALM AHVEDLIIKT
 321 IISAELAIAT ACKTFVPHRS SCFELYGFDV LIDSTLKPWL
 361 LEVNLSPSLA CDAPLDLKIK ASMISDMFTV VGFVCQDPAQ
 401 RASTRPTYPT FESSRRNPFQ KPQRCRPLSA SDAEMKNLVG
 441 SAREKGPGKL GGSVLGLSME EIKVLRRVKE ENDRRGGFIR
 481 IFPTSETWEI YGSYLEHKTS MNYMLATRLF QDRMTADGAP
 521 ELKIESLNSK AKLHAALYER KLLSLEVRKR RRRSSRLRAM
 561 RPKYPVITQP AEMNVKTETE SEEEEEVALD NEDEEQEASQ
 601 EESAGFLREN QAKYTPSLTA LVE
```

The following STAMP polypeptide fragment, with amino acids 834-956 has the N-terminal portion the RID regions of STAMP (SEQ ID NO:16).

```
 834                                          GDHPETI
 841 MEEVKIKPPK QQQTTEIHSD KLSRFTTSAE KEAKLVYSNS
 881 SSGPTATLQK IPNTHLSSVT TSDLSPGPCH HSSLSQIPSA
 921 IPSMPHQPTI LLNTVSASAS PCLHPGAQNI PSPTGL
```

Moreover, according to the invention, STAMP-related polypeptides with sequences similar but not necessarily identical to SEQ ID NO:1 can be used in the compositions of the invention. Thus, for example, a sequence related to human STAMP has been newly deposited as Genbank Accession No. NP 055887 (gi: 50658079). According to the invention, this STAMP-related polypeptide, and fragments thereof, can be used in the compositions and methods of the invention. This STAMP-related polypeptide sequence is provided below for easy reference (SEQ ID NO:63).

```
    1 MPIVMARDLE ETASSSEDEE VISQEDHPCI MWTGGCRRIP
   41 VLVFHADAIL TKDNNIRVIG ERYHLSYKIV RTDSRLVRSI
   81 LTAHGFHEVH PSSTDYNLMW TGSHLKPFLL RTLSEAQKVN
  121 HFPRSYELTR KDRLYKNIIR MQHTHGFKAF HILPQTFLLP
  161 AEYAEFCNSY SKDRGPWIVK PVASSRGRGV YLINNPNQIS
  201 LEENILVSRY INNPLLIDDF KFDVRLYVLV TSYDPLVIYL
  241 YEEGLARFAT VRYDQGAKNI RNQFMHLTNY SVNKKSGDYV
  281 SCDDPEVEDY GNKWSMSAML RYLKQEGRDT TALMAHVEDL
  321 IIKTIISAEL AIATACKTFV PHRSSCFELY GFDVLIDSTL
  361 KPWLLEVNLS PSLACDAPLD LKIKASMISD MFTVVGFVCQ
  401 DPAQRASTRP IYPTFESSRR NPFQKPQRCR PLSASDAEMK
  441 NLVGSAREKG PGKLGGSVLG LSMEEIKVLR RVKEENDRRG
  481 GFIRIFPTSE TWEIYGSYLE HKTSMNYMLA TRLFQDRMTA
  521 DGAPELKIES LNSKAKLHAA LYERKLLSLE VRKRRRSSR
  561 LRAMRPKYPV ITQPAEMNVK TETESEEEEE VALDNEDEEQ
  601 EASQEESAGF LRENQAKYTP SLTALVENTP KENSMKVREW
  641 NNKGGHCCKL ETQELEPKFN LMQILQDNGN LSKMQARIAF
  681 SAYLQHVQIR LMKDSGGQTF SASWAAKEDE QMELVVRFLK
  721 RASNNLQHSL RMVLPSRRLA LLERRRILAH QLGDFIIVYN
  761 KETEQMAEKK SKKKVEEEEE DGVNMENFQE FIRQASEAEL
  801 EEVLTFYTQK NKSASVFLGT HSKISKNNNN YSDSGAKGDH
  841 PETIMEEVKI KPPKQQQTTE IHSDKLSRFT TSAEKEAKLV
  881 YSNSSSGPTA TLQKIPNTHL SSVTTSDLSP GPCHHSSLSQ
  921 IPSAIPSMPH QPTILLNTVS ASASPCLHPG AQNIPSPTGL
  961 PRCRSGSHTI GPFSSFQSAA HIYSQKLSRP SSAKAGSCYL
 1001 NKHHSGIAKT QKEGEDASLY SKRYNQSMVT AELQRLAEKQ
 1041 AARQYSPSSH INLLTQQVTN LNLATGIINR SSASAPPTLR
 1081 PIISPSGPTW STQSDPQAPE NHSSSPGSRS LQTGGFAWEG
 1121 EVENNVYSQA TGVVPQHKYH PTAGSYQLQF ALQQLEQQKL
 1161 QSRQLLDQSR ARHQAIFGSQ TLPNSNLWTM NNGAGCRISS
 1201 ATASGQKPTT LPQKVVPPPS SCASLVPKPP PNHEQVLRRA
 1241 TSQKASKGSS AEGQLNGLQS SLNPAAFVPI TSSTDPAHTK
 1281 I
```

An orangutan (Pongo pygmaeus) sequence related to human STAMP has been newly deposited as Genbank Accession No. NP CAH91681 (gi: 55729911). According to the invention, this STAMP-related polypeptide, and fragments thereof, can be used in the compositions and methods of the invention. This STAMP-related orangutan polypeptide sequence is provided below for easy reference (SEQ ID NO:64).

```
    1 MPIVMARDLE ETASSSEDEE VISQEDHPCI MWTGGCRRIP
   41 VLVFHADAIL TKDNNIRVIG ERYHLSYKIV RTDSRLVRSI
   81 LTAHGFHEVH PSSTDYNLMW TGSHLKPFLL RTLSEAQKVN
  121 HFPRSYELTR KDRLYKNIIR MQHTHGFKAF HILPQTELLP
  161 AEYAEFCNSY SKDRGPWIVK PVASSRGRGV YLINNPNQIS
  201 LEENILVSRY INNPLLIDDF KFDVRLYVLV TSYDPLVIYL
  241 YEEGLARFAT VRYDQGAKNI RNQFMHLTNY SVNKKSGDYV
  281 SCDDPEVEDY GNKWSMSAML RYLKQEGRDT TALMAHVEDL
  321 IIKTIISAEL AIATACKTFV PHRSSCFELY GFDVLIDSTL
  361 KPWLLEVNLS PSLACDAPLD LKIKASMISD MFTVVGFVCQ
  401 DPAQRASTRP IYPTFESSRR NPFQKPQRCR PLSASDAEMK
  441 NLVGSAREKG PGKLGGSVLG LSMEEIKVLR RVKEENDRRG
  481 GFIRIFPTSE TWEIYGSYLE HKTSMNYMLA TRLFQDRGNP
  521 RRSLLTGRTR MTADGAPELK IESLNSKAKL HAALYERKLL
  561 SLEVRKRRRR SSRLRAMRPK YPVITQPAEM NVKTETESEE
  601 EEEVALDNEE EEQEASQEES AGFLRENQAK YTPSLTALVE
  641 NTPKEHSMKV REWNNKGGHC CKLETQELEP KFNLVQILQD
  681 NGNLSKVQAR IAFSAYLQHV QIRLMKDSGG QTFSASWAAK
  721 EDEQMELVVR FLKRASNNLQ HSLRMVLPSR RLALLERRRI
  761 LAHQLGDFII VYNKETEQMA EKKSKKKVEE EEDGVNMEN
  801 FQEFIRQASE AELEEVLTFY TQKNKSASVF LGTHSKSSKN
  841 NNSYSDSGAK GDHPETIMEE VKIKPPKQQQ TTEIHSDKLS
  881 RFTTSAEKEA KLVYSNSSST PFSGPTATLQ KIPNTHLSSV
  921 TTSDLSPGPG HHSSLSQIPS AIPSMPHQPT VLLNTVSASA
  961 SPCLHTGTQN IPNPAGLPRC RSGSHTIGPF SSFQSAAHIY
 1001 SQKLSRPSSA KAAGSCYLNK HHSGIAKTQK EGEDASSYSK
 1041 RYNQSMVTAE LQRLAEKQAA RQYSPSSHIN LLTQQVTNLN
```

```
1081 LATGIINRSS ASTPPTLRPI ISPSGPTWST QSDPQAPENH

1121 SSPPGSRSLQ TGVFAWEGEV ENNVYSKATG VVPQHKYHPT

1161 AGSYQLHFAL QQLEQQKLQS RQLLDQSRAR HQAIFGSQTL

1201 PNSNLWTMNN GAGCRISSAT ASGQKPTTLP QKVVPPPSSC

1241 ASLVPKPPPN HKQVLRRATS QRASKGSSAE GQLNGLQSSL

1281 NPAAFVPITS STDPAHTKI
```

A human STAMP polypeptide with a 1281 amino acid sequence, where translation began at the first start codon has SEQ ID NO:70, provided below. The amino acid numbering provided below is used simply to illustrate the N-terminal extension that constitutes the difference between the predominant form of STAMP (SEQ ID NO:1) and the 1281 amino acid form of STAMP with SEQ ID NO:70.

```
  -4 MPIV

1 MARDLEETAS SSEDEEVISQ EDHPCIMWTG GCRRIPVLVF

41 HADAILTKDN NIRVIGERYH LSYKIVRTDS RLVRSILTAH

81 GFHEVHPSST DYNLMWTGSH LKPFLLRTLS EAQKVNHFPR

121 SYELTRKDRL YKNIIRMQHT HGFKVFHILP QTFLLPAEYA

161 EFCNSYSKDR GPWIVKPVAS SRGRGVYLIN NPNQISLEEN

201 ILVSRYINNP LLIDDFKFDV RLYVLVTSYD PLVIYLYEEG

241 LARFATVRYD QGAKNIRNQF MHLTNYSVNK KSGDYVSCDD

281 PEVEDYGNKW SMSAMLRYLK QEGRDTTALM AHVEDLIIKT

321 IISAELAIAT ACKTFVPHRS SCFELYGFDV LIDSTLKPWL

361 LEVNLSPSLA CDAPLDLKIK ASMISDMFTV VGFVCQDPAQ

401 RASTRPIYPT FESSRRNPFQ KPQRCRPLSA SDAEMKNLVG

441 SAREKGPGKL GGSVLGLSME EIKVLRRVKE ENDRRGGFIR

481 IFPTSETWEI YGSYLEHKTS MNYMLATRLF QDRMTADGAP

521 ELKIESLNSK AKLHAALYER KLLSLEVRKR RRRSSRLRAM

561 RPKYPVITQP AEMNVKTETE SEEEEEVALD NEDEEQEASQ

601 EESAGFLREN QAKYTPSLTA LVENTPKENS MKVREWNNKG

641 GHCCKLETQE LEPKFNLMQI LQDNGNLSKM QARIAFSAYL

681 QHVQIRLMKD SGGQTFSASW AAKEDEQMEL VVRFLKRASN

721 NLQHSLRMVL PSRRLALLER RRILAHQLGD FIIVYNKETE

761 QMAEKKSKKK VEEEEEDGVN MENFQEFIRQ ASEAELEEVL

801 TFYTQKNKSA SVFLGTHSKI SKNNNNYSDS GAKGDHPETI

841 MEEVKIKPPK QQQTTEIHSD KLSRFTTSAE KEAKLVYSNS

881 SSGPTATLQK IPNTHLSSVT TSDLSPGPCH HSSLSQIPSA

921 IPSMPHQPTI LLNTVSASAS PCLHPGAQNI PSPTGLPRCR

961 SGSHTTGPFS SFQSAAHIYS QKLSRPSSAK AGSCYLNKHH

1001 SGIAKTQKEG EDASLYSKRY NQSMVTAELQ RLAEKQAARQ

1041 YSPSSHINLL TQQVTNLNLA TGIINRSSAS APPTLRPIIS

1081 PSGPTWSTQS DPQAPENHSS SPGSRSLQTG GFAWEGEVEN

1121 NVYSQATGVV PQHKYHPTAG SYQLQFALQQ LEQQKLQSRQ

1161 LLDQSRARHQ AIFGSQTLPN SNLWTMNNGA GCRISSATAS

1201 GQKPTTLPQK VVPPPSSCAS LVPKPPPNHE QVLRRATSQK

1241 ASKGSSAEGQ LNGLQSSLNP AASVPITSST DPAHTKI
```

The invention is directed to all these STAMP polypeptides and to functionally active fragments thereof.

STAMP Nucleic Acids

As described herein STAMP polypeptides are encoded by STAMP nucleic acids, for example, a nucleic acid comprising SEQ ID NO:2 or SEQ ID NO:61. In one embodiment, the invention provides STAMP sense and/or anti-sense nucleic acids, as well as related RNA or DNA molecules. Such STAMP sense and/or anti-sense nucleic acids, as well as related RNA or DNA molecules can be used to modulate STAMP expression, translation and/or the degradation of STAMP transcripts. For example, an anti-sense RNA or DNA that can hybridize to a nucleic acid having SEQ ID NO:2 or SEQ ID NO:61 can be used for diminishing the expression of STAMP. The degradation of STAMP mRNA may also be increased upon exposure to small duplexes of synthetic double-stranded RNA through the use of RNA interference (RNAi) technology (Scherr, M. et al. 2003, Curr. Med. Chem. 10:245; Martinez, L. A. et al. 2002 PNAS 99: 14849).

In one embodiment, a disease where glucocorticoid responsive gene expression is undesirably active, or inactive, can be treated by administering to a mammal a nucleic acid that can inhibit, or augment, the functioning of a STAMP RNA. Nucleic acids that can inhibit the function of a STAMP RNA can be generated from coding and non-coding regions of the STAMP gene. However, nucleic acids that can inhibit the function of a STAMP RNA are often selected to be complementary to sequences near the 5' end of the coding region. Hence, in some embodiments, the nucleic acid that can inhibit the functioning of a STAMP RNA can be complementary to sequences near the 5' end of SEQ ID NO:2. In other embodiments, nucleic acids that can inhibit the function of a STAMP RNA can be complementary to SEQ ID NO:2 or to STAMP RNAs from other species (e.g., mouse or a monkey STAMP RNA).

A nucleic acid that can inhibit the functioning of a STAMP RNA need not be 100% complementary to a selected region of SEQ ID NO:2. Instead, some variability the sequence of the nucleic acid that can inhibit the functioning of a STAMP RNA is permitted. It has recently been shown that a string of eleven nucleotides in a 21-23 RNA duplex is sufficient to complex with an mRNA species and cause silencing of expression from the gene encoding this mRNA. See Jackson et al. (2003) Nat. Biotechnol. 21: 635-37. Thus, perfect complementarity of a 21-23 bp siRNA is not needed for gene silencing. A nucleic acid that can inhibit the functioning of a mouse STAMP RNA, for example, can therefore be complementary to a nucleic acid encoding a mouse or monkey STAMP gene product. A nucleic acid encoding African green monkey (Cercopithecus aethiops) STAMP gene product, for example, can be found in the NCBI database at GenBank Accession No. AY383558). This monkey STAMP cDNA is 98% identical to the human STAMP cDNA (FIG. 3D; alignment from BLAST on GCG). The sequence for this monkey STAMP cDNA is as follows (SEQ ID NO:61).

```
   1 TGAATCTGCt aGGAAAGGtc tcTGAGGCCC CGTCTGCCG
  41 ACTGCATGAC AAACCCTAAA GGAAATGCCA GTCGTGATGG
  81 CCCGGGACCT GGAGGAAACA GCATCATCCT CAGAGGATGA
 121 GGAGGTCATA AGTCAAGAGG ATCATCCATG CATCATGTGG
 161 ACTGGAGGCT GTAGGAGAAT TCCAGTTTTG GTATTCCATG
 201 CCGACGCTAT TCTTACAAAG GACAACAATA TTAGAGTAAT
 241 TGGAGAACGT TATCATTTGT CTTATAAGAT TGTACGAACG
 281 GACAGTCGCC TAGTACGCAG CATTCTGACA GCCCATGGAT
 321 TTCATGAAGT TCACCCAAGC AGCACTGACT ATAACCTAAT
 361 GTGGACAGGA TCCCACCTGA AGCCCTTCTT ACTGCGCACC
 401 CTCTCTGAAG CACAAAAAGT TAATCACTTT CCCAGGTCTT
 441 ATGAACTTAC CCGGAAGGAC CGACTGTACA AAAACATTAT
 481 TCGAATGCAg CATACACATG GATTCAAGGC TTTtCACATC
 521 CTCCCCCaGA CCTTCCTCCT GCCAGCTGAG TACGCGGAAT
 561 TTTGTAATTC ATATTCGAAG GACCGGGGAC CTTGGATAGT
 601 AAAACCAGTG GCATCTTCTA GGGGGCGGGG CGTCTACCTG
 641 ATCAACAATC CAAACCAGAT TTCCCTGGAA GAAAACATTC
 681 TGGTCTCCCG TTATATTAAC AACCCCCTGC TCATAGATGA
 721 TTTCAAGTTT GATGTGCGCC TCTATGTGCT GGTGACTTCC
 761 TATGATCCTC TTGTCATCTA TCTCTATGAA GAAGGATTGG
 801 CTAGGTTTGC AACTGTGCGA TATGATCAAG GAGCCAAGAA
 841 CATTCGGAAC CAGTTCATGC ATCTGACAAA CTACAGTGTG
 881 AACAAGAAGA GTGGAGACTA CGTCAGTTGT GATGATCCAG
 921 AAgtGGAGGA CTATGGAAAC AAATGGAGCA TGAgTGCTAT
 961 GCTTAGGTAC CTGAAACAAG AAGGCAGAGA TACAACTGCA
1001 TTGATGGCCC ATGTAGAAGA CCTGATCATT AAGACTATAA
1041 TCTCTGCTGA ACTAGCTATT GCTACTGCCT GTAAAACCTT
1081 TGTTCCTCAT CGCAGCAGTT GTTTTGAACT CTATGGCTTT
1121 GACGTGCTCA TAGATGCTAC TCTGAAGCCA TGGTTGTTGG
1161 AAGTGAATCT CTCTCCTTCT TTGGCCTGTG ATGCACCTCT
1201 GGACCTAAAG ATTAAAGCCA GTATGAtTTC AGATATGTTC
1241 ACTGTTGTTG GATTTGTGTG CCAAGATCCT GCCCAGCGGG
1281 CATCAACCCG GCCAATTTAT CCCACCTTTG AGTCTTCCAG
1321 GCGAAACCCT TTCCAGAAAC CTcagcgtcc acttccagca
1361 cagtttcatt catcagagcc aaagCAGCgT TCCCGTCCAC
1401 TCTCTGCcAg TgatGCGGAA ATGAAAAACC TCGTGGGCTC
1441 AGCCCGGGAG AAAGGGCCAG GGAAGTTGGG TGGTTCTGTG
1481 CTTGGTCTGT CAATGGAGGA GATCAAAGTT TTACGGAGGG
1521 TGAAGGAGGA GAATGATCGG AGAGGTGGAT TTATTCGCAT
1561 ATTTCCTACA TCTGAGACAT GGGAAATATA TGGGTCCTAC
1601 CTCGAGCATA AGACCTCAAT GAACTATATG CTGGCAACAC
1641 GCCTCTTCCA GGACAGAatg ACtGCtGAtG GAGCACCAGA
1681 ATTGAAGATA GAGGGCCTGA ATTCAAAGGC CAAGCTGCAT
1721 GCTGCACTTT ACGAGAGGAA GCTCCTGTCT CTGGAGGTGC
1761 GAAAACGTAG ACGACGGAGT AGCAGATTGA GGGCAATGAG
1801 GCCAAAATAC CCAGTGATTA CCCAACCAGC TGAAATGAAT
1841 GTTAAAACTG AGACAGAGAG TGAAGAGGAG GAAGAAGTCG
1881 CATTAGACAA TGAAGATGAA GAGCAGGAAG CTTCCCAGGA
1921 GGAGTCTGCA GGATTTCTTA GAgAAAATCA AGCCAAAGAT
1961 ACACCCTCAT TGACAACTTT GGTAGAAAAT ACACCCAAAG
2001 AAAATTCCGT GAAAGTTCGT GAATGGAGTA aAAAAGGTGA
2041 ACGGTGCTGC AAACTTGAGA CTCAGGAGCT GGAGCCTAAA
2081 TTTAACCTGA TGCAGGTTCT TCAAGATAAC GGCAATCTTA
2121 GCAAAGTGCA GGCCCGAATA GCATTCTCTA CCTATCTCCA
2161 GCATGTTCAA ATTCGCCTGA TGAAAGACAG TGGAGGTCAG
2201 ACGTTCAGTG CCAGTTGGGC TGCCAAAGAG GATGAACAGA
2241 TGGAGCTGGT CGTTCGTTTC CTCAAGCGAG CATCAAATAA
2281 CCTTCAGCAG TCACTGAGGA TGGTATTACC CAGCCGACGA
2321 TTGGCACTTC TGGAACGCAG AAGAATCCTG GCCCACCAGC
2361 TGGGTGACTT TATCATTGTA TACAACAAGG AAACAGAACA
2401 AATGGCTGAA AAGAAaTCAA AGAAGAAAGT TGAAGAAGAA
2441 GAGGAgGATG GaGTGAATAT GGAAAACTTT CAGGAGTTCA
2481 TCAGACAAGC AAGTGAGGCT GAACTGGAGG AGGTGTTGAC
2521 TTTTTATACC CAAAAGAACA AGTCTGCTAG TGTCTTCCTG
2561 GGGACTCACT CTAAAAGTTC TAAGAACAAC AACAGTTATT
2601 CTGATAGTGG GGCAAAAGGT GATCACCCTG AGACTGTAAT
2641 GGAAGAAGCG AAAATGAAGC CGCCTAAACA GCAACAGACA
2681 ACAGAAATTC ACTCTGATAA ATTATCTCGA TTTACCACTT
2721 CAGCAgAAAA AGAGGCAAAA TTAGTTTATA CCAGTTCTTC
2761 GTCGaCTCCT TTCTCTGGTC CTACTGCTAC TCTGCAGAAA
2801 ATTCCCAACA CCCATTTGTC ATCTGTTACA ACCTCAGACC
2841 TCTCTCCAGG GCCTGGCCAC CATTCTTCTT TATCTCAAAT
2881 TCCTTCAGCT ATCCCCAGCA TGCCTCACCA GCCAACAATT
2921 TTACTGAACA CAGTCTCTGC CAGTGCTTCT CCCTCCCTAC
2961 ATCCTGGGAC ACAGAACATC CCAAGCCCTG CTGGCCTGCC
3001 TCGCTGTCGA TCAGGAAGTC ACACCATTGG CTCCTTTTCT
3041 TCCTTCCAAA GTGCTGCACA CATCTATAGC CAGAAACTGT
3081 CTCGTCCCTC TTCAGCAAAG GCAGGATCgT GCTaTCTAaa
```

-continued

```
3121 cAAgCATCAT TCAgGAAtAG CCAAaACACA ACAAGAGGGA

3161 GAAGATGCTT CTTTATATAG CAAACGGTAC AACCAAAGTA

3201 TGGTTACAGC TgAACTTCAG CGgCTAGCtG AGAAGCAGGC

3241 AGCGAGACAG TATTCTCCAt CCAGCCACAT CAACCTCCTC

3281 ACCCAACAGG TGACAAACTT GAATTTGGCC ACTGGCATCA

3321 TAAACAGAAG CAGTGCTTCA ACTCCCCCA CCCTCCAACC

3361 CATCATCAGC CCTAGTGGCC CCACATGGTT GGTGCAGTCG

3401 GACCCTCAAG CTCCTGAGAA TCACTCCAGC CCTCCCAGAA

3441 GCAGGAGCCT CCAGACAGGT GGGTTTGCCT GGGAAGGAGA

3481 GGTAGAAAAC AACGTGTACA GCAAGGCTAC CGGGGTGGTC

3521 CCCCAGCACA AGTATCACCC CACAGCAGGC AGCTATCAGC

3561 TCCATTTTGC CCTGCAGCAA CTTGAACAAC AAAAACTTCA

3601 GTCCCGGCAG CTCCTGGACC AGAGTCGAGc CCGGCACCAG

3641 GCAATCTTTG GCAGCCAGAC ACTACCTAAC TCCAATTTAT

3681 GGACAATGAA TAATGGTGCA ggTTGTAGAA TTTCCAGTGC

3721 CACAGCTAGT GGCCAGAAGC CAACCACTCT GCCACAAAAA

3761 GCAGTACCAC CTCCAAGCTC TTGCGCCTCC CTGGTCCCCA

3801 AACCCCCTCC CAACCACAAA CAAGTGCTCA GAAGGGCAAC

3841 ATCCCAgAGC GCTTCCAAAG GGTCCTCgGC AtATGCGCAG

3881 CTGAaTGGAC TCCAgAGCAg CCTTaAcccT GCAgCCTcTG

3921 TGCCCATCAC CAGCTCCACA GATCCTGCTC ACACTAAAAG

3961 ATGAACCACA AACACACAGA GAAACGAcCT GTTCACCACT

4001 CCTGGGGTGC ATCTAGAGCA T
```

This green monkey cDNA clone is predicted to encode a protein that is 97% identical to the human STAMP protein (FIG. 3E). The green monkey STAMP polypeptide has the following sequence (SEQ ID NO:62).

```
  1 MPVVMARDLE ETASSSEDEE VISQEDHPCI MWTGGCRRIP

41 VLVFHADAIL TKDNNIRVIG ERYHLSYKIV RTDSRLVRSI

81 LTAHGFHEVH PSSTDYNLMW TGSHLKPFLL RTLSEAQKVN

121 HFPRSYELTR KDRLYKNIIR MQHTHGFKAF HILPQTFLLP

161 AEYAEFCNSY SKDRGPWIVK PVASSRGRGV YLINNPNQIS

201 LEENILVSRY INNPLLIDDF KFDVRLYVLV TSYDPLVIYL

241 YEEGLARFAT VRYDQGAKNI RNQFMHLTNY SVNKKSGDYV

281 SCDDPEVEDY GNKWSNSAML RYLKQEGRDT TALMAHVEDL

321 IIKTIISAEL AIATACKTFV PHRSSCFELY GFDVLIDATL

361 KPWLLEVNLS PSLACDAPLD LKIKASMISD MFTVVGFVCQ

401 DPAQRASTRP IYPTFESSRR NPFQKPQRPL PAQFHSSEPK

441 QRSRPLSASD AEMKNLVGSA REKGPGKLGG SVLGLSMEEI

481 KVLRRVKEEN DRRGGEIRIF PTSETWEIYG SYLEHKTSMN

521 YMLATRLFQD RMTADGAPEL KIEGLNSKAK LHAALYERKL

561 LSLEVRKRRR RSSRLRAMRP KYPVITQPAE MNVKTETESE

601 EEEEVALDNE DEEQEASQEE SAGFLRENQA KDTPSLTTLV

641 ENTPKENSVK VREWSKKGER CCKLETQELE PKFNLMQVLQ

681 DNGNLSKVQA RIAFSTYLQH VQIRLMKDSG GQTFSASWAA

721 KEDEQMELVV RFLKRASNNL QQSLRMVLPS RRLALLERRR

761 ILAHQLGDFI IVYNKETEQM AEKKSKKKVE EEEEDGVNME

801 NFQEFIRQAS EAELEEVLTF YTQKNKSASV FLGTHSKSSK

841 NNNSYSDSGA KGDHPETVME EAKMKPPKQQ QTTEIHSDKL

881 SRFTTSAEKE AKLVYTSSSS TPFSGPTATL QKIPNTHLSS

921 VTTSDLSPGP GHHSSLSQIP SAIPSMPHQP TILLNTVSAS

961 ASPSLHPGTQ NIPSPAGLPR CRSGSHTIGS FSSEQSAAHI

1001 YSQKLSRPSS AKAGSCYLNK HHSGIAKTQQ EGEDASLYSK

1041 RYNQSMVTAE LQRLAEKQAA RQYSPSSHIN LLTQQVTNLN

1081 LATGIINRSS ASTPPTLQPI ISPSGPTWLV QSDPQAPENH

1121 SSPPRSRSLQ TGGFAWEGEV ENNVYSKATG VVPQKYHPT

1161 AGSYQLHFAL QQLEQQKLQS RQLLDQSRAR HQAIFGSQTL

1241 PNSNLWTMNN GAGCRISSAT ASGQKPTTLP QKAVPPPSSC

1281 ASLVPKPPPN HKQVLRRATS QRASKGSSAY AQLNGLQSSL

1321 NPAASVPITS STDPAHTKR
```

Mice contain a cDNA encoding a protein of unknown function that is 89% identical to the human STAMP cDNA (GenBank Accession No. XM_126935). Similarly, nucleic acids encoding STAMP-related polypeptides such as those provided herein as SEQ ID NO:63-65 are sufficiently closely related to the human STAMP sequence to be used for generating STAMP-related polypeptides or for making nucleic acids that can inhibit the functioning of a STAMP RNA. Thus, a cDNA sequence for STAMP-related polypeptide having SEQ ID NO:63 is available in the NCBI database at accession number NM 015072 (gi: 50658078). A cDNA sequence for STAMP-related orangutan polypeptide having SEQ ID NO:64 is available in the NCBI database at accession number CR859514 (gi: 55729910). Therefore, variant STAMP sequences exist and the STAMP gene and protein are conserved among different species.

Moreover, nucleic acids that can hybridize under moderately or highly stringent hybridization conditions are sufficiently complementary to inhibit the functioning of a STAMP RNA and can be utilized in the compositions of the invention. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal pointing point of the selected sequence, depending upon the desired degree of stringency as otherwise qualified herein. In some embodiments, the nucleic acids that can inhibit the functioning of STAMP RNA can hybridize to a STAMP RNA under physiological conditions, for example, physiological temperatures and salt concentrations.

Precise complementarity is therefore not required for successful duplex formation between a nucleic acid that can inhibit a STAMP RNA and the complementary coding sequence of a STAMP RNA. Inhibitory nucleic acid molecules that comprise, for example, 2, 3, 4, or 5 or more stretches of contiguous nucleotides that are precisely complementary to a STAMP coding sequence, each separated by a stretch of contiguous nucleotides that are not complementary to adjacent STAMP coding sequences, can inhibit the function of STAMP mRNA. In general, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of a nucleic acid hybridized to a sense nucleic acid to estimate the degree of mismatching that will be tolerated between a particular nucleic acid for inhibiting expression of a particular STAMP RNA.

In some embodiments a nucleic acid that can inhibit the function of an endogenous STAMP RNA is an anti-sense oligonucleotide. The anti-sense oligonucleotide is complementary to at least a portion of the coding sequence of a gene comprising SEQ ID NO:2 or SEQ ID NO:61. Such anti-sense oligonucleotides are generally at least six nucleotides in length, but can be about 8, 12, 15, 20, 25, 30, 35, 40, 45, or 50 nucleotides long. Longer oligonucleotides can also be used. STAMP anti-sense oligonucleotides can be provided in a DNA construct and introduced into cells whose division is to be decreased, for example, into cells expressing a glucocorticoid receptor such as immune cells or lymphocyte precursor cells.

In one embodiment of the invention, expression of a STAMP gene is decreased using a ribozyme. A ribozyme is an RNA molecule with catalytic activity. See, e.g., Cech, 1987, Science 236: 1532-1539; Cech, 1990, Ann. Rev. Biochem. 59:543-568; Cech, 1992, Curr. Opin. Struct. Biol. 2: 605-609; Couture and Stinchcomb, 1996, Trends Genet. 12: 510-515. Ribozymes can be used to inhibit gene function by cleaving an RNA sequence, as is known in the art (see, e.g., Haseloff et al., U.S. Pat. No. 5,641,673).

STAMP nucleic acids complementary to SEQ ID NO:2 or SEQ ID NO:61 can be used to generate ribozymes that will specifically bind to mRNA transcribed from a STAMP gene. Methods of designing and constructing ribozymes that can cleave other RNA molecules in trans in a highly sequence specific manner have been developed and described in the art (see Haseloff et al. (1988), Nature 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). The target sequence can be a segment of about 10, 12, 15, 20, or 50 contiguous nucleotides selected from a nucleotide sequence having SEQ ID NO:2 or SEQ ID NO:61. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

RNA interference (RNAi) involves post-transcriptional gene silencing (PTGS) induced by the direct introduction of dsRNA into a cell or organism. Small interfering RNAs (siRNAs) are generally 21-23 nucleotide dsRNAs and can mediate post-transcriptional gene silencing in mammalian cells. siRNAs can also be produced in vivo by cleavage of dsRNA introduced directly or via a transgene or virus. Amplification by an RNA-dependent RNA polymerase may occur in some organisms. siRNAs are incorporated into the RNA-induced silencing complex, guiding the complex to the homologous endogenous mRNA where the complex cleaves the transcript.

Rules for designing siRNAs are available. See, e.g., Elbashir S M, Harborth J, Lendeckel W, Yalcin A, Weber K, Tuschl T (2001). Duplexes of 21-nucleotide RNAs mediate RNA interference in mammalian cell culture. *Nature* 411: 494-498; J. Harborth, S. M. Elbashir, K. Vandenburgh, H. Manninga, S. A. Scaringe, K. Weber and T. Tuschl (2003). Sequence, chemical, and structural variation of small interfering RNAs and short hairpin RNAs and the effect on mammalian gene silencing, *Antisense Nucleic Acid Drug Dev.* 13: 83-106.

Thus, an effective siRNA can be made by selecting target sites within SEQ ID NO:2 or SEQ ID NO:61 that begin with AA, that have 3' UU overhangs for both the sense and antisense siRNA strands, and that have an approximate 50% G/C content. For example, a siRNA of the invention can be a double-stranded RNA having one strand with the following sequence:

```
AAGCAGCCGUCGGCGGCUGUU       (SEQ ID NO: 17)

AACCAUGGGAAGAUGAGACUU       (SEQ ID NO: 18)

AAUCUGUGCCAUCCAAAUUUU       (SEQ ID NO: 19)

AAAGGUCUCUGAGGCCCCCUU       (SEQ ID NO: 20)

AAACCCUAAAGGAAAUGCCUU       (SEQ ID NO: 21)

AAACAGCAUCAUCCUCAGAUU       (SEQ ID NO: 22)

AAAAAGUUAAUCACUUUCCUU       (SEQ ID NO: 23)

AAAACAUUAUUCGAAUGCAUU       (SEQ ID NO: 24)

AAGGUUUUUCACAUCCUCCUU       (SEQ ID NO: 25)

AAUUUUGUAAUUCAUAUUCUU       (SEQ ID NO: 26)

AAGGACCGGGGACCUUGGAUU       (SEQ ID NO: 27)

AAACCAGUGGCAUCUUCAAUU       (SEQ ID NO: 28)

AACAAUCCAAACCAGAUCUUU       (SEQ ID NO: 29)

AAGAGAACAUUUUGGUCUCUU       (SEQ ID NO: 30)

AACCCCCUGCUCAUAGAUGAUU      (SEQ ID NO: 31)

AAGAAGGAUUGGCUAGGUUUU       (SEQ ID NO: 32)

CAGCACUGACUAUAACCUAAUUU     (SEQ ID NO: 33)
```

-continued

CACCCUCUCUGAAGCACAAAAUU (SEQ ID NO: 34)

GCCAGCUGAGUACGCGGAAUUUU (SEQ ID NO: 35)

GAGGGCAAUGAGGCCAAAAUAUU (SEQ ID NO: 36)

Examples of siRNAs that seem to work in preliminary experiments are the double stranded RNAs corresponding to the following DNA sequences of human STAMP:

490-CAGCACTGACTATAACCTAAT-510 (SEQ ID NO: 37)

547-CACCCTCTCTGAAGCACAAA-567 (SEQ ID NO: 38)

691-GCCAGCTGAGTACGCGGAATT-711 (SEQ ID NO: 39)

1897-GAGGGCAATGAGGCCAAAATA-1917 (SEQ ID NO: 40)

Hence, the invention contemplated RNAi and siRNAs that can be used to control STAMP expression. In some embodiments, the mechanism used to decrease expression of the STAMP, whether by ribozyme, anti-sense, siRNA, or antibody, decreases expression of the gene by 50%, 55%, 60%, 65%, 70%, 75% or 80%. In other embodiments, expression of the STAMP gene is decreased by 85%, 90%, 95%, 99%, or 100%. The effectiveness of the mechanism chosen to alter expression of the gene can be assessed using methods well known in the art, such as hybridization of nucleotide probes to mRNA from the human or monkey STAMP cDNA, quantitative RT-PCR, or detection of a STAMP protein using antibodies of the invention.

Anti-sense oligonucleotides, ribozymes and siRNAs can be composed of deoxyribonucleotides, ribonucleotides, or a combination of both. Oligonucleotides can be synthesized endogenously from transgenic expression cassettes or vectors as described herein. Alternatively, such oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, Meth. Mol. Biol. 20:1-8; Sonveaux, 1994, Meth. Mol. Biol. 26:1-72; Uhlmann et al., 1990, Chem. Rev. 90:543-583.

STAMP anti-sense oligonucleotides, ribozymes and siRNAs can be modified without affecting their ability to hybridize to a STAMP coding sequence. These modifications can be internal or at one or both ends of the selected nucleic acid. For example, internucleoside phosphate linkages can be modified by adding peptidyl, cholesteryl or diamine moieties with varying numbers of carbon residues between these moieties and the terminal ribose. Modified bases and/or sugars, such as arabinose instead of ribose, or a 3', 5'-substituted oligonucleotide in which the 3' hydroxyl group or the 5' phosphate group are substituted, can also be employed in a modified nucleic acid or oligonucleotide. These modified nucleic acids and oligonucleotides can be prepared by methods available in the art. Agrawal et al., 1992, Trends Biotechnol. 10:152-158; Uhlmann et al., 1990, Chem. Rev. 90:543-584; Uhlmann et al., 1987, Tetrahedron. Lett. 215:3539-3542.

Receptors, Coactivators and Other Factors

Compositions and methods employing STAMP polypeptides and nucleic acids can also include other factors, for example, hormones, receptor agonists, other coactivators, repressors, receptors, receptor ligands and factors that modulate gene expression. As described herein STAMP can bind to glucocorticoid receptors, and to the coactivators such as transcription intermediary factor-2 (TIF2) and steroid receptor coactivator-1 (SRC-1). These and other factors can be included in the compositions of the invention.

Glucocorticoid receptors (GRs) mediate both gene induction and gene repression by increasing or decreasing the rates of transcription from glucocorticoids-responsive genes. For gene induction, GR binds directly to a glucocorticoid response element that consists of a consensus palindromic sequence of six nucleotides (TGTTCT, SEQ ID NO:41), each of which is separated by three additional nucleotides. No such common DNA sequence exists among those genes that are down-regulated by GRs due to the diversity of mechanisms involved in GR-mediated repression.

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells (P. J. Barnes, Clin. Sci., 1998, 94, pp. 557-572; P. J. Barnes et al., Trends Pharmacol. Sci., 1993, 14, pp. 436-441). In addition to these effects, glucocorticoids stimulate glucose production in the liver and catabolism of proteins, play a role in electrolyte and water balance, reduce calcium absorption, and inhibit osteoblast function.

The anti-inflammatory and immune suppressive activities of endogenous glucocorticoids have stimulated the development of synthetic glucocorticoid derivatives including dexamethasone, prednisone, and prednisolone (L. Parente, Glucocorticoids, N. J. Goulding and R. J. Flowers (eds.), Boston: Birkhauser, 2001, pp. 35-54). These have found wide use in the treatment of inflammatory, immune, and allergic disorders including rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease (COPD), and other immune and inflammatory diseases including Crohn's disease, ulcerative colitis, systemic lupus erythematosus, autoimmune chronic active hepatitis, osteoarthritis, tendonitis, and bursitis (J. Toogood, Glucocorticoids, N. J. Goulding and R. J. Flowers (eds.), Boston: Birkhauser, 2001, pp. 161-174). They have also been used to help prevent rejection in organ transplantation.

The responses in GR-regulated induction, and often in GR-directed repression, are augmented by cofactors including coactivators such as transcription intermediary factor-2 (TIF2) and hBRM. Voegel et al., 1996, EMBO J. 15, 3667-3675; Hong et al., 1996, Proc. Natl. Acad. Sci. USA 93, 4948-4952; He et al., 2002, J. Biol. Chem. 277, 49256-49266; Rogatsky et al., 2001, EMBO. J. 20, 6071-6083; Rogatsky et al., 2002, Proc. Natl. Acad. Sci. U. S. A. 99, 16701-16706; Singh et al., 2001, J. Biol. Chem. 276, 13762-13770. These coactivators are recruited to DNA-associated receptors. Two activation domains called AD1 and AD2 have been found to be required for the ability of the p160 coactivators, such as TIF2, to increase the total levels of transactivation.

As described herein, the coactivators TIF2 and SRC-1 bind to STAMP. The regions of the coactivators TIF2 and SRC-1 that participate in the modulation of the $EC_{50}$ and partial agonist activity of glucocorticoid receptor complexes are separable from the AD1 and AD2 domains that are critical for increasing the total levels of gene activation. Moreover, TIF2 can modulate the activities of several receptors, including androgen receptors, estrogen receptors, mineralocorticoid receptors, progesterone receptors, thyroid receptors, retinoid receptors (RAR and RXR), and peroxisome proliferator-activated receptors (PPARs).

Hence, the invention contemplates compositions containing STAMP polypeptides or STAMP nucleic acids along with hormones, receptor agonists, antisteroids, other coactivators, repressors, steroid receptors, nuclear receptors, and factors that modulate glucocorticoid-responsive gene expression. Examples of receptors that STAMP can influence include steroid and nuclear receptors such as glucocorticoid receptors, androgen receptors, estrogen receptors, mineralocorticoid receptors, progesterone receptors, thyroid receptors, retinoid receptors (RAR and RXR), and peroxisome proliferator-activated receptors (PPARs).

Nucleic acid and amino acid sequences for coactivators, repressors, glucocorticoid receptors, and factors that modulate glucocorticoid-responsive gene expression can be found in the art, for example, in the NCBI database. See website at ncbi.nlm.nih.gov. For example, one amino acid sequence for human transcription intermediary factor-2 (TIF2) can be found in the NCBI database as accession number Q15596 (gi: 13626594). See website at ncbi.nlm.nih.gov. This sequence is provided below as follows (SEQ ID NO:42).

```
  1 MSGMGENTSD PSRAETRKRK ECPDQLGPSP KRNTEKRNRE

41 QENKYIEELA ELIFANFNDI DNFNEKPDKC AILKETVKQI

81 RQIKEQEKAA AANIDEVQKS DVSSTGQGVI DKDALGPMML

121 EALDGFFFVV NLEGNVVFVS ENVTQYLRYN QEELMNKSVY

161 SILHVGDHTE FVKNLLPKSI VNGGSWSGEP PRRNSHTFNC

201 RMLVKPLPDS EEEGHDNQEA HQKYETMQCF AVSQPKSIKE

241 EGEDLQSCLI CVARRVPMKE RPVLPSSESF TTRQDLQGKI

281 TSLDTSTMRA AMKPGWEDLV RRCIQKFHAQ HEGESVSYAK

321 RHHHEVLRQG LAFSQIYRFS LSDGTLVAAQ TKSKLIRSQT

361 TNEPQLVISL HMLHREQNVC VMNPDLTGQT MGKPLNPISS

401 NSPAHQALCS GNPGQDMTLS SNINFPINGP KEQMGMPMGR

441 FGGSGGMNHV SGMQATTPQG SNYALKMNSP SQSSPGMNPG

481 QPTSMLSPRH RMSPGVAGSP RIPPSQFSPA GSLHSPVGVC

521 SSTGNSHSYT NSSLNALQAL SEGHGVSLGS SLASPDLKMG

561 NLQNSPVNMN PPPLSKMGSL DSKDCFGLYG EPSEGTTGQA

601 ESSCHPGEQK ETNDPNLPPA VSSERADGQS RLHDSKGQTK

641 LLQLLTTKSD QMEPSPLASS LSDTNKDSTG SLPGSGSTHG

681 TSLKEKHKIL HRLLQDSSSP VDLAKLTAEA TGKDLSQESS

721 STAPGSEVTI KQEPVSPKKK ENALLRYLLD KDDTKDIGLP
```

-continued

```
761 EITPKLERLD SKTDPASNTK LIAMKTEKEE MSFEPGDQPG

801 SELDNLEEIL DDLQNSQLPQ LFPDTRPGAP AGSVDKQAII

841 NDLMQLTAEN SPVTPVGAQK TALRISQSTF NNPRPGQLGR

881 LLPNQNLPLD ITLQSPTGAG PFPPIRNSSP YSVIPQPGMM

921 GNQGMIGNQG NLGNSSTGMI GNSASRPTMP SGEWAPQSSA

961 VRVTCAATTS AMNRPVQGGM IRNPAASIPM RPSSQPGQRQ

1001 TLQSQVMNIG PSELEMNMGG PQYSQQQAPP NQTAPWPESI

1041 LPIDQASFAS QNRQPFGSSP DDLLCPHPAA ESPSDEGALL

1081 DQLYLALRNF DGLEEIDRAL GIPELVSQSQ AVDPEQFSSQ

1121 DSNIMLEQKA PVFPQQYASQ AQMAQGSYSP MQDPNFHTMG

1161 QRPSYATLRM QPRPGLRPTG LVQNQPNQLR LQLQHRLQAQ

1201 QNRQPLMNQI SNVSNVNLTL RPGVPTQAPI NAQMLAQRQR

1241 EILNQHLRQR QMHQQQQVQQ RTLMMRGQGL NMTPSMVAPS

1281 GMPATMSNPR IPQANAQQFP FPPNYGISQQ PDPGFTGATT

1321 PQSPLMSPRM AHTQSPMMQQ SQANPAYQAP SDINGWAQGN

1361 MGGNSMFSQQ SPPHFGQQAN TSMYSNNMNI NVSMATNTGG

1401 MSSMNQMTGQ ISMTSVTSVP TSGLSSMGPE QVNDPALRGG

1441 NLFPNQLPGM DMIKQEGDTT RKYC
```

See also, Voegel et al., 1998, EMBO J. 17, 507-519.

As described herein, STAMP interacts with a region of the coactivator TIF2 defined by amino acids 623-834. The TIF2 coactivator modulates the properties of not only glucocorticoid receptors but also of progesterone (Giannoukos et al., 2001, Mol. Endocrinol., 15, 255-270) and mineralocorticoid (data not shown) receptors. Thus, a target of STAMP (i.e., TIF2) does modulate the dose-response curve and partial agonist activity of several steroid receptors and can affect the properties of steroid and nuclear receptors such as androgen receptors, estrogen receptors, mineralocorticoid receptors, progesterone receptor, thyroid receptors, retinoid receptors (RAR and RXR), and peroxisome proliferator-activated receptors (PPARs). Hence, STAMP can be included in compositions and methods for modulating such receptors.

One example of a sequence for a human steroid receptor coactivator-1 (SRC-1) has accession number AAC50631 (gi: 1480646). See website at ncbi.nlm.nih.gov. This sequence for this human glucocorticoid receptor is provided below (SEQ ID NO:43).

```
  1 MSGLGDSSSD PANPDSHKRK GSPCDTLASS TEKRRREQEN

41 KYLEELAELL SANISDIDSL SVKPDKCKIL KKTVDQIQLM

81 KRMEQEKSTT DDDVQKSDIS SSSQGVIEKE SLGPLLLEAL

121 DGFFFVVNCE GRIVFVSENV TSYLGYNQEE LMNTSVYSIL

161 HVGDHAEFVK NLLPKSLVNG VPWPQEATRR NSHTFNCRML

201 IHPPDEPGTE NQEACQRYEV MQCFTVSQPK SIQEDGEDFQ

241 SCLICIARRL PRPPAITGVE SFMTKQDTTG KIISIDTSSL

281 RAAGRTGWED LVRKCIYAFF QPQGREPSYA RQLFQEVMTR
```

```
321 GTASSPSYRF ILNDGTMLSA HTKCKLCYPQ SPDMQPFIMG
361 IHIIDREHSG LSPQDDTNSG MSIPRVNPSV NPSISPAHGV
401 ARSSTLPPSN SNMVSTRINR QQSSDLHSSS HSNSSNSQGS
441 FGCSPGSQIV ANVALNQGQA SSQSSNPSLN LNNSPMEGTG
481 ISLAQFMSPR RQVTSGLATR PRMPNNSFPP NISTLSSPVG
521 MTSSACNNNN RSYSNIPVTS LQGMNEGPNN SVGFSASSPV
561 LRQMSSQNSP SRLNIQPAKA ESKDNKEIAS ILNEMIQSDN
601 SSSDGKPLDS GLLHNNDRLS DGDSKYSQTS HKLVQLLTTT
641 AEQQLRHADI DTSCKDVLSC TGTSNSASAN SSGGSCPSSH
681 SSLTERHKIL HRLLQEGSPS DITTLSVEPD KKDSASTSVS
721 VTGQVQGNSS IKLELDASKK KESKDHQLLR YLLDKDEKDL
761 RSTPNLSLDD VKVKVEKKEQ MDPCNTNPTP MTKPTPEEIK
801 LEAQSQFTAD LDQFDQLLPT LEKAAQLPGL CETDRMDGAV
841 TSVTIKSEIL PASLQSATAR PTSRLNRLPE LELEAIDNQF
881 GQPGTGDQIP WTNNTVTAIN QSKSEDQCIS SQLDELLCPP
921 TTVEGRNDEK ALLEQLVSFL SGKDETELAE LDRALGIDKL
961 VQGGGLDVLS ERFPPQQATP PLIMEERPNL YSQPYSSPSP
1001 TANLPSPFQG MVRQKPSLGT MPVQVTPPRG AFSPGMGMQP
1041 RQTLNRPPAA PNQLRLQLQQ RLQGQQQLIH QNRQAILNQF
1081 AATAPVGINM RSGMQQQITP QPPLNAQMLA QRQRELYSQQ
1121 HRQRQLIQQQ RAMLMRQQSF GNNLPPSSGL PVQMGNPRLP
1161 QGAPQQFPYP PNYGTNPGTP PASTSPFSQL AANPEASLAN
1201 RNSMVSRGMT GNIGGQFGTG INPQMQQNVF QYPGAGMVPQ
1241 GEANFAPSLS PGSSMVPMPI PPPQSSLLQQ TPPASGYQSP
1281 DMKAWQQGAI GNNNVFSQAV QNQPTPAQPG VYNNMSITVS
1321 MAGGNTNVQN MNPMMAQMQM SSLQMPGMNT VCPEQINDPA
1361 LRHTGLYCNQ LSSTDLLKTE ADGTQVQQVQ VEADVQCTVN
1401 LVGGDPYLNQ PGPLGTQKPT SGPQTPQAQQ KSLLQQLLTE
```

See also, Takeshita et al., *Molecular cloning and properties of a full-length putative thyroid hormone receptor coactivator*, Endocrinology 137 (8), 3594-3597 (1996).

Numerous sequences for human glucocorticoid receptor isoforms and variants are available, for example, in the NCBI database. One example of a sequence for a human glucocorticoid receptor has accession number P04150 (gi: 121069). See website at ncbi.nlm.nih.gov. This sequence for this human glucocorticoid receptor is provided below (SEQ ID NO:44).

```
  1 MDSKESLTPG REENPSSVLA QERGDVMDFY KTLRGGATVK
 41 VSASSPSLAV ASQSDSKQRR LLVDFPKGSV SNAQQPDLSK
 81 AVSLSMGLYM GETETKVMGN DLGFPQQGQI SLSSGETDLK
121 LLEESIANLN RSTSVPENPK SSASTAVSAA PTEKEFPKTH
161 SDVSSEQQHL KGQTGTNGGN VKLYTTDQST FDILQDLEFS
201 SGSPGKETNE SPWRSDLLID ENCLLSPLAG EDDSFLLEGN
241 SNEDCKPLIL PDTKPKIKDN GDLVLSSPSN VTLPQVKTEK
281 EDFIELCTPG VIKQEKLGTV YCQASFPGAN IIGNKMSAIS
321 VHGVSTSGGQ MYHYDMNTAS LSQQQDQKPI FNVIPPIPVG
361 SENWNRCQGS GDDNLTSLGT LNFPGRTVFS NGYSSPSMRP
401 DVSSPPSSSS TATTGPPPKL CLVCSDEASG CHYGVLTCGS
441 CKVFFKRAVE GQHNYLCAGR NDCIIDKIRR KNCPACRYRK
481 CLQAGMNLEA RKTKKKIKGI QQATTGVSQE TSENPGNKTI
521 VPATLPQLTP TLVSLLEVIE PEVLYAGYDS SVPDSTWRIM
561 TTLNMLGGRQ VIAAVKWAKA IPGFRNLHLD DQMTLLQYSW
601 MFLMAFALGW RSYRQSSANL LCFAPDLIIN EQRMTLPCMY
641 DQCKHMLYVS SELHRLQVSY EEYLCMKTLL LLSSVPKDGL
681 KSQELFDEIR MTYIKELGKA IVKREGNSSQ NWQREYQLTK
721 LLDSMHEVVE NLLNYCFQTF LDKTMSIEFP EMLAEIITNQ
761 IPKYSNGNIK KLLFHQK
```

One of skill in the art can readily obtain the sequence for other human glucocorticoid receptor, human transcription intermediary factor-2 and steroid receptor coactivator-1 in the art, for example, in the NCBI database. Compositions containing a STAMP polypeptide of the invention and such other human glucocorticoid receptors, human transcription intermediary factor-2 or steroid receptor coactivator-1 can readily be made by one of skill in the art.

The invention also contemplates a method of identifying a factor that can interact with a STAMP polypeptide that involves contacting the STAMP polypeptide with a test factor and observing whether a complex forms between the STAMP polypeptide and the test factor. Formation of a complex can be identified by immunoprecipitation, western analysis, yeast two-hybrid assays and other procedures available to one of skill in the art. Factors that can be tested include, for example, receptors, coactivators, agonists, antagonists and cDNA libraries encoding segments of known and unknown proteins.

Modulating Glucocorticoid-Responsive Gene Expression

Compositions containing STAMP that may also contain any available GR coactivators, agonists, partial agonists, steroids, antisteroids and antagonists can be used to modulate glucocorticoid-responsive gene expression and glucocorticoid receptor-mediated diseases. As such, these compounds can be used to influence several systems in the body, including carbohydrate, protein and lipid metabolism, electrolyte and water balance, and the functions of the cardiovascular, kidney, central nervous, immune, skeletal muscle and other organ and tissue systems. In this regard, GR modulators are used for the treatment of diseases or conditions associated with an excess or a deficiency of steroids and/or glucocorticoids in the body. As such, they may be used to treat the following: obesity, diabetes, cardiovascular disease, hypertension, cancer, Syndrome X, depression, anxiety, glaucoma, human immunodeficiency virus (HIV) or acquired immunodeficiency syndrome (AIDS), neurodegeneration (for example, Alzheimer's disease and Parkinson's disease), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. In some embodiments, the disease or condition that can be treated by the compositions of the invention include conception (prevention or enhancement of the probability of conception), contraception, infertility, diabetes, menopause, cancer (e.g., hormone- or steroid-sensitive cancers, such as prostate and breast cancer), hypertension, and osteoporosis.

The present invention relates to methods of treating conditions and disorders such as the following: endocrine disorders (such as primary or secondary adrenocortical insufficiency; congenital adrenal hyperplasia, nonsuppurative thyroiditis and hypercalcemia associated with cancer); hormone-sensitive cancer, steroid-sensitive cancer, conception (prevention of conception or enhancement of the probability of conception), contraception, infertility, arthritis (such as osteoarthritis; psoriatic arthritis; rheumatoid arthritis; juvenile rheumatoid arthritis; ankylosing spondylitis; acute and subacute bursitis; acute nonspecific tenosynovitis; acute gouty arthritis; post-traumatic osteoarthritis; synovitis of osteoarthritis and epicondylitis); collagen diseases (such as exacerbation or as maintenance therapy in systemic lupus erythematosus, acute rheumatic carditis and systemic dermatomyositis (polymyositis)); dermatologic diseases (such as pemphigus, bullous dermatitis herpetiformis, erythema multiforme, Stevens-Johnson syndrome, exfoliative dermatitis, mycosis fungoides; psoriasis and seborrheic dermatitis); allergic states (such as control of severe or incapacitating allergic conditions intractable to adequate trials of conventional treatment, rhinitis including seasonal or perennial allergic rhinitis, asthma including bronchial asthma, contact dermatitis, atopic dermatitis, serum sickness, food allergies and drug hypersensitivity reactions); ophthalmic diseases (such as the treatment of severe acute and chronic allergic and inflammatory processes involving the eye and its adnexa, such as allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis and sympathetic ophthalmia); ameliorating or treating postmenopausal symptoms; respiratory diseases (such as chronic obstructive pulmonary disease, acute respiratory distress syndrome, symptomatic sarcoidosis, Loeffler's syndrome; berylliosis, fulminating or disseminated pulmonary tuberculosis and aspiration pneumonitis); hematologic disorders (such as idiopathic thrombocytopenic purpura, secondary thrombocytopenia, acquired (autoimmune) hemolytic anemia, erythroblastopenia (RBC anemia) and congenital (erythroid) hypoplastic anemia); neoplastic diseases (such as leukemias and lymphomas); edematous states (such as to induce a diuresis or remission of proteinuria in the nephrotic syndrome, without uremia, of the idiopathic type or that due to lupus erythematosus); gastrointestinal diseases (such as ulcerative colitis, inflammatory bowel diseases, Crohns disease and regional enteritis); tuberculosis, tuberculosis meningitis, trichinosis with neurological or myocardial involvement, immunomodulation such as graft vs. host transplant rejection, multiple sclerosis, glucocorticoid insufficiency and systemic fungal infections, in a mammal comprising administering to said mammal a therapeutically effective amount of a composition of the invention.

Cancers that can be treated by the present compositions and methods include autoimmune deficiency syndrome-associated Kaposi's sarcoma, cancer of the adrenal cortex, cancer of the cervix, cancer of the breast, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. Information regarding numerous types of cancer can be found e.g., from the American Cancer Society, or from, e.g., Wilson et al. (1991) Harrison's Principles of Internal Medicine, $12^{th}$ Edition, McGraw-Hill, Inc. Both human and veterinary uses are contemplated.

The compositions of the present invention, and pharmaceutically acceptable salts thereof, are useful to induce weight loss in mammals needing or desiring to lose weight. While not intending to limit the present invention to a specific mechanism of action, the compositions of the present invention, and salts thereof, are able to induce weight loss by a variety of mechanisms, such as appetite suppression, decreasing food intake and stimulation of the metabolic rate in peripheral tissue, thereby increasing energy expenditure. In addition, the compositions of the present invention, and salts thereof are useful to induce a more favorable partitioning of nutrients from fat to muscle tissue in mammals. Thus, while not necessarily resulting in weight loss, this increase in muscle mass may be useful in preventing or treating diseases, such as obesity and frailty. In addition, the compounds of the present invention, prodrugs and pharmaceutically acceptable salts thereof, may also be useful to increase lean meat deposition, improve lean meat to fat ratio, and trim unwanted fat from non-human animals.

Furthermore, it will be understood by those skilled in the art that the compositions and pharmaceutically acceptable salts thereof can be used in a wide variety of combination therapies to treat the conditions and diseases described above. Thus, the compositions of the present invention can be used in conjunction with (e.g., simultaneously or sequentially) other pharmaceutical agents for the treatment of the disease/conditions described herein. For example, they may be used in combination with pharmaceutical agents that treat obesity, diabetes, inflammatory disease, immunodefficiency, hypertension, cardiovascular disease, viral infection, HIV, Alzheimer's disease, Parkinson's disease, anxiety, depression, or psychosis. In combination therapy treatment, both the compositions of this invention and the other drug therapies are administered to mammals (e.g., humans, male or female) by conventional methods.

Thus, the STAMP polypeptides of the invention can be formulated into compositions containing a variety of other active and inactive agents. For example, the compositions can also contain glucocorticoid receptor agonists that are efficacious for the treatment of various inflammatory diseases. Such treatment is often accompanied by undesirable side effects such as metabolic effects, weight gain, muscle wasting, decalcification of the skeleton, osteoporosis, thinning of the skin and thinning of the skeleton. However, according to the present invention, glucocorticoid receptor modulators may be used in combination with glucocorticoid receptor agonists to minimize or reduce the incidence of these side effects, without inhibiting the efficacy of the treatment. As demonstrated by the inventors, STAMP can shift the dose response curve of steroids and glucocorticoid receptor agonists to lower concentrations of ligand, thereby reducing the dosage required for activity of such steroids and glucocorticoid receptor agonists and minimizing or eliminating their side effects.

Thus, any glucocorticoid receptor agonist may be used as an additional active agent in the STAMP compositions of the present invention. This composition can be used in the treatment of various inflammatory diseases, such as arthritis (osteo and rheumatoid), asthma, rhinitis, or immunomodulation.

Examples of additional glucocorticoid receptor modulators that can be used in the compositions of the invention include those known in the art as well as the polypeptides, compounds and other agents described herein. Examples of glucocorticoid receptor modulators known in the art include, but are not limited to, certain nonsteroidal compounds, such as 5H-chromeno[3,4-f]quinolines, which are selective modulators of steroid receptors, as disclosed in U.S. Pat. No. 5,696,127; and certain steroid compounds which possess antiglucocorticoid activity, and some of which have glucocorticoid activity, as disclosed in Published European Patent Application 0 188 396, published Jul. 23, 1986. Examples of glucocorticoid receptor agonists include prednisone (17,21-dihydroxypregnane-1,4-diene-3,11,20-trione), progesterone, prednylidene ((11β)-11,17,21-trihydroxy-16-methylenepregna-1,4-diene-3,20-dione), prednisolone ((11β)-11,17,21-trihydroxypregna-1,4-diene-3,20-dione), cortisone (17α,21-dihydroxy-4-pregnene-3,11,20-trione), dexamethasone ((11β,16α)-9-fluoro-11,17,21-trihydroxy-16-methylpregna-1,4-diene-3,20-dione), hydrocortisone (11β,17α,21-trihydroxypregn-4-ene-3,20-dione), androgen (e.g., 5α-dihydrotestosterone, testosterone and/or methyltrienolone), and/or 5H-chromeno[3,4-f]quinoline. Another highly potent glucocorticoid agonist that may be used in the compositions of the invention is deacylcortivazol. See Simons Jr. et al. (1979) Biochem. Biophys. Res. Comm. 86: 793-800.

These glucocorticoid receptor modulators and agonists will generally be administered in the form of a dosage unit at a therapeutically effective amount of such compound. For example, prednisone or an equivalent compound may be administered from about 5 to about 80 mg, depending on the condition; hydrocortisone may be administered from about 100 to about 400 mg, depending on the condition; and dexamethasone may be administered from about 4 to about 16 mg, depending on the condition. These doses are typically administered once to twice daily, and for maintenance purposes, sometimes on alternate days.

The compositions of the invention can also include antisteroids. Antisteroids are defined as compounds that block the action of agonist steroids. For example, certain dexamethasone derivatives can act as antiglucocorticoids or antiprogestins, that block or partially block the activities of glucocorticoids and progestin. See. U.S. Patent Application 20030207854.

For the treatment of Alzheimer's disease, any cholinomimetic drug, such as donepezil hydrochloride (ARICEPT™), may be used in the compositions of this invention.

For the treatment of Parkinson's disease, any anti-Parkinson's drug, such as L-dopa, bromocriptine, or selegiline, may be used in the compositions of this invention.

For the treatment of anxiety, any antianxiolytic drug, such as benzodiazepine, valium, or librium, may be used in the compositions of this invention.

For the treatment of depression, any tricyclic antidepressant such as, desipramine, or any selective serotonin reuptake inhibitor (SSRI's), such as sertraline hydrochloride or fluoxetine hydrochloride, may be used in the compositions of this invention.

For the treatment of psychosis, any typical or atypical antipsychotic drug, such as haloperidol or clozapine may be used in the compositions of this invention.

For the treatment of diabetes, any aldose reductase inhibitor may be used in the compositions of this invention. The term aldose reductase inhibitor refers to a compound, which inhibits the bioconversion of glucose to sorbitol catalyzed by the enzyme aldose reductase. Such inhibition is readily determined by those skilled in the art according to standard assays (J. Malone, Diabetes, 29:861-864, 1980, "Red Cell Sorbitol, an Indicator of Diabetic Control"). A variety of aldose reductase inhibitors are available in the art. Examples of aldose reductase inhibitors include compounds such as those disclosed and described in WO 99/43663, published Sep. 2, 1999.

Any glycogen phosphorylase inhibitor may be used in the compositions of this invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described in WO 99/43664, published Sep. 2, 1999). A variety of these compounds are described in the following published international patent applications: WO 96139384, published Dec. 12, 1996, WO 96/39385, published Dec. 12, 1996, and WO 99143663, published Sep. 2, 1999.

Any sorbitol dehydrogenase inhibitor may be used in the compositions of this invention. The term sorbitol dehydrogenase inhibitor refers to a compound that inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below. However other sorbitol dehydrogenase inhibitors are available to those skilled in the art. For example, U.S. Pat. No. 5,728,704 discloses substituted pyrimidines that inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy.

Any known, commercially marketed antidiabetic compound may be used in the compositions of this invention. A variety of such compounds are available to those skilled in the art. Examples of such compounds useful in the compositions and methods of this invention include, for example, insulin, inhaled insulin, metformin, and sulfonylureas, such as glipazide (GLUCOTROL™), glyburide (GLYNASE™, MICRONASE™) and chlorpropamide (DIABINASE™).

Any β-adrenergic agonist may be used in the compositions of this invention. β-Adrenergic agents have been categorized into $β_1$, $β_2$, and $β_3$ subtypes. Agonists of β receptors promote the activation of adenyl cyclase. Activation of $β_1$ receptors invokes increases in heart rate. Activation of $β_2$ receptors induces relaxation of smooth muscle tissue which produces a drop in blood pressure and the onset of skeletal muscle tremors. Activation of $β_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate $\beta_3$ receptors are therefore useful as anti-obesity agents. Compounds that are $\beta_3$-receptors agonists have hypoglycemic and/or anti-diabetic activity. Such activity is readily determined by those skilled in the art according to standard assays (International Patent Application, Publication No. WO 96/35671). Several $\beta_3$-adrenergic agonists are available to those skilled in the art. For example, International Patent Application, Publication No. WO 96/35671 discloses compounds, such as substituted aminopyridines, which are β-adrenergic agonists. International Patent Application, Publication No. 93/16189 discloses the use of selective $\beta_3$ receptor agonists in combination with compounds which modify eating behavior for the treatment of obesity.

Any thyromimetic antiobesity agent may be used in the compositions of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effect is readily measured by those skilled in the art according to standard assays. A variety of these compounds will be known to those skilled in the art. It is well known to one of ordinary skill in the art that selectivity of the thermogenic effect is an important requirement for a useful therapeutic agent in the treatment of, for example, obesity and related conditions.

Any eating behavior modifying compound may be used in the compositions of this invention. Compounds that modify eating behavior include anorectic agents, which are compounds that diminish the appetite. Such classes and compounds of anorectic agents are available to one of ordinary skill in the art. For example, the following are antiobesity agents: phenylpropanolamine, ephedrine, pseudoephedrine, phentermine, a Neuropeptide Y (hereinafter also referred to as "NPY") antagonist, a cholecystokinin-A (hereinafter referred to as CCK-A) agonist, a monoamine reuptake inhibitor (such as sibutramine), a sympathomimetic agent, a serotoninergic agent (such as fenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a galanin antagonist or a GI lipase inhibitor or decreaser (such as orlistat). Other antiobesity agents include phosphatase 1B inhibitors, bombesin agonists, dehydroepiandrosterone or analogs thereof, glucocorticoid receptor antagonists, orexin receptor antagonists, urocortin binding protein antagonists or glucagon-like peptide-1 (insulinotropin) agonists. A particularly preferred monoamine reuptake inhibitor is sibutramine, which can be prepared as disclosed in U.S. Pat. No. 4,929,629. Preferred serotoninergic agents include fenfluramine and fenfluramine, which can be prepared as disclosed in U.S. Pat. No. 3,198,834. A particularly preferred dopamine agonist is bromocriptine, which can be prepared as disclosed in U.S. Pat. Nos. 3,752,814 and 3,752,888. Another preferred anorectic agent is phentermine, which can be prepared as disclosed in U.S. Pat. No. 2,408,345.

Any NPY receptors antagonist may be used in the compositions of this invention. The term NPY receptors antagonist refers to compounds that interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays (such as those described in International Patent Application, Publication No. WO 99/07703). A number of NPY receptors antagonist are available to those skilled in the art. For example, International Patent Application, Publication No. WO 99107703 discloses certain 4-aminopyrrole (3,2-d) pyrimidines as neuropeptide Y receptor antagonists. International patent application, Publication No. WO 96/14307, published May 17, 1996; International patent application, Publication No. WO 96/40660, published Dec. 19, 1996; International patent application, Publication No. WO 98/03492; International patent application, Publication No. WO 98/03494; International patent application, Publication No. WO 98/03493; International patent application, Publication No. WO 96114307, published May 17, 1996; International patent application, Publication No. WO 96/40660, published Dec. 19, 1996; disclose additional compounds, such as substituted benzylamine derivatives, which are useful as neuropeptide Y receptors specific ligands.

Antibodies

The invention also contemplates antibodies that can bind to a STAMP polypeptide of the invention. In another embodiment, a disease where glucocorticoid-responsive gene expression is undesirably active can be treated by administering to a mammal an antibody that can bind to STAMP polypeptide. Such an antibody may block STAMP activity or activate STAMP. For example, the antibody can be directed against a STAMP polypeptide comprising any one of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:62, SEQ ID NO:63, SEQ ID NO:64, SEQ ID NO:70, or a combination thereof.

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector function, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. The present invention contemplates the use of any specificity of an antibody, polyclonal or monoclonal, and is not limited to antibodies that recognize and immunoreact with a specific epitope. In some embodiments, however, the antibodies of the invention may react with selected epitopes within the CID, RID or other domains of the STAMP protein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments retain some ability to selectively bind with its antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The preparation of polyclonal antibodies is well-known to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Methods of in vitro and in vivo manipulation of monoclonal antibodies are also available to those skilled in the art. For example, the monoclonal antibodies to be used in accordance with the present invention may be made by the hybridoma method first described by Kohler and Milstein, Nature 256, 495 (1975), or they may be made by recombinant methods, for example, as described in U.S. Pat. No. 4,816,567. The monoclonal antibodies for use with the present invention may also be isolated from antibody libraries using the techniques described in Clackson et al. Nature 352: 624-628 (1991), as well as in Marks et al., J. Mol Biol. 222: 581-597 (1991).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Another method for generating antibodies involves a Selected Lymphocyte Antibody Method (SLAM). The SLAM technology permits the generation, isolation and manipulation of monoclonal antibodies without the process of hybridoma generation. The methodology principally involves the growth of antibody forming cells, the physical selection of specifically selected antibody forming cells, the isolation of the genes encoding the antibody and the subsequent cloning and expression of those genes.

More specifically, an animal is immunized with a source of specific antigen. The animal can be a rabbit, mouse, rat, or any other convenient animal. This immunization may consist of purified protein, in either native or recombinant form, peptides, DNA encoding the protein of interest or cells expressing the protein of interest. After a suitable period, during which antibodies can be detected in the serum of the animal (usually weeks to months), blood, spleen or other tissues are harvested from the animal. Lymphocytes are isolated from the blood and cultured under specific conditions to generate antibody-forming cells, with antibody being secreted into the culture medium. These cells are detected by any of several means (complement mediated lysis of antigen-bearing cells, fluorescence detection or other) and then isolated using micromanipulation technology. The individual antibody forming cells are then processed for eventual single cell PCR to obtain the expressed Heavy and Light chain genes that encode the specific antibody. Once obtained and sequenced, these genes are cloned into an appropriate expression vector and recombinant, monoclonal antibody produced in a heterologous cell system. These antibodies are then purified via standard methodologies such as the use of protein A affinity columns. These types of methods are further described in Babcook, et al., Proc. Natl. Acad. Sci. (USA) 93: 7843-7848 (1996); U.S. Pat. No. 5,627,052; and PCT WO 92/02551 by Schrader.

Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998). The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the antibody is obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5 S Fab=monovalent fragments. Alternatively, an enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention further contemplates human and humanized forms of non-human (e.g. murine) antibodies. Such humanized antibodies can be chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework, sequences. These modifications are made to further refine and optimize antibody performance. In general, humanized antibodies can comprise substantially all of at least one, and typically two, variable domains, in which all or substantially all of the CDR regions correspond to those of a non-human immunoglobulin and all or substantially all of the Fv regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Inununol., 81:105-115 (1998); U.S. Pat. Nos. 4,816,567 and 6,331,415; PCT/GB84/00094; PCT/US86/02269; PCT/US89/00077; PCT/US88/02514; and WO91/09967, each of which is incorporated herein by reference in its entirety.

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or non-proteinaceous solutes. The term "isolated antibody" also includes antibodies within recombinant cells because at least one component of the antibody's natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In some embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomassie blue or, preferably, silver stain.

Expression of STAMP Nucleic Acids

Mammalian expression of STAMP sense, anti-sense, ribozyme, and siRNA nucleic acids can be accomplished as described in Dijkema et al., EMBO J. (1985) 4: 761, Gorman et al., Proc. Natl. Acad. Sci. USA (1982b) 79: 6777, Boshart et al., Cell (1985) 41: 521 and U.S. Pat. No. 4,399,216. Other features of mammalian expression can be facilitated as described in Ham and Wallace, Meth. Enz. (1979) 58: 44, Barnes and Sato, Anal. Biochem. (1980) 102: 255, U.S. Pat. Nos. 4,767,704, 4,657,866, 4,927,762, 4,560,655, WO 90/103430, WO 87/00195, and U.S. Pat. No. RE 30,985. Use of such STAMP nucleic acids can augment or inhibit the expression of STAMP polypeptides.

STAMP nucleic acids can be placed within linear or circular molecules. They can be placed within autonomously replicating molecules or within molecules without replication sequences. They can be regulated by their own or by other regulatory sequences, as is known in the art.

STAMP nucleic acids can be used in expression cassettes or gene delivery vehicles, for the purpose of delivering an mRNA or oligonucleotide (with a sequence from a native mRNA or its complement), a full-length protein, a fusion protein, a polypeptide, a ribozyme, a siRNA or a single-chain antibody, into a cell, preferably a eukaryotic cell. According to the present invention, a gene delivery vehicle can be, for example, naked plasmid DNA, a viral expression vector comprising a sense or anti-sense nucleic acid of the invention, or a sense or anti-sense nucleic acid of the invention in conjunction with a liposome or a condensing agent.

STAMP nucleic acids can be introduced into suitable host cells using a variety of techniques that are available in the art, such as transferrin-polycation-mediated DNA transfer, transfection with naked or encapsulated nucleic acids, liposome-mediated DNA transfer, intracellular transportation of DNA-coated latex beads, protoplast fusion, viral infection, electroporation, use of nucleic acid microprojectile procedures and calcium phosphate-mediated transfection.

In one embodiment of the invention, the gene delivery vehicle comprises a promoter and one of the STAMP nucleic acids disclosed herein. Preferred promoters are tissue-specific promoters and promoters that are activated by cellular proliferation, such as the thymidine kinase and thymidylate synthase promoters. Other preferred promoters include promoters that are activated by infection with a virus, such as the α- and β-interferon promoters, and promoters that can be activated by a hormone, such as estrogen. Other promoters that can be used include the Moloney virus LTR, the CMV promoter, and the mouse albumin promoter.

A gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In some embodiments, the gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91102805).

Examples of retroviruses that can be utilized include avian leukosis virus (ATCC Nos. VR-535 and VR-247), bovine leukemia virus (VR-1315), murine leukemia virus (MLV), mink-cell focus-inducing virus (Koch el al., J. Vir. 49:828, 1984; and Oliff et al., J. Vir. 48:542, 1983), murine sarcoma virus (ATCC Nos. VR-844, 45010 and 45016), reticuloendotheliosis virus (ATCC Nos. VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Strains of MLV from which recombinant retroviruses can be generated include 4070A and 1504A (Hartley and Rowe, J. Vir. 19:19, 1976), Abelson (ATCC No. VR-999), Friend (ATCC No. VR-245), Graffi (Ru et al., J. Vir. 67:4722, 1993; and Yantchev Neopksma 26:397, 1979), Gross (ATCC No. VR-590), Kirsten (Albino et al., J. Exp. Med. 164:1710, 1986), Harvey sarcoma virus (Manly el al., J. Vir. 62:3540, 1988; and Albino et al., J. Exp. Med. 164:1710, 1986) and Rauscher (ATCC No. VR-998), and Moloney MLV (ATCC No. VR-190). A non-mouse retrovirus that can be used is Rous sarcoma virus, for example, Bratislava (Manly et al., J. Vir. 62:3540, 1988; and Albino et al., J. Exp. Med. 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., Neoplasma 27:159, 1980), Engelbreth-Holm (Laurent et al., Biochem Biophys Acta 908:241, 1987), Harris, Prague (e.g., ATCC Nos. VR-772, and 45033), or Schmidt-Ruppin (e.g. ATCC Nos. VR-724, VR-725, VR-354) viruses.

Any of the above retroviruses can be readily utilized in order to assemble or construct retroviral gene delivery vehicles given the disclosure provided herein and standard recombinant techniques (e.g., Sambrook et al., Molecular Cloning: A Laboratory Manual, $2^{nd}$ Edition (1989), Sambrook et al., Molecular Cloning: A Laboratory Manual, $3^{rd}$ Edition (2001), and Kunkle, Proc. Natl. Acad. Sci. U.S.A. 82:488, 1985). Portions of retroviral expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 071800,921, filed Nov. 29, 1991).

Recombinant retroviruses can be produced that direct the site-specific integration of the recombinant retroviral genome into specific regions of the host cell DNA. Such site-specific integration is useful for mutating the endogenous STAMP gene. Site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see WO 92/05266) and used to create producer cell lines (also termed vector cell lines or "VCLs") for production of recombinant viral particles. In preferred embodiments of the present invention, packaging cell lines are made from human (e.g., HT1080 cells) or mink parent cell lines, thereby allowing production of recombinant retroviral gene delivery vehicles that are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines. Similarly, adenovirus gene delivery vehicles can also be readily prepared and utilized given the disclosure provided herein (see also Berkner, Biotechniques 6:616-627, 1988, and Rosenfeld et al., Science 252:431-434, 1991, WO 93/07283, WO 93/06223, and WO 93/07282).

A gene delivery vehicle can also be a recombinant adenoviral gene delivery vehicle. Such vehicles can be readily prepared and utilized given the disclosure provided herein (see also Berkner, Biotechniques 6:616, 1988, and Rosenfeld et al., Science 252:431, 1991, WO 93/07283, WO 93/06223, and WO 93/07282). Adeno-associated viral gene delivery vehicles can also be constructed and used to deliver proteins or nucleic acids of the invention to cells in vitro or in vivo. The use of adeno-associated viral gene delivery vehicles in vitro is described in Chatteijee et al., Science 258: 1485-1488 (1992), Walsh et al., Proc. Nat'l. Acad. Sci. 89: 7257-7261 (1992), Walsh et al., J. Clin. Invest. 94: 1440-1448 (1994), Flotte et al., J. Biol. Chem. 268: 3781-3790 (1993), Ponnazhagan et al., J. Exp. Med. 179: 733-738 (1994), Miller et al., Proc. Nat'l Acad. Sci. 91: 10183-10187 (1994), Einerhand et al., Gene Ther. 2: 336-343 (1995), Luo et al., Exp. Hematol. 23: 1261-1267 (1995), and Zhou et al., Gene Therapy 3: 223-229 (1996). In vivo use of these vehicles is described in Flotte et al., Proc. Nat'l Acad. Sci. 90: 10613-10617(1993), and Kaplitt et al., Nature Genet. 8:148-153 (1994).

In another embodiment of the invention, a gene delivery vehicle is derived from a togavirus. Such togaviruses include alphaviruses such as those described in U.S. Ser. No. 08/405, 627, filed Mar. 15, 1995, WO 95/07994. Alpha viruses, including Sindbis and ELVS viruses can be gene delivery vehicles for nucleic acids of the invention. Alpha viruses are described in WO 94/21792, WO 92/10578 and WO 95/07994. Several different alphavirus gene delivery vehicle systems can be constructed and used to deliver nucleic acids to a cell according to the present invention. Representative examples of such systems include those described in U.S. Pat. Nos.

5,091,309 and 5,217,879. Preferred alphavirus gene delivery vehicles for use in the present invention include those that are described in WO 95/07994.

The recombinant viral vehicle can also be a recombinant alphavirus viral vehicle based on a Sindbis virus. Sindbis constructs, as well as numerous similar constructs, can be readily prepared. Sindbis viral gene delivery vehicles typically comprise a 5' sequence capable of initiating Sindbis virus transcription, a nucleotide sequence encoding Sindbis non-structural proteins, a viral junction region inactivated so as to prevent fragment transcription, and a Sindbis RNA polymerase recognition sequence. Optionally, the viral junction region can be modified so that nucleic acid transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region that has been inactivated in order to prevent transcription of the nucleic acid and a second viral junction region that has been modified such that nucleic acid transcription is reduced. An alphavirus-derived vehicle can also include a 5' promoter capable of initiating synthesis of viral RNA from cDNA and a 3' sequence that controls transcription termination.

Other recombinant togaviral gene delivery vehicles that can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578.

Other viral gene delivery vehicles suitable for use in the present invention include, for example, those derived from poliovirus (Evans et al., Nature 339:385, 1989, and Sabin et al., J. Biol. Standardization 1:115, 1973) (ATCC VR-58); rhinovirus (Arnold et al., J. Cell. Biochem. L401, 1990) (ATCC VR-1110); pox viruses, such as canary pox virus or vaccinia virus (Fisher-Hoch et al., PROC. NATL. ACAD. SCI. U.S.A. 86:317, 1989; Flexner et al., Ann. N.Y. Acad. Sci. 569:86, 1989; Flexner et al., Vaccine 8:17, 1990; U.S. Pat. Nos. 4,603,112 and 4,769,330; WO 89/01973) (ATCC VR-111; ATCC VR-2010); SV40 (Mulligan et al., Nature 277:108, 1979) (ATCC VR-305), (Madzak et al., J. Gen. Vir. 73:1533, 1992); influenza virus (Luytjes et al., Cell 59:1107, 1989; McMicheal et al., The New England Journal of Medicine 309:13, 1983; and Yap et al., Nature 273:238, 1978) (ATCC VR-797); parvovirus such as adeno-associated virus (Samulski et al., J. Vir. 63:3822, 1989, and Mendelson et al., Virology 166:154, 1988) (ATCC VR-645); herpes simplex virus (Kit et al., Adv. Exp. Med. Biol. 215:219, 1989) (ATCC VR-977; ATCC VR-260); Nature 277: 108, 1979); human immunodeficiency virus (EPO 386,882, Buchschacher et al., J. Vir. 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., Proc. Soc. Exp. Biol. Med. 121:190, 1966) (ATCC VR-740).

A nucleic acid of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, a nucleic acid is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell that has internalized the liposome, thereby releasing its contents into the cytoplasm. Prior to interaction with the surface of a cell, however, the liposome membrane acts as a relatively impermeable barrier that sequesters and protects its contents, for example, from degradative enzymes. Additionally, because a liposome is a synthetic structure, specially designed liposomes can be produced that incorporate desirable features. See Stryer, Biochemistry, pp. 236-240, 1975 (W. H. Freeman, San Francisco, Calif.); Szoka et al., Biochim. Biophys. Acta 600:1, 1980; Bayer et al., Biochim. Biophys. Acta. 550:464, 1979; Rivnay et al., Meth. Enzymol. 149:119, 1987; Wang et al., PROC. NATL. ACAD. SCI. U.S.A. 84: 7851, 1987, Plant et al., Anal. Biochem. 176:420, 1989, and U.S. Pat. No. 4,762,915. Liposomes can encapsulate a variety of nucleic acid molecules including DNA, RNA, plasmids, and expression constructs comprising nucleic acids such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., Proc. Natl. Acad. Sci. USA 84:7413-7416, 1987), mRNA (Malone et al., Proc. Natl. Acad. Sci. USA 86:6077-6081, 1989), and purified transcription factors (Debs et al, J. Biol. Chem. 265:10189-10192, 1990), in functional form. Cationic liposomes are readily available. For example, N[1-2,3-dioleyloxy)propyl]-N,N,N-triethylammonium (DOTMA) liposomes are available under the trademark Lipofectin™, from GIBCO BRL, Grand Island, N.Y. See also Feigner et al., Proc. Natl. Acad. Sci. US491: 5148-5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA 75:4194-4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE) and the like. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512-527; Szoka et al., Proc. Natl. Acad. Sci. USA 87:3410-3414, 1990; Papahadjopoulos et al., Biochim. Biophys. Acta 394:483, 1975; Wilson et al., Cell 17:77, 1979; Deamer and Bangham, Biochim. Biophys. Acta 443: 629, 1976; Ostro et al., Biochem. Biophys. Res. Commun. 76:836, 1977; Fraley et al., Proc. Natl. Acad Sci. USA 76:3348, 1979; Enoch and Strittmatter, Proc. Natl. Acad Sci. USA 76:145, 1979; Fraley et al., J. Biol. Chem. 255:10431, 1980; Szoka and Papahadjopoulos, Proc. Natl. Acad. Sci. USA 75:145, 1979; and Schaefer-Ridder et al., Science 215: 166, 1982.

In addition, lipoproteins can be included with a nucleic acid of the invention for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of nucleic acids to cells expressing lipoprotein receptors. Preferably, if lipoproteins are included with a nucleic acid, no other targeting ligand is included in the composition.

Receptor-mediated targeted delivery of STAMP nucleic acids to specific tissues can also be used. Receptor-mediated DNA delivery techniques are described in, for example, Findeis et al. (1993), Trends in Biotechnol. 11, 202-05; Chiou et al. (1994), GENE THERAPEUTICS: METHODS AND APPLICATIONS OF DIRECT GENE TRANSFER (J. A. Wolff, ed.); Wu & Wu (1988), J. Biol. Chem. 263, 621-24; Wu et al. (1994), J. Biol. Chem. 269, 542-46; Zenke et al. (1990), Proc. Natl. Acad. Sci. U.S.A. 87, 3655-59; Wu et al. (1991), J. Biol. Chem. 266, 338-42.

In another embodiment, naked nucleic acid molecules are used as gene delivery vehicles, as described in WO 90/11092 and U.S. Pat. No. 5,580,859. Such gene delivery vehicles can be either DNA or RNA and, in certain embodiments, are linked to killed adenovirus. Curiel et al., Hum. Gene. Ther. 3:147-154, 1992. Other suitable vehicles include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad Sci. 84:7851-7855, 1987) and microprojectiles (Williams et al., Proc. Natl. Acad. Sci. 88:2726-2730, 1991).

One can increase the efficiency of naked nucleic acid uptake into cells by coating the nucleic acids onto biodegradable latex beads. This approach takes advantage of the observation that latex beads, when incubated with cells in culture, are efficiently transported and concentrated in the perinuclear region of the cells. The beads will then be transported into cells when injected into muscle. Nucleic acid-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of nucleic acids into the cytoplasm.

STAMP-specific siRNA, ribozymes and anti-sense nucleic acids can be introduced into cells in a similar manner. The nucleic acid construct encoding the siRNA, ribozyme or anti-sense nucleic acid may include transcriptional regulatory elements, such as a promoter element, an enhancer or UAS element, and a transcriptional terminator signal, for controlling transcription of the ribozyme in the cells. Mechanical methods, such as microinjection, liposome-mediated transfection, electroporation, or calcium phosphate precipitation, can be used to introduce the siRNA, ribozyme or anti-sense DNA construct into cells whose division it is desired to decrease, as described above. Alternatively, if it is desired that the cells stably retain the DNA construct, the DNA construct can be supplied on a plasmid and maintained as a separate element or integrated into the genome of the cells, as is known in the art.

Expression of an endogenous STAMP gene in a cell can also be altered by introducing in frame with the endogenous STAMP gene a DNA construct comprising a STAMP targeting sequence, a regulatory sequence, an exon, and an unpaired splice donor site by homologous recombination, such that a homologous recombinant cell comprising the DNA construct is formed. The new transcription unit can be used to turn the STAMP gene on or off as desired. This method of affecting endogenous gene expression is taught in U.S. Pat. No. 5,641,670.

Integration of a delivered STAMP nucleic acid into the genome of a cell line or tissue can be monitored by any means known in the art. For example, Southern blotting of the delivered STAMP nucleic acid can be performed. A change in the size of the fragments of a delivered nucleic acid indicates integration. Replication of a delivered nucleic acid can be monitored inter alia by detecting incorporation of labeled nucleotides combined with hybridization to a STAMP probe. Expression of a STAMP nucleic acid can be monitored by detecting production of STAMP mRNA that hybridizes to the delivered nucleic acid or by detecting STAMP protein. STAMP protein can be detected immunologically.

Compositions

The STAMP polypeptides and antibodies of the invention, including their salts, as well as the STAMP siRNA, ribozymes, sense and anti-sense nucleic acids are administered to modulate glucocorticoid responsive gene expression, modulate STAMP activity or to achieve a reduction in at least one symptom associated with a condition, indication, infection or disease associated with inappropriate glucocorticoid-responsive gene expression. Other agents can be included as described herein such as glucocorticoid receptors, glucocorticoid agonists, glucocorticoid antagonists and/or glucocorticoid coactivators.

To achieve the desired effect(s), the STAMP polypeptide, nucleic acid, antibody, and combinations with other agents thereof, may be administered as single or divided dosages. For example, STAMP polypeptides and antibodies can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the polypeptide or antibody chosen, the disease, the weight, the physical condition, the health, the age of the mammal, whether prevention or treatment is to be achieved, and if the polypeptide or antibody is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the polypeptides, nucleic acids and antibodies of the invention may be essentially continuous over a preselected period of time or may be in a series of spaced doses. Both local and systemic administration is contemplated.

To prepare the composition, polypeptides, nucleic acids and antibodies are synthesized or otherwise obtained, purified as necessary or desired and then lyophilized and stabilized. The polypeptide, nucleic acid or antibody can then be adjusted to the appropriate concentration, and optionally combined with other agents. The absolute weight of a given polypeptide, nucleic acid or antibody included in a unit dose can vary widely. For example, about 0.01 to about 2 g, or about 0.1 to about 500 mg, of at least one polypeptide, nucleic acid or antibody of the invention, or a plurality of polypeptides, nucleic acids and antibodies specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the polypeptides, nucleic acids or antibodies of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic polypeptides, nucleic acids or antibodies of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste. Orally administered therapeutic agents of the invention can also be formulated for sustained release, e.g., the therapeutic agents can be coated, micro-encapsulated, or otherwise placed within a sustained delivery device. The total active ingredients in such formulations comprise from 0.001 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic agents of the invention can be prepared by procedures known in the art using well-known and readily available ingredients. For example, the therapeutic agents can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more therapeutic agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active polypeptides, nucleic acids or antibodies and other ingredients may form suspensions, solutions, or emulsions in oily or aqueous vehicles, and may contain formulatory agents such as suspending, stabilizing and/or dispersing agents. Alternatively, the active polypeptides, nucleic acids or antibodies and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the polypeptides or antibodies are well suited to formulation as sustained release dosage forms and the like. The formulations can be so constituted that they release the therapeutic agents, for example, in a particular part of the intestinal or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the polypeptide or antibody can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The therapeutic agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.001% to 95% of the total weight of the formulation, and typically 0.01-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agents may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The therapeutic agents of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid polypeptide, nucleic acid or antibody particles that are not dissolved or suspended in a liquid are also useful in the practice of the present invention. Polypeptides, nucleic acids or antibodies of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, antimicrobial agents, bronchodilators and the like, whether for the conditions described or some other condition.

The present invention further pertains to a packaged pharmaceutical composition for modulating glucocorticoid responsive gene expression such as a kit or other container. The kit or container holds a therapeutically effective amount of a pharmaceutical composition for modulating glucocorticoid responsive gene expression and instructions for using the pharmaceutical composition for modulating glucocorticoid responsive gene expression. The pharmaceutical composition includes at least one STAMP polypeptide, siRNA, ribozyme, anti-sense nucleic acid or antibody of the present invention, in a therapeutically effective amount such that glucocorticoid responsive gene expression is modulated. The composition can also contain a glucocorticoid receptor, a glucocorticoid agonist, a glucocorticoid antagonist and/or a glucocorticoid coactivator.

In another embodiment, the invention provides a packaged pharmaceutical composition for modulating STAMP activity. The kit or container holds a therapeutically effective amount of a pharmaceutical composition for modulating STAMP activity and instructions for using the pharmaceutical composition for modulating STAMP activity. The pharmaceutical composition includes at least one siRNA, ribozyme, anti-sense nucleic acid or antibody of the present invention, in a therapeutically effective amount such that STAMP activity is modulated.

The invention will be further described by reference to the following detailed examples, which are given for illustration of the invention, and are not intended to be limiting thereof.

EXAMPLE 1

Materials and Methods

This Example illustrates some of the materials and methods used for demonstrating the utility of the compositions and methods of the invention.

Unless otherwise indicated, all operations were performed at 0° C.

Chemicals

Dexamethasone (Dex) and phorbol 12-myristate 13-acetate (PMA) were purchased from Sigma. Dexamethasone-21-mesylate (Dex-Mes) (Simons Jr. et al., 1980, J. Org. Chem., 45, 3084-3088) and Dexamethasone-oxetanone (Dex-Ox) (Pons and Simons Jr., 1981, J. Org. Chem., 46, 3262-3264) were synthesized as described. [$^{35}$S]methionine and [$^{32}$P]dATP were from Amersham. Restriction enzymes and DNA polymerase were obtained from New England Biolabs, Amersham Biosciences, or Promega.

Antibodies

Anti-HA mouse monoclonal antibody (Roche), anti-FLAG mouse monoclonal antibody (Sigma), anti-GR monoclonal antibody (BUBR-2; Affinity BioReagents), and mouse monoclonal anti-GAL DBD and anti-VP16 antibodies (Santa Cruz Biotechnology) are commercially available.

Plasmids and STAMP Cloning

GR, GREtkLUC, TIF2, TIF2.4, TIF2.4m123, SRC1, SRC1-1139C, VP16-GR, pBAL-GR, GST-TIF2.4, GAL-TIF2.4, GRIP (HA-GRIP) have been described in He et al. (2002) J. Biol. Chem. 277, 49256-49266. VP16 chimeras of full length androgen, estrogen (α and β), thyroid (β), and retinoid (α) receptors are described in Chang et al. (1999) Mol. Cell. Biol 19:8226-39. KIAA0998 plasmid was donated by Takahiro Nagase (Kazusa DNA Research Institute, Japan). AP-1-Luc (Inez Rogatsky, UCSF Medical School, San Francisco, Calif.) and AR, AREtkLUC, VP16/PPARγ, and VP16/RXRα (Kai Ge, NIDDK, NIH) were gifts. pSos-TIF2.4 was constructed by inserting the NcoI/NotI fragment of Gal-TIF2.4 into pSos (Stratagene). Full length STAMP was constructed by assembling the BamHI/XbaI fragment of KIAA0998 clone (Japanese Kazusa DNA Institute) with the EcoRV/BamHI fragment of IMAGE clone 3632160 (Open Biosystems) and inserting the product into the EcoRV/XbaI sites of pCMV-Sport6 (Invitrogen).

pSos-TIF2.4 was constructed by inserting the NcoI/NotI fragment of Gal-TIF2.4 into pSos (Stratagene).

Full length STAMP was constructed by assembling the BamHI/XbaI fragment of KIAA0998 clone (Japanese Kazusa DNA Institute) with the EcoRV/BamHI fragment of IMAGE clone 3632160 (Open Biosystems) and inserting the product into the EcoRV/XbaI sites of pCMV-Sport6 (Invitrogen). The following primers were used to construct different fragments of STAMP or other constructs:

```
STAMP 3' PRIMER 2:
                                        (SEQ ID NO: 45)
5'-GCT CTA GAT GCA CCC AGG AGT GGT GAA CAG G-3'.

STAMP 5' PRIMER 2:
                                        (SEQ ID NO: 46)
5'-AAG ATG AGA CAG GAA TCT GTG CC-3'.
```

-continued

220F:
(SEQ ID NO: 47)
5'-TAC GAT ATC TGA TGG CCC GGG ACC TGG AGG AAA C-3'.

525R:
(SEQ ID NO: 48)
5'-AGT AAG AAG GGC TTC AGG-3'.

Xb2092R:
(SEQ ID NO: 49)
5'-CGT CTA GAC TAC CAA AGC TGT CAA TGA GGG TG-3'.

ER2093F:
(SEQ ID NO: 50)
5'-GGA ATT CGA AAA TAC ACC CAA AGA AAA TTC C-3'.

Xb2729R:
(SEQ ID NO: 51)
5'-GCT CTA GAC ACC TTT TGC CCC ACT ATC AGA A-3'.

ER2728F:
(SEQ ID NO: 52)
5'-GGA ATT CGA TCA CCC TGA GAC TAT AAT GG-3'.

Xb3091R:
(SEQ ID NO: 53)
5'-CGT CTA GAG GCC AGT AGG GCT TGG GAT GTT C-3'.

ER3091F:
(SEQ ID NO: 54)
5'-GGA ATT CCT GCC ACG CTG TCG ATC AGG AAG-3'.

ER3605F:
(SEQ ID NO: 55)
5'-GGA ATT CAC AGG GGT GGT CCC CCA GCA C-3'.

Xb3605R:
(SEQ ID NO: 56)
5'-CGT CTA GAT AGC CTG GCT GTA CAC GTT GTT TTC-3'.

TIF2-1140F:
(SEQ ID NO: 57)
5'-GGA ATT CGC ACA AAT GGC CCA GGG TAG C-3'.

TIF2-1464R:
(SEQ ID NO: 58)
5'-CGG GAT CCT CAG CAA TAT TTC CGT GTT GTG TC-3'.

HA-pSG5-STAMP (HA/STAMP) was constructed by joining the EcoRV/BamHI fragment of the 5' STAMP PCR product of 220F and 525R primers with the BamHI/NotI fragment of KIAA0998 followed by insertion into the EcoRV/NotI site of a modified HA-pSG5. The modified HA-pSG5 was prepared by inserting the annealed double-strand oligonucleotide (GAA TTC CCG GGA TAT CGT CGA CCC ACG CGT CCG GGG CGG CCG CTC TAG AGT ATC CCT CGA GGA TCC (SEQ ID NO:59) into the EcoRI/BamHI Sites of HA-pSG5 (from Mike Stallcup, USC, Los Angeles, Calif.), thus introducing new EcoRV and NotI Sites.

pFlag/STAMP (Flag/STAMP) was constructed by inserting the EcoRV/XbaI fragment of HA/STAMP into pFlag-CMV2 (Sigma).

GAL/STAMP(623-834) (Gal/6-6CL1) and VP16/6-6CL1 were constructed by inserting the 1.2 Kb EcoRI fragment of the original 6-6CL1 clone from the yeast library screening into the PM and VP16 plasmids (Clontech) respectively.

GAL/STAMP(N623): the PCR amplified fragment prepared with 220F and Xb2092R primers was then cut and insert into the EcoRV/XbaI sites of PM plasmid.

GAL/STAMP(N834): the PCR amplified fragment prepared with 220F and Xb2729R primers was then cut and inserted into the EcoRV/XbaI sites of PM plasmid.

GAL/STAMP(834C): the PCR amplified fragment prepared with ER2728F and STAMP 3' primer 2 was then cut and inserted into the EcoR1/XbaI sites of PM plasmid.

GAL/STAMP(1127C): the PCR amplified fragment prepared with ER3605F and STAMP 3' primer 2 was then cut and inserted into the EcoR1/XbaI sites of PM plasmid.

GAL/STAMP(834-956): the PCR amplified fragment prepared with ER2728F and Xb3091R primers was then cut and inserted into the EcoR1/XbaI sites of PM plasmid.

GAL/STAMP(956-1127): the PCR amplified fragment prepared with ER3091F and Xb3605R primers were then cut and inserted into the EcoR1+XbaI sites of PM plasmid.

GST/STAMP(956C): the PCR amplified fragment prepared with ER3091F and STAMP 3' primers 2 was then cut and inserted into the EcoR1/XhoI sites of pGEX6p1 (Amersham Pharmacia).

VP16/SRC(1139C) was constructed by inserting the EcoRI/XbaI fragment of SRC1-1139C into VP16. VP16/TIF2(1140C) was constructed by inserting into VP16 the EcoR1/BamHI fragment from the PCR product of TIF2 with the TIF2-1140F and TIF2-1464R primers.

Cell Culture, Transient Transfection and Reporter Analysis

The culturing and transiently transfection of CV-1 cells was performed generally as described in He et al. (2002) J. Biol. Chem. 277, 49256-49266 or with some modification of the procedures described in Rogatsky et al. (2002) Proc. Natl. Acad. Sci. U. S. A. 99, 16701-16706. Triplicate samples of U2OS.rGR cells were seeded into 24-well plates in DMEM/10% FBS at 20,000 cells per well and transfected the following day in FBS-free DMEM by using 0.8 µl of Lipofectamine and 1.6 µl of PLUS reagent (Invitrogen) per well according to the manufacturer's instructions. The total transfected DNA was adjusted to 150 ng/well of a 24-well plate with pBluescriptII SK$^+$ (Stratagene). The molar amount of plasmids expressing different protein constructs was kept constant with added empty plasmid or plasmid expressing human serum albumin (Wang et al., Mol. Endocrinol. 18: 1376-95 (2004)). phRG-TK Renilla (Promega) (10 ng/well of a 24-well plate) was included as an internal control. After transfection (3 h), cells were re-fed with DMEM/10% FBS, allowed to recover for 3 h, and re-fed with DMEM/10% FBS containing appropriate hormone dilutions. Twelve hours later, the cells were lysed and assayed for reporter gene activity using the Dual Luciferase Assay reagents according to manufacturer's instruction (Promega, Madison, Wis.). Luciferase activity was measured by an EG&G Berthhold's luminometer (Microlumat LB 96P). The data were normalized either for total protein or Renilla null luciferase activity.

Yeast Sos-Ras Two-hybrid Library Screen

The yeast Sos-Recruitment two-hybrid system (Cyto Trap Vector Kit) and the Human Fetal Brain Cyto Trap Plasmid cDNA Library were purchased from Stratagene and employed according to the manufacturer's instructions. Thus, about 50 µg of pSos bait construct (pSos-TIF2.4) and 50 µg pMyr cDNA plasmid library (Statagene) were cotransformed into 10 ml of cdc25H yeast competent cells, spread onto forty 100 mm plates of SD/glu (-UL), and grown for 2-4 days at 25° C. Colonies were replica plated onto SD/gal (-UL) plates and grown for 6 days at 37 C. Candidate "interactor" colonies were selected and "patched" onto SD/glu (-UL) plates, grown for 2 days at 25° C. for Gal repression. These colonies were "repatched" onto two serial interaction plates for 4 days at 37° C.: one with SD/glu (-UL) and the other with SD/gal (-UL). Those colonies that grew on SD/gal (-UL), but not on SD/glu (-UL), plates were selected for further study. The cDNA plasmid from these putative colonies was isolated and cotransformed with bait or empty pSos plasmid into cdc25H yeast cells to see whether the candidate cDNA clone specifically interacted with the bait in yeast.

mRNA, Total RNA Extraction and RT-PCR

Human Testis Poly A+ RNA was purchased from BD Clontech. CV-1 cell total RNA was prepared by growing CV-1 cells to confluence in 60 mm dishes for 2 days, lysing the cells with TRIzol (Invitrogen) Reagent, and extracting the total RNA according to the manufacturer's instructions. First-Strand cDNA was synthesized by SuperScript II RNase H-Reverse Transcriptase (Invitrogen). As suggested by the manufacturer, 5 µg of total CV-1 RNA or 0.5 µg human testis mRNA was mixed with 500 ng Oligo (dT)12-18 (Invitrogen), 1 µl 10 mM dNTP, 2 µl 0.1M DTT, 4 µl 5× buffer, 1 µl RNaseOUT Ribonuclease Inhibitor (Invitrogen), 1 µl (200U) SuperScript II Transcriptase at 42° C. for 50 min. PCR was performed with STAMP 5' primer 2 and 3' primer 2 and PfuUltra High-Fidelity DNA Polymerase (Stratagene) according to the manufacturer's instructions to amplify the full length STAMP.

Northern Blots

STAMP(2093-2426, SEQ ID NO:60) probe was prepared by cutting the original 6-6CL1 clone with EcoR1/Sal1 and purifying the 300 bp fragment from an agarose (2%) gel. The probe (along with a control β-actin probe from BD Clontech) was labeled with [$^{32}$P]dATP using Prime-a-Gene Labeling System (Promega) according to the manufacturer's instructions. Multiple Tissue Northern Blot (BD Clontech) membranes were prehybridized in 5 ml ExpressHyb Solution at 68° C. for 30 min according to the manufacturer's instructions. The ExpressHyb Solution was replaced with fresh solution containing denatured radio-labeled probe and the membrane was incubated at 68° C. for 1 hr, rinsed in Wash Solution 1 several times at room temperature, washed in Wash Solution 2 for 40 min at 50° C., and subjected to radio-autography at −70° C.

Mammalian Two-hybrid Assays

These assays were conducted as described (He et al., 2002). In particular, the recommended procedure for the Mammalian Matchmaker two-hybrid assay kit (Clontech) was modified slightly by changing from a chloramphenicol acetyltransferase reporter to a Luciferase Reporter pFRLuc (Stratagene), which is under the control of five repeats of the upstream activating sequence for the binding of GAL4.

Bacterial Expression of Proteins

The pGEX series of plasmids were transformed into *Escherichia coli* (BL21; Amersham Biosciences) according to the manufacturer's recommendations. A single colony was picked and inoculated into 3 ml of LB broth with 100 ng/ml ampicillin. After overnight culture, 1 ml of bacterial culture was diluted into 50 ml of LB broth containing 100 ng/ml ampicillin, shaken at 37° C. for 2 hr, adjusted to 0.1 mM isopropyl-1-thio-D-galactopyranoside (IPTG), and shaken at 37° C. for another 3 hr. The cells were harvested by centrifugation, washed once with phosphate-buffered saline, resuspended in 10 ml of phosphate-buffered saline, and sonicated for 30 cycles at 30% of maximum power. The supernatant was collected for use after centrifugation (5000×g for 20 min).

In Vitro Transcription and Translation Assays

Template DNA plasmids (1 µg), 40 µl of Promega TNT (SP6) quick coupled transcription/translation system master mixture, and 2 µl of [$^{35}$S]methionine (Amersham Biosciences) were brought up to a total volume of 50 µl with H$_2$O and incubated at 30° C. for 90 min according to the manufacturer's (Promega) recommendations. If hormone stimulation is needed, hormones (Dex, etc) were added into the transcription-translation reaction during the 30° C. incubation to both increase the stability of the synthesized GR and to cause activation of the GR-steroid complexes.

Pull-down Assays

These assays were conducted generally as described (He et al., 2002). Sonicated bacterial lysates (1 ml) containing overexpressed GST, GST/TIF2.4, or GST/STAMP-956C were incubated with 160 µl of glutathione-Sepharose 4B beads for 1 hr at 0° C. The mixture was centrifuged (12,000×g), the supernatant was discarded, and the pellet was washed with phosphate-buffered saline (3×1 ml). Each 20-µl sample of immobilized GST or GST-chimera was then incubated overnight with 10 µl of $^{35}$S-labeled in vitro translation product. The matrix was washed with phosphate-buffered saline (4×1 ml). The immobilized proteins were removed from the beads by heating at 90° C. for 5 min in 20 µl of 2×SDS loading buffer. The proteins were separated on 8-10% SDS-PAGE gels and detected by radio-autoradiography.

Immunoprecipitation Assays

Immunoprecipitations were conducted as generally described in Wang et al. (2004) Mol. Endocrinol. 18: 1476-95, with slight modifications. The day before transfection, Cos-7 cells were seeded into 150 mm dishes at 200,000 cells per dish containing 20 ml of media. On the next day, about 30 µg of DNA/dish was transfected with 60 µl of FuGene reagent. After 2 days growth, cells were treated with EtOH±Dex, washed once with 20 ml PBS 2 hr later, lysed for 5 min at room temperature with 1.6 ml CytoBuster Protein Extraction Reagent (Novagen) containing protease inhibitor cocktail (Roche) per 150 mm dish, collected with a cell scraper, and centrifuged for 5 min at 16,000×g (4° C.). Aliquots (700 µl) of supernatant were incubated on a roller drum (3 rpm) with either 50 µl of HA-matrix (Roche) (overnight at 4° C.) or 80 µl or 50% slurry protein-G (Amersham Pharmacia) (4° C. for 1 hr) and then centrifuged for 1 min at 13,000 rpm (4° C.). The supernatant was incubated with 10 µl of antibody for 1 hr (4° C. on a roller drum) and then overnight at 4° C. with 70µ of protein-G. On the next day, the antibody complexes were centrifuged (1 min/13,000 rpm (16,000×g) at 4° C.), washed 3 times with 1 ml lysis buffer (50 mM Tris, pH 7.5; 150 mM NaCl; 0.1% NP-40), extracted with 20 µl of 2×SDS-loading buffer (95° C. for 3 min), and separated by gel electrophoresis (8-10% SDS-PAGE).

Immunocytochemistry

Cells were cultured in phenol-red free medium with 10% charcoal/dextran-stripped fetal bovine serum and transiently transfected in 2-4 chambers per slide (Nalge Nunc). Twenty four to 48 hrs after transfection, the cells were treated with steroid (some controls received no steroid), washed with 1 ml cold PBS and fixed with 1 ml of freshly prepared 4% paraformaldehyde (PFA) for 20 min at room temperature. The cells were washed with PBS (5 min), treated with 1 ml of 100% methanol (10 min), washed with PBS (10 min) and treated with 1 ml of blocking buffer (1×PBS, 0.1% Tween 20, 3% BSA) for 30 min, all at room temperature. After incubation with 250 µl of the first antibody in blocking buffer (room temperature for 2 hrs), the cells were washed twice with PBS+0.05% Tween 20 (each for 10 min) and then treated with 250 µl of the fluorescence-coupled second antibody (anti-mouse; Jackson ImmunoResearch) in blocking buffer (room temperature for 1 hr in the dark) before being washed (1 ml of PBS+0.05% Tween 20, 10 min) and treated with 1 µg/ml of 4,6-diamidino-2-phenyindole (DAPI from Sigma) in PBS+

0.05% Tween 20 (5 min in the dark). The cells were washed (PBS+0.05% Tween 20, 10 min) before being examined with a fluorescent microscope.

ChIP Assays

The basic method of Ma et al. (Ma et al. (2003) Methods Enzymol. 364: 284-2966, was used with modifications. Two days before harvest, U2OS.rGR cells were seeded into 150 mm dishes at 3,000,000 cells per dish in phenol-red free medium with 10% charcoal/dextran-stripped fetal bovine serum. Each dish was transfected on the next day with 15 µg HA-STAMP and 60 µl Liopfectamine. On the third day, after brief ligand treatment, formaldehyde (37%) was added directly into the medium to a final concentration of 1% (37° C., 10 min), which was followed by glycine to a final concentration of 0.125 M (room temperature, 5 min with shaking). Cells were washed with (4° C.) cold PBS twice and harvested by scraping into 5 ml of cold (4° C.) PBS with a protease inhibitor cocktail (Roche). After centrifuge (1200×g, 10 min), the cell pellet was resuspended in 1 ml hypotonic buffer (0° C., 10 min) and lysed by passing through a #25 gauge needle five times. The nuclei are collected by centrifugation (15,000×g, 10 min) and resuspended in 250 µl of nuclear lysis buffer per dish (0° C., 10 min). The nuclear pellet is sonicated with a Fisher Scientific Ultrasonic Dismembrator (model 500) (3-5 pulses of 15 s pulse on, 45 s pulse off, 25% power). After centrifugation (15,000×g, 10 min), 100 µl of supernatant is diluted into 1 ml of IP dilution buffer and treated with 20 µl pre-blocked protein G beads (Amersham Pharmacia) with gentle mixing (4° C., 1 hr on a rotating drum at 4 rpm). After centrifugation (15,000×g, 10 min), the supernatant was treated with 2 µg of anti-GR (Affinity BioReagents, PA1-511A) or anti-HA (Santa Cruz, sc7392) antibody (4° C., overnight). The next morning, 40 µl of pre-blocked protein G beads were added (4° C., 2 hr). The pellet was centrifuged (5500 g, 1 min), washed sequentially by 1 ml each of wash buffers I, II, and III, three times with 1 ml TE, and then eluted with 2×150 µl elution buffer. The eluents were combined, adjusted to 300 mM NaCl (65° C., overnight, total volume=300 µl) to reverse the cross-linking and then treated with 10 µl EDTA (0.5 M), 40 µl Tris-HCl (1 M, pH 6.5) and 2 µl proteinase K (10 µg/µl, Sigma) at 45° C. for 1 hr. The DNA was purified by a Qiagen PCR Purification Kit according to the manufacture's instructions. The immunoprecipitated DNA was amplified by PCR using the published primers for the collagenase 3 (Rogatsky et al., EMBO J. 20:6071-83 (2001)) and β-actin (Kim et al., Mol. Cell 12: 1537-49 (2003)) genes.

siRNA Assays

Four different siRNA oligonucleotides for STAMP were designed and synthesized by Qiagen:

```
1) GCCAGCTGAGTACGCGGAATT;      (SEQ ID NO: 39)

2) CACCCTCTCTGAAGCACAAAA;      (SEQ ID NO: 38)

3) CAGCACTGACTATAACCTAAT;      (SEQ ID NO: 37)
and

4) GAGGGCAATGAGGCCAAAATA.      (SEQ ID NO: 40)
```

A control β-actin siRNA was also purchased from Qiagen. U2OS.rGR cells were seeded at 50,000 cells per well in 24 wells plate the day before transfection. DNA (STAMP plasmid and AP-1/Luc reporter; total=150 ng) together with 500 ng siRNA were mixed with 1.6 µl Lipofectamine 2000 (Invitrogen), allowed to stand at room temperature for 15 min, and then added to FBS-free DMEM pre-washed cells. Four hours later, the cells were re-fed with DMEM/10% FBS (containing G418), allowed to recover for 2 h, and re-fed with DMEM/10% FBS (containing G418) containing appropriate hormone dilutions±PMA. The cells were harvested and Luciferase activity was determined as described above in the standard transient transfection studies.

EXAMPLE 2

STAMP Isolation and Characterization

This Example describes the isolation and characterization of the STAMP factor.

Isolation of a TIF2.4 Binding Protein by Yeast Two-hybrid Library Screening

The activity of TIF2 and its derivatives (FIG. 1) in modulating glucocorticoid receptor transactivation properties was assessed by quantifying the ability of exogenous coactivator to shift the $EC_{50}$ value of the dose-response curve to lower concentrations of agonist steroid and to increase the partial agonist activity of an anti-glucocorticoid. Szapary et al. (1996) J. Biol. Chem. 271, 30576-30582; Szapary et al. (1999) Mol. Endocrinol. 13, 2108-2121; Chen et al. (2000) J. Biol. Chem. 275, 40810-40816; He et al. (2002) J. Biol. Chem. 277, 49256-49266. Using this assay in CV-1 cells, the inventors previously established that TIF2.4 retains most of the modulatory activity of TIF2. He et al. (2002) J. Biol. Chem. 277, 49256-49266. As shown in FIG. 1 of He et al. (2002), TIF2.37 and TIF2.38 competitively inhibit the actions of TIF2.4, suggesting that a protein present in CV-1 cells may bind to TIF2.37 and TIF2.38.

These results suggested that TIF2.37 and/or TIF2.38 could be used to isolate the protein or proteins that bind to these TIF2 fragments. Unfortunately, both TIF2.37 and TIF2.38 show strong autonomous transactivation activity when used as bait in the conventional yeast two-hybrid screen (data not shown). Therefore, a Sos-Ras system (FIG. 1C) was used that involved a membrane-bound yeast-two hybrid screen that displays no activity with bait but that has intrinsic transactivation activity on reporter genes. See also, Aronheim (1997) Nucleic Acids Res 25, 3373-3374. In this system, TIF2.4 was used as the bait with a human fetal brain library.

Figure 2A:
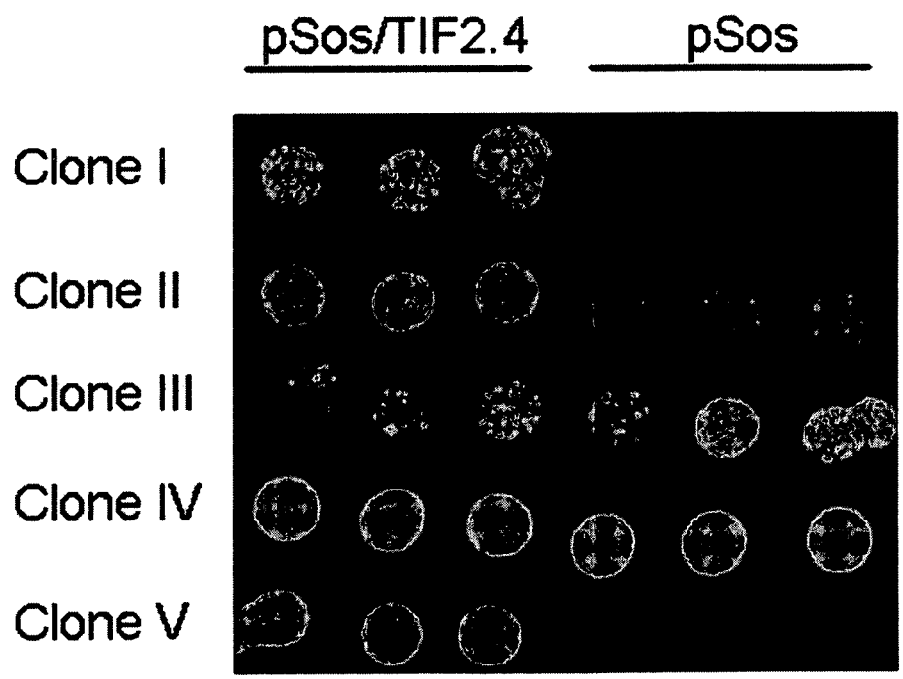
FIG. 2A-2C illustrate the isolation and characterization of the partial clone of the protein that binds to TIF2.4.
Figure 2B:
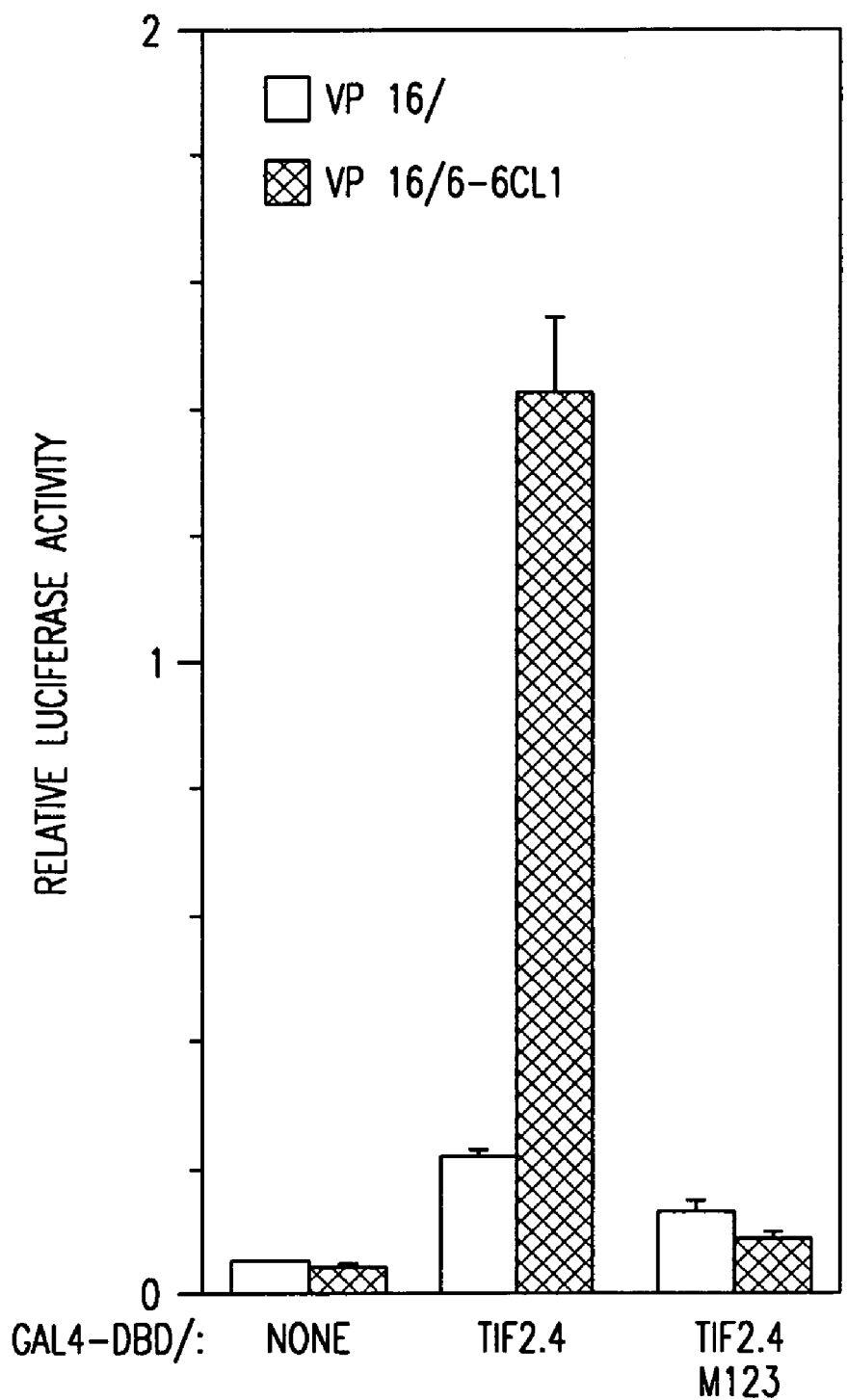
Figure 2C:
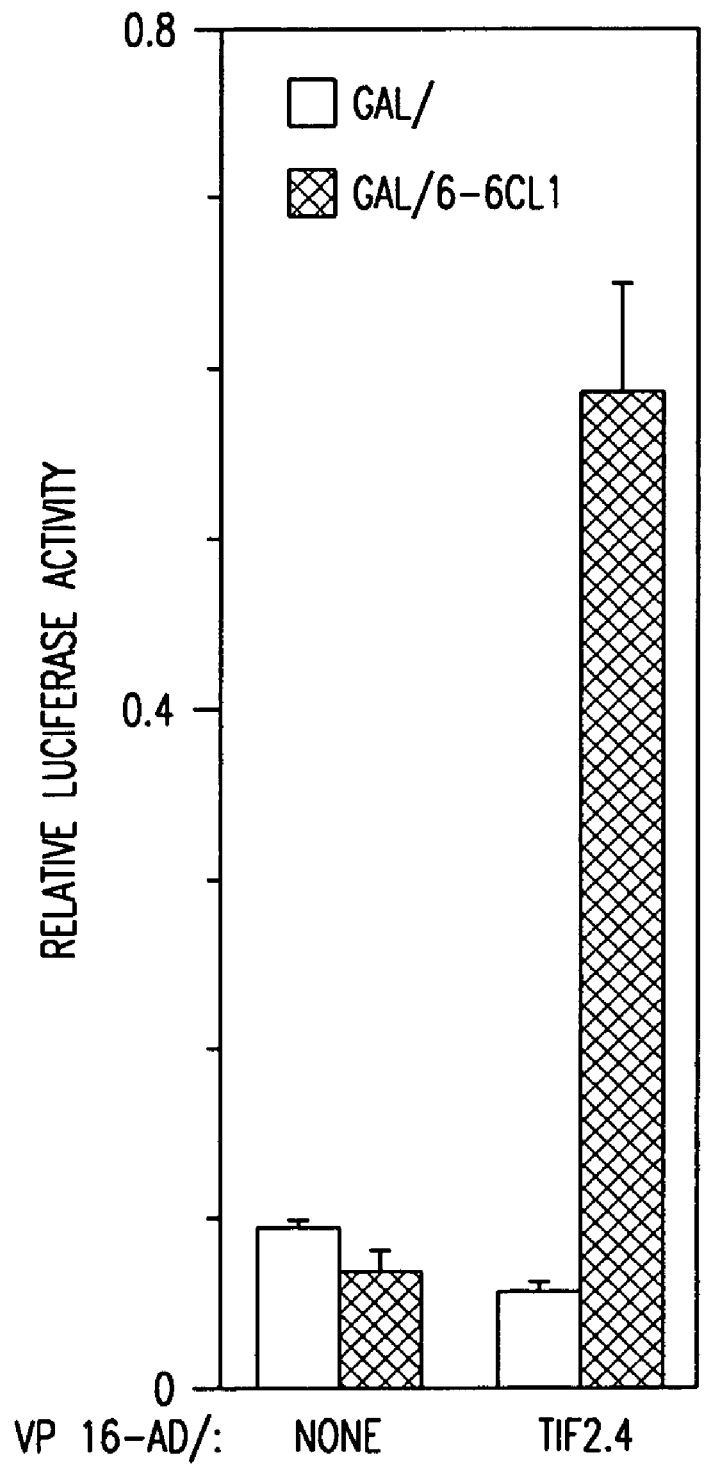

Using the Sos-Ras system with the procedures described in Example 1, a clone was isolated named 6-6CL1 (clone 1 in FIG. 2A), which had an open reading frame of 214 amino acids. In a mammalian two-hybrid assay, the 6-6CL1 clone (fused to the VP16 activation domain) did interact with TIF2.4 but did not interact with equal amounts of TIF2.4m123 protein (see FIGS. 1 and 2B). These results indicate that TIF2.4m123 could not block the TIF2.4-induced changes in GR dose-response curve and partial agonist activity (data not shown). This may be an indirect effect of the mutated RIDs present in TIF2.4m 123, because previous results obtained by the inventors indicate that TIF2.4 fragments which lack the RIDs domains (e.g. TIF2.37 and TIF2.38 shown in FIG. 1A) do not inhibit the modulatory actions of TIF2.4 (see He et al. (2002) J. Biol. Chem. 277, 49256-49266). The same two-hybrid assay revealed negligible association of 6-6CL1 with p300, CBP, and PCAF (data not shown), which are cofactors known to interact with GR/TIF2 complexes. See Chen et al., 1997, Cell 90, 569-580; Voegel et al., 1998, EMBO J. 17, 507-519; Ma et al., 1999, Mol. Cell. Biol. 19, 6164-6173; Chen et al., 2000, J. Biol. Chem. 275, 40810-40816. The 6-6CL1 gene product also interacted with TIF2.4 when using the opposite orientation of fusion constructs (FIG. 2C).

Figure 2D:
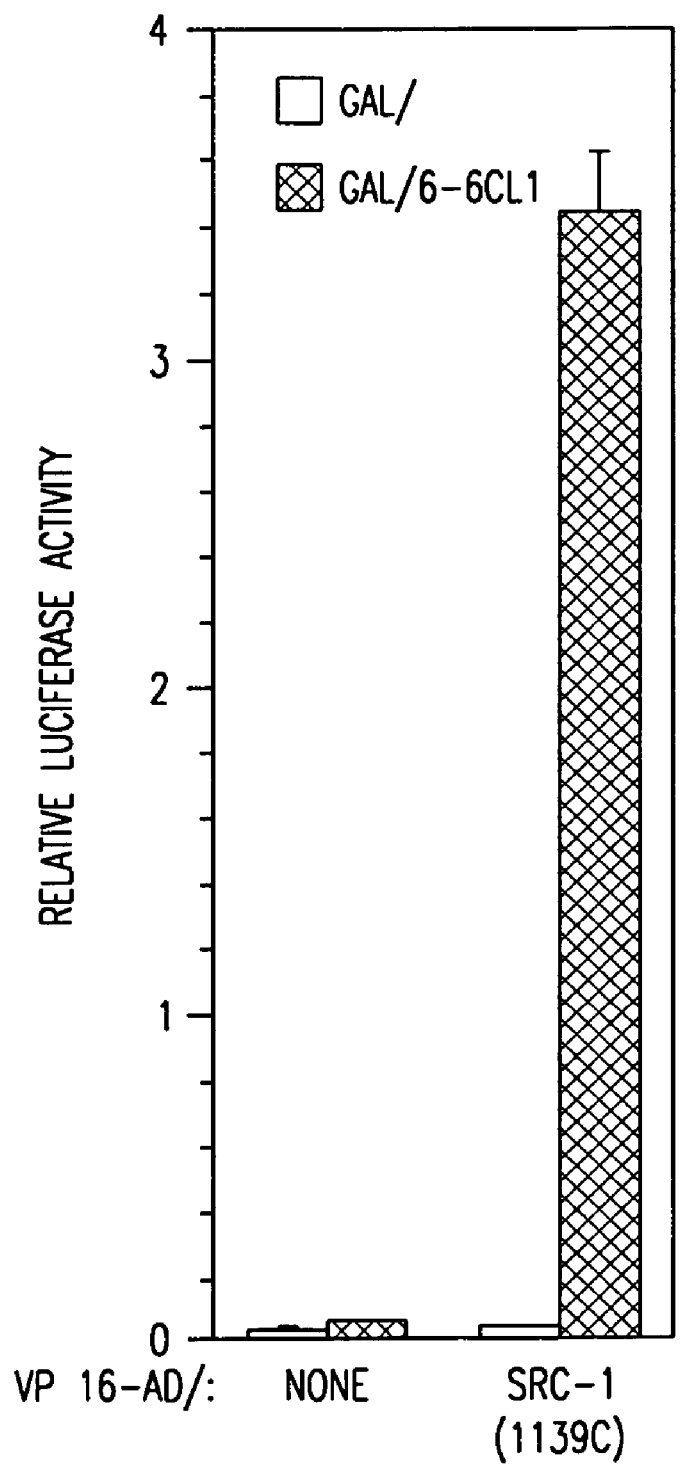
FIG. 2D and FIG. 2E provide a comparison of binding to 6-6CL1 by similarly positioned domains of SRC-1 and TIF2. Triplicate samples of CV-1 cells in 24-well plates were analyzed as in (B&C) after being transiently transfected with GAL±6-6CL1 constructs and pFRLuc reporter along with VP16 chimeras of SRC-1 (FIG. 2D) or TIF2 (FIG. 2E) segments. Similar results for SRC-1 were obtained in two additional experiments (ND=not determined). Western blots (FIG. 2F) indicate that the low activity of TIF2(1140C) (see FIG. 1) is not due to inadequate protein expression.
Figure 2E:
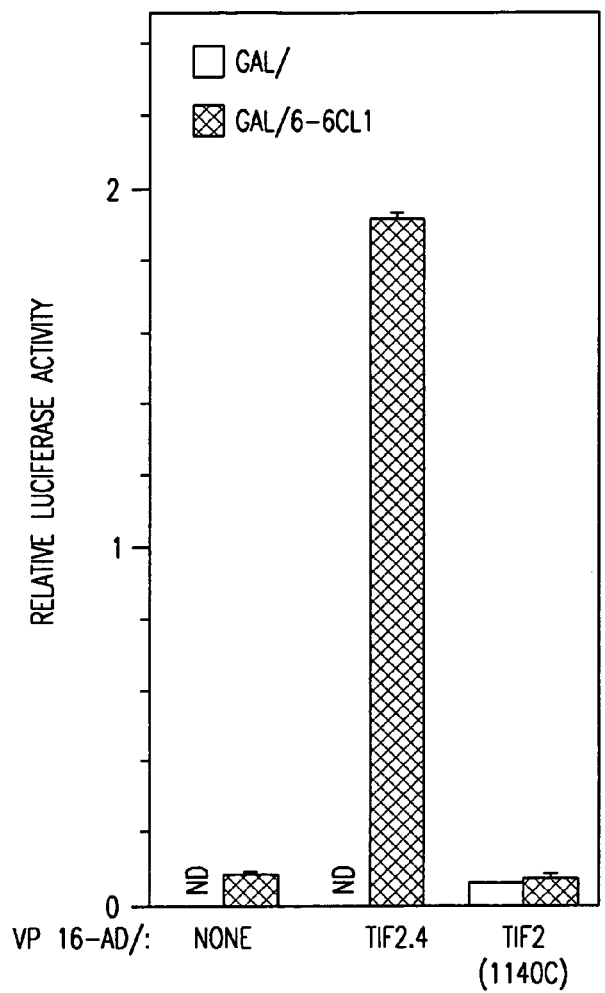
Figure 2F:
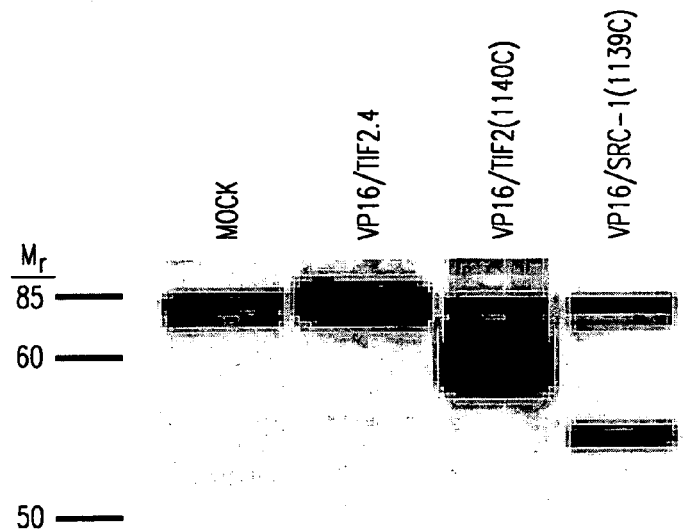

SRC-1, like TIF2, can modulate the dose-response curve and partial agonist activity of GR complexes. Szapary et al., 1999, Mol. Endocrinol. 13, 2108-2121. The C-terminal 303 amino acid SRC-1 fragment (termed 1139C in FIG. 1) was previously found to possess the greatest GR modulatory activity of other SRC-1 peptides tested. He et al., 2002, J. Biol. Chem. 277, 49256-49266. Interestingly, this same C-terminal portion of SRC-1 strongly interacted with the 6-6CL1 polypeptide in the mammalian two-hybrid assay (FIG. 2D). In contrast, while the TIF2 and SRC-1 domains are similarly organized (McKenna and O'Malley, 2002, Cell 108, 465-474; Xu and Li, 2003, Mol. Endocrinol. 17, 1681-1692), the segment of TIF2 that is spatially analogous to the 1139C fragment (i.e. the TIF2(1140C) fragment shown in FIG. 1), does not interact with the 6-6CL1 clone (FIG. 2E). Western blots showed that such inactivity by the TIF2(1140C) fragment was not due to poor expression of the protein (FIG. 2F). These data indicate that distinct (not analogous) domains of TIF2, and SRC-1 modulate GR transactivation properties. These data also indicate that the 6-6CL1 polypeptide is part of a protein that can interact with SRC-1, as well as TIF2. The name STAMP (SRC-1 and TIF2 associated modulatory protein) was chosen for the predicted full length protein that contains the 6-6CL1 sequence.

Isolation of the Full Length Clone of STAMP

Examination of the sequences available in GenBank revealed that 6-6CL1 corresponded to part of a human protein of unknown function. See Nagase et al., 1999, DNA Res 6, 63-70 (GenBank Accession Nos. AB023215, NM_015072, BC002766). The presence of an EST (IMAG:3632160) that extended upstream from the 5' end of those clones containing 6-6CL1 indicated that the full length clone for STAMP had not yet been isolated.

Figure 3A1:
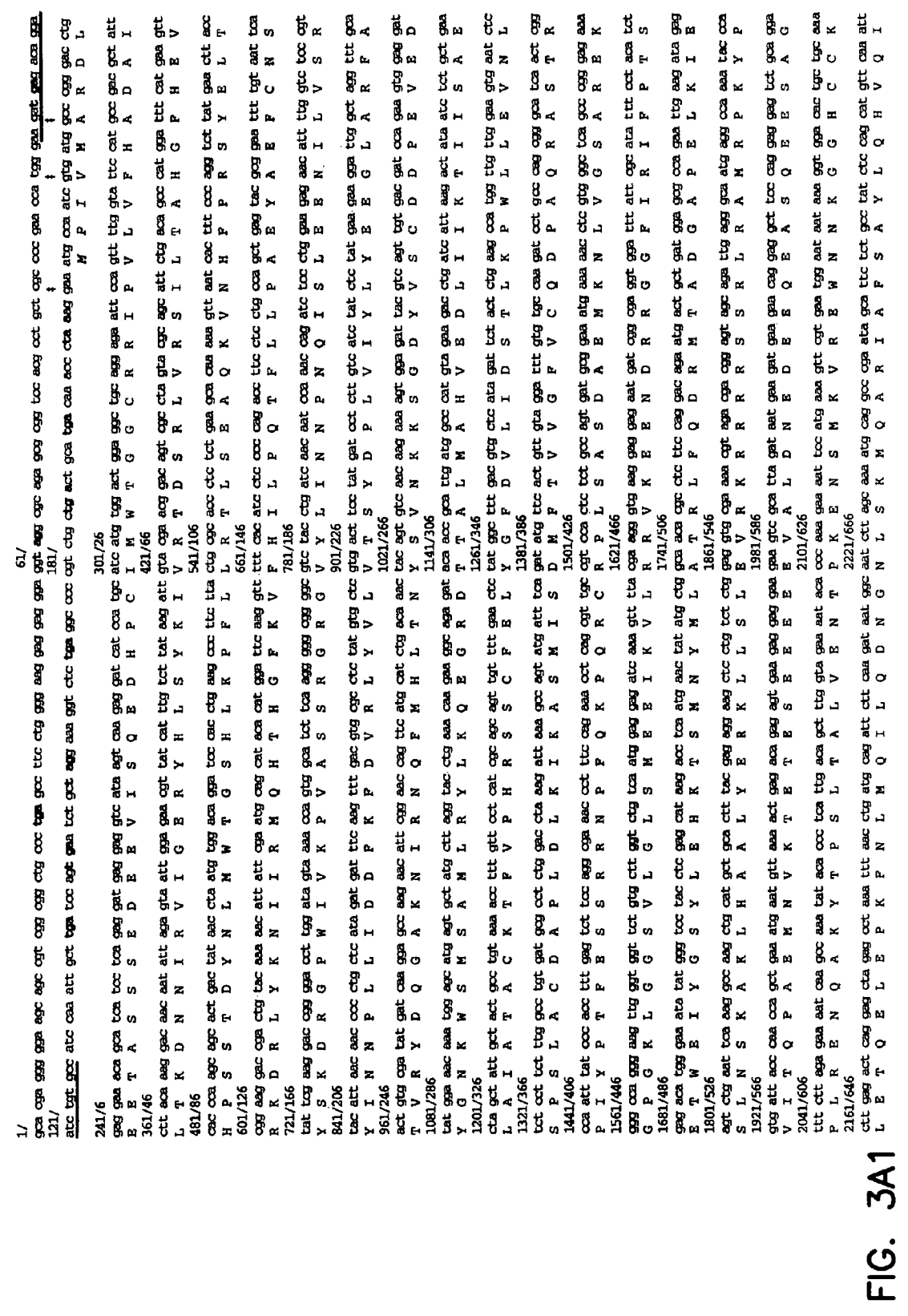
Figure 3A2:
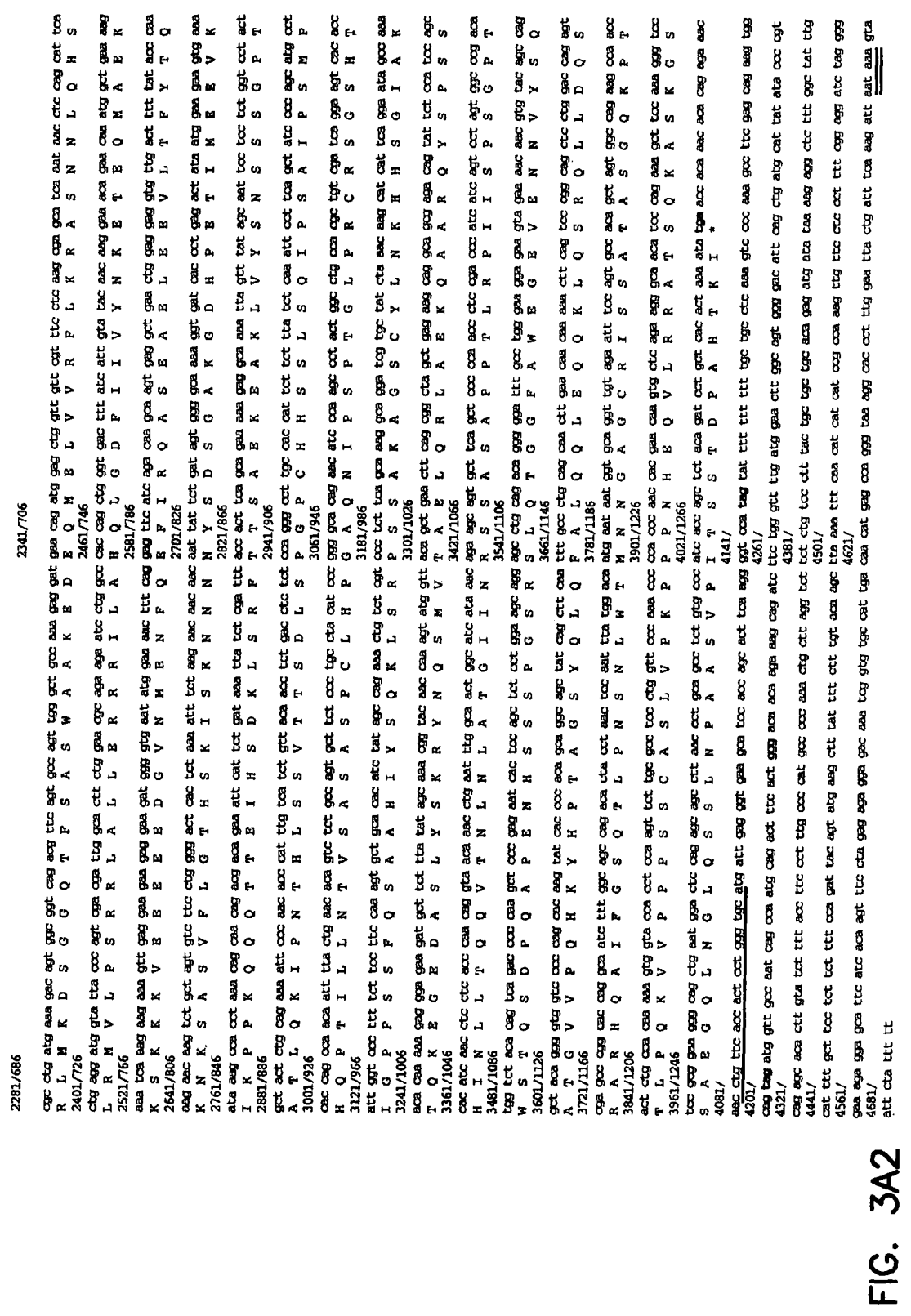

Therefore, a full-length STAMP clone was isolated using the primers described in Example 1. Sequence analysis of the full-length STAMP sequence indicated that the 1277 amino acid STAMP polypeptide is encoded in a 4.6 kb cDNA (GenBank Accession No. AY237126) (FIG. 3A). The STAMP polypeptide had a predicted molecular weight of 143 kDa and is encoded in a locus residing on chromosome 14q24.3 with 32 introns (GenBank Accession No. NM_015072). There is a weaker Kozak sequence (purine at −3 but no G at +4) (Kozak (1989) J. Cell Biol. 108, 229-241) for an alternative start site that is 4 amino acids upstream of the predicted major start site (italicized residues in FIG. 3A). Therefore, there may be heterogeneity in the amino terminal sequence of the STAMP protein in some tissues. The presence of multiple stop codons in all reading frames upstream of the start of translation and several in-frame stop codons at the end of the open reading frame argue that this clone encodes the full length of the protein STAMP.

Figure 3B:
Figure 3C:
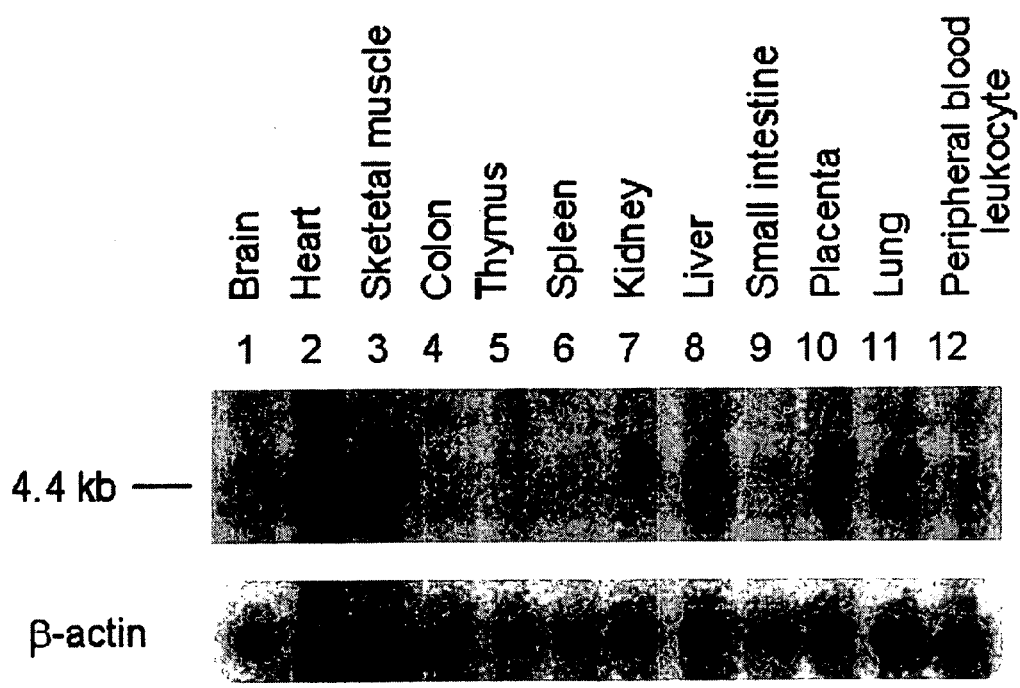

Reverse transcription-Polymerase Chain Reaction (RT-PCR) amplification of an mRNA preparation from human testis (Clontech) using internal primers (underlined sequences in FIG. 3A) produced the correct size for the STAMP cDNA of 4.1 kb (FIG. 3B). These data indicate that a mRNA encoding the full length STAMP protein exists in intact cells. Northern blots reveal the existence of the predicted 4.6 kb mRNA in 12 different tissues (FIG. 3C). The levels of the STAMP mRNA were highest in heart and skeletal muscle. The STAMP mRNA levels were usually low in the other tissues examined suggesting that the STAMP protein levels in these tissues may also be low. However, these data also indicate that STAMP is a ubiquitously expressed protein in humans.

RT-PCR of the mRNA from CV-1 cells, followed by sequencing, showed that monkey cells contain a cDNA (GenBank Accession No. AY383558) that is 98% identical to the human STAMP cDNA (FIG. 3D; alignment from BLAST on GCG). This monkey clone is predicted to encode a protein that is 97% identical to the human STAMP protein (FIG. 3E). Mice contain a cDNA encoding a protein of unknown function (GenBank Accession No. XM_126935) that is 83.3% identical to the C-terminal 705 amino acids of the human STAMP protein. Thus the STAMP gene and protein are conserved among these different species.

Whole Cell Localization of STAMP

Indirect immunofluorescence, using HA-tagged full-length STAMP revealed that STAMP has a diverse cellular localization in U2OS.rGR (FIG. 3F1-6) and CV-1 cells (data not shown) in the absence of dexamethasone (Dex). STAMP was usually observed in the cytoplasm (red in the original) and associated with glucocorticoid receptors (GRs, green in the original), as indicated by the lighter shades in FIG. 3. Twenty minutes after the addition of Dex, STAMP colocalized with GRs in the nucleus of numerous cells (lighter shades in FIG. 3F). In both cases, the amount of STAMP-GR complexes was variable, presumably due to different ratios of STAMP to GR in the cells.

Activity of STAMP in GR-mediated Induction

Tests were run to determine whether exogenous STAMP can modulate the $EC_{50}$ of glucocorticoids and the partial agonist activity of antiglucocorticoids in the transient transfection assays where GR induced gene expression from a GREtkLUC reporter. See Szapary et al., 1996, J. Biol. Chem. 271, 30576-30582; Szapary et al., 1999, Mol. Endocrinol. 13, 2108-2121; Chen et al., 2000, J. Biol. Chem. 275, 40810-40816; He et al., 2002, J. Biol. Chem. 277, 49256-49266.

In the absence of exogenous coactivators and low concentrations of GR, STAMP caused a weak but statistically significant shift in the dose-response curve to lower steroid concentrations (1.54±0.12 fold, S.E.M., n=6, P=0.0074) and an increase in the partial agonist activity of the antagonist Dex-Mes (1.16±0.05 fold higher from 39% to 45% activity, S.E.M., n=6, P=0.023). It should be noted that STAMP also had a small effect on the total amount of gene product induced by 1 μM Dex (1.26±0.05 fold increase, S.E.M., n=6) but there is no change in the fold induction by 1 μM Dex (0.93±0.08 fold increase, S.E.M., n=6). Addition of TIF2 alone had a similar, small effect (FIG. 4A1).

However, a significant further left-shift in the dose-response curve occurs when both STAMP and TIF2 are added (FIG. 4A1, see also FIG. 4A2). When the fold change in $EC_{50}$ from four independent experiments is normalized to that of GR alone, STAMP plus TIF2 produces a greater change in $EC_{50}$ to lower steroid concentrations than expected from the responses of STAMP and TIF2 alone (FIG. 4B). Similarly, the effect of STAMP plus TIF2 on the partial agonist activity of Dex-Mes is greater than the sum of the individual factors (FIG. 4B). This is consistent with STAMP being a limiting factor in the presence of exogenous GR and TIF2. At the same time, STAMP increases the fold induction (above basal activity) with 1 μM Dex both with and without added TIF2 (FIG. 4B).

Activity of STAMP in GR-mediated Repression

Rogatsky et al. have reported that TIF2 augments GR repression of an AP-1 induced gene. Rogatsky et al., (2002) Proc. Natl. Acad. Sci. U. S. A. 99, 16701-16706; Rogatsky et al. (2001) EMBO J. 20: 6071-6083. The TIF2 domain identified as having TIF2 activity in GR repression was the same as used to isolate STAMP. In order to determine if STAMP was active in GR-mediated gene repression as well as induction, the ability of STAMP to increase the repressive activity of GR in the AP-1 responsive whole cell bioassay system was assessed using U2OS.rGR cells.

As seen in FIG. 5A, the fold induction by PMA was unchanged by the presence of TIF2, STAMP, or TIF2+STAMP. However, when dexamethasone was added, the level of GR-related expression (without added TIF2 or STAMP) was reduced by about 5-fold. Addition of TIF2 reduced the level of GR-related expression even further (about 9-fold). See also, Rogatsky et al., 2002, Proc. Natl. Acad. Sci. U. S. A. 99, 16701-16706. The presence of exogenous STAMP, without added TIF2, increased the repression by Dex-bound glucocorticoid receptors to 16-fold. This response may reflect the ability of exogenous STAMP to supplement limiting concentrations of endogenous STAMP that interact naturally with endogenous TIF2. Significantly, addition of STAMP with TIF2 reduced induction of AP-1 expression in the presence of Dex-bound GRs even further, to about 31-fold (P=0.029; Mann-Whitney test). These data indicate that STAMP and TIF2 act cooperatively to modulate glucocorticoid receptor activity.

The enhancement of STAMP activity by TIF2 was investigated by comparing the fold repression seen with the wild type TIF2 to the mutant TIF2ml23 (FIG. 1A), which does not interact with GR (Voegel et al., 1998; Ding et al., 1998; He et al., 2002) and appears not to bind to STAMP (FIG. 2B). In these experiments, less STAMP (50 vs. 100 ng) was added in order to reduce the fold repression due STAMP alone. FIG. 5B shows that TIF2m123 was unable to augment GR-mediated repression either by itself or in combination with STAMP. Therefore, these results indicate that STAMP activity requires the RID domains that mediate TIF2 binding to GR and/or STAMP.

The endogenous collagenase-3 (coll3) gene in U2OS.rGR cells is repressed by GR. TIF2 potentiates GR repression of coll3 and is recruited to the coll3 promoter in concert with GR-agonist complexes (Rogatsky et al., 2001). Because STAMP augments the ability of TIF2 to increase GR repression of a transiently transfected gene (FIG. 5A), chromatin immunoprecipitation assays were used to ascertain whether STAMP is also recruited by GR/TIF2 complexes to the endogenous coll3 gene. FIG. 5C shows that both GR and STAMP were induced to localize on the coll3 promoter after 20 min of steroid treatment. This is the same time period in which nuclear colocalization of GR and STAMP is seen (FIG. 6). The time-dependent promoter binding by both GR and STAMP also indicates that, in intact cells, this binding is not due simply to increased protein levels following transient transfection.

Inhibition of STAMP Actions by STAMP siRNA

Experiments were performed to ascertain whether STAMP siRNAs can reduce STAMP protein levels and reverse the effects of STAMP. Four siRNAs were prepared that were based upon STAMP cDNA. The probability that each siRNA would have at least 11 nucleotides in common with any other gene, and thus silence the expression of a gene other than STAMP, was exceedingly small. As shown in FIG. 5D1 and 5D2, each STAMP siRNA significantly reduced the level of overexpressed STAMP protein, with little or no effect on ectopic GR protein levels, while a non-specific control (β-actin siRNA) had negligible effects on either protein. Thus, the STAMP siRNAs were STAMP-specific in that they reduced the levels of expressed STAMP protein.

As shown in FIG. 5E, each STAMP siRNA was also very effective in reversing the ability of transfected STAMP to increase the fold repression by GR of an AP-1 reporter relative to the β-actin siRNA control. STAMP siRNAs #3 and 4 were then used to lower the levels of endogenous STAMP. As shown in FIG. 5F, these siRNAs can reduce the repressive activity of GR-agonist complexes, indicating that endogenous STAMP is present in U2OS.rGR cells and assists in GR-mediated inhibition of an AP-1 induced gene.

Identification of Regions of STAMP Interacting with Other Proteins

FIG. 2 indicates that the clone 6-6CL1, which encompasses amino acids 623-834 of STAMP, binds to TIF2.4. In order to determine the specificity of this binding, the interactions of other regions of STAMP with TIF2.4 were examined in the mammalian two hybrid assay. FIG. 6A shows that most of the STAMP domain that interacts with TIF2.4 resides between amino acids 623 and 834 of STAMP. This interaction domain is called the CID, or coactivator interaction domain. Western blots (data not shown) and the biological activity assays (see below) indicated that the weak response of the amino and carboxyl fragments (N623 and 834C) in FIG. 6A was not due to poor levels of protein expression. It should be noted that no segment of STAMP (FIG. 6A), nor the full length STAMP (data not shown), displayed any intrinsic transactivation activity, as determined from the inability of each GAL/STAMP chimera to induce the FRLuc reporter in the absence of TIF2.4.

Interestingly, a region of STAMP more C-terminal than the CID interacted with GR in a steroid-responsive manner (FIG. 6B). Again, Western blots (data not shown) and the activity in FIG. 6A argue that the relative inactivity of GAL/N834 and/ 623-834 is not due to inadequate protein expression. The numbers in parentheses above the bar for VP16/GR (with Dex) represent the fold induction by with and without Dex. While there was increased association of steroid-free GR with the STAMP segment of amino acids 834-956, the largest agonist-induced changes in GR interaction with STAMP occurred when the C-terminal STAMP domain was used, including amino acids 834-1277 (=834C) (FIG. 6B). There is substantial ligand-independent association of GR with STAMP(834-956) while the largest agonist-induced changes in GR interaction with STAMP are restricted to the two domains of amino acids 956-1127 and 1127-1277 (=1127C) (FIG. 6B). Neither half of GR (N-terminal [N523] or C-terminal [407C] half) interacted with STAMP834C in this assay under conditions that give a strong response with GR407C and the receptor interaction domain of TIF2 (TIF2.4; data not shown; S3 file "STAMP-GRdomain/2Hybrid"). Thus, it appears that both N- and C-terminal domains of GR are required for the interaction of wild type GR with STAMP.

Importantly, STAMP834C also interacted with agonist-bound, full length PRs (B-form) and androgen receptors (ARs) but not estrogen (α or β), PPARγ2, thyroid (TR) (β), RXR α, or retinoid (α) receptors (FIG. 6C). The lack of interaction with all but GR, PR, and AR is not due to low expression of the other receptors as seen by their robust activity with GAL/TIF2.4 (FIG. 6C). The ability of STAMP to supplement the whole cell actions of TIF2 with full length AR and TRβ was therefore examined. As shown in FIG. 6D, STAMP augments the left-shift of the dose-response curve of ARs in the presence of TIF2 but not when added by itself. Conversely, STAMP increases the fold induction by AR but has no additional effect with TIF2. In contrast to AR, added STAMP has little ability with TRβ either to cause a left-shift in the dose-response curve or to increase the fold induction regardless of whether TIF2 is present (FIG. 6D). Collectively, these data suggest that STAMP association and activity with receptors is more discriminatory than that of the coactivator TIF2 and may be selective for the sub-class of receptors that bind to a glucocorticoid receptor enhancer (GRE) (Beato et al. (1989) J. Steroid Biochem. 32:737-48).

The binding of [$^{35}$S]methionine-labeled, in vitro translated STAMP constructs to GST/TIF2.4 in a pulldown assay further indicates that a weak interaction exists between TIF2.4 and the full length STAMP, but STAMP fragments encompassing amino acids 623-834 shows strong binding to TIF2.4 (FIG. 7A). This binding is selective in that neither the amino terminal (N623) nor the C-terminal (834C) fragments exhibit significantly more binding to GST/TIF2.4 than to GST itself (FIG. 7A). However, the STAMP 623-824 fragment exhibits strong TIF binding. Similarly, the pulldown assays that show [$^{35}$S]methionine-labeled full length glucocorticoid receptor (GR) bound to GST/STAMP(956C), although this binding is steroid-independent (FIG. 7B).

The N-terminal domain of STAMP contains the only previously characterized, functional domain, which is a tubulin-tyrosine ligase (TTL) domain at amino acids 113-391 (FIG. 7A). A comparison of the actions of Flag/STAMP with and without the TTL domain (STAMP623C) in the presence of transfected GR and TIF2 shows that STAMP lacking the TTL domain retains 85% of the capacity of full length STAMP to increase the fold induction with Dex. Moreover, STAMP lacking the TTL domain retained 40% of its ability to increase the partial agonist activity of Dex-Mes and decreased the EC$_{50}$ for Dex induction (FIG. 8). Therefore, it appears that the TTL domain is not essential for any of the identified activities of STAMP.

Whole Cell Interaction of STAMP with GR and TIF2

The data provided in FIGS. 5 and 7 indicate that the biological effects of STAMP (see, e.g., FIG. 4-5) are mediated by the binding of STAMP to TIF2, and possibly to GR. FIGS. 7 and 8 further indicate that STAMP and TIF2 and/or STAMP and GR functionally interact with one another. To detect whether STAMP can interact with TIF2 and/or GR in intact cells, Cos-7 cells were cotransfected with HA-GRIP 1 (GRIP 1 is the mouse homolog of TIF2), GR, and Flag-STAMP or Flag itself, and cell lysates were subjected to immunoprecipitation with various antibodies. Anti-Flag antibody was used to precipitate Flag-STAMP and associated proteins.

The immunoprecipitation results provided in FIG. 7C show that GRIP1 and GR are both co-immunoprecipitated with STAMP in a manner that requires the presence of STAMP (in FIG. 7C1 compare lanes 2 and 3 with Flag-STAMP to lane 4 with just Flag). Consistent with the pull-down data shown in FIG. 7B, the presence or absence of the agonist Dex does not alter the ability of GR to be co-immunoprecipitated by STAMP (FIG. 7C3, lane 2 vs. 3). Similarly, GR and STAMP were co-immunoprecipitated with the chimera HA/GRIP by anti-HA antibody (data not shown).

Thus, the invention provides novel STAMP polypeptides that interact with the biologically active domains of TIF2 and SRC-1. The association of STAMP with TIF2 is mediated by a central domain within STAMP, while the C-terminal domain of STAMP binds to glucocorticoid receptors. A mutation of TIF2 (to give TIF2m123) that prevents TIF2 binding to STAMP and GR also eliminates the ability of TIF2 to augment GR repressive activity with or without STAMP. While STAMP can be found in both the cytoplasm and the nucleus, STAMP and glucocorticoid receptor polypeptides do co-localize in the nucleus, especially in the presence of dexamethasone. The addition of STAMP to GR-responsive whole cells increases the modulatory activity of TIF2 for a GR-induced gene expression and accentuates the repressive effects of TIF2 for a GR-suppressed gene activity. STAMP affects multiple aspects of GR regulated gene expression in whole cells, including both GR-mediated induction and repression. The repressive activity of endogenous and exogenous STAMP is largely abrogated by addition of STAMP siRNAs. These data indicate that STAMP is an important new factor in the glucocorticoid regulatory network and can act as a modulator of both GR-mediated gene activation and GR-mediated gene repression. As illustrated herein GR-mediated gene activation and repression can be modulated by addition of STAMP polypeptides or STAMP siRNAs.

Articles

Aronheim, A. (1997). Improved efficiency sos recruitment system: expression of the mammalian GAP reduces isolation of Ras GTPase false positives. Nucleic Acids Res 25, 3373-3374.

Beato, M., Chalepakis, G., Schauer, M., and Slater, E. P. (1989). DNA regulatory elements for steroid hormones. J. Steroid Biochem. 32, 737-748.

Brown, K., Chen, Y., Underhill, T. M., Mymryk, J. S., and Torchia, J. (2003). The coactivator p/CIP/SRC-3 facilitates retinoic acid receptor signaling via recruitment of GCN5. J Biol Chem 278, 39402-39412.

Chen, D., Huang, S. M., and Stallcup, M. R. (2000). Synergistic, p160 coactivator-dependent enhancement of estrogen receptor function by CARM1 and p300. J. Biol. Chem. 275, 40810-40816.

Chen, D., Ma, H., Hong, H., Koh, S. S., Huang, S.-M., Schurter, B. T., Aswad, D. W., and Stallcup, M. R. (1999). Regulation of transcription by a protein methyltransferase. Science 284, 2174-2177.

Chen, H., Lin, R. J., Schiltz, R. L., Chakravarti, D., Nash, A., Nagy, L., Privalsky, M. L., Nakatani, Y., and Evans, R. M. (1997). Nuclear receptor coactivator ACTR is a novel histone acetyltransferase and forms a multimeric activation complex with P/CAF and CBP/p300. Cell 90, 569-580.

Chen, S., Sarlis, N. J., and Simons, Jr., S. S. (2000). Evidence for a common step in three different processes for modulating the kinetic properties of glucocorticoid receptor-induced gene transcription. J. Biol. Chem. 275, 30106-30117.

Cheng, S., Brzostek, S., Lee, S. R., Hollenberg, A. N., and Balk, S. P. (2002). Inhibition of the dihydrotestosterone-activated androgen receptor by nuclear receptor corepressor. Mol. Endocrinol. 16, 1492-1501.

Cosma, M. P. (2002). Ordered recruitment: gene-specific mechanism of transcription activation. Mol. Cell 10, 227-236.

Darimont, B. D., Wagner, R. L., Apriletti, J. W., Stallcup, M. R., Kushner, P. J., Baxter, J. D., Fletterick, R. J., and Yamamoto, K. R. (1998). Structure and specificity of nuclear receptor-coactivator interactions. Genes and Develop. 12, 3343-3356.

Dotzlaw, H., Moehren, U., Mink, S., Cato, A. C., Iniguez, L. J. A., and Baniahmad, A. (2002). The amino terminus of the human AR is target for corepressor action and antihormone agonism. Mol. Endocrinol. 16, 661-673.

Giannoukos, G., Szapary, D., Smith, C. L., Meeker, J. E. W., and Simons, Jr., S. S. (2001). New antiprogestins with partial agonist activity: potential selective progesterone receptor modulators (SPRMs) and probes for receptor- and coregulator-induced changes in progesterone receptor induction properties. Mol. Endocrinol. 15, 255-270.

He, Y., Szapary, D., and Simons, Jr., S. S. (2002). Modulation of induction properties of glucocorticoid receptor-agonist and -antagonist complexes by coactivators involves binding to receptors but is independent of ability of coactivators to augment transactivation. J. Biol. Chem. 277, 49256-49266.

Hong, H., Kohli, K., Trivedi, A., Johnson, D. L., and Stallcup, M. R. (1996). GRIP1, a novel mouse protein that serves as a transcriptional coactivator in yeast for the hormone binding domains of steroid receptors. Proc. Natl. Acad. Sci. USA 93, 4948-4952.

Kalkhoven, E., Valentine, J. E., Heery, D. M., and Parker, M. G. (1998). Isoforms of steroid receptor co-activator 1 differ in their ability to potentiate transcription by the oestrogen receptor. EMBO J. 17, 232-243.

Karin, M., and Chang, L. (2001). AP-1—glucocorticoid receptor crosstalk taken to a higher level. J Endocrinol 169, 447-451.

Kaul, S., Blackford, Jr., J. A., Cho, S., and Simons, Jr., S. S. (2002). Ubc9 is a novel modulator of the induction properties of glucocorticoid receptors. J. Biol. Chem. 277, 12541-12549.

Kim, J. H., Li, H., and Stallcup, M. R. (2003). CoCoA, a nuclear receptor coactivator which acts through an N-terminal activation domain of p160 coactivators. Mol Cell 12, 1537-1549.

Koh, S. S., Chen, D., Lee, Y. H., and Stallcup, M. R. (2001). Synergistic enhancement of nuclear receptor function by p160 coactivators and two coactivators with protein methyltransferase activities. J. Biol. Chem. 276, 1089-1098.

Kozak, M. (1989). The scanning model of translation: an update. J. Cell Biol. 108, 229-241.

Lavinsky, R. M., Jepsen, K., Heinzel, T., Torchia, J., Mullen, T.-M., Schiff, R., Del-Rio, A. L., Ricote, M., Ngo, S., Gemsch, J., Hilsenbeck, S. G., Osborne, C. K., Glass, C. K., Rosenfeld, M. G., and Rose, D. W. (1998). Diverse signaling pathways modulate nuclear receptor recruitment of N-CoR and SMRT complexes. Proc. Natl. Acad. Sci. USA 95, 2920-2925.

Lee, Y. H., Koh, S. S., Zhang, X., Cheng, X., and Stallcup, M. R. (2002). Synergy among nuclear receptor coactivators: selective requirement for protein methyltransferase and acetyltransferase activities. Mol. Cell Biol. 22, 3621-3632.

Ma, H., Hong, H., Huang, S.-M., Irvine, R. A., Webb, P., Kushner, P. J., Coetzee, G. A., and Stallcup, M. R. (1999). Multiple signal input and output domains of the 160-kilodalton nuclear receptor coactivator proteins. Mol. Cell. Biol. 19, 6164-6173.

McInerney, E. M., Rose, D. W., Flynn, S. E., Westin, S., Mullen, T.-M., Krones, A., Inostroza, J., Torchia, J., Nolte, R. T., Assa-Munt, N., Milburn, M. V., Glass, C. K., and Rosenfeld, M. G. (1998). Determinants of coactivator LXXLL motif specificity in nuclear receptor transcriptional activation. Genes and Develop. 12, 3357-3368.

McKenna, N. J., Lanz, R. B., and O'Malley, B. W. (1999). Nuclear receptor coregulators: cellular and molecular biology. Endocrine Reviews 20, 321-344.

McKenna, N. J., and O'Malley, B. W. (2002). Combinatorial control of gene expression by nuclear receptors and coregulators. Cell 108, 465-474.

Nagase, T., Ishikawa, K., Suyama, M., Kikuno, R., Hirosawa, M., Miyajima, N., Tanaka, A., Kotani, H., Nomura, N., and Ohara, O. (1999). Prediction of the coding sequences of unidentified human genes. XIII. The complete sequences of 100 new cDNA clones from brain which code for large proteins in vitro. DNA Res 6, 63-70.

Onate, S. A., Boonyaratanakornkit, V., Spencer, T. E., Tsai, S. Y., Tsai, M.-J., Edwards, D. P., and O'Malley, B. W. (1998). The steroid receptor coactivator-1 contains multiple receptor interacting and activation domains that cooperatively enhance the activation function 1 (AF1) and AF2 domains of steroid receptors. J. Biol. Chem. 273, 12101-12108.

Onate, S. A., Tsai, S. Y., Tsai, M.-J., and O'Malley, B. W. (1995). Sequence and characterization of a coactivator for the steroid hormone receptor superfamily. Science 270, 1354-1357.

Oshima, H., and Simons, Jr., S. S. (1993). Sequence-selective interactions of transcription factor elements with tandem glucocorticoid-responsive elements at physiological steroid concentrations. J. Biol. Chem. 268, 26858-26865.

Pons, M., and Simons, Jr., S. S. (1981). Facile, high yield synthesis of spiro C-17-steroidal oxetan-3'-ones. J. Org. Chem. 46, 3262-3264.

Robyr, D., Wolffe, A. P., and Wahli, W. (2000). Nuclear hormone receptor coregulators in action: diversity for shared tasks. Mol. Endocrinol. 14, 329-347.

Rogatsky, I., Trowbridge, J. M., and Garabedian, M. J. (1997). Glucocorticoid receptor-mediated cell cycle arrest is achieved through distinct cell-specific transcriptional regulatory mechanisms. Mol Cell Biol 17, 3181-3193.

Rogatsky, I., Luecke, H. F., Leitman, D. C., and Yamamoto, K. R. (2002). Alternate surfaces of transcriptional coregulator GRIP1 function in different glucocorticoid receptor activation and repression contexts. Proc. Natl. Acad. Sci. U. S. A. 99, 16701-16706.

Rogatsky, I., Zarember, K. A., and Yamamoto, K. R. (2001). Factor recruitment and TIF2/GRIP1 corepressor activity at a collagenase-3 response element that mediates regulation by phorbol esters and hormones. EMBO. J. 20, 6071-6083.

Schaaf, M. J., and Cidlowski, J. A. (2002). Molecular mechanisms of glucocorticoid action and resistance. J Steroid Biochem Mol Biol 83, 37-48.

Schulz, M., Eggert, M., Baniahmad, A., Dostert, A., Heinzel, T., and Renkawitz, R. (2002). RU486-induced glucocorticoid receptor agonism is controlled by the receptor N terminus and by corepressor binding. J. Biol. Chem. 277, 26238-26243.

Simons, Jr., S. S. (2003). The importance of being varied in steroid receptor transactivation. TIPS 24, 253-259.

Simons, Jr., S. S., Pons, M., and Johnson, D. F. (1980). □-Keto mesylate: a reactive thiol-specific functional group. J. Org. Chem. 45, 3084-3088.

Singh, P., Chan, S. W., and Hong, W. (2001). Retinoblastoma protein is functionally distinct from its homologues in affecting glucocorticoid receptor-mediated transcription and apoptosis. J. Biol. Chem. 276, 13762-13770.

Song, L.-N., Huse, B., Rusconi, S., and Simons, Jr., S. S. (2001). Transactivation specificity of glucocorticoid vs. progesterone receptors: role of functionally different interactions of transcription factors with amino- and carboxyl-terminal receptor domains. J. Biol. Chem. 276, 24806-24816.

Szapary, D., Huang, Y., and Simons, Jr., S. S. (1999). Opposing effects of corepressor and coactivators in determining the dose-response curve of agonists, and residual agonist activity of antagonists, for glucocorticoid receptor regulated gene expression. Mol. Endocrinol. 13, 2108-2121.

Szapary, D., Xu, M., and Simons, Jr., S. S. (1996). Induction properties of a transiently transfected glucocorticoid-responsive gene vary with glucocorticoid receptor concentration. J. Biol. Chem. 271, 30576-30582.

Torchia, J., Rose, D. W., Inostroza, J., Kamei, Y., Westin, S., Glass, C. K., and Rosenfeld, M. G. (1997). The transcriptional co-activator p/CIP binds CBP and mediates nuclear-receptor function. Nature 387, 677-684.

Truss, M., and Beato, M. (1993). Steroid hormone receptors: interaction with deoxyribonucleic acid and transcription factors. Endocrine Reviews 14, 459-479.

Tsai, M.-J., and O'Malley, B. W. (1994). Molecular mechanisms of action of steroid/thyroid receptor superfamily members. Annu. Rev. Biochem. 63, 451-486.

Voegel, J. J., Heine, M. J. S., Tini, M., Vivat, V., Chambon, P., and Gronemeyer, H. (1998). The coactivator TIF2 contains three nuclear receptor-binding motifs and mediates transactivation through CBP binding-dependent and -independent pathways. EMBO J. 17, 507-519.

Voegel, J. J., Heine, M. J. S., Zechel, C., Chambon, P., and Gronemeyer, H. (1996). TIF2, a 160 kDa transcriptional mediatior for the ligand-dependent activation function AF-2 of nuclear receptors. EMBO J. 15, 3667-3675.

Wagner, B. L., Norris, J. D., Knotts, T. A., Weigel, N. L., and McDonnell, D. P. (1998). The nuclear corepressors NCoR and SMRT are key regulators of both ligand- and 8-bromo-cyclic AMP-dependent transcriptional activity of the human progesterone receptor. Mol. Cell. Biol. 18, 1369-1378.

Wang, Q., Blackford, Jr., J. A., Song, L.-N., Huang, Y., and Simons, Jr., S. S. (2004). Equilibrium interactions of corepressors and coactivators modulate the properties of agonist and antagonist complexes of glucocorticoid receptors. Mol. Endocrinol. 18, 1376-1395.

Wang, Q., Richter, W. F., Anzick, S. L., Meltzer, P. S., and Simons, Jr., S. S. (b). Effects of changing concentrations of receptor, coactivator, and corepressor on the transcriptional properties of mineralocorticoid and estrogen receptors. Under Review Woychik, N. A., and Hampsey, M. (2002). The RNA polymerase II machinery: structure illuminates function. Cell 108, 453-463.

Wu, Z., Belanger, G., Brennan, B. B., Lum, J. K., Minter, A. R., Rowe, S. P., Plachetka, A., Majmudar, C. Y., and Mapp, A. K. (2003). Targeting the transcriptional machinery with unique artificial transcriptional activators. J Amer Chem Soc 125, 12390-12391.

Xu, J., and Li, Q. (2003). Review of the in vivo functions of the p160 steroid receptor coactivator family. Mol. Endocrinol. 17, 1681-1692.

Xu, L., Glass, C. K., and Rosenfeld, M. G. (1999). Coactivator and corepressor complexes in nuclear receptor function. Current Opin. Cell Biol. 9, 140-147.

Yao, T.-P., Ku, G., Zhou, N., Scully, R., and Livingston, D. M. (1996). The nuclear hormone receptor coactivator SRC-1 is a specific target of p300. Proc. Natl. Acad. Sci. USA 93, 10626-10631.

Zeng, H., Plisov, S. Y., and Simons, Jr., S. S. (2000). Ability of the glucocorticoid modulatory element (GME) to modify glucocorticoid receptor transactivation indicates parallel pathways for the expression of GME and glucocorticoid response element activities. Mol. Cell. Endo. 162, 221-234.

Zhang, X., Jeyakumar, M., Petukhow, S., and Bagchi, M. K. (1998). A nuclear receptor corepressor modulates transcriptional activity of antagonist-occupied steroid hormone receptor. Mol. Endocrinol. 12, 513-524.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of modulating the activity of a steroid or nuclear receptor selected from the group consisting of a glucocorticoid receptor, a progesterone receptor, an androgen receptor and a mineralocorticoid receptor, in a mammal comprising administering to the mammal a composition comprising a carrier and an effective amount of a Steroid receptor coactivator-1 and Transcription intermediary factor 2 Associated Modulatory Protein (STAMP) polypeptide selected from the group consisting of SEQ ID NO: 1, SEQ ID NO:5, SEQ ID NO:6, SEQ ID NO:70 and a combination thereof.

2. The method of claim 1, wherein the receptor is a glucocorticoid receptor.

3. The method of claim 1, wherein the composition also comprises a ligand, coactivator, agonist, partial agonist or antagonist for the receptor.

* * * * *